United States Patent
Bálint et al.

(10) Patent No.: US 10,618,909 B2
(45) Date of Patent: Apr. 14, 2020

(54) BICYCLIC DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Balázs Bálint, Fót (HU); Márton Csékei, Dunakeszi (HU); Zoltán Szabó, Budapest (HU); Zoltán Szlávik, Budapest (HU); András Kotschy, Törökbálint (HU); Maïa Chanrion, Issy les Moulineaux (FR); Olivier Geneste, Rueil-Malmaison (FR); I-Jen Chen, Cambridge (GB); James Edward Paul Davidson, Great Shelford (GB); James Brooke Murray, Linton (GB); Szabolcs Sipos, Budapest (HU); Levente Ondi, Veresegyház (HU); Ágnes Proszenyák, Budapest (HU)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 16/394,308

(22) Filed: Apr. 25, 2019

(65) Prior Publication Data
US 2019/0248805 A1    Aug. 15, 2019

Related U.S. Application Data

(63) Continuation of application No. 15/738,186, filed as application No. PCT/EP2016/064418 on Jun. 22, 2016.

(30) Foreign Application Priority Data

Jun. 23, 2015  (FR) .................................... 15 55750

(51) Int. Cl.
| | | |
|---|---|---|
| A61K 31/519 | (2006.01) |
| C07D 495/04 | (2006.01) |
| C07D 403/12 | (2006.01) |
| C07D 333/56 | (2006.01) |
| C07D 405/04 | (2006.01) |
| C07D 405/12 | (2006.01) |
| C07D 409/12 | (2006.01) |
| C07D 471/04 | (2006.01) |
| C07D 487/04 | (2006.01) |
| C07D 491/04 | (2006.01) |
| C07D 209/12 | (2006.01) |
| C07D 307/80 | (2006.01) |
| C07D 307/81 | (2006.01) |
| A61P 35/02 | (2006.01) |
| C07D 491/048 | (2006.01) |
| A61K 45/06 | (2006.01) |

(52) U.S. Cl.
CPC ............ *C07D 495/04* (2013.01); *A61P 35/02* (2018.01); *C07D 209/12* (2013.01); *C07D 307/80* (2013.01); *C07D 307/81* (2013.01); *C07D 333/56* (2013.01); *C07D 403/12* (2013.01); *C07D 405/04* (2013.01); *C07D 405/12* (2013.01); *C07D 409/12* (2013.01); *C07D 471/04* (2013.01); *C07D 487/04* (2013.01); *C07D 491/04* (2013.01); *C07D 491/048* (2013.01); *A61K 45/06* (2013.01); *A61K 2300/00* (2013.01)

(58) Field of Classification Search
CPC ........................... A61K 31/496; A61K 31/519
USPC .................................................. 514/253, 258
See application file for complete search history.

(56) References Cited

U.S. PATENT DOCUMENTS

2015/0051189 A1    2/2015    Le Diguarher

FOREIGN PATENT DOCUMENTS

| EP | 2484678 | 8/2012 |
|---|---|---|
| WO | WO97/02266 | 1/1997 |
| WO | WO 2007/017678 A1 | 2/2007 |
| WO | WO 2007/064993 A2 | 6/2007 |
| WO | WO 2013/067260 A1 | 5/2013 |
| WO | WO 2013/072694 A1 | 5/2013 |

(Continued)

OTHER PUBLICATIONS

Akgul, et al., FEBS Letter, 2000, 478, 72-76.

(Continued)

*Primary Examiner* — Charanjit Aulakh
(74) *Attorney, Agent, or Firm* — Hueschen and Sage

(57) ABSTRACT

Compounds of formula (I):

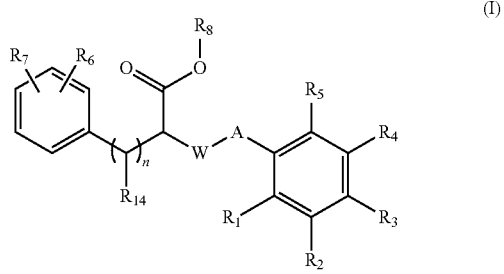

wherein $R_1$, $R_2$, $R_3$, $R_4$, $R_5$, $R_6$, $R_7$, $R_8$, $R_{14}$, W, A and n are as defined in the description.
Medicinal products containing the same which are useful in treating conditions requiring a pro-apoptotic agent.

33 Claims, No Drawings

(56) References Cited

FOREIGN PATENT DOCUMENTS

WO    WO 2013/110890 A1    8/2013

OTHER PUBLICATIONS

Allaeys, et al., PLoS One, 2014, 9, e109256.
Beroukhim, et al., Nature, 2010, 463, 899-905.
Cordeu, et al., Bioorganic and Medicinal Chemistry, vol. 15, No. 4, p. 1659-1669, Jan. 14, 2007.
Glaser, et al., Genes Dev, 2012, 26, 120-125.
Gong, et al., Blood, 2016, 128, 1834-1844.
Goodwin, et al., Cell Death and Differentiation, 2015, 22, 2098-2106.
Gross, et al., Genes Dev., 1999, 13, 1899-1911.
Hanahan and Weinberg, Cell, 2000, 100, 57-70.
Hanahan and Weinberg, Cell, 2011, 144, 646-674.
International Search Reprot for PCT/EP2016/064418 dated Oct. 6, 2016.
Juin, et al., Nature Reviews Cancer, 2013, 13, 455-465.
Kelly, et al., Genes Dev, 2014, 28, 58-70.
Kemnitzer, W. et al., Bioorganic and Medicinal Chemistry Letters, vol. 19, No. 13, p. 3536-2540, Jul. 1, 2009.
Kozopas, et al., Proc. Natl. Acad. Sci. USA, 1993, 90, 3516-3520.
Leverson, et al., Cell Death Dis., 2015, 6, e1590.
Liu, et al., Arthritis Rheum, 2006, 54, 3174-3181.
Liu, et al., J. Immunol., 2005, 175, 8337-8345.
Marsden and Strasser, Annu. Rev. Immunol., 2003, 21, 71-105.
Park, et al., J. Med. Chem., 2008, 51, 6902-6915.
Perciavalle and Opferman, Trends Cell Biol., 2013, 23, 22-29.
Phillips, et al., Blood Cancer J., 2015, 5, e368.
Phillips, et al., Blood Cancer J., 2016, 6, e403.
Roberts, et al., J. Clin. Oncol., 2012, 30, 488-496.
Souers, et al., Nat. Med., 2013, 19, 202-208.
Vaux and Flavell, Curr. Opin. Immunol., 2000, 12, 719-724.
Wei, et al., Cancer Cell, 2012, 21, 547-562.
Xiao, et al., Mol. Cancer Ther., 2015, 14, 1837-1847.
Youle and Strasser, Nat. Rev. Mol. Cell Biol., 2008, 9, 47-59.

BICYCLIC DERIVATIVES, A PROCESS FOR THEIR PREPARATION AND PHARMACEUTICAL COMPOSITIONS CONTAINING THEM

The present invention relates to new bicyclic derivatives, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, lymphoma, myeloma, acute myeloid leukemia, pancreatic cancer, etc. Overexpression of the anti-apoptotic proteins of the Bcl-2 family is involved in tumorigenesis, in resistance to chemotherapy and in the clinical prognosis of patients affected by cancer. Notably, Mcl-1, an anti-apoptotic Bcl-2 family member, is overexpressed in various types of cancer (Beroukhim R. et al., Nature 2010, 899-905). There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of immune and auto-immune diseases.

The present invention relates more especially to compounds of formula (I):

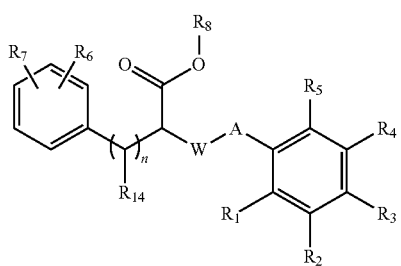

wherein:

A represents the group

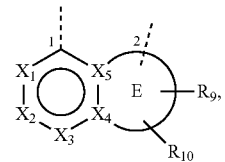

in which 1 is linked to the W group and 2 is linked to the phenyl ring, wherein:
E represents a furyl, thienyl or pyrrolyl ring,
$X_1$, $X_3$, $X_4$ and $X_5$ independently of one another represent a carbon atom or a nitrogen atom,
$X_2$ represents a C—$R_{21}$ group or a nitrogen atom, and

means that the ring is aromatic,
$R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_{11}R_{11}$', —O-alkyl($C_1$-$C_6$)—$NR_{11}R_{11}$', —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', —$SO_2$-alkyl($C_1$-$C_6$),
$R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}$', —O-alkyl($C_1$-$C_6$)—$NR_{11}R_{11}$', —O-alkyl ($C_1$-$C_6$)—$R_{12}$, —C(O)—$OR_1$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$),
or the substituents of the pair ($R_1$, $R_2$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by from 1 to 2 groups selected from halogen, linear or branched ($C_1$-$C_6$)alkyl, -alkyl($C_0$-$C_6$)—$NR_{11}R_{11}$', —$NR_{13}R_{13}$', -alkyl($C_0$-$C_6$)-$Cy_1$ or oxo,
$R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, —$SO_2$-alkyl($C_1$-$C_6$), or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}'$, -alkyl($C_0$-$C_6$)-$Cy_1$ or an oxo, W represents a —$CH_2$— group, a —NH— group or an oxygen atom, $R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_9$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{15}$, or —C(O)—$NR_{15}R_{15}'$, $R_{10}$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, an arylalkyl($C_1$-$C_6$) group, a cycloalkylalkyl($C_1$-$C_6$) group, a linear or branched ($C_1$-$C_6$)polyhaloalkyl, -alkyl($C_1$-$C_6$)—O-$Cy_4$, or the substituents of the pair ($R_9$, $R_{10}$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, $R_{11}$ and $R_{11}'$ independently of one another represent a hydrogen atom, a linear or branched ($C_1$-$C_6$)alkyl group, or the substituents of the pair ($R_{11}$, $R_{11}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched ($C_1$-$C_6$)alkyl group, $R_{12}$ represents -$Cy_5$, -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl($C_0$-$C_6$)-$Cy_7$, —C(O)—$NR_{11}R_{11}'$, —$NR_{11}R_{11}'$, —$OR_{11}$, —$NR_{11}$—C(O)—$R_{11}'$, —O-alkyl($C_1$-$C_6$)—$OR_{11}$, —$SO_2$—$R_{11}$, —C(O)—$OR_{11}$, or —NH—C(O)—NH—$R_{11}$, $R_{13}$, $R_{13}'$, $R_{15}$ and $R_{15}'$ independently of one another represent a hydrogen atom, or an optionally substituted linear or branched ($C_1$-$C_6$)alkyl group, $R_{14}$ represents a hydrogen atom, a hydroxy group or a hydroxy($C_1$-$C_6$)alkyl group, $R_{21}$ represents a hydrogen atom, a halogen atom, a linear or branched ($C_1$-$C_6$)alkyl group, or a cyano group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$ independently of one another represent a hydrogen atom, a linear or branched ($C_1$-$C_8$)alkyl group, a cycloalkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched ($C_1$-$C_6$)alkyl group, $Cy_1$, $Cy_2$, $Cy_3$, $Cy_4$, $Cy_5$, $Cy_6$ and $Cy_7$ independently of one another, represent a cycloalkyl group, a heterocycloalkyl group, an aryl group, or a heteroaryl group, n is an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy groups, to be substituted by from 1 to 4 groups selected from optionally substituted linear or branched ($C_1$-$C_6$)alkyl, optionally substituted linear or branched ($C_2$-$C_6$)alkenyl, optionally substituted linear or branched ($C_2$-$C_6$)alkynyl, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)($O^-M^+$)$_2$, linear or branched ($C_1$-$C_6$)polyhaloalkyl, trifluoromethoxy, halogen, or an aldohexose of formula:

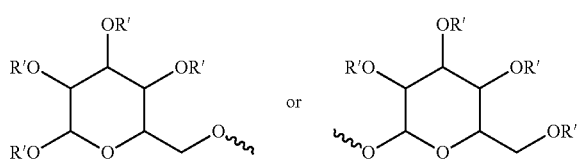

in which each R' is independent;

it being understood that R' and R" independently of one another represent a hydrogen atom or an optionally substituted linear or branched ($C_1$-$C_6$)alkyl group, and $M^+$ represents a pharmaceutically acceptable monovalent cation, with the proviso that

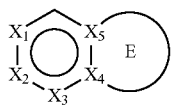

cannot represent

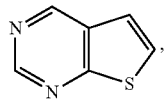

their enantiomers, diastereoisomers and atropisomers, and addition salts thereof with a pharmaceutically acceptable acid or base.

Advantageously, the present invention relates to compounds of formula (I) wherein:
- $R_1$ and $R_2$ independently of one another represent a halogen atom, a linear or branched $(C_1-C_6)$alkyl group, a hydroxy group, a linear or branched $(C_1-C_6)$alkoxy group,
- or the substituents of the pair $(R_1, R_2)$ form together with the carbon atoms carrying them an aromatic ring composed of from 5 to 7 ring members, which may contain from 1 to 3 nitrogen atoms,
- $R_3$ represents a hydrogen atom, a halogen atom, a linear or branched $(C_1-C_6)$alkyl group, a hydroxy group, a linear or branched $(C_1-C_6)$alkoxy group, or —O-alkyl $(C_1-C_6)$—$NR_{11}R_{11}'$,
- $R_4$ and $R_5$ independently of one another represent a hydrogen atom, a halogen atom, a linear or branched $(C_1-C_6)$alkyl group, a hydroxy group, a linear or branched $(C_1-C_6)$alkoxy group,
- $R_6$ and $R_7$ independently of one another represent a hydrogen atom, a halogen atom, a linear or branched $(C_1-C_6)$alkyl group, a linear or branched $(C_1-C_6)$polyhaloalkyl group, a hydroxy group, a linear or branched $(C_1-C_6)$alkoxy group, a cyano group, a nitro group, -alkyl$(C_0-C_6)$—$NR_{11}R_{11}'$, -alkyl$(C_0-C_6)$-$Cy_1$, —O-alkyl$(C_1-C_6)$—$R_{12}$, or —C(O)—$NR_{11}R_{11}'$,
- $R_8$ represents a hydrogen atom, a linear or branched $(C_1-C_8)$alkyl group, or a —$CHR_aR_b$ group,
- $R_9$ represents a hydrogen atom, a linear or branched $(C_1-C_6)$alkyl group, a linear or branched $(C_2-C_6)$alkenyl group, a linear or branched $(C_2-C_6)$alkynyl group, -$Cy_2$, or a halogen atom,
- $R_{10}$ represents a hydrogen atom, a linear or branched $(C_1-C_6)$alkyl group, a linear or branched $(C_2-C_6)$alkenyl group, a linear or branched $(C_2-C_6)$alkynyl group, an arylalkyl$(C_1-C_6)$ group, a cycloalkylalkyl$(C_1-C_6)$ group, a linear or branched $(C_1-C_6)$polyhaloalkyl, or -alkyl$(C_1-C_6)$—O-$Cy_4$,
- or the substituents of the pair $(R_9, R_{10})$ when grafted onto two adjacent carbon atoms, form together with the carbon atoms carrying them a non-aromatic ring composed of from 5 to 7 ring members, which may contain from 1 to 3 heteroatoms selected from oxygen, sulphur and nitrogen,
- $R_{11}$ and $R_{11}'$ independently of one another represent a hydrogen atom, a linear or branched $(C_1-C_6)$alkyl group,
- or the substituents of the pair $(R_{11}, R_{11}')$ form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched $(C_1-C_6)$alkyl group,
- $R_{12}$ represents -$Cy_5$ or -$Cy_5$-alkyl$(C_0-C_6)$-$Cy_6$,
- W represents a —NH— group or an oxygen atom, it being possible for the aryl, heteroaryl, cycloalkyl and heterocycloalkyl groups so defined and the alkyl, alkenyl, alkynyl, alkoxy groups, to be substituted by from 1 to 4 groups selected from optionally substituted linear or branched $(C_1-C_6)$alkyl, optionally substituted linear or branched $(C_1-C_6)$alkoxy, hydroxy, oxo (or N-oxide where appropriate), —C(O)—OR', —C(O)—NR'R", —O—C(O)—NR'R", —NR'R", —O—P(O)(OR')$_2$, —O—P(O)(O$^-$M$^+$)$_2$, linear or branched $(C_1-C_6)$polyhaloalkyl, halogen, or an aldohexose of formula:

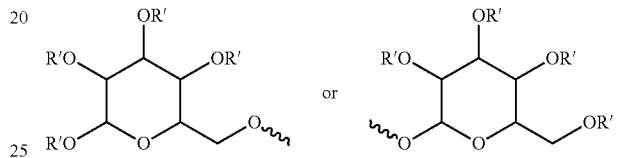

in which each R' is independent;

it being understood that R' and R" independently of one another represent a hydrogen atom or an optionally substituted linear or branched $(C_1-C_6)$alkyl group and M$^+$ represents a pharmaceutically acceptable monovalent cation.

More especially, compounds of formula (I) to which preference is given are compounds wherein n is an integer equal to 1.

In another embodiment of the invention, an advantageous possibility consists of compounds of formula (I-a):

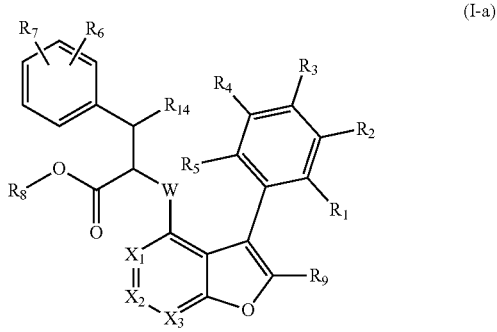

(I-a)

wherein $R_1$, $R_2$, $R_3$, $R_4$, $R_5$, $R_6$, $R_7$, $R_8$, $R_9$, $R_{14}$, $X_1$, $X_2$, $X_3$ and W are as defined for formula (I). More especially, compounds of formula (I-a) to which preference is given are compounds wherein

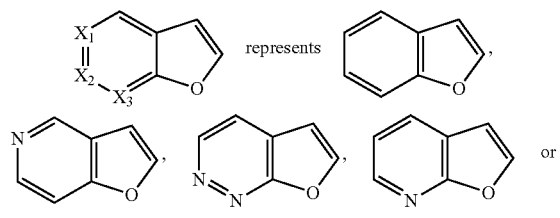

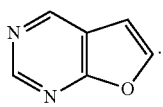

More particularly, compounds of formula (I-a) to which preference is given are compounds wherein

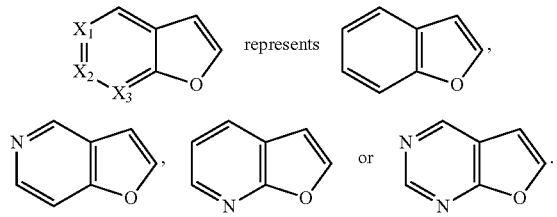

Advantageously,

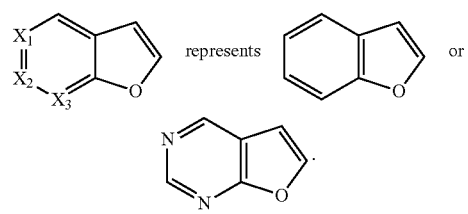

In another embodiment of the invention, an advantageous possibility consists of compounds of formula (I-b):

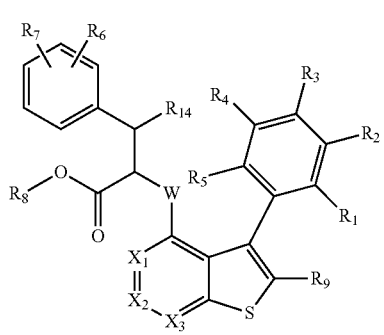

(I-b)

wherein $R_1$, $R_2$, $R_3$, $R_4$, $R_5$, $R_6$, $R_7$, $R_8$, $R_9$, $R_{14}$, $X_1$, $X_2$, $X_3$ and W are as defined for formula (I). More especially, compounds of formula (I-b) to which preference is given are compounds wherein

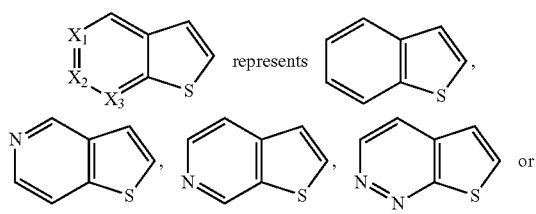

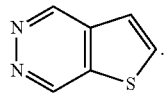

Advantageously,

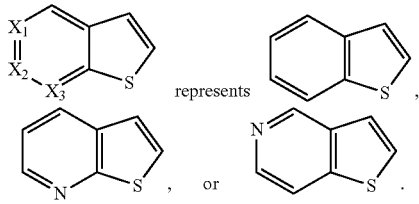

In another embodiment of the invention, an advantageous possibility consists of compounds of formula (I-c):

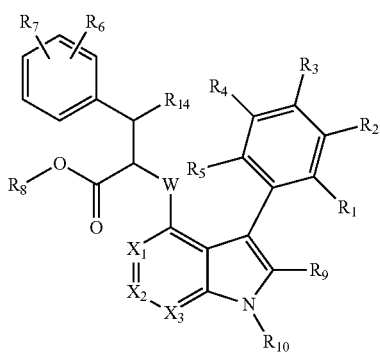

(I-c)

wherein $R_1$, $R_2$, $R_3$, $R_4$, $R_5$, $R_6$, $R_7$, $R_8$, $R_9$, $R_{10}$, $R_{14}$, $X_1$, $X_2$, $X_3$ and W are as defined for formula (I). More especially, compounds of formula (I-c) to which preference is given are compounds wherein

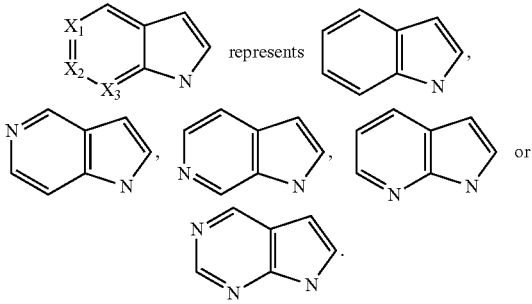

More particularly, compounds of formula (I-c) to which preference is given are compounds wherein

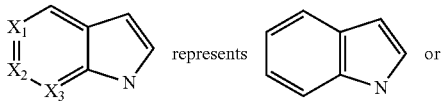

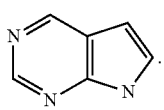

In another embodiment of the invention, an advantageous possibility consists of compounds of formula (I-d):

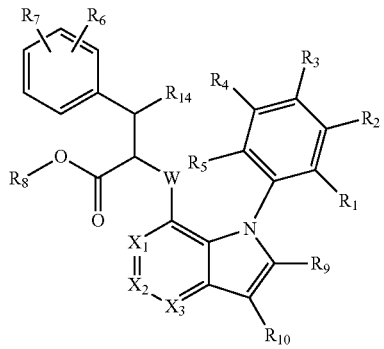

(I-d)

wherein $R_1$, $R_2$, $R_3$, $R_4$, $R_5$, $R_6$, $R_7$, $R_8$, $R_9$, $R_{10}$, $R_{14}$, $X_1$, $X_2$, $X_3$ and W are as defined for formula (I). More especially, compounds of formula (I-d) to which preference is given are compounds wherein

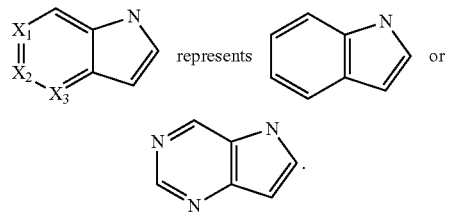

In another embodiment of the invention, an advantageous possibility consists of compounds of formula (I-e):

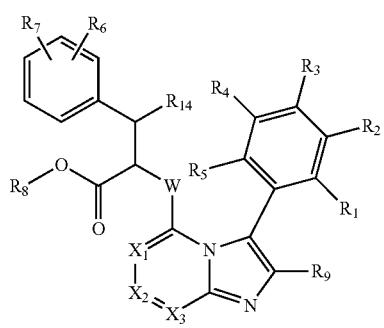

(I-e)

wherein $R_1$, $R_2$, $R_3$, $R_4$, $R_5$, $R_6$, $R_7$, $R_8$, $R_9$, $R_{14}$, $X_1$, $X_2$, $X_3$ and W are as defined for formula (I). More especially, compounds of formula (I-e) to which preference is given are compounds wherein

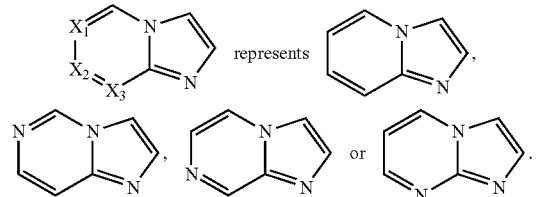

Advantageously,

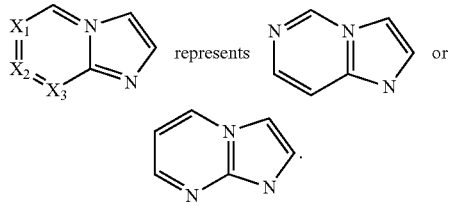

Compounds of formulae (I-a), (I-b), (I-c) and (I-e) are particularly preferred. Compounds of formulae (I-a) and (I-b) are even more preferred.

In another embodiment of the invention, an advantageous possibility consists of compounds of formula (I-f):

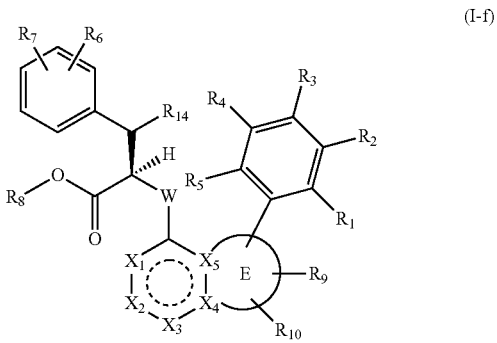

(I-f)

wherein E, $R_1$, $R_2$, $R_3$, $R_4$, $R_5$, $R_6$, $R_7$, $R_8$, $R_9$, $R_{10}$, $R_{14}$, $X_1$, $X_2$, $X_3$, $X_4$, $X_5$ and W are as defined for formula (I).

Atropisomers are stereoisomers arising because of hindered rotation about a single bond, where energy differences due to steric strain or other contributors create a barrier to rotation that is high enough to allow for isolation of individual conformers. For example, for compounds of formula (I-b) (the same can be done for compounds of formula (I-a), (I-c), (I-d) and (I-e)), atropisomers are as follows:

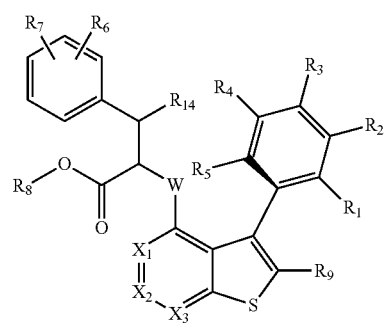

-continued

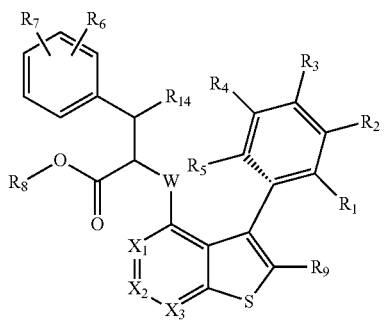

Preferred atropisomer is ($S_a$) for compounds of formula (I-a), (I-b), (I-c) and (I-d). Preferred atropisomer is ($R_a$) for compounds of formula (I-e).

Advantageously, at least one of the groups selected from $R_2$, $R_3$, $R_4$ and $R_5$ does not represent a hydrogen atom.

Preferably, $R_{14}$ represents a hydrogen atom.

$R_{21}$ represents preferably a hydrogen atom, a fluorine atom, a methyl group or a cyano group. More preferably, $R_{21}$ represents a hydrogen atom or a fluorine atom. Even more preferably, $R_{21}$ represents a hydrogen atom.

In the preferred compounds of the invention, $R_1$ represents a linear or branched ($C_1$-$C_6$)alkyl group or a halogen atom. More preferably, $R_1$ represents a methyl group, an ethyl group, a bromine atom or a chlorine atom. Even more preferably, $R_1$ represents a methyl group or an ethyl group.

Advantageously, $R_2$ represents a halogen atom, a hydroxy group, a linear or branched ($C_1$-$C_6$)alkoxy group. More preferably, $R_2$ represents a methoxy group, a hydroxy group, a fluorine atom, a bromine atom or a chlorine atom. Even more preferably, $R_2$ represents a chlorine atom.

In some preferred embodiment of the invention, when the substituents of the pair ($R_1$, $R_2$) form together with the carbon atoms carrying them an aromatic ring,

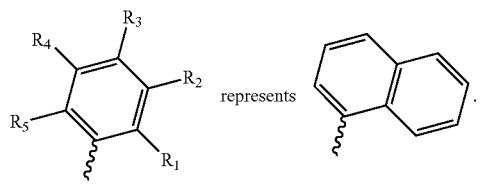

$R_3$ advantageously represents a hydrogen atom, a hydroxy group, a linear or branched ($C_1$-$C_6$)alkoxy group or —O-alkyl($C_1$-$C_6$)—$NR_{11}R_{11}$'. Advantageously, $R_3$ represents —O-alkyl($C_1$-$C_6$)—$NR_{11}R_{11}$'.

$R_4$ and $R_5$ preferably represent a hydrogen atom.

In an advantageous embodiment, the substituents of the pair ($R_1$, $R_5$) are identical and the substituents of the pair ($R_2$, $R_4$) are identical. In the preferred compounds of the invention, the substituents of the pair ($R_1$, $R_5$) are identical and represent a ($C_1$-$C_6$)alkyl group, preferably a methyl group, whereas the substituents of the pair ($R_2$, $R_4$) are identical and represent a halogen atom, preferably a chlorine atom, or a hydrogen atom.

In the preferred compounds of the invention,

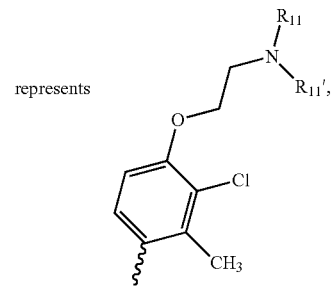

wherein $R_{11}$ and $R_{11}$' are as defined for formula (I).

In another embodiment of the invention, $R_6$ represents a hydrogen atom, an optionally substituted linear or branched ($C_1$-$C_6$)alkoxy group or a —O-alkyl($C_1$-$C_6$)—$R_{12}$ group.

Advantageously, $R_6$ represents a 2,2,2-trifluoroethoxy group, a methoxy group, or a —O-alkyl($C_1$-$C_6$)—$R_{12}$ group.

$R_7$ preferably represents a hydrogen atom.

In the preferred compounds of the invention,

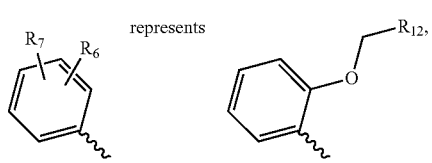

wherein $R_{12}$ is as defined for formula (I).

In another embodiment of the invention, an advantageous possibility consists of compounds of formula (I-g):

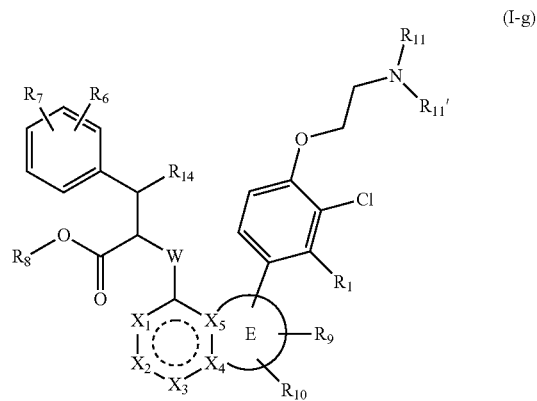

(I-g)

wherein $R_1$, $R_6$, $R_7$, $R_8$, $R_9$, $R_{10}$, $R_{11}$, $R_{11}$', $R_{14}$, $X_1$, $X_2$, $X_3$, $X_4$, $X_5$, W and E are as defined for formula (I).

Preferably, $R_8$ represents a hydrogen atom, a —$CHR_aR_b$ group, an optionally substituted linear or branched ($C_1$-$C_8$) alkyl group, or a heteroarylalkyl($C_1$-$C_6$) group. Preferably, $R_8$ represents a —$CHR_aR_b$ group in which $R_a$ represents a hydrogen atom or a methyl group and $R_b$ represents a —O—C(O)—O—($C_1$-$C_8$)alkyl group; a —O—C(O)—O-cycloalkyl group; a —O—C(O)—$NR_cR_c$' group, in which $R_c$ and $R_c$' independently of one another represent a hydrogen atom, a linear or branched ($C_1$-$C_8$)alkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c$') form together with the nitrogen atom carrying them a non-aromatic ring composed of from 5 to 7 ring members, which may contain in addition to the nitrogen atom from 1 to 3 heteroatoms selected from oxygen and nitrogen; or a —O—P(O)(OH)$_2$ group. Preferred $R_8$ groups are as follows: hydrogen; methyl; ethyl; (5-methyl-2-oxo-1,3-dioxol-4-yl)methyl; a —CHR$_a$R$_b$ group in which R$_a$ represents a methyl group and R$_b$ represents a —O—C(O)—O—CH$_2$CH$_3$ group or a —O—C(O)—N(CH$_3$)$_2$ group. Even more preferably, $R_8$ represents hydrogen.

In the preferred compounds of the invention, $R_9$ represents a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, an aryl group or a heteroaryl group. More preferably, $R_9$ represents a prop-1-yn-1-yl group, a phenyl group or a furan-2-yl group. In a more preferred embodiment, $R_9$ represents a prop-1-yn-1-yl group, a 4-fluorophenyl group or a 5-fluorofuran-2-yl group. Even more preferentially, $R_9$ represents a 4-fluorophenyl group.

In the advantageous possibility consisting in compounds of formula (I-c), preferred $R_{10}$ groups are as follows: hydrogen; methyl; isopropyl; 2,2,2-trifluoroethyl; benzyl; 4-methoxybenzyl; phenethyl; 3-phenyl-propyl; cyclopropylmethyl; cyclopentylethyl; naphthalen-1-ylmethyl; 2-(naphthalen-1-yloxy)ethyl; but-2-yn-1-yl; prop-2-en-1 yl; but-3-en-1-yl. In another embodiment, the substituents of the pair ($R_9$, $R_{10}$) when grafted onto two adjacent atoms, form together with the carbon and nitrogen atoms carrying them a non-aromatic ring composed of from 5 to 6 ring members.

In the advantageous possibility consisting in compounds of formula (I-d), $R_{10}$ preferably represents a hydrogen atom or a halogen atom.

In the preferred compounds of the invention, $R_{11}$ and $R_{11}'$ independently of one another represent a linear or branched (C$_1$-C$_6$)alkyl group, or the substituents of the pair ($R_{11}$, $R_{11}'$) form together with the nitrogen atom carrying them a non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, a linear or branched (C$_1$-C$_6$)alkyl group. More preferably, $R_{11}$ and $R_{11}'$ represent a methyl group, or the substituents of the pair ($R_{11}$, $R_{11}'$) form together a 4-methyl-piperazinyl group or a 4-ethyl-piperazinyl group. In a more preferred embodiment, the substituents of the pair ($R_{11}$, $R_{11}'$) form together a 4-methyl-piperazinyl group. In another preferred embodiment, $R_{11}$ and $R_{11}'$ represent a methyl group.

Advantageously, $R_{12}$ represents -Cy$_5$ or -Cy$_5$-alkyl(C$_0$-C$_6$)-Cy$_6$. Preferably, $R_{12}$ represents -Cy$_5$ or -Cy$_5$-Cy$_6$.

Cy$_5$ preferably represents a heteroaryl group, particularly, a pyrimidinyl group, a pyrazolyl group, a triazolyl group, a pyrazinyl group or a pyridinyl group. More preferably, Cy$_5$ represents a pyrimidin-4-yl group, a pyrazol-5-yl group, or a pyrazin-2-yl group. In the preferred compounds of the invention, Cy$_5$ represents a pyrimidin-4-yl group.

In another embodiment of the invention, Cy$_5$ represents a heteroaryl group which is substituted by an optionally substituted linear or branched (C$_1$-C$_6$)alkyl group, an optionally substituted linear or branched (C$_1$-C$_6$)alkoxy group, a —NR'R" group, or a linear or branched (C$_1$-C$_6$) polyhaloalkyl group, it being understood that R' and R" independently of one another represent a hydrogen atom or an optionally substituted linear or branched (C$_1$-C$_6$)alkyl group.

Cy$_6$ preferably represents a phenyl group.

Other compounds of the invention to which preference is given are those wherein,
$R_{12}$ represents,

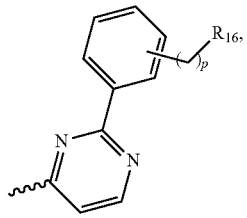

in which p is an integer equal to 0 or 1 and $R_{16}$ represents a hydrogen atom, a hydroxy group, an optionally substituted linear or branched (C$_1$-C$_6$)alkyl group, a linear or branched (C$_1$-C$_6$)alkoxy group, a —O—(CHR$_{17}$—CHR$_{18}$—O)$_q$—R' group, a —O—P(O)(OR')$_2$ group, a —O—P(O)(O$^-$M$^+$)$_2$ group, a —O—C(O)—NR$_{19}$R$_{20}$ group, a di(C$_1$-C$_6$)alkylamino(C$_1$-C$_6$)alkoxy group, a halogen atom, or an aldohexose of formula:

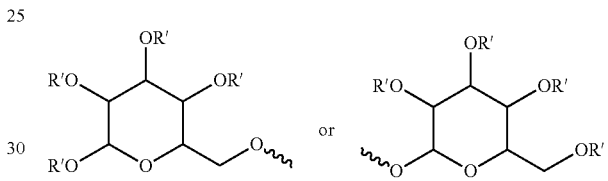

in which each R' is independent;
it being understood that:
R' represents a hydrogen atom or a linear or branched (C$_1$-C$_6$)alkyl group,
$R_{17}$ represents a hydrogen atom or a (C$_1$-C$_6$)alkoxy(C$_1$-C$_6$)alkyl group,
$R_{18}$ represents a hydrogen atom or a hydroxy(C$_1$-C$_6$)alkyl group,
$R_{19}$ represents a hydrogen atom or a (C$_1$-C$_6$)alkoxy(C$_1$-C$_6$)alkyl group,
$R_{20}$ represents a (C$_1$-C$_6$)alkoxy(C$_1$-C$_6$)alkyl group, a —(CH$_2$)$_r$—NR$_{11}$R$_{11}'$ group or a —(CH$_2$)$_r$—O—(CHR$_{17}$—CHR$_{18}$—O)$_q$—R' group,
q is an integer equal to 1, 2 or 3 and r is an integer equal to 0 or 1,
M$^+$ represents a pharmaceutically acceptable monovalent cation.

The aldohexose according to the invention is preferably D-mannose. Preferably, the group —(CH$_2$)$_p$—R$_{16}$ is located at ortho position of the phenyl group.

Among the preferred compounds of the invention there may be mentioned:
(2R)-2-{[5-{3-chloro-2-methyl-4-[2-(4-methylpiperazin-1-yl)ethoxy]phenyl}-6-(4-fluorophenyl)furo[2,3-d]pyrimidin-4-yl]oxy}-3-(2-{[2-(2-methoxyphenyl) pyrimidin-4-yl]methoxy}phenyl)propanoic acid;
(2R)-2-{[5-{3-chloro-2-ethyl-4-[2-(4-methylpiperazin-1-yl) ethoxy]phenyl}-6-(4-fluorophenyl)furo[2,3-d]pyrimidin-4-yl]oxy}-3-(2-{[2-(2-methoxyphenyl) pyrimidin-4-yl] methoxy}phenyl)propanoic acid;
N-[(5S$_a$)-5-{3-chloro-2-methyl-4-[2-(4-methylpiperazin-1-yl)ethoxy]phenyl}-6-(4-fluorophenyl)furo[2,3-d]pyrimidin-4-yl]-2-{[2-(2-methoxyphenyl)pyrimidin-4-yl] methoxy}-D-phenylalanine;

(2R)-2-{[(3S$_a$)-3-{3-chloro-2-methyl-4-[2-(4-methylpiperazin-1-yl)ethoxy]phenyl}-2-(4-fluorophenyl)-1-benzothiophen-4-yl]oxy}-3-(2-{[2-(2-methoxyphenyl)pyrimidin-4-yl]methoxy}phenyl)propanoic acid;

(2R)-2-{[(3S$_a$)-3-{3-chloro-2-methyl-4-[2-(4-methylpiperazin-1-yl)ethoxy]phenyl}-2-(4-fluorophenyl)-1-benzofuran-4-yl]oxy}-3-(2-{[2-(2-methoxyphenyl)pyrimidin-4-yl]methoxy}phenyl)propanoic acid;

(2R)-2-{[(3S$_a$)-3-{3-chloro-2-methyl-4-[2-(4-methylpiperazin-1-yl)ethoxy]phenyl}-6-fluoro-2-(4-fluorophenyl)-1-benzofuran-4-yl]oxy}-3-(2-{[2-(2-methoxyphenyl)pyrimidin-4-yl]methoxy}phenyl)propanoic acid;

(2R)-2-{[3-{(3S$_a$)-3-chloro-2-methyl-4-[2-(4-methylpiperazin-1-yl)ethoxy]phenyl}-2-(4-fluorophenyl)-1-methyl-1H-indol-4-yl]oxy}-3-(2-{[2-(2-methoxyphenyl) pyrimidin-4-yl]methoxy}phenyl)propanoic acid;

(2R)-2-{[(3S$_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl) pyrimidin-4-yl]methoxy}phenyl)propanoic acid;

(2R)-2-[5-[3-chloro-2-methyl-4-[2-(4-methylpiperazin-1-yl)ethoxy]phenyl]-6-(4-fluorophenyl)-7-methyl-pyrrolo[2,3-d]pyrimidin-4-yl]oxy-3-[2-[[2-(2-methoxy phenyl)pyrimidin-4-yl]methoxy]phenyl]propanoic acid;

1-[(dimethylcarbamoyl)oxy]ethyl (2R)-2-{[(3S$_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl)propanoate;

1-[(ethoxycarbonyl)oxy]ethyl (2R)-2-{[(3S$_a$)-3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl)propanoate;

N-[3-{3-chloro-2-methyl-4-[2-(4-methylpiperazin-1-yl)ethoxy]phenyl}-2-(4-fluorophenyl)thieno[2,3-b]pyridin-4-yl]-2-{[2-(2-methoxyphenyl)pyrimidin-4-yl]methoxy}-D-phenylalanine;

N-[3-{3-chloro-2-methyl-4-[2-(4-methylpiperazin-1-yl)ethoxy]phenyl}-2-(4-fluorophenyl)thieno[3,2-c]pyridin-4-yl]-2-{[2-(2-methoxyphenyl)pyrimidin-4-yl]methoxy}phenylalanine;

2-{[(3R$_a$)-3-{3-chloro-2-methyl-4-[2-(4-methylpiperazin-1-yl)ethoxy]phenyl}-2-(4-fluorophenyl)imidazo[1,2-c]pyrimidin-5-yl]oxy}-3-(2-{[2-(2-methoxyphenyl) pyrimidin-4-yl]methoxy}phenyl)propanoic acid.

The invention relates also to a process for the preparation of compounds of formula (I), which process is characterized in that there is used as starting material the compound of formula (II-a):

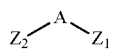

(II-a)

wherein $Z_1$ represents bromine or iodine, $Z_2$ represents chlorine, bromine or hydroxy, and A is as defined for formula (I) in which 1 is linked to the $Z_2$ group and 2 is linked to the $Z_1$ group, which compound of formula (II-a) is subjected to coupling with a compound of formula (III):

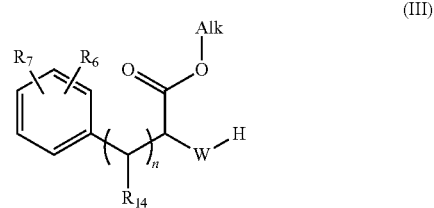

(III)

wherein $R_6$, $R_7$, $R_{14}$, W and n are as defined for formula (I), and Alk represents a linear or branched $(C_1-C_6)$alkyl group, to yield the compound of formula (IV):

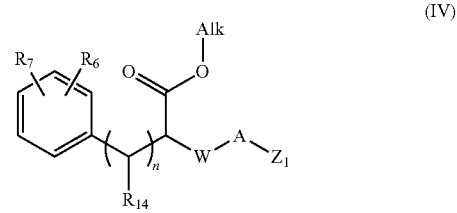

(IV)

wherein $R_6$, $R_7$, $R_{14}$, A, W and n are as defined for formula (I), and $Z_1$ and Alk are as defined before,
compound of formula (IV) which is further subjected to coupling with compound of formula (V):

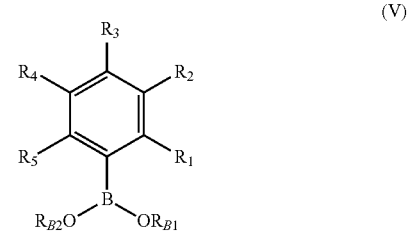

(V)

wherein $R_1$, $R_2$, $R_3$, $R_4$ and $R_5$ are as defined for formula (I), and $R_{B1}$ and $R_{B2}$ represent a hydrogen atom, a linear or branched $(C_1-C_6)$ alkyl group, or $R_{B1}$ and $R_{B2}$ form with the oxygen carrying them an optionally methylated ring, to yield the compound of formula (VI):

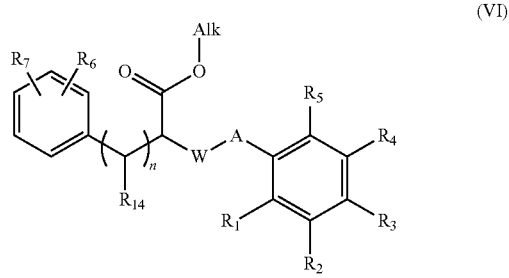

(VI)

wherein $R_1$, $R_2$, $R_3$, $R_4$, $R_5$, $R_6$, $R_7$, $R_{14}$, A, W and n are as defined for formula (I) and Alk is as defined before,
the Alk-O—C(O)— ester function of which compound of formula (VI) is hydrolyzed to yield the carboxylic acid, which may optionally be reacted with an alcohol of formula $R_8'$—OH or a chlorinated compound of formula $R_8'$—Cl wherein $R_8'$ represents a linear or branched $(C_1$-$C_8)$alkyl group, a —$CHR_aR_b$ group, an aryl group, a heteroaryl group, an arylalkyl$(C_1$-$C_6)$ group, or a heteroarylalkyl$(C_1$-$C_6)$ group, $R_a$ and $R_b$ are as defined for formula (I), to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

In another embodiment of the invention, compounds of formula (I) may be obtained using an alternative process, which process is characterised in that there is used as starting material the compound of formula (II-b):

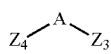
(II-b)

wherein $Z_3$ represents iodine, $Z_4$ represents chlorine, hydroxy, and A is as defined for formula (I) in which 1 is linked to the $Z_4$ group and 2 is linked to the $Z_3$ group, which compound of formula (II-b) is subjected to coupling with a compound of formula (V):

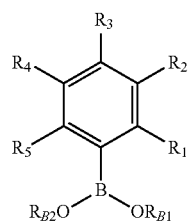
(V)

wherein $R_1$, $R_2$, $R_3$, $R_4$ and $R_5$ are as defined for formula (I), and $R_{B1}$ and $R_{B2}$ represent a hydrogen atom, a linear or branched $(C_1$-$C_6)$ alkyl group, or $R_{B1}$ and $R_{B2}$ form with the oxygen carrying them an optionally methylated ring, to yield the compound of formula (VII):

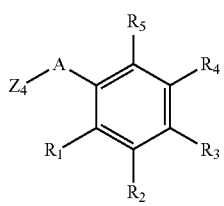
(VII)

wherein $R_1$, $R_2$, $R_3$ $R_4$, $R_5$ and A are as defined for formula (I), and $Z_4$ is as defined before, compound of formula (VII) which is further subjected to coupling with compound of formula (III):

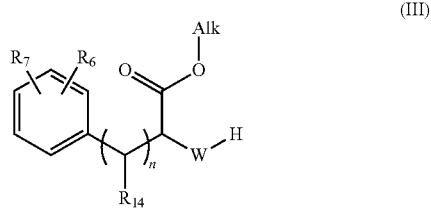
(III)

wherein $R_6$, $R_7$, $R_{14}$, W and n are as defined for formula (I), and Alk represents a linear or branched $(C_1$-$C_6)$alkyl group, to yield the compound of formula (VI):

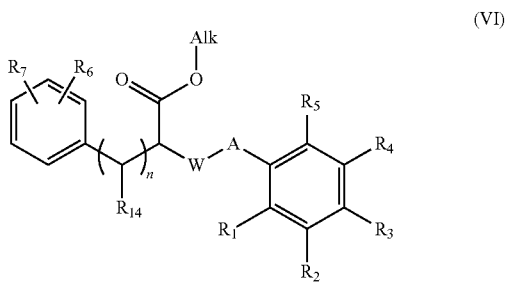
(VI)

wherein $R_1$, $R_2$, $R_3$ $R_4$, $R_5$, $R_6$, $R_7$, $R_{14}$, A, W and n are as defined for formula (I) and Alk is as defined before, the Alk-O—C(O)— ester function of which compound of formula (VI) is hydrolyzed to yield the carboxylic acid, which may optionally be reacted with an alcohol of formula $R_8'$—OH or a chlorinated compound of formula $R_8'$—Cl wherein $R_8'$ represents a linear or branched $(C_1$-$C_8)$alkyl group, a —$CHR_aR_b$ group, an aryl group, a heteroaryl group, an arylalkyl$(C_1$-$C_6)$ group, or a heteroarylalkyl$(C_1$-$C_6)$ group, $R_a$ and $R_b$ are as defined for formula (I), to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II-a), (II-b), (III), (V), $R_8'$—OH and $R_8'$-CL are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers.

Among the cancer treatments envisaged there may be mentioned, without implying any limitation, treatment of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

Advantageously, the present invention relates to the combination of a compound of formula (I) with an EGFR inhibitor, and also to pharmaceutical compositions comprising that type of combination.

In another embodiment, the present invention relates to the combination of a compound of formula (I) with a mTOR/PI3K inhibitor, and also to pharmaceutical compositions comprising that type of combination.

In a preferred embodiment, the present invention relates to the combination of a compound of formula (I) with a MEK inhibitor, and also to pharmaceutical compositions comprising that type of combination.

Preferably, the present invention relates to the combination of a compound of formula (I) with a HER2 inhibitor, and also to pharmaceutical compositions comprising that type of combination.

Advantageously, the present invention relates to the combination of a compound of formula (I) with a RAF inhibitor, and also to pharmaceutical compositions comprising that type of combination.

In another embodiment, the present invention relates to the combination of a compound of formula (I) with a EGFR/HER2 inhibitor, and also to pharmaceutical compositions comprising that type of combination.

In a preferred embodiment, the present invention relates to the combination of a compound of formula (I) with a taxane, and also to pharmaceutical compositions comprising that type of combination.

In another embodiment, the present invention relates to the combination of a compound of formula (I) with a proteasome inhibitor, an immunomodulator or an alkylating agent, and also to pharmaceutical compositions comprising that type of combination.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of the invention may also be used in combination with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn. 2000, 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol. 2001, 74(4):257-75), the protein Z derivative from the domain B of staphylococcal protein A, thioredoxin A or any protein with a repeated domain such as an "ankyrin repeat" (Kohl et al., PNAS 2003, 100(4), 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention but do not limit it in any way.

GENERAL PROCEDURES

All reagents obtained from commercial sources were used without further purification.

Anhydrous solvents were obtained from commercial sources and used without further drying.

Flash chromatography was performed on ISCO CombiFlash Rf 200i with pre-packed silica-gel cartridges (RediSep® $R_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an Armen Spot Liquid Chromatography system with a Gemini- NX® 10 μM C18, 250 mm×50 mm i.d. column running at a flow rate of 118 mL min$^{-1}$ with UV diode array detection (210-400 nm) using 25 mM aqueous NH$_4$HCO$_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/H$_2$O (1:1) with 5 μL loop injection. LCMS analyses were performed on two instruments, one of which was operated with basic, and the other with acidic eluents.

Basic LCMS: Gemini-NX, 3 μm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 μm, 50 mm×4.6 mm i.d. column at 40° C., at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-d$_6$ or CDCl$_3$ as solvent. $^1$H NMR data is in the form of delta values, given in part per million (ppm), using the residual peak of the solvent (2.50 ppm for DMSO-d$_6$ and 7.26 ppm for CDCl$_3$) as internal standard. Splitting patterns are designated as: s (singlet), d (doublet), t (triplet), q (quartet), quint (quintet), m (multiplet), br s (broad singlet), dd (doublet of doublets), td (triplet of doublets), dt (doublet of triplets), ddd (doublet of doublet of doublets).

Combination gas chromatography and low resolution mass spectrometry were performed on Agilent 6850 gas chromatograph and Agilent 5975C mass spectrometer using 15 m×0.25 mm column with 0.25 m HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI+/−, ionization voltage: (+−)4.5 kV. Mass resolution min. 10000.

Elementary analyses were performed on a Thermo Flash EA 1112 Elemental Analyzer.

List of Abbreviations

| Abbreviation | Name |
|---|---|
| 2-Me-THF | 2-methyl-tetrahydrofurane |
| abs. | absolute |
| Ac | acetyl |
| AIBN | 2-[(1-cyano-1-methyl-ethyl)azo]-2-methyl-propanenitrile |
| AtaPhos | bis(di-tert-butyl(4-dimethylaminophenyl)phosphine)dichloropalladium(II) |
| BINAP | (2,2'-bis(diphenylphosphino)-1,1'-binaphthyl) |
| cc. | concentrated |
| dba | dibenzylideneacetone |
| DCM | methylene chloride |
| DEAD | diethyl azodicarboxylate |
| DEE | diethyl ether |
| DIPA | diisopropylamine |

-continued

| Abbreviation | Name |
|---|---|
| DIPEA | diisopropylethylamine |
| DMA | dimethylacetamide |
| DME | 1,2-dimethoxyethane |
| DMF | dimethylformamide |
| DMSO | dimethyl sulfoxide |
| dppf | 1,1'-bis(diphenylphosphino)ferrocene |
| DTAD | di-tert-butyl azodicarboxylate |
| EDC · HCl | N-(3-dimethylaminopropyl)-N'-ethylcarbodiimide hydrochloride |
| eq. | equivalent |
| Et | ethyl |
| HILIC | hydrophilic interaction liquid chromatography |
| HMDS | hexamethyldisilazane |
| $^i$Pr | isopropyl |
| LDA | lithium diisopropylamide |
| MCPBA | meta-chloroperoxybenzoic acid |
| Me | methyl |
| MeCN | acetonitrile |
| MTBE | methyl tert-butyl ether |
| MW | microwave |
| NBS | N-bromosuccinimide |
| $^n$Bu | n-butyl |
| NCS | N-chlorosuccinimide |
| Ph | phenyl |
| PPA | polyphospholic acid |
| rac. | racemic |
| r.t. | room temperature |
| S$_2$Me$_2$ | dimethyl disulfide |
| SPhos | 2-dicyclohexylphosphino-2',6'-dimethoxybiphenyl |
| TBAF | tetrabutyl ammonium fluoride |
| TBAOH | tetrabutyl ammonium hydroxyde |
| $^t$Bu | tert-butyl |
| TEA | triethylamine |
| TFA | trifluoroacetic acid |
| THF | tetrahydrofurane |
| TIPSCl | triisopropylsilyl chloride |
| TLC | thin layer chromatography |
| Ts | tosyl |
| X-Phos | 2-dicyclohexylphosphino-2',4',6'-triisopropylbiphenyl |

General Procedure Ia 1 eq. Preparation 1a, 2 eq. from the appropriate lactic ester derivative, 10 mL/mmol $^t$BuOH and 5 eq. Cs$_2$CO$_3$ were placed in a flask and stirred at 55° C. until no further conversion was observed. Then the mixture was concentrated under reduced pressure, neutralized with IM aqueous HCl solution, diluted with brine and extracted with EtOAc. The combined organic phases were dried over Na$_2$SO$_4$, filtered and the filtrate was concentrated under reduced pressure. The crude product was purified via flash chromatography using heptane and EtOAc as eluents unless otherwise stated.

General Procedure Ib 1 eq. Preparation 1a, 2 eq. from the appropriate amino acid derivative, 10 mL/mmol DMSO and 3 eq. K$_2$CO$_3$ were placed in a flask and stirred at 45° C. until no further conversion was observed. Then the mixture was neutralized with 1 M aqueous HCl solution, diluted with brine and extracted with DCM. The combined organic phases were dried over Na$_2$SO$_4$, filtered and the filtrate was concentrated under reduced pressure. The crude product was purified via HILIC chromatography unless otherwise stated.

General Procedure II

Step A 1 eq. from the appropriate 5-bromo-furo[2,3-d]pyrimidyl-lactic ester derivative, 1.25 eq. from the appropriate boronic acid derivative, 10 mol % AtaPhos and 3 eq. Cs$_2$CO$_3$ were dissolved in a 1:1 mixture of dioxane and water (10 mL/mmol 5-bromo-furo[2,3-d]pyrimidyl-lactic ester derivative) and stirred at 105° C. in a MW reactor until no further conversion was observed. Then the mixture was neutralized with 1M aqueous HCl solution, diluted with brine and extracted with THF. The combined organic phases were dried over MgSO$_4$, filtered and the filtrate was concentrated under reduced pressure. The crude product was purified using preparative reversed phase chromatography using 25 mM aqueous NH$_4$HCO$_3$ solution and MeCN as eluents.

Step B

The obtained intermediate was dissolved in a 1:1 mixture of dioxane and water (25 mL/mmol) and 10 eq. LiOH×H$_2$O was added. The mixture was stirred at r.t. until no further conversion was observed. Then it was diluted with brine, neutralized with 2M aqueous HCl, extracted with DCM. The combined organic phases were dried over Na$_2$SO$_4$, filtered and the filtrate was concentrated under reduced pressure. The diastereoisomers were purified and separated by preparative reversed phase chromatography using 25 mM aqueous NH$_4$HCO$_3$ solution and MeCN as eluents.

General Procedure III 1 eq. from the appropriate 4-chloro-pyrrolo[2,3-d]pyrimidine derivative, 3 eq. from the appropriate amino acid derivative, 10 mL/mmol DMSO and 4 eq. K$_2$CO$_3$ were stirred at 150° C. until no further conversion was observed. The mixture was acidified with 1M aqueous HCl solution, the precipitate was filtered and purified via preparative reversed phase chromatography using 25 mM aqueous NH$_4$HCO$_3$ solution and MeCN as eluents.

General Procedure IVa 1 eq. from the appropriate 5-bromo-pyrrolo[2,3-d]pyrimidine derivative, 3 eq. from the appropriate boronic acid derivative, 3 eq. TBAOH, 0.2 eq. palladium acetate, 0.4 eq. tricyclohexylphosphonium tetrafluoroborate and 3.5 mL/mmol DME were stirred under N$_2$ atmosphere at 120° C. in a MW reactor until no further conversion was observed. Then the mixture was filtered through Celite and washed with MTBE and water. The layers were separated, the aqueous layer was washed with MTBE. The combined organic layers were washed with brine, dried over MgSO$_4$, filtered and the filtrate was concentrated under reduced pressure. The crude product was purified via preparative reversed phase chromatography using 40 mM aqueous NH$_4$OAc (pH=4) solution and MeCN as eluents.

General Procedure IVb 1 eq. from the appropriate 5-iodo-pyrrolo[2,3-d]pyrimidine derivative, 3 eq. from the appropriate boronic acid derivative, 3 eq. TBAOH, 0.2 eq. palladium acetate, 0.4 eq. butyldi-1-adamantylphosphine and 7 mL/mmol DME were stirred under N$_2$ atmosphere at reflux until no further conversion was observed. Then the mixture was filtered through Celite and concentrated under reduced pressure. The residue was purified via flash chromatography using DCM and MeOH as eluents.

General Procedure V 1 eq. from the appropriate benzofuran-4-ol derivative, 2.5 eq. from the appropriate lactic ester derivative, 2.5 eq. DTAD and 2.5 eq. PPh$_3$ were dissolved in dry toluene (20 mL/mmol) and stirred at 55° C. until no further conversion was observed. Then the mixture was concentrated and the residue was purified via flash chromatography using heptane and EtOAc as eluents.

General Procedure VI 1 eq. from the appropriate 3-bromo-benzofuran derivative, 2 eq. from the appropriate boronic acid derivative, 2 eq. Cs$_2$CO$_3$, 10 mol % Ataphos, 1.5 eq. tri-tert-butylphosphonium tetrafluoroborate and THF (10 mL/mmol) and water (4 mL/mmol) were stirred under N$_2$ atmosphere at 110° C. in a MW reactor until no further conversion was observed.

Then the mixture was acidified with 1M aqueous HCl solution and extracted with DCM. The combined organic layers were washed with brine, dried over MgSO$_4$, filtered and the filtrate was concentrated under reduced pressure. The crude product was purified via preparative reversed phase chromatography using 25 mM aqueous NH$_4$HCO$_3$ solution and MeCN as eluents. The obtained intermediate was dissolved in dioxane:water 1:1 (10 mL/mmol), 10 eq. LiOH×H$_2$O was added and the mixture was stirred at r.t. until no further conversion was observed. Then the mixture was diluted with water, acidified with 1M aqueous HCl solution and extracted with DCM. The combined organic phases were dried over Na$_2$SO$_4$, filtered and the filtrate was concentrated under reduced pressure. The crude product was purified via preparative reversed phase chromatography using 25 mM aqueous NH$_4$HCO$_3$ solution and MeCN as eluents.

Preparation 1a: 5-bromo-4-chloro-6-(4-fluorophenyl)furo[2,3-d]pyrimidine

Step A: 2-(4-fluorobenzoyl)propanedinitrile 81 mL 1M NaOEt solution in EtOH (81 mmol) was cooled to 0° C. and 6.14 g malononitrile (93 mmol) was added. The mixture was stirred at 0° C. for 1 hour, then 16.8 g 2-bromo-1-(4-fluorophenyl)ethanone (77.4 mmol) was added. The mixture was stirred at 0° C. for 1 hour, then at r.t. until no further conversion was observed. The volatiles were removed under reduced pressure, and the residue was purified via flash chromatography using heptane and EtOAc as eluents to obtain 2-(4-fluorobenzoyl)propanedinitrile.
$^1$H NMR (400 MHz, CDCl$_3$): 8.1 (m, 2H), 7.24 (m, 2H), 4.41 (t, 1H), 3.75 (d, 2H).

Step B: 2-amino-5-(4-fluorophenyl)furan-3-carbonitrile 6.56 g 2-(4-fluorobenzoyl)propanedinitrile (28.5 mmol) was dissolved in 140 mL AcOH and 6 g Amberlite 15H$^+$ was added. The mixture was stirred at 90° C. until no further conversion was observed. Then the mixture was filtered, the filtrate was concentrated under reduced pressure. The residue was recrystallized from DCM to obtain 2-amino-5-(4-fluorophenyl)furan-3-carbonitrile. $^1$H NMR (400 MHz, DMSO-d$_6$): 7.69 (m, 2H), 7.24 (m, 2H), 6.96 (s, 1H)

Step C: 6-(4-fluorophenyl)-3H-furo[2,3-d]pyrimidin-4-one 1290 mg 2-amino-5-(4-fluorophenyl)furan-3-carbonitrile (6.38 mmol) and 25.5 mL acetic formic anhydride were placed in a flask and stirred at r.t. for 30 minutes. Then, the volatiles were evaporated under reduced pressure. The residue was dissolved in 51 mL AcOH and heated in a MW reactor at 160° C. for 30 minutes, then at 180° C. for 15 minutes. Then the mixture was cooled to r.t., and the precipitate was filtered to obtain 6-(4-fluorophenyl)-3H-furo[2,3-d]pyrimidin-4-one. $^1$H NMR (500 MHz, DMSO-d$_6$): 12.66 (br s, 1H), 8.15 (s, 1H), 7.99 (m, 2H), 7.47 (s, 1H), 7.33 (m, 2H)

Step D: 5-bromo-6-(4-fluorophenyl)-3H-furo[2,3-d]pyrimidin-4-one 1704 mg 6-(4-fluorophenyl)-3H-furo[2,3-d]pyrimidin-4-one (7.4 mmol) was dissolved in 74 mL AcOH, then 1182 mg bromine (7.4 mmol) was added. The mixture was stirred at r.t. until no further conversion was observed. The mixture was then filtered, the filtrate was concentrated under reduced pressure. The residue was digerated with 15 mL MeOH, filtered and dried on air to obtain 5-bromo-6-(4-fluorophenyl)-3H-furo[2,3-d]pyrimidin-4-one. MS: $(M-H)^+=309.0$ Step E: Preparation 1a 1680 mg 5-bromo-6-(4-fluorophenyl)-3H-furo[2,3-d]pyrimidin-4-one (5.44 mmol) was dissolved in 12.7 mL $POCl_3$ (136 mmol) and 690 μL DMA (5.44 mmol) was added. The mixture was stirred at 110° C. until no further conversion was observed. The mixture was then cooled to 0° C. and poured into ice-water. The crude product was isolated by filtration and purified via flash chromatography using heptane and EtOAc as eluents to obtain Preparation 1a. $^1$H NMR (400 MHz, DMSO-$d_6$): 8.87 (s, 1H), 8.16 (m, 2H), 7.47 (m, 2H) Preparation 1b: 5-bromo-4-chloro-6-ethyl-7H-pyrrolo[2,3-d]pyrimidine Step A: 6-amino-5-[(2-ethyl-1,3-dioxolan-2-yl)methyl]pyrimidin-4-ol 257 mg 6-amino-5-[(2-ethyl-1,3-dioxolan-2-yl)methyl]-2-sulfanyl-pyrimidin-4-ol (0.1 mmol), 0.77 mL aqueous cc. $NH_3$ solution, 768 mg Raney-Ni and 11 mL water were placed in a flask under $N_2$ atmosphere and heated to reflux until no further conversion was observed. The warm reaction mixture was then filtered through Celite and washed with warm water. The filtrate was concentrated under reduced pressure. The crude product (6-amino-5-[(2-ethyl-1,3-dioxolan-2-yl)methyl]pyrimidin-4-ol) was used without further purification.

$^1$H NMR (400 MHz, DMSO-$d_6$) δ: 11.44 (br s, 1H), 7.70 (s, 1H), 6.07 (s, 2H), 3.89 (m, 4H), 2.62 (s, 2H), 1.53 (m, 2H), 0.81 (t, 3H)
MS (M+H): 226.2

Step B: 6-ethyl-7H-pyrrolo[2,3-d]pyrimidin-4-ol 4.193 g 6-amino-5-[(2-ethyl-1,3-dioxolan-2-yl)methyl]pyrimidin-4-ol (18.6 mmol) was dissolved in 280 mL 0.2M aqueous HCl solution. The mixture was stirred at r.t. until no further conversion was observed. The precipitate was filtered, washed with water and dried to obtain 6-ethyl-7H-pyrrolo[2,3-d]pyrimidin-4-ol.

$^1$H NMR (400 MHz, DMSO-$d_6$) δ: 11.67 (s, 1H), 7.75 (s, 1H), 6.12 (t, 1H), 2.56 (m, 2H), 1.21 (t, 3H)
MS (M+H): 164.2

Step C: 5-bromo-6-ethyl-7H-pyrrolo[2,3-d]pyrimidin-4-ol 1.63 g 6-ethyl-7H-pyrrolo[2,3-d]pyrimidin-4-ol (10 mmol) was dissolved in 20 mL DMF and cooled to 0° C. 1 mL bromine (20 mmol) was added and the mixture was stirred at r.t. until no further conversion was observed. Then it was diluted with water and aqueous $Na_2SO_3$ solution and extracted with DCM. The combined organic layers were washed with brine, dried over $MgSO_4$, filtered and the filtrate was concentrated under reduced pressure to obtain 5-bromo-6-ethyl-7H-pyrrolo[2,3-d]pyrimidin-4-ol.

$^1$H NMR (400 MHz, DMSO-$d_6$) δ: 12.08 (s, 1H), 11.83 (s, 1H), 7.80 (d, 1H), 2.60 (q, 2H), 1.16 (t, 3H) MS (M+H): 243.8

Step D: Preparation 1b 1936 mg 5-bromo-6-ethyl-7H-pyrrolo[2,3-d]pyrimidin-4-ol (8 mmol), 4.5 mL $POCl_3$ and 969 mg N,N-dimethylaniline (8 mmol) were placed in a flask and stirred at 100° C. until no further conversion was observed. The mixture was then poured into ice-water and extracted with DCM. The combined organic layers were washed with brine, dried over $MgSO_4$, filtered and the filtrate was concentrated under reduced pressure to obtain Preparation 1b.

$^1$H NMR (400 MHz, $CDCl_3$) δ: 9.79 (s, 1H), 8.59 (s, 1H), 2.91 (q, 2H), 1.37 (t, 3H)
MS (M+H): 260.0

Preparation 1c:
3-bromo-2-(4-fluorophenyl)benzofuran-4-ol

Step A: 2-(4-fluorophenyl)benzofuran-4-ol 2.37 g 2-bromoresorcinol (12.5 mmol) was dissolved in 30 mL dry THF under $N_2$ atmosphere and 4.17 mL TEA (30 mmol) and 1.92 mL AcCl (27 mmol) were added respectively. After stirring the mixture for 5 minutes, 2.4 g 1-ethynyl-4-fluorobenzene (20 mmol), 561 mg $Pd(OAc)_2$ (2.5 mmol), 1.45 g tri-tert-butylphosphonium tetrafluoroborate (5 mmol), 476 mg CuI (2.5 mmol) and 10 mL dry DIPA were added and the mixture was stirred at 80° C. until no further conversion was observed. Then 2 g $LiOH \times H_2O$ was added and the mixture was stirred at 80° C. until no further conversion was observed. The mixture was then concentrated under reduced pressure and purified via preparative reversed phase chromatography using 25 mM aqueous $NH_4HCO_3$ solution and MeCN as eluents to obtain 2-(4-fluorophenyl)benzofuran-4-ol. $^1$H NMR (400 MHz, DMSO-$d_6$) δ: 10.00 (s, 1H), 7.91 (m, 2H), 7.38 (s, 1H), 7.31 (t, 2H), 7.10 (t, 1H), 7.04 (d, 1H), 6.63 (dd, 1H)

Step B: [2-(4-fluorophenyl)benzofuran-4-yl] acetate 456 mg 2-(4-fluorophenyl)benzofuran-4-ol (2 mmol) was dissolved in 10 mL dry THF then 156 μL AcCl (2.2 mmol) and then 306 μL TEA (2.2 mmol) were added carefully. The mixture was stirred under $N_2$ atmosphere until no further conversion was observed. The solvent was then removed under reduced pressure, and the residue was purified via flash chromatography using heptane and EtOAc as eluents to obtain [2-(4-fluorophenyl) benzofuran-4-yl] acetate. $^1$H NMR (400 MHz, $CDCl_3$) δ: 7.84 (m, 2H), 7.42 (d, 1H), 7.28 (t, 1H), 7.15 (t, 2H), 7.02 (d, 1H), 6.86 (s, 1H), 2.42 (s, 3H)

Step C: [3-bromo-2-(4-fluorophenyl)benzofuran-4-yl] acetate 688 mg [2-(4-fluorophenyl)benzofuran-4-yl] acetate (2.54 mmol) and 589 mg NBS (3.31 mmol) were dissolved in 20 mL MeCN and stirred at 70° C. until no further conversion was observed. The solvent was then removed under reduced pressure, and the residue was purified via flash chromatography using heptane and EtOAc as eluents to obtain [3-bromo-2-(4-fluorophenyl)benzofuran-4-yl] acetate. $^1$H NMR (400 MHz, $CDCl_3$) δ: 8.11 (m, 2H), 7.44 (dd, 1H), 7.34 (t, 1H), 7.19 (m, 2H), 7.00 (dd, 1H), 2.45 (s, 3H)

Step D: Preparation 1c 175 mg [3-bromo-2-(4-fluorophenyl)benzofuran-4-yl] acetate (0.5 mmol) and 150 μL 1M NaOEt in EtOH solution and 5 mL EtOH were stirred at r.t. under N$_2$ atmosphere until no further conversion was observed. The mixture was diluted with 50 mL aqueous cc. NH$_4$Cl solution and extracted with DCM. The combined organic phases were dried over Na$_2$SO$_4$, filtered and the filtrate was concentrated to give Preparation 1c. $^1$H NMR (400 MHz, DMSO-d$_6$) δ: 10.16 (br s, 1H), 8.08 (m, 2H), 7.38 (m, 2H), 7.17 (t, 1H), 7.08 (d, 1H), 6.70 (d, 1H)

Preparation 1d:
3-bromo-6-fluoro-2-(4-fluorophenyl)benzofuran-4-ol

Step A: 5-fluoro-2-iodo-benzene-1,3-diol 3.81 g (29.7 mmol) 5-fluorobenzene-1,3-diol was dissolved in 600 mL water and 8.08 g (31.8 mmol) iodine was added at 0° C. and the mixture was stirred for 30 minutes. Then pH was adjusted to 3 with NaHCO$_3$ solution and the mixture was stirred until no further conversion was observed. Then pH was adjusted to 8 (with NaHCO$_3$ solution), 20 g Na$_2$SO$_3$ was added and the mixture was extracted with EtOAc. Combined organic phases were dried over Na$_2$SO$_4$, filtered and the filtrate was concentrated and purified via flash chromatography using heptane and EtOAc as eluents to obtain 5-fluoro-2-iodo-benzene-1,3-diol. $^1$H NMR (400 MHz, DMSO-d$_6$): 10.54 (s, 2H), 6.19 (d, 2H)

Step B: (3-acetoxy-5-fluoro-2-iodo-phenyl) acetate 4.78 g 3-bromo-6-fluoro-2-(4-fluorophenyl)benzofuran-4-ol (18.8 mmol) was dissolved in 150 mL THF and 5.70 g TEA (56.5 mmol) was added, then 4.267 g Ac$_2$O (41.4 mmol) was added dropwise at r.t. The mixture was stirred until no further conversion was observed. The mixture was then concentrated under reduced pressure and purified via flash chromatography using heptane and EtOAc as eluents to obtain (3-acetoxy-5-fluoro-2-iodo-phenyl) acetate. $^1$H NMR (400 MHz, DMSO-d$_6$): 7.24 (d, 2H), 2.34 (s, 6H)

Step C: 6-fluoro-2-(4-fluorophenyl)benzofuran-4-ol 5.9 g (3-acetoxy-5-fluoro-2-iodo-phenyl) acetate (17.45 mmol) was dissolved in 70 mL dry THF and 70 mL dry DIPA under N$_2$ atmosphere, then 3.77 g 1-ethynyl-4-fluorobenzene (31.4 mmol), 587 mg Pd(OAc)$_2$ (2.62 mmol), 1.52 g tri-tert-butylphosphonium tetrafluoroborate (5.24 mmol), and 500 mg CuI (2.62 mmol) were added and the mixture was stirred at 60° C. until no further conversion was observed. Then 2.93 g LiOH×H$_2$O was added and the mixture was stirred at 60° C. until no further conversion was observed. The mixture was then concentrated under reduced pressure and purified via preparative reversed phase chromatography using 25 mM aqueous NH$_4$HCO$_3$ solution and MeCN as eluents to obtain 6-fluoro-2-(4-fluorophenyl)benzofuran-4-ol. $^1$H NMR (400 MHz, DMSO-d$_6$): 10.60 (s, 1H), 7.89 (m, 2H), 7.38 (s, 1H), 7.32 (m, 2H), 6.99 (m, 1H), 6.48 (dd, 1H)

Step D: [6-fluoro-2-(4-fluorophenyl)benzofuran-4-yl] acetate 2.49 mg 6-fluoro-2-(4-fluorophenyl)benzofuran-4-ol (10.1 mmol) was dissolved in 50 mL dry THF then 791 μL AcCl (11.1 mmol) and then 1.55 mL TEA (11.1 mmol) were added carefully. The mixture was stirred under N$_2$ atmosphere until no further conversion was observed. The solvent was then removed under reduced pressure, the residue was purified via flash chromatography using heptane and EtOAc as eluents to obtain [6-fluoro-2-(4-fluorophenyl)benzofuran-4-yl] acetate. $^1$H NMR (400 MHz, DMSO-d$_6$): 7.95 (m, 2H), 7.57 (m, 1H), 7.46 (s, 1H), 7.37 (m, 2H), 7.09 (dd, 1H), 2.40 (s, 3H)

Step E: [3-bromo-6-fluoro-2-(4-fluorophenyl)benzofuran-4-yl] acetate 2.96 g [6-fluoro-2-(4-fluorophenyl)benzofuran-4-yl] acetate (10.27 mmol) and 2.28 g NBS (12.84 mmol) were dissolved in 120 mL MeCN and stirred at 60° C. until no further conversion was observed. The solvent was then removed under reduced pressure, the residue was purified via flash chromatography using heptane and EtOAc as eluents to obtain [3-bromo-6-fluoro-2-(4-fluorophenyl)benzofuran-4-yl] acetate. $^1$H NMR (400 MHz, DMSO-d$_6$): 8.07 (m, 2H), 7.69 (dd, 1H), 7.44 (m, 1H), 7.19 (m, 2H), 7.09 (dd, 1H), 2.41 (s, 3H)

Step F: Preparation 1d 3.35 g [3-bromo-6-fluoro-2-(4-fluorophenyl)benzofuran-4-yl] acetate (9.12 mmol) and 8.67 mL 1M NaOEt in EtOH solution and 90 mL EtOH were stirred at r.t. under N$_2$ atmosphere until no further conversion was observed. The mixture was diluted with 50 mL aqueous cc. NH$_4$Cl solution and extracted with DCM. The combined organic phases were dried over Na$_2$SO$_4$, filtered and the filtrate was concentrated to give Preparation 1d. $^1$H NMR (400 MHz, DMSO-d$_6$): 10.78 (s, 1H), 8.06 (m, 2H), 7.40 (m, 2H), 7.06 (dd, 1H), 6.54 (dd, 1H)

Preparation 2a: Ethyl
(2R)-2-acetoxy-3-(2-hydroxyphenyl)propanoate and

Preparation 2b: Ethyl
(2S)-2-acetoxy-3-(2-hydroxyphenyl)propanoate

Step A: [2-(Bromomethyl)phenyl]acetate 60.07 g 2-methylphenyl acetate (400 mmol) and 106.8 g NBS (600 mmol) were placed in a 1 L flask. 500 mL cyclohexane was added, and then with intensive stirring 3.284 g AIBN (20 mmol) was added over 30 minutes. The mixture was stirred at 80° C. until no further conversion was observed, then cooled to r.t. The precipitate was filtered off and washed with cyclohexane. The mother liquor was concentrated under reduced pressure, and the crude product was used in Step B without further purification.

Step B: Preparations 2a and 2b 23.10 g anhydrous LiCl (545 mmol) and 65.36 g anhydrous ZnCl$_2$ (479.6 mmol) were placed in a 2 L flask, then dried at 160° C. under 0.1 mmHg for 1 hour. After cooling to r.t. under argon atmosphere, 26.49 g magnesium turnings (1090 mmol) and 1 L dry pre-cooled (0° C.) THF were added. The resulting mixture was immersed into an ice-bath, and then stirred for 30 minutes. 100 g [2-(bromomethyl) phenyl] acetate (crude product from Step A, ~436 mmol) was dissolved in 120 mL dry THF and was added to the precooled inorganics over 15 minutes. After addition of the reagent the resulting mixture was stirred for 45 minutes while keeping the temperature between 0-5° C. Then 64.82 mL ethyl 2-oxoacetate (654 mmol, 50% in toluene) was added over 5 minutes and the resulting mixture was stirred for another 15 minutes. The remaining inorganics were removed by filtration, and the filtrate was diluted with 500 mL MeOH. It was stirred until the intramolecular acetyl group migration from the phenolic oxygen to the alkyl oxygen was complete. Then 30 mL acetic acid was added the volatiles were evaporated under reduced pressure. 350 mL water was added to the residue and it was extracted with EtOAc. The combined organic layers were washed with saturated aqueous NaHCO$_3$ and with brine, and then dried over MgSO$_4$, filtered and the filtrate was concentrated under reduced pressure. Then 100 mL hexane was added and it was stirred for 30 minutes at 0° C. The formed white crystals were collected by filtration and washed with hexane. $^1$H NMR (500 MHz, DMSO-d$_6$) δ: 9.53 (s, 1H), 7.06 (t, 1H), 7.04 (d, 1H), 6.79 (d, 1H), 6.71 (t, 1H), 5.10 (dd, 1H), 4.05 (q, 2H), 3.06 (dd, 1H), 2.94 (dd, 1H), 2.00 (s, 3H), 1.09 (t, 3H)

The enantiomers were separated via chiral chromatography. Column: OD; Eluents: heptane/EtOH; the enantiomer eluting earlier was collected as Preparation 2b with 99.8% ee and the enantiomer eluting later was collected as Preparation 2a with 99.9% ee.

Preparation 2c: Ethyl (2R)-2-hydroxy-3-[2-[[2-(2-methoxyphenyl)pyrimidin-4-yl]methoxy]phenyl] propanoate Step A: (2R)-2-hydroxy-3-[2-[[2-(2-methoxyphenyl) pyrimidin-4-yl]methoxy]phenyl]propanoic Acid 30.3 g Preparation 2a (120 mmol), 38.9 g Preparation 5b (180 mmol) and 47.2 g triphenyl phosphine (180 mmol) were dissolved in 120 mL dry toluene, then 82 mL DEAD (180 mmol, 40% in toluene) was added. The mixture was stirred at 50° C. under nitrogen atmosphere until no further conversion was observed. The volatiles were evaporated under reduced pressure. Then 300 mL DEE was added, the mixture was sonicated and filtered, washed with DEE. The filtrate was concentrated under reduced pressure. The residue was dissolved in 125 mL THF, then 24 g NaOH (0.6 mol) dissolved in 125 mL water was added. The mixture was stirred at 50° C. until no further conversion was observed. The pH was set to 5 with cc. HCl, and the volatiles were removed under reduced pressure. 100 mL water and 350 mL DCM were added, the mixture was stirred at 0° C. and the precipitate was filtered, washed with cold water and DCM and dried under reduced pressure to obtain (2R)-2-hydroxy-3-[2-[[2-(2-methoxyphenyl)pyrimidin-4-yl]methoxy]phenyl]propanoic acid. $^1$H-NMR (400 MHz, DMSO-d$_6$) δ: 8.88 (d, 1H), 7.80 (d, 1H), 7.55 (dd, 1H), 7.49-7.44 (m, 1H), 7.26 (dd, 1H), 7.17-7.11 (m, 2H), 7.06 (t, 1H), 6.98 (d, 1H), 6.88 (t, 1H), 5.22 (s, 2H), 4.50 (d, 1H), 3.81 (dd, 1H), 3.77 (s, 3H), 3.73 (dd, 1H), 2.44 (dd, 1H)

Step B: Preparation 2c 51.7 g (2R)-2-hydroxy-3-[2-[[2-(2-methoxyphenyl)pyrimidin-4-yl]methoxy]phenyl]propanoic acid (136 mmol) was dissolved in 520 mL EtOH, then 20 mL cc. H$_2$SO$_4$ was added. The mixture was stirred at 60° C. until no further conversion was observed. Then it was diluted with water, neutralized with aqueous saturated NaHCO$_3$ solution and extracted with dichloromethane. The combined organic phases were dried over Na$_2$SO$_4$, filtered and the filtrate was concentrated under reduced pressure and purified via flash chromatography using EtOAc and MeOH as eluents to obtain Preparation 2c. HRMS calculated for C$_{23}$H$_{24}$N$_2$O$_5$: 408.1685, found: 409.1757 (M+H).

Preparation 2d: Ethyl (2S)-2-hydroxy-3-[2-[[2-(2-methoxyphenyl)pyrimidin-4-yl]methoxy]phenyl] propanoate Preparation 2d was synthesized the way as Preparation 2c, but starting from Preparation 2b instead of Preparation 2a.

Preparation 2e: Ethyl (2R)-2-hydroxy-3-(2-methoxyphenyl)propanoate and

Preparation 2f: Ethyl (2S)-2-hydroxy-3-(2-methoxyphenyl)propanoate

The enantiomers of ethyl 2-hydroxy-3-(2-methoxyphenyl)propanoate were separated via chiral chromatography; Column: AD, Eluent: 2-PrOH; the enantiomer eluting earlier was collected as Preparation 2e with 99.8% ee. The enantiomer eluting later was collected as Preparation 2f with 97.8% ee.

Preparation 2g: Ethyl (2R)-2-hydroxy-3-[2-(pyrazin-2-ylmethoxy)phenyl]propanoate Step A: Ethyl (2R)-2-acetoxy-3-[2-(pyrazin-2-ylmethoxy)phenyl]propanoate 1 eq. Preparation 2a, 2 eq. of pyrazin-2-ylmethanol and 2 eq. triphenylphosphine were dissolved in dry toluene (0.2M for the phenol), then 2 eq. DTAD was added. The mixture was stirred at 50° C. under nitrogen atmosphere. After reaching an appropriate conversion the volatiles were removed under reduced pressure. The crude intermediate was purified via flash chromatography using heptane and EtOAc as eluents to obtain ethyl (2R)-2-acetoxy-3-[2-(pyrazin-2-ylmethoxy)phenyl]propanoate.

Step B: Preparation 2g

Ethyl (2R)-2-acetoxy-3-[2-(pyrazin-2-ylmethoxy)phenyl] propanoate was dissolved in ethanol (0.5M) then 2 mol % NaOEt solution (1.0M in ethanol) was added. The resulting mixture was stirred at r.t. Additional NaOEt solution was added if conversion was not complete. The mixture was concentrated to half of its volume, then water and brine was added, and it was extracted with EtOAc. The combined organics were dried over Na$_2$SO$_4$, filtered and the filtrate was concentrated under reduced pressure. The crude product was purified via flash chromatography using DCM and methanol as eluents to obtain Preparation 2g. $^1$H NMR (400 MHz, DMSO-d$_6$) δ: 8.88 (s, 1H), 8.64 (dd, 2H), 7.22-7.16 (m, 2H), 7.06 (d, 1H), 6.89 (t, 1H), 5.46 (d, 1H), 5.27 (dd, 2H), 4.29 (dq, 1H), 4.00 (q, 2H), 3.09 (dd, 1H), 2.79 (dd, 1H), 1.08 (t, 3H)

Preparation 2h: Ethyl (2S)-2-hydroxy-3-[2-(2,2,2-trifluoroethoxy)phenyl]propanoate Step A: Ethyl (2S)-2-hydroxy-3-(2-hydroxyphenyl)propanoate 13.633 g Preparation 2b (54 mmol) was dissolved in 200 mL dry EtOH, then 30 mL NaOEt solution (IM in EtOH) was added and the mixture was stirred at r.t. If needed, the addition of the NaOEt solution was repeated until the cleavage of the acetyl group was complete. The mixture was diluted with 600 mL water and it was extracted with EtOAc. The combined organic layers were dried over Na$_2$SO$_4$, filtered and the filtrate was concentrated under reduced pressure. The obtained ethyl (2S)-2-hydroxy-3-(2-hydroxyphenyl)propanoate was used in the next step without further purification.

Step B: Preparation 2h 9.18 g ethyl (2S)-2-hydroxy-3-(2-hydroxyphenyl)propanoate (43.7 mmol) was dissolved in 130 mL dry DMF, then 6.040 g K$_2$CO$_3$ (43.7 mmol) was added. After 5 minutes stirring 7.7 mL 2,2,2-trifluoroethyl trifluoromethanesulfonate (48 mmol) was added over 5 minutes. The resulting mixture was stirred until no further conversion was observed. The reaction mixture was diluted with brine, then extracted with EtOAc. The combined organic layers were dried over Na$_2$SO$_4$, filtered and the filtrate was concentrated under reduced pressure. The crude product was purified via flash chromatography using heptane and EtOAc as eluents.
$^1$H NMR (500 MHz, DMSO-d$_6$) δ: 7.23 (t, 1H), 7.18 (d, 1H), 7.06 (d, 1H), 6.95 (t, 1H), 5.50 (d, 1H), 4.75 (q, 2H), 4.22 (m, 1H), 4.02 (q, 2H), 3.00 (dd, 1H), 2.76 (dd, 1H), 1.09 (t, 3H)

Preparation 2i: (2R)-2-amino-3-[2-[[2-(2-methoxyphenyl)pyrimidin-4-yl]methoxy]phenyl]propanoic Acid

Step A: ethyl (2R)-2-amino-3-(2-hydroxyphenyl)propanoate hydrochloride 653 mg (2R)-2-amino-3-(2-hydroxyphenyl)propanoic acid hydrochloride (3.0 mmol) was dissolved in 6 mL HCl (1.25 M in EtOH) and stirred at 60° C. until no further conversion was observed. Then the reaction mixture was carefully diluted with 10% aqueous NaHCO$_3$ solution and extracted with DCM. The combined organic phase was dried over Na$_2$SO$_4$, filtered and the filtrate was concentrated under reduced pressure. The product should be stored in freezer.
$^1$H NMR (500 MHz, DMSO-d$_6$) δ: 7.05-6.95 (m, 2H), 6.72 (dm, 1H), 6.69-6.63 (m, 1H), 4.02 (q, 2H), 3.65 (dd, 1H), 2.84 (dd, 1H), 2.78 (dd, 1H), 1.12 (t, 3H)
HRMS calculated for C$_{11}$H$_{15}$NO$_3$: 209.1052; found: 210.1128 (M+H).

Step B: ethyl (2R)-2-amino-3-[2-[[2-(2-methoxyphenyl)pyrimidin-4-yl]methoxy]phenyl]propanoate 3.96 g ethyl (2R)-2-amino-3-(2-hydroxyphenyl)propanoate hydrochloride (18.9 mmol) was dissolved in 200 mL dry toluene, then 5.69 g PPh$_3$ (21.7 mmol), 4.69 g Preparation 5b (21.7 mmol) were added and the mixture was heated to 35° C., then 5.0 g DTAD (21.7 mmol) was added and the mixture was stirred at 45° C. until no further conversion was observed. Then the mixture was concentrated under reduced pressure and purified via flash chromatography using EtOAc and MeOH as eluents.
$^1$H NMR (500 MHz, DMSO-d$_6$) δ: 8.92 (d, 1H), 7.61 (d, 1H), 7.55 (dd, 1H), 7.46 (td, 1H), 7.20 (td, 1H), 7.17 (dd, 1H), 7.15 (dd, 1H), 7.06 (td, 1H), 7.04 (dd, 1H), 6.91 (td, 1H), 5.27/5.23 (d, 2H), 4.01 (q, 2H), 3.76 (s, 3H), 3.68 (dd, 1H), 3.08 (br, 2H), 3.03/2.83 (dd, 2H), 1.07 (t, 3H)

HRMS calculated for C$_{23}$H$_{25}$N$_3$O$_4$: 407.1845; found: 408.1928 (M+H).

Step C: Preparation 2i 3.20 g ethyl (2R)-2-amino-3-[2-[[2-(2-methoxyphenyl)pyrimidin-4-yl]methoxy]phenyl]propanoate (7.85 mmol) was dissolved in 10 mL THF, then 10 mL water and 420 mg LiOH×H$_2$O (10 mmol) were added and the mixture was stirred at r.t. until the hydrolysis was complete. Then it was diluted with water and neutralized with 2 M aqueous HCl solution. The formed precipitate was filtered, washed with water and dried to obtain Preparation 2i.
$^1$H NMR (500 MHz, DMSO-d$_6$) δ: 8.88 (d, 1H), 7.82 (d, 1H), 7.54 (dd, 1H), 7.47 (m, 1H), 7.27 (dd, 1H), 7.23 (t, 1H), 7.16 (d, 1H), 7.06 (t, 1H), 7.05 (d, 1H), 6.93 (t, 1H), 5.26 (s, 2H), 3.76 (s, 3H), 3.59 (dd, 1H), 3.49/2.83 (dd, 2H) HRMS calculated for C$_{21}$H$_{21}$N$_3$O$_4$: 379.1532; found: 380.1610 (M+H).

Preparation 3a: 2-Chloro-3-methyl-4-(4,4,5,5-tetramethyl-1,3,2-dioxaborolan-2-yl) phenol

Step A: (4-Bromo-2-chloro-phenoxy)-trimethyl-silane 20.8 g 4-bromo-2-chloro-phenol (100 mmol) was dissolved in 150 mL dry THF then 24.2 g HMDS (150 mmol) was added. The reaction mixture was stirred at 85° C. under argon atmosphere for 1.5 hours then concentrated under reduced pressure. The resulted crude product was used without further purification. $^1$H NMR (200 MHz, CDCl$_3$): 7.49 (d, 1H), 7.23 (dd, 1H), 6.75 (d, 1H), 0.26 (s, 9H)

Step B: 4-Bromo-2-chloro-3-methyl-phenol 48 mL "BuLi solution in hexanes (120 mmol, 2.5M in hexanes) was added dropwise to a solution of 12.1 g dry DIPA (120 mmol) in 250 mL dry THF at −78° C. under argon atmosphere. The mixture was stirred for 30 minutes at the same temperature then 28.0 g (4-bromo-2-chloro-phenoxy)-trimethyl-silane (100 mmol) was added dropwise. After 2.5 hours, 21.3 g MeI (150 mmol) was added dropwise then the cooling bath was removed and the mixture was stirred overnight. The reaction was quenched with 100 mL aqueous NH$_3$ solution and 200 mL saturated aqueous NH$_4$Cl solution and extracted with EtOAc. The organic phase was dried over Na$_2$SO$_4$, filtered and the filtrate was concentrated under reduced pressure. The resulting dark mass was refluxed with pure hexane several times (150-150 mL aliquots) and decanted leaving a black tar behind. The combined organic phases were concentrated under reduced pressure affording 19.0 g crude product, which was used without further purification. $^1$H NMR (200 MHz, CDCl$_3$) δ: 7.32 (d, 1H), 6.76 (d, 1H), 5.62 (s, 1H), 2.49 (s, 3H).

Step C: (4-Bromo-2-chloro-3-methyl-phenoxy)-trimethyl-silane 20.8 g HMDS (129 mmol) was added to the solution of 19.0 g 4-bromo-2-chloro-3-methyl-phenol (86.0 mmol) in 150 mL dry THF. The mixture was stirred at 85° C. under argon balloon for 1.5 hours and then concentrated under reduced pressure. The obtained product was used without further purification. $^1$H NMR (200 MHz, CDCl$_3$) δ: 7.30 (d, 1H), 6.63 (d, 1H), 2.50 (s, 3H), 0.28 (s, 9H)

Step D: Preparation 3a

A solution of 25.2 g (4-bromo-2-chloro-3-methyl-phenoxy)-trimethyl-silane (86.0 mmol) in 250 mL dry THF was cooled to −78° C. under argon and then 38 mL ″BuLi solution (94.6 mmol, 2.5M in hexanes) was added dropwise. After 5 minutes, 19.2 g 2-isopropoxy-4,4,5,5-tetramethyl-1,3,2-dioxaborolane (103 mmol) was added dropwise. The cooling bath was removed and the mixture was slowly allowed to warm up to r.t. Then the mixture was added to 200 mL saturated aqueous NH$_4$Cl solution and extracted with EtOAc. The combined organic layers were concentrated under reduced pressure and passed through a pad of silica gel using hexane and EtOAc as eluents. The crude product was recrystallized from a mixture of EtOAc and hexane to obtain Preparation 3a. $^1$H NMR (500 MHz, DMSO-d$_6$) δ: 10.40 (s, 1H), 7.42 (d, 1H), 6.80 (d, 1H), 2.49 (s, 3H), 1.27 (s, 12H)

Preparation 3b: 1-[2-[2-Chloro-3-methyl-4-(4,4,5,5-tetramethyl-1,3,2-dioxaborolan-2-yl)phenoxy]ethyl]-4-methyl-piperazine 10.0 g Preparation 3a (37.2 mmol), 8.7 g 2-(4-methylpiperazin-1-yl)ethanol (60.3 mmol) and 15.8 g PPh$_3$ (60.3 mmol) were dissolved in 100 mL dry toluene and then 27 mL DEAD (60.3 mmol, 40% solution in toluene) was added dropwise. The mixture was stirred at 50° C. under argon atmosphere until no further conversion was observed. The volatiles were evaporated under reduced pressure and 100 mL Et$_2$O was added. The precipitated white crystals were filtered off and washed with Et$_2$O. The filtrate was concentrated under reduced pressure and purified via flash chromatography using CHCl$_3$ and MeOH as eluents. The resulting light brown oil was crystallized from hexane to give Preparation 3b as an off-white solid. $^1$H NMR (500 MHz, DMSO-d$_6$) δ: 7.56 (d, 1H), 6.99 (d, 1H), 4.15 (t, 2H), 2.72 (t, 2H), 2.51 (s, 3H), 2.50 (br s, 4H), 2.29 (br s, 4H), 2.13 (s, 3H), 1.29 (s, 12H)

Preparation 3c: 2-(3-chloro-2-methyl-phenyl)-5,5-dimethyl-1,3,2-dioxaborinane 4.94 g (3-chloro-2-methylphenyl)boronic acid (29 mmol) and 3.021 g neopentyl-glycol (29 mmol) were stirred at r.t. in the presence of Amberlite 15H$^+$ (dried with toluene) until no further conversion was observed. The mixture was then filtered through Celite and washed with 2-Me-THF. The filtrate was concentrated under reduced pressure to obtain Preparation 3c. $^1$H NMR (400 MHz, CDCl$_3$): 7.59 (dd, 1H), 7.38 (dd, 1H), 7.10 (t, 1H), 3.79 (s, 4H), 2.57 (s, 3H), 1.05 (s, 6H)

Preparation 4: Ethyl (2R)-2-[5-bromo-6-(4-fluorophenyl)furo[2,3-d]pyrimidin-4-yl]oxy-3-[2-[[2-(2-methoxyphenyl)pyrimidin-4-yl]methoxy]phenyl]propanoate Using General procedure 1a and Preparation 2c as the appropriate lactic ester derivative, Preparation 4 was obtained. MS: (M+H)$^+$=700.4

Preparation 5a: (E)-4-(Dimethylamino)-1,1-dimethoxy-but-3-en-2-one 502.1 g 1,1-dimethoxypropan-2-one (4.25 mol) and 506.4 g 1,1-dimethoxy-N,N-dimethyl-methanamine (4.25 mol) were mixed in a 2 L flask and stirred at 105° C. for 3 hours. The formed MeOH was removed continuously via distillation. When MeOH formation stopped (at 65° C. head temperature) the reaction mixture was vacuum distilled (decreasing the pressure slowly to 30 mbar) to remove side products and unreacted starting materials. The crude product was distilled at 0.1 mbar. Fractions were collected between 107-118° C. head temperature (bath temperature 160-165° C.) to give a yellow oil. $^1$H NMR (500 MHz, DMSO-d$_6$) δ: 7.59 (d, 1H), 5.17 (d, 1H), 4.42 (s, 1H), 3.25 (s, 6H), 3.09 (s, 3H), 2.78 (s, 3H)

Preparation 5b: [2-(2-Methoxyphenyl)pyrimidin-4-yl]methanol

Step A: 4-(dimethoxymethyl)-2-(2-methoxyphenyl)pyrimidine

To the mixture of 1.2 eq. 2-methoxybenzamidine acetic acid salt and 1 eq. Preparation 5a in dry methanol (0.5 mL/mmol), 1.2 eq. NaOEt was added portionwise and the mixture was stirred at 75° C. until no further conversion was observed. Then the reaction mixture was cooled and concentrated under reduced pressure. Water was added to the residue and it was extracted with DCM. The combined organic layers were dried over MgSO$_4$, filtered and the filtrate was concentrated under reduced pressure. The crude product was purified via flash chromatography using heptane and EtOAc as eluents to give 4-(dimethoxymethyl)-2-(2-methoxyphenyl)pyrimidine. $^1$H NMR (400 MHz, DMSO-d$_6$) δ: 8.93 (d, 1H), 7.55-7.44 (m, 3H), 7.16 (d, 1H), 7.06 (m, 1H), 5.31 (s, 1H), 3.76 (s, 3H), 3.37 (s, 6H)

Step B: Preparation 5b 261 mg 4-(dimethoxymethyl)-2-(2-methoxyphenyl)pyrimidine (1.0 mmol) was dissolved in 2 mL HCl in dioxane (4M solution), then 2 mL water was added and this mixture was stirred at 50° C. for 16 hours. The reaction mixture was cooled to 0° C., then 320 mg NaOH (8.0 mmol) was added portionwise. The pH was adjusted to 8 using 10% aqueous K$_2$CO$_3$ solution, then 76 mg sodium borohydride (2.0 mmol) was added and the mixture was stirred for 30 minutes at 0° C. The reaction mixture was diluted with 5 mL water and extracted with EtOAc. The combined organic phases were dried over Na$_2$SO$_4$, filtered and the filtrate was concentrated under reduced pressure. The crude product was purified via flash chromatography using heptane and EtOAc as eluents to give Preparation 5b. $^1$H NMR (400 MHz, DMSO-d$_6$) δ: 8.84 (d, 1H), 7.50-7.42 (m, 3H), 7.14 (d, 1H), 7.03 (m, 1H), 5.66 (t, 1H), 4.58 (d, 2H), 3.75 (s, 3H)

Preparation 6: (2R)-2-[(7-benzyl-5-bromo-6-ethyl-pyrrolo[2,3-d]pyrimidin-4-yl) amino]-3-phenyl-propanoic Acid

Step A: 7-benzyl-5-bromo-4-chloro-6-ethyl-pyrrolo[2,3-d]pyrimidine 255 mg NaH (6.38 mmol) and 50 mL dry THF were charged into a 50 mL Schlenk tube under N$_2$ atmosphere and the slurry was cooled to 0° C. Then 1.792 g Preparation 1b (5.8 mmol) was added. After stirring the mixture for 30 minutes at 0° C., 773 µL benzyl bromide (6.38 mmol) was added and the mixture was allowed to warm up to r.t., and stirred until no further conversion was observed. The mixture was then diluted with saturated aqueous NH$_4$Cl solution, and extracted with DCM. The combined organic layers were washed with brine, dried over MgSO$_4$, filtered and the filtrate was concentrated under reduced pressure. The crude product was purified via flash chromatography using heptane and EtOAc as eluents to obtain 7-benzyl-5-bromo-4-chloro-6-ethyl-pyrrolo[2,3-d]pyrimidine.

$^1$H NMR (400 MHz, CDCl$_3$) δ: 8.60 (s, 1H), 7.33-7.26 (m, 3H), 7.06-7.04 (m, 2H), 5.54 (s, 2H), 2.79 (q, 2H), 1.07 (t, 3H)

MS (M+H): 351.8

Step B: Preparation 6

Using General Procedure III and 7-benzyl-5-bromo-4-chloro-6-ethyl-pyrrolo[2,3-d]pyrimidine as the appropriate 4-chloro-pyrrolo[2,3-d]pyrimidine derivative and D-phenylalanine as the appropriate amino acid derivative, Preparation 6 was obtained.

MS (M+H): 279.2

Preparation 7a: N-[2-benzyloxy-6-(2,2-dibromovinyl)phenyl]-3-chloro-2-methyl-4-triisopropylsilyloxy-aniline Step A: (4-Bromo-2-chloro-phenoxy)-triisopropyl-silane 200 g 4-bromo-2-chloro-phenol (0.97 mol) and 126 mL TIPSCl (1.18 mol) were dissolved in 1.6 L DCM. 167 g imidazole (2.45 mol) was added and the mixture was stirred at r.t. for 2 hours. Then the volatiles were evaporated under reduced pressure and the residue was dissolved in 1.5 L EtOAc. The mixture was washed with brine, dried over Na$_2$SO$_4$, filtered and the filtrate was concentrated under reduced pressure. The triisopropylsilyl hydroxide impurity was removed by distillation (120° C. at 0.01 mmHg). The residue was filtered through a short pad of silica with hexane and concentrated under reduced pressure. The product (colourless oil) was used in the next step without further purification.

$^1$H NMR (400 MHz, CDCl$_3$) δ: 7.49 (d, 1H), 7.21 (dd, 1H), 6.78 (d, 1H), 1.31 (septet, 3H), 1.14 (d, 18H)

MS (EI, 70 eV) m/z (% relative intensity, [ion]): 63 (30), 79 (24), 93 (41), 170 (17), 235 (19), 251 (16), 265 (24), 293 (23), 319 (77), 321 (100), 323 (28), 362 (1, [M$^+$])

Step B: (4-Bromo-2-chloro-3-methyl-phenoxy)-triisopropyl-silane 76.0 mL dry DIPA (0.54 mol) was dissolved in 1.2 L dry THF under argon atmosphere and 51.2 mL "BuLi solution (0.512 mol, 10M in hexanes) was added dropwise at −78° C. The mixture was stirred for 45 minutes at the same temperature. Then 178 g (4-bromo-2-chloro-phenoxy)-triisopropyl-silane (0.488 mol) was added dropwise at −78° C. and the white suspension was stirred until no further conversion was observed. Then 36.5 mL MeI (0.586 mmol) was added at this temperature and the reaction mixture was stirred overnight without further cooling. The volatiles were evaporated under reduced pressure. The residue was dissolved in 1.5 L EtOAc, washed with brine. The organic phase was dried over Na$_2$SO$_4$, filtered and the filtrate was concentrated under reduced pressure. The crude product was filtered through a short pad of silica using hexane as eluent and concentrated under reduced pressure to obtain the product as pale yellow oil. $^1$H NMR (400 MHz, CDCl$_3$) δ: 7.30 (d, 1H), 6.68 (d, 1H), 2.53 (s, 3H), 1.32 (septet, 3H), 1.14 (d, 18H)

Step C: N-benzyl-3-chloro-2-methyl-4-triisopropylsilyloxy-aniline 7.56 g (4-bromo-2-chloro-3-methyl-phenoxy)-triisopropyl-silane (20 mmol) and 4.29 g benzylamine (40 mmol) were dissolved in 16 mL dry toluene, then 450 mg Pd$_2$dba$_3$ (0.5 mmol), 450 mg X-Phos (1 mmol) and 9.77 g Cs$_2$CO$_3$ (30 mmol) were added and the mixture was stirred at 100° C. until no further conversion was observed. Then it was filtered through Celite, and the filtrate was concentrated under reduced pressure. The crude product was purified via flash chromatography using hexane and EtOAc as eluents to obtain N-benzyl-3-chloro-2-methyl-4-triisopropylsilyloxy-aniline.

Step D: 3-chloro-2-methyl-4-triisopropylsilyloxy-aniline 3.50 g N-benzyl-3-chloro-2-methyl-4-triisopropylsilyloxy-aniline (8.66 mmol) was dissolved in 100 mL MeOH and 20 mL EtOAc, then 80 mg 10% Pd/C was added and the mixture was stirred under 1 bar H$_2$ atmosphere until no further conversion was observed. Then it was filtered through Celite, and the filtrate was concentrated under reduced pressure. The crude product was purified via flash chromatography using hexane and EtOAc as eluents to obtain 3-chloro-2-methyl-4-triisopropylsilyloxy-aniline.

$^1$H NMR (400 MHz, DMSO-d$_6$) δ: 6.58 (d, 1H), 6.50 (d, 1H), 4.68 (s, 2H), 2.11 (s, 3H), 1.24 (m, 3H), 1.06 (d, 18H)

MS: (M+H)$^+$=314.2

Step E: 3-benzyloxy-2-bromo-benzaldehyde 4.554 g 2-bromo-3-hydroxybenzaldehyde (22.65 mmol), 4.262 g benzyl bromide (24.92 mmol) and 4.696 g K$_2$CO$_3$ (33.98 mmol) were dissolved in 20 mL DMSO and stirred at 50° C. until no further conversion was observed. The mixture was then poured into water. The precipitate was filtered to give 3-benzyloxy-2-bromo-benzaldehyde. MS (EI, 70 eV) m/z (% relative intensity, [ion]): 65 (10), 91 (100), 290 (5, [M$^+$]), 292 (5, [M$^+$])

Step F: 3-benzyloxy-2-(3-chloro-2-methyl-4-triisopropylsilyloxy-anilino)benzaldehyde 5.0 g 3-benzyloxy-2-bromo-benzaldehyde (17.17 mmol), 5.391 g 3-chloro-2-methyl-4-triisopropylsilyloxy-aniline (17.17 mmol), 16.782 g Cs$_2$CO$_3$ (51.51 mmol), 393 mg Pd$_2$dba$_3$ (0.43 mmol) and 535 mg rac. BINAP (0.86 mmol) were mixed in 85 mL toluene and stirred at 120° C. until no further conversion was observed. The volatiles were removed under reduced pressure, the residue was purified via flash chromatography using heptane and EtOAc as eluents to obtain 3-benzyloxy-2-(3-chloro-2-methyl-4-triisopropylsilyloxy-anilino) benzaldehyde. MS: (M+H)$^+$ =524.2

Step G: Preparation 7a 7.7 g 3-benzyloxy-2-(3-chloro-2-methyl-4-triisopropylsilyloxy-anilino)benzaldehyde (14.69 mmol) and 7.308 g carbon tetrabromide (22.03 mmol) were dissolved in 160 mL DCM at 0° C., then 11.56 g PPh$_3$ (44.07 mmol) was added.

The mixture was stirred at r.t. until no further conversion was observed. Then the solvent was removed under reduced pressure, the residue was dissolved in $Et_2O$. Then heptane was added and the formed precipitate was filtered, the filtrate was concentrated under reduced pressure. Then heptane was added, and the mixture was stirred for 10 minutes and filtered again. The filtrate was concentrated under reduced pressure and purified via flash chromatography using heptane and EtOAc as eluents to give Preparation 7a.

$^1$H NMR (400 MHz, DMSO-$d_6$) δ: 7.28-7.23 (m, 5H), 7.19 (s, 1H), 7.11 (dd, 2H), 7.05 (d, 1H), 6.60 (d, 1H), 6.41 (s, 1H), 6.22 (d, 1H), 5.08 (s, 2H), 2.30 (s, 3H), 1.25 (m, 3H), 1.05 (d, 18H)

MS: $(M+H)^+=680.0$

Preparation 7b: Ethyl (2R)-2-[1-[3-chloro-2-methyl-4-[2-(4-methylpiperazin-1-yl) ethoxy]phenyl]-2-(4-fluorophenyl)indol-7-yl]oxy-3-(2-methoxyphenyl) propanoate

Step A: [4-[7-benzyloxy-2-(4-fluorophenyl)indol-1-yl]-2-chloro-3-methyl-phenoxy]-triisopropyl-silane 2720 mg Preparation 7a (4 mmol), 1119 mg 4-fluorophenylboronic acid (8 mmol), 4245 mg $K_3PO_4$ (20 mmol), 90 mg $Pd(OAc)_2$ (0.4 mmol) and 328 mg SPhos (0.8 mmol) were mixed in 60 mL dry toluene under $N_2$ atmosphere and stirred at 100° C. until no further conversion was observed. Then the solvent was removed under reduced pressure, the residue was purified via flash chromatography using heptane and EtOAc as eluents to give [4-[7-benzyloxy-2-(4-fluorophenyl)indol-1-yl]-2-chloro-3-methyl-phenoxy]-triisopropyl-silane. $^1$H NMR (400 MHz, $CDCl_3$) δ: 7.33 (d, 2H), 7.29-t.22 (m, 2H), 7.18 (d, 1H), 7.16 (d, 1H), 7.10 (t, 2H), 6.94 (d, 1H), 6.92-6.84 (m, 4H), 6.73 (s, 1H), 6.61 (d, 1H), 4.94 (d, 1H), 4.89 (d, 1H), 1.97 (s, 3H), 1.31 (m, 3H), 1.13 (t, 18H)

Step B: 4-[7-benzyloxy-2-(4-fluorophenyl)indol-1-yl]-2-chloro-3-methyl-phenol 2600 mg [4-[7-benzyloxy-2-(4-fluorophenyl)indol-1-yl]-2-chloro-3-methyl-phenoxy]-triisopropyl-silane (2.96 mmol), 2.96 mL TBAF solution (2.96 mmol, IM in THF) and 50 mL THF were stirred at r.t. until no further conversion was observed. The solvent was then removed under reduced pressure, the residue was purified via flash chromatography using heptane and EtOAc as eluents to give 4-[7-benzyloxy-2-(4-fluorophenyl)indol-1-yl]-2-chloro-3-methyl-phenol.

$^1$H NMR (400 MHz, DMSO-$d_6$) δ: 10.27 (br s, 1H), 7.28-7.18 (m, 6H), 7.10 (t, 2H), 7.07-6.99 (m, 2H), 6.85-6.77 (m, 3H), 6.75 (s, 1H), 6.72 (d, 1H), 4.95 (d, 1H), 4.90 (d, 1H), 1.75 (s, 3H)

MS: $(M+H)^+=458.0$.

Step C: 7-benzyloxy-1-[3-chloro-2-methyl-4-[2-(4-methylpiperazin-1-yl)ethoxy]phenyl]-2-(4-fluorophenyl)indole 1.2 g 4-[7-benzyloxy-2-(4-fluorophenyl)indol-1-yl]-2-chloro-3-methyl-phenol (2.1 mmol), 606 mg 1-(2-hydroxyethyl)-4-methylpiperazine (4.2 mmol) and 2.1 g $PPh_3$ (6.3 mmol) were dissolved in 50 mL dry toluene under $N_2$ atmosphere and the mixture was cooled to 0° C. Then 1451 mg DTAD (6.3 mmol) was added and the mixture was heated to 45° C. and stirred until no further conversion was observed. The solvent was then removed under reduced pressure, the residue was purified via flash chromatography using heptane and EtOAc and MeOH as eluents to give 7-benzyloxy-1-[3-chloro-2-methyl-4-[2-(4-methylpiperazin-1-yl)ethoxy]phenyl]-2-(4-fluorophenyl)indole. MS: $(M+H)^+=584.2$

Step D: 1-[3-chloro-2-methyl-4-[2-(4-methylpiperazin-1-yl)ethoxy]phenyl]-2-(4-fluoro phenyl)indol-7-ol 1280 mg 7-benzyloxy-1-[3-chloro-2-methyl-4-[2-(4-methylpiperazin-1-yl)ethoxy]phenyl]-2-(4-fluorophenyl)indole (2.19 mmol) was dissolved in 100 mL EtOH, then 100 mg 10% Pd/C was added. The mixture was stirred under 1 bar $H_2$ atmosphere at r.t. until no further conversion was observed. Then the mixture was filtered through Celite and the filtrate was concentrated to give 1-[3-chloro-2-methyl-4-[2-(4-methylpiperazin-1-yl)ethoxy]phenyl]-2-(4-fluorophenyl)indol-7-ol.

$^1$H NMR (400 MHz, DMSO-$d_6$) δ: 9.04 (br s, 1H), 7.25 (dd, 2H), 7.17-7.03 (m, 4H), 6.94 (d, 1H), 6.86 (t, 1H), 6.70 (s, 1H), 6.47 (d, 1H), 4.13 (m, 2H), 2.72 (t, 2H), 2.58-2.42 (br s, 4H), 2.40-2.17 (br s, 4H), 2.14 (s, 3H), 1.86 (s, 3H)

MS: $(M+H)^+=494.2$

Step E: Preparation 7b 494 mg 1-[3-chloro-2-methyl-4-[2-(4-methylpiperazin-1-yl)ethoxy]phenyl]-2-(4-fluoro phenyl)indol-7-ol (1 mmol), 449 mg Preparation 2f (2 mmol) and 786 mg $PPh_3$ (3 mmol) were dissolved in 10 mL dry toluene under $N_2$ atmosphere and the mixture was cooled to 0° C. Then 691 mg DTAD (3 mmol) was added and the mixture was heated to 45° C. and stirred until no further conversion was observed. The solvent was then removed under reduced pressure, the residue was purified via flash chromatography using heptane and EtOAc and MeOH as eluents to give Preparation 7b as a mixture of diastereoisomers.

$^1$H NMR (500 MHz, DMSO-$d_6$) δ: 7.43/6.98 (d, 1H), 7.28 (m, 2H), 7.23/7.24 (d, 1H), 7.17/7.18 (t, 1H), 7.14 (m, 2H), 7.12/6.88 (d, 1H), 6.95/6.94 (t, 1H), 6.91/6.91 (d, 1H), 6.79/6.78 (s, 1H), 6.73/6.75 (t, 1H), 6.52/6.60 (d, 1H), 6.46/6.40 (d, 1H), 4.85/4.76 (dd, 1H), 4.25-4.01 (m, 2H), 4.01-3.89 (m, 2H), 3.77/3.76 (s, 3H), 2.70-2.60 (m, 3H), 2.54-2.30 (m, 5H), 2.21 (br s, 4H), 2.13/2.09 (s, 3H), 1.59/2.08 (s, 3H), 0.99/0.98 (t, 3H)

MS: $(M+H)^+=700.0$

Example 1: (2R)-2-{[5-{3-chloro-2-methyl-4-[2-(4-methylpiperazin-1-yl)ethoxy]phenyl}-6-(4-fluorophenyl)furo[2,3-d]pyrimidin-4-yl]oxy}-3-(2-{[2-(2-methoxyphenyl) pyrimidin-4-yl]methoxy}phenyl) propanoic Acid Using General Procedure II and Preparation 4 as the appropriate 5-bromo-furo[2,3-d]pyrimidine derivative and Preparation 3b as the appropriate boronic acid derivative, Example 1 was obtained as a mixture of diastereoisomers. HRMS calculated for $C_{47}H_{44}ClFN_6O_7$: 858.2944, found: 430.1547 and 430.1555 (M+2H).

Example 2: (2R)-2-{[5-{3-chloro-2-ethyl-4-[2-(4-methylpiperazin-1-yl)ethoxy]phenyl}-6-(4-fluorophenyl)furo[2,3-d]pyrimidin-4-yl]oxy}-3-(2-{[2-(2-methoxyphenyl) pyrimidin-4-yl]methoxy}phenyl) propanoic Acid Step A: 1-[2-(4-bromo-2-chloro-phenoxy)ethyl]-4-methyl-piperazine 10.373 g 4-bromo-2-chlorophenol (50 mmol), 14.442 g 2-(4-methylpiperazin-1-yl)ethanol (100 mmol) and 26.229 g PPh$_3$ (100 mmol) were dissolved in 250 mL dry toluene under N$_2$ atmosphere, then 23.027 g DTAD (100 mmol) was added. The mixture was stirred at 50° C. until no further conversion was observed. The volatiles were evaporated under reduced pressure and the residue was purified via flash chromatography using EtOAc and MeOH as eluents. MS (M+H): 333.0

Step B: 1-[2-(4-bromo-2-chloro-3-ethyl-phenoxy)ethyl]-4-methyl-piperazine 2.0 g 1-[2-(4-bromo-2-chloro-phenoxy)ethyl]-4-methyl-piperazine (6 mmol) was dissolved in 50 mL dry THF under N$_2$ atmosphere and was cooled to −78° C. 6 mL LDA solution (12 mmol in 2M THF) was added and the mixture was stirred for 3 hours, then 982 mg iodoethane (6.3 mmol) was added and the mixture was allowed to warm up to r.t. It was quenched with saturated aqueous NH$_4$Cl solution, extracted with EtOAc. The combined organic layer was dried over Na$_2$SO$_4$, filtered and the filtrate was concentrated under reduced pressure. MS (M+H): 360.8

Step C: 1-[2-[2-chloro-3-ethyl-4-(4,4,5,5-tetramethyl-1,3,2-dioxaborolan-2-yl)phenoxy]ethyl]-4-methyl-piperazine 2099 mg 1-[2-(4-bromo-2-chloro-3-ethyl-phenoxy)ethyl]-4-methyl-piperazine (5.8 mmol) was dissolved in 30 mL dry THF under N$_2$ atmosphere and was cooled to −78° C. 4.65 mL ″BuLi solution (11.61 mmol in 2.5M THF) was added dropwise. It was stirred for 5 hours, then 2.6 mL 2-isopropoxy-4,4,5,5-tetramethyl-1,3,2-dioxaborolane (12.77 mmol) was added and the mixture was stirred for 30 minutes. Then it was allowed to warm up to r.t. and it was concentrated under reduced pressure. The crude product was purified via flash chromatography using EtOAc and MeOH as eluents. MS (M+H): 409.2

Step D: Example 2

Using General Procedure II and Preparation 4 as the appropriate 5-bromo-furo[2,3-d]pyrimidine derivative and 1-[2-[2-chloro-3-ethyl-4-(4,4,5,5-tetramethyl-1,3,2-dioxaborolan-2-yl)phenoxy]ethyl]-4-methyl-piperazine as the appropriate boronic acid derivative, Example 2 was obtained as a mixture of diastereoisomers. HRMS calculated for C$_{48}$H$_{46}$ClFN$_6$O$_7$: 872.3101, found: 437.1620 and 437.1620 (M+2H).

Example 3: (2R)-2-{[5-{3-chloro-2-methyl-4-[2-(4-methylpiperazin-1-yl)ethoxy]phenyl}-6-(4-fluorophenyl)furo[2,3-d]pyrimidin-4-yl]oxy}-3-(2-methoxyphenyl) propanoic Acid Step A: Ethyl (2R)-2-[5-bromo-6-(4-fluorophenyl)furo[2,3-d]pyrimidin-4-yl]oxy-3-(2-methoxyphenyl) propanoate Using General procedure 1a and Preparation 2e as the appropriate lactic ester derivative, ethyl (2R)-2-[5-bromo-6-(4-fluorophenyl)furo[2,3-d]pyrimidin-4-yl]oxy-3-(2-methoxy phenyl)propanoate was obtained. $^1$H NMR (400 MHz, DMSO-d$_6$): 8.53 (s, 1H), 8.10 (m, 2H), 7.47-7.36 (m, 3H), 7.23 (m, 1H), 6.96 (m, 1H), 6.89 (t, 1H), 5.58 (m, 1H), 4.12 (q, 2H), 3.79 (s, 3H), 3.36 (m, 1H), 3.21 (m, 1H), 1.11 (t, 3H)

Step B: Example 3

Using General Procedure II and ethyl (2R)-2-[5-bromo-6-(4-fluorophenyl)furo[2,3-d]pyrimidin-4-yl]oxy-3-(2-methoxyphenyl)propanoate as the appropriate 5-bromo-furo[2,3-d]pyrimidine derivative and Preparation 3b as the appropriate boronic acid derivative, Example 3 was obtained as a mixture of diastereoisomers. HRMS calculated for C$_{36}$H$_{36}$ClFN$_4$O$_6$: 674.2307, found: 675.2367 and 675.2364 (M+H).

Example 4: (2R)-2-{[5-{3-chloro-2-methyl-4-[2-(4-methylpiperazin-1-yl)ethoxy]phenyl}-6-(4-fluorophenyl)furo[2,3-d]pyrimidin-4-yl]oxy}-3-[2-(pyrazin-2-ylmethoxy) phenyl]propanoic Acid Step A: Ethyl (2R)-2-[5-bromo-6-(4-fluorophenyl)furo[2,3-d]pyrimidin-4-yl]oxy-3-[2-(pyrazin-2-yl-methoxy)phenyl]propanoate Using General procedure 1a and Preparation 2g as the appropriate lactic ester derivative, ethyl (2R)-2-[5-bromo-6-(4-fluorophenyl)furo[2,3-d]pyrimidin-4-yl]oxy-3-[2-(pyrazin-2-ylmethoxy)phenyl]propanoate was obtained. MS: (M+H)$^+$=595.0

Step B: Example 4

Using General Procedure II and ethyl (2R)-2-[5-bromo-6-(4-fluorophenyl)furo[2,3-d]pyrimidin-4-yl]oxy-3-[2-(pyrazin-2-ylmethoxy)phenyl]propanoate as the appropriate 5-bromo-furo[2,3-d]pyrimidine derivative and Preparation 3b as the appropriate boronic acid derivative, Example 4 was obtained as a mixture of diastereoisomers. HRMS calculated for C$_{40}$H$_{38}$ClFN$_6$O$_6$: 752.2525, found: 753.2645 and 753.2606 (M+H).

Example 5: (2R)-2-{[6-(5-chlorofuran-2-yl)-5-{3-chloro-2-methyl-4-[2-(4-methyl piperazin-1-yl)ethoxy]phenyl}furo[2,3-d]pyrimidin-4-yl]oxy}-3-[2-(pyrazin-2-yl methoxy)phenyl]propanoic Acid Step A: 2-[2-(2-furyl)-2-oxo-ethyl]propanedinitrile 46.2 mL IM NaOEt solution in EtOH (46.2 mmol) and 400 mL EtOH were cooled to 0° C. and 3.2 g malononitrile (48.4 mmol) was added. The mixture was stirred at 0° C. for 1 hour, then 8.35 g 2-bromo-1-(2-furyl)ethanone (44 mmol) was added. The mixture was stirred at 0° C. for 1 hour, then at r.t. until no further conversion was observed. The volatiles were removed under reduced pressure, the residue was digerated in Et$_2$O, filtered, then purified via flash chromatography using DCM and EtOAc as eluents to obtain 2-[2-(2-furyl)-2-oxo-ethyl]propanedinitrile. MS: (M+H)+=175.2

Step B: 2-amino-5-(2-furyl)furan-3-carbonitrile 4.587 g 2-[2-(2-furyl)-2-oxo-ethyl]propanedinitrile (26.34 mmol) was dissolved in 150 mL EtOH and 4.6 g Amberlite 15H$^+$ was added. The mixture was stirred at 90°

C. until no further conversion was observed. The mixture was then filtered, washed with DCM and EtOAc. The filtrate was concentrated under reduced pressure and purified via flash chromatography using heptane and EtOAc as eluents to obtain 2-amino-5-(2-furyl)furan-3-carbonitrile. MS: (M+H)+=175.4

Step C: 6-(2-furyl)-3H-furo[2,3-d]pyrimidin-4-one 1310 mg 2-amino-5-(2-furyl)furan-3-carbonitrile (7.52 mmol) and 30 mL acetic formic anhydride were placed in a flask and stirred at r.t. for 30 minutes. Then the volatiles were evaporated under reduced pressure and the residue was dissolved in 60 mL AcOH, and irradiated at 180° C. for 50 minutes. The mixture was cooled to r.t., and the crude product was purified via flash chromatography using heptane and EtOAc as eluents to obtain 6-(2-furyl)-3H-furo[2,3-d]pyrimidin-4-one. $^1$H NMR (400 MHz, DMSO-d$_6$): 12.68 (br s, 1H), 8.14 (s, 1H), 7.84 (m, 1H), 7.08 (s, 1H), 6.94 (d, 1H), 6.67 (m, 1H)

Step D: 6-(5-chloro-2-furyl)-3H-furo[2,3-d]pyrimidin-4-one 1.183 g 6-(2-furyl)-3H-furo[2,3-d]pyrimidin-4-one (5.85 mmol) was dissolved in 55 mL THF and 860 mg NCS (6.44 mmol) was added. The mixture was stirred at 40° C. until no further conversion was observed. The mixture was cooled to 0° C., and the precipitate was filtered, and dried to obtain 6-(5-chloro-2-furyl)-3H-furo[2,3-d]pyrimidin-4-one. MS: (M+H)+=237.0

Step E: 5-bromo-6-(5-chloro-2-furyl)-3H-furo[2,3-d]pyrimidin-4-one)

1000 mg 6-(5-chloro-2-furyl)-3H-furo[2,3-d]pyrimidin-4-one (4.23 mmol) was dissolved in 40 mL AcOH, then 776 mg bromine (4.86 mmol) was added. The mixture was stirred at 40° C. until no further conversion was observed. Then the volatiles were removed under reduced pressure. The residue was digerated with DCM then filtered to obtain 5-bromo-6-(5-chloro-2-furyl)-3H-furo[2,3-d]pyrimidin-4-one. MS: (M−H)+=314.8

Step F: 5-bromo-4-chloro-6-(5-chloro-2-furyl)furo[2,3-d]pyrimidine 1110 mg 5-bromo-6-(5-chloro-2-furyl)-3H-furo[2,3-d]pyrimidin-4-one (3.52 mmol) was dissolved in 8.21 mL POCl$_3$ (88.1 mmol) then 447 μL DMA (3.52 mmol) was added. The mixture was stirred at 110° C. until no further conversion was observed. The mixture was then cooled to −78° C. and ice was added. It was sonicated then the precipitate was filtered. The crude product was purified via flash chromatography using heptane and EtOAc as eluents to obtain 5-bromo-4-chloro-6-(5-chloro-2-furyl)furo[2,3-d]pyrimidine. MS: (M+H)+=335.0

Step G: Ethyl (2R)-2-[5-bromo-6-(5-chloro-2-furyl)furo[2,3-d]pyrimidin-4-yl]oxy-3-[2-(pyrazin-2-ylmethoxy)phenyl]propanoate 1 eq. 5-bromo-4-chloro-6-(5-chloro-2-furyl)furo[2,3-d]pyrimidine, 2 eq. Preparation 2g, 10 mL/mmol $^t$BuOH and 5 eq. Cs$_2$CO$_3$ were placed in a flask and stirred at 55° C. until no further conversion was observed. The mixture was then concentrated under reduced pressure, diluted with brine, neutralized with 1M aqueous HCl solution, and extracted with EtOAc. The combined organic phases were dried over Na$_2$SO$_4$, filtered and the filtrate was concentrated under reduced pressure. The crude product was purified via flash chromatography using heptane and EtOAc as eluents to give ethyl (2R)-2-[5-bromo-6-(5-chloro-2-furyl)furo[2,3-d]pyrimidin-4-yl]oxy-3-[2-(pyrazin-2-ylmethoxy)phenyl]propanoate. MS: (M+H)+=601.0

Step H: Example 5

Using General Procedure II and ethyl (2R)-2-[5-bromo-6-(5-chloro-2-furyl)furo[2,3-d]pyrimidin-4-yl]oxy-3-[2-(pyrazin-2-ylmethoxy)phenyl]propanoate as the appropriate 5-bromo-furo[2,3-d]pyrimidine derivative and Preparation 3b as the appropriate boronic acid derivative, Example 5 was obtained as a mixture of diastereoisomers. HRMS calculated for $C_{38}H_{36}Cl_2N_6O_7$: 758.2023, found: 759.2119 and 759.2156 (M+H).

Example 6: (2R)-3-{2-[(1-tert-butyl-1H-pyrazol-5-yl)methoxy]phenyl}-2-{[5-{3-chloro-4-[2-(dimethylamino)ethoxy]-2-methylphenyl}-6-(4-fluorophenyl)furo[2,3-d]pyrimidin-4-yl]oxy}propanoic Acid Step A: 1-tert-butyl-5-(dimethoxymethyl)-1H-pyrazole 1.2 eq. tert-butylhydrazine hydrochloride and 1 eq. Preparation 5a was dissolved in dry methanol (0.5 mL/mmol), then 1.2 eq NaOEt was added portionwise and the mixture was stirred at 75° C. for 2 hours. The reaction mixture was cooled and concentrated under reduced pressure. The residue was diluted with water and it was extracted with DCM. The combined organic phases were dried over MgSO$_4$, filtered and the filtrate was concentrated under reduced pressure. The crude product was purified via flash chromatography using heptane and EtOAc as eluents to give 1-tert-butyl-5-(dimethoxymethyl)-1H-pyrazole. $^1$H NMR (400 MHz, DMSO-d$_6$) δ: 7.34 (d, 1H), 6.34 (d, 1H), 5.74 (s, 1H), 3.24 (s, 6H), 1.57 (s, 9H). We also obtained 1-tert-butyl-3-(dimethoxymethyl)-1H-pyrazole. $^1$H NMR (400 MHz, DMSO-d$_6$) δ: 7.75 (d, 1H), 6.18 (d, 1H), 5.34 (s, 1H), 3.24 (s, 6H), 1.50 (s, 9H)

Step B: (1-tert-Butyl-1H-pyrazol-5-yl)methanol 1 eq. 1-tert-butyl-5-(dimethoxymethyl)-1H-pyrazole was stirred with 1M aqueous HCl solution (3 mL/mmol) at 50° C. until no further conversion was observed. The reaction mixture was cooled to 0° C., then 2.85 eq. solid NaOH was added portionwise. The pH was adjusted to 8 using 10% aqueous K$_2$CO$_3$ solution, then 2 eq. sodium borohydride was added portionwise, keeping the temperature below 5° C. and stirred at 0° C. until no further conversion was observed. The mixture was extracted with EtOAc, the combined organic phases were dried over Na$_2$SO$_4$, filtered and the filtrate was concentrated under reduced pressure. The crude product was purified via flash chromatography using heptane and EtOAc to obtain (1-tert-butyl-1H-pyrazol-5-yl)methanol. $^1$H NMR (400 MHz, DMSO-d$_6$) δ: 7.27 (d, 1H), 6.19 (d, 1H), 5.31 (t, 1H), 4.61 (d, 2H), 1.56 (s, 9H)

Step C: (2R)-3-[2-[(2-tert-butylpyrazol-3-yl)methoxy]phenyl]-2-hydroxy-propanoic Acid 2.51 g Preparation 2a (9.96 mmol), 2.0 g (1-tert-butyl-1H-pyrazol-5-yl)methanol (13 mmol) and 3.39 g triphenyl phosphine (13 mmol) were dissolved in 12 mL dry toluene, then 5.9 mL DEAD (13 mmol) was added. The mixture was stirred at 50° C. under nitrogen atmosphere until no further conversion was observed. The volatiles were evaporated under reduced pressure. Then 30 mL Et$_2$O was added, the mixture was sonicated and filtered (to remove PPh$_3$ and PPh$_3$O). The filtrate was concentrated under reduced pressure. The residue was dissolved in THF, and then 2 g NaOH dissolved in 8 mL water was added. The mixture was stirred at 50° C. until no further conversion was observed. Then it was acidified with 2M aqueous HCl solution, and THF was removed under reduced pressure. The residue was extracted with DCM, dried over Na$_2$SO$_4$, filtered and the filtrate was concentrated under reduced pressure to obtain (2R)-3-[2-[(2-tert-butylpyrazol-3-yl)methoxy]phenyl]-2-hydroxy-propanoic acid. MS (M+H): 319.0

Step D: Ethyl (2R)-3-[2-[(2-tert-butylpyrazol-3-yl)methoxy]phenyl]-2-hydroxy-propanoate 7.2 g (2R)-3-[2-[(2-tert-butylpyrazol-3-yl)methoxy]phenyl]-2-hydroxy-propanoic acid was dissolved in 75 mL EtOH, then 2 mL cc. H$_2$SO$_4$ was added. The mixture was stirred at 60° C. until no further conversion was observed. Then it was diluted with water, neutralized with saturated aqueous NaHCO$_3$ solution and extracted with dichloromethane. The combined organic phases were dried over Na$_2$SO$_4$, filtered and the filtrate was concentrated under reduced pressure and purified via flash chromatography using EtOAc and MeOH as eluents to obtain ethyl (2R)-3-[2-[(2-tert-butylpyrazol-3-yl)methoxy]phenyl]-2-hydroxy-propanoate. MS (M+H): 347.0

Step E: Ethyl (2R)-2-[5-bromo-6-(4-fluorophenyl)furo[2,3-d]pyrimidin-4-yl]oxy-3-[2-[(2-tert-butylpyrazol-3-yl)methoxy]phenyl]propanoate Using General procedure 1a and ethyl (2R)-3-[2-[(2-tert-butylpyrazol-3-yl)methoxy]phenyl]-2-hydroxy-propanoate as the appropriate lactic ester derivative, ethyl (2R)-2-[5-bromo-6-(4-fluorophenyl)furo[2,3-d]pyrimidin-4-yl]oxy-3-[2-[(2-tert-butyl-pyrazol-3-yl) methoxy]phenyl]propanoate was obtained. MS (M+H): 636.6-638.6

Step F: 2-[2-chloro-3-methyl-4-(4,4,5,5-tetramethyl-1,3,2-dioxaborolan-2-yl)phenoxy]-N,N-dimethyl-ethanamine 10.0 g Preparation 3a (37.2 mmol), 5.366 g N,N-dimethylethanolamine (60.3 mmol) and 15.8 g PPh$_3$ (60.3 mmol) were dissolved in 100 mL dry toluene and then 27 mL DEAD (60.3 mmol, 40% solution in toluene) was added dropwise. The mixture was stirred at 50° C. under argon atmosphere until no further conversion was observed. The volatiles were evaporated under reduced pressure and 100 mL Et$_2$O was added. The precipitated white crystals were filtered off and washed with Et$_2$O. The filtrate was concentrated under reduced pressure and purified via flash chromatography using CHCl$_3$ and MeOH as eluents. The resulting light brown oil was crystallized from hexane to give 2-[2-chloro-3-methyl-4-(4,4,5,5-tetramethyl-1,3,2-dioxaborolan-2-yl)phenoxy]-N,N-dimethyl-ethanamine.
$^1$H NMR (200 MHz, CDCl$_3$) δ: 7.63 (d, 1H), 6.75 (d, 1H), 4.15 (t, 2H), 2.81 (t, 2H), 2.60 (s, 3H), 2.38 (s, 6H), 1.33 (s, 12H)
MS (M+H): 340.1

Step G: Example 6

Using General Procedure II and ethyl (2R)-2-[5-bromo-6-(4-fluorophenyl)furo[2,3-d]pyrimidin-4-yl]oxy-3-[2-[(2-tert-butylpyrazol-3-yl)methoxy]phenyl]propanoate as the appropriate 5-bromo-furo[2,3-d]pyrimidine derivative and 2-[2-chloro-3-methyl-4-(4,4,5,5-tetramethyl-1,3,2-dioxaborolan-2-yl)phenoxy]-N,N-dimethyl-ethanamine as the appropriate boronic acid derivative, Example 6 was obtained. HRMS calculated for C$_{40}$H$_{41}$ClFN$_5$O$_6$: 741.2729, found: 742.2813 and 742.2808 (M+H) for the two diastereomers.

Example 7: N-[(5S$_a$)-5-{3-chloro-2-methyl-4-[2-(4-methylpiperazin-1-yl)ethoxy]phenyl}-6-(4-fluorophenyl)furo[2,3-d]pyrimidin-4-yl]-2-methoxy-D-phenylalanine Step A: (2R)-2-[[5-bromo-6-(4-fluorophenyl)furo[2,3-d]pyrimidin-4-yl]amino]-3-(2-methoxyphenyl)propanoic Acid Using General Procedure Ib and (2R)-2-amino-3-(2-methoxyphenyl)propanoic acid as the appropriate amino acid derivative, (2R)-2-[[5-bromo-6-(4-fluorophenyl)furo[2,3-d]pyrimidin-4-yl]amino]-3-(2-methoxyphenyl)propanoic acid was obtained. MS: (M+H)+=487.8

Step B: Example 7

1 eq. (2R)-2-[[5-bromo-6-(4-fluorophenyl)furo[2,3-d]pyrimidin-4-yl]amino]-3-(2-methoxy phenyl)propanoic acid, 1.5 eq. Preparation 3b, 5 mol % AtaPhos and 2 eq. Cs$_2$CO$_3$ were stirred in a 1:1 mixture of THF and water (10 mL/mmol 5-bromo-furo[2,3-d]pyrimidine derivative) and heated to 110° C. in a MW reactor until no further conversion was observed. Then the mixture was diluted with brine, the pH was set to 4 with IM aqueous HCl solution, and was extracted with DCM. The combined organic phases were dried over MgSO$_4$, filtered and the filtrate was concentrated under reduced pressure. The obtained mixture of diastereoisomers were purified and separated via HILIC chromatography. Example 7 was obtained as the later eluting diastereoisomer. HRMS calculated for C$_{36}$H$_{37}$ClFN$_5$O$_5$: 673.2467, found: 337.6286 (M+2H).

Example 8: N-[(5S$_a$)-5-{3-chloro-2-methyl-4-[2-(4-methylpiperazin-1-yl)ethoxy]phenyl}-6-(4-fluorophenyl)furo[2,3-d]pyrimidin-4-yl]-2-{[2-(2-methoxyphenyl)pyrimidin-4-yl]methoxy}-D-phenylalanine and Example 9: N-[(5R$_a$)-5-{3-chloro-2-methyl-4-[2-(4-methylpiperazin-1-yl)ethoxy]phenyl}-6-(4-fluorophenyl)furo[2,3-d]pyrimidin-4-yl]-2-{[2-(2-methoxyphenyl)pyrimidin-4-yl]methoxy}-D-phenylalanine Step A: (2R)-2-[[5-bromo-6-(4-fluorophenyl)furo[2,3-d]pyrimidin-4-yl]amino]-3-(2-hydroxyphenyl)propanoic Acid Using General Procedure Ib and D-(R)-2-amino-3-(2-hydroxy-phenyl)-propionic acid as the appropriate amino acid derivative, (2R)-2-[[5-bromo-6-(4-fluorophenyl)furo[2, 3-d]pyrimidin-4-yl]amino]-3-(2-hydroxyphenyl)propanoic acid was obtained. MS: (M+H)$^+$=473.6

Step B: Ethyl (2R)-2-[[5-bromo-6-(4-fluorophenyl) furo[2,3-d]pyrimidin-4-yl]amino]-3-[2-[[2-(2-methoxyphenyl)pyrimidin-5-yl]methoxy]phenyl] propanoate 163 mg (2R)-2-[[5-bromo-6-(4-fluorophenyl)furo[2,3-d]pyrimidin-4-yl]amino]-3-(2-hydroxyphenyl)propanoic acid was dissolved in 3 mL HCl solution (1.25M in EtOH) and stirred at 60° C. until no further conversion was observed. The mixture was concentrated under reduced pressure, diluted with water. The precipitate was filtered and purified via flash chromatography using heptane and EtOAc as eluents to obtain ethyl (2R)-2-[[5-bromo-6-(4-fluorophenyl)furo[2,3-d]pyrimidin-4-yl]amino]-3-(2-hydroxyphenyl) propanoate. MS: (M+H)$^+$=501.6

Step C: Ethyl (2R)-2-[[5-bromo-6-(4-fluorophenyl) furo[2,3-d]pyrimidin-4-yl]amino]-3-[2-[[2-(2-methoxyphenyl) pyrimidin-5-yl]methoxy]phenyl] propanoate 500 mg ethyl (2R)-2-[[5-bromo-6-(4-fluorophenyl)furo[2,3-d]pyrimidin-4-yl]amino]-3-(2-hydroxyphenyl)propanoate (1 mmol), 540 mg Preparation 5b (2.5 mmol) and 656 mg PPh$_3$ (2.5 mmol) were dissolved in 20 mL dry toluene under N$_2$ atmosphere, then 576 mg DTAD (2.5 mmol) was added. The mixture was stirred at 60° C. until no further conversion was observed. The mixture was then concentrated under reduced pressure and purified via flash chromatography using heptane and EtOAc as eluents to give ethyl (2R)-2-[[5-bromo-6-(4-fluorophenyl)furo[2,3-d]pyrimidin-4-yl]amino]-3-[2-[[2-(2-methoxyphenyl) pyrimidin-5-yl]methoxy]phenyl]propanoate. HRMS (M+H)+: 698.1402

Step D: Examples 8 and 9

1 eq. ethyl (2R)-2-[[5-bromo-6-(4-fluorophenyl)furo[2,3-d]pyrimidin-4-yl]amino]-3-[2-[[2-(2-methoxyphenyl)pyrimidin-5-yl]methoxy]phenyl]propanoate, 1.5 eq. Preparation 3b, 5 mol % AtaPhos and 2 eq. Cs$_2$CO$_3$ were stirred in a 1:1 mixture of THF and water (10 mL/mmol 5-bromo-furo[2,3-d]pyrimidine derivative) and heated to 70° C. and stirred until no further conversion was observed. Then the mixture was diluted with brine, the pH was set to 4 with IM aqueous HCl solution, and was extracted with DCM. The combined organic phases were dried over MgSO$_4$, filtered and the filtrate was concentrated under reduced pressure. The crude intermediate was purified via flash chromatography using DCM and MeOH as eluents. Then it was dissolved in dioxane:water 1:1 (20 mL/mmol) and 10 eq. LiOH×H$_2$O was added. The mixture was stirred at r.t. until no further conversion was observed. Then it was diluted with brine, neutralized with 2M aqueous HCl solution, extracted with DCM. The combined organic phases were dried over Na$_2$SO$_4$, filtered and the filtrate was concentrated under reduced pressure to obtain a mixture of diastereoisomers. They were separated and purified via preparative reversed phase chromatography using 25 mM aqueous NH$_4$HCO$_3$ solution and MeCN as eluents. Example 8 was obtained as the earlier eluting diastereoisomer. HRMS calculated for C$_{47}$H$_{45}$ClFN$_7$O$_6$: 857.3104, found: 429.6637 (M+2H).

Example 9 was obtained as the later eluting diastereoisomer. HRMS calculated for C$_{47}$H$_{45}$ClFN$_7$O$_6$: 857.3104, found: 429.6648 (M+2H).

Example 10: N-[7-methyl-5-(naphthalen-1-yl)-7H-pyrrolo[2,3-d]pyrimidin-4-yl]-D-phenylalanine Step A: 4-chloro-5-iodo-7-methyl-pyrrolo[2,3-d] pyrimidine Into a 50 mL Schlenk tube under N$_2$ atmosphere 220 mg NaH (5.5 mmol) and 40 mL dry THF were charged and the slurry was cooled to 0° C. Then 1471 mg 4-chloro-5-iodo-7H-pyrrolo[2,3-d]pyrimidine (5 mmol) was added. After 30 minutes stirring, 346 µL MeI (5.5 mmol) was added and the mixture was allowed to warm up to r.t., and stirred until no further conversion was observed. The mixture was then diluted with saturated aqueous NH$_4$Cl solution, and extracted with DCM. The combined organic layers were washed with brine, dried over MgSO$_4$, filtered and the filtrate was concentrated under reduced pressure to obtain 4-chloro-5-iodo-7-methyl-pyrrolo[2,3-d]pyrimidine.
$^1$H NMR (400 MHz, DMSO-d$_6$) δ: 8.65 (s, 1H), 7.98 (s, 1H), 3.83 (s, 3H)
MS: (M+H)$^+$=294.0

Step B: 4-chloro-7-methyl-5-(1-naphthyl)pyrrolo[2, 3-d]pyrimidine 1 eq. 4-chloro-5-iodo-7-methyl-pyrrolo[2,3-d]pyrimidine, 1.1 eq. 1-naphthaleneboronic acid neopentyl glycol ester, 1.1 eq. silver carbonate, 0.15 eq. Pd(PPh$_3$)$_4$ and 2-Me-THF (15 mL/mmol 5-iodo-pyrrolo[2,3-d]pyrimidine derivative) were stirred under N$_2$ atmosphere at 110° C. until no further conversion was observed. The mixture was diluted with brine, neutralized with IM aqueous HCl solution, and extracted with DCM. The combined organic phases were dried over Na$_2$SO$_4$, filtered and the filtrate was concentrated under reduced pressure. The crude product was purified via flash chromatography using heptane and EtOAc as eluents to give 4-chloro-7-methyl-5-(1-naphthyl)pyrrolo [2,3-d]pyrimidine. MS: (M+H)$^+$=294.2

Step C: Example 10

Using General Procedure III and 4-chloro-7-methyl-5-(1-naphthyl)pyrrolo[2,3-d]pyrimidine as the appropriate 4-chloro-pyrrolo[2,3-d]pyrimidine derivative and D-phenylalanine as the appropriate amino acid derivative, Example 10 was obtained. HRMS calculated for C$_{26}$H$_{22}$N$_4$O$_2$: 422.1743, found: 423.1804 (M+H).

Example 11: N-[5-(naphthalen-1-yl)-7H-pyrrolo[2, 3-d]pyrimidin-4-yl]-D-phenylalanine Step A: 7-(benzenesulfonyl)-4-chloro-5-iodo-pyrrolo[2,3-d]pyrimidine Into a 50 mL Schlenk tube under N$_2$ atmosphere 220 mg NaH (5.5 mmol) and 40 mL dry THF were charged and the slurry was cooled to 0° C. Then 1471 mg 4-chloro-5-iodo-7H-pyrrolo[2,3-d]pyrimidine (5 mmol) was added. After 30 minutes stirring, 1.4 mL benzenesulfonyl chloride (5.25 mmol) was added and the mixture was allowed to warm up to r.t., and stirred until no further conversion was observed. The mixture was then diluted with saturated aqueous NH$_4$Cl solution, and extracted with DCM. The combined organic layers were washed with brine, dried over MgSO₄, filtered and the filtrate was concentrated under reduced pressure. Then it was digerated with MTBE, then filtered to obtain 7-(benzenesulfonyl)-4-chloro-5-iodo-pyrrolo[2,3-d]pyrimidine.

$^1$H NMR (400 MHz, CDCl₃) δ: 8.75 (s, 1H), 8.22 (m, 2H), 7.95 (s, 1H), 7.67 (m, 1H), 7.56 (m, 2H)

MS: (M+H)⁺=419.8

Step B: 7-(benzenesulfonyl)-4-chloro-5-(1-naphthyl)pyrrolo[2,3-d]pyrimidine 1 eq. 7-(benzenesulfonyl)-4-chloro-5-iodo-pyrrolo[2,3-d]pyrimidine, 1.1 eq. 1-naphthaleneboronic acid neopentyl glycol ester, 1.1 eq. silver carbonate, 0.15 eq. Pd(PPh₃)₄ and 2-Me-THF (15 mL/mmol 5-iodo-pyrrolo[2,3-d]pyrimidine derivative) were stirred under N₂ atmosphere at 110° C. until no further conversion was observed. The mixture was diluted with brine, neutralized with IM aqueous HCl solution, and extracted with DCM. The combined organic phases were dried over Na₂SO₄, filtered and the filtrate was concentrated under reduced pressure. The crude product was purified via flash chromatography using heptane and EtOAc as eluents to give 7-(benzenesulfonyl)-4-chloro-5-(1-naphthyl)pyrrolo[2,3-d]pyrimidine.

$^1$H NMR (400 MHz, CDCl₃) δ: 8.82 (s, 1H), 8.31 (m, 2H), 7.94 (m, 2H), 7.84 (s, 1H), 7.71 (m, 1H), 7.60 (m, 2H), 7.56-7.48 (m, 3H), 7.48-7.38 (m, 2H)

MS: (M+H)⁺=420.0

Step C: Example 11

Using General Procedure III and 7-(benzenesulfonyl)-4-chloro-5-(1-naphthyl)pyrrolo[2,3-d]pyrimidine as the appropriate 4-chloro-pyrrolo[2,3-d]pyrimidine derivative and D-phenylalanine as the appropriate amino acid derivative, Example 11 was obtained. HRMS calculated for $C_{25}H_{20}N_4O_2$: 408.1586, found: 409.1670 (M+H).

Example 12: N-[7-benzyl-6-ethyl-5-(naphthalen-1-yl)-7H-pyrrolo[2,3-d]pyrimidin-4-yl]-D-phenylalanine, diastereoisomer 1 and Example 13: N-[7-benzyl-6-ethyl-5-(naphthalen-1-yl)-7H-pyrrolo[2,3-d]pyrimidin-4-yl]-D-phenylalanine, diastereoisomer 2

Using General Procedure IVa and Preparation 6 as the appropriate 5-bromo-pyrrolo[2,3-d]pyrimidine derivative and 1-naphthaleneboronic acid neopentyl glycol ester as the appropriate boronic acid derivative, Example 12 was obtained as the earlier eluting diastereoisomer. HRMS calculated for $C_{34}H_{30}N_4O_2$: 526.2369, found: 527.2431 (M+H). Example 13 was obtained as the later eluting diastereoisomer. HRMS calculated for $C_{34}H_{30}N_4O_2$: 526.2369, found: 527.2423 (M+H).

Example 14: N-{6-ethyl-5-(naphthalen-1-yl)-7-[2-(naphthalen-1-yloxy)ethyl]-7H-pyrrolo[2,3-d]pyrimidin-4-yl}-D-phenylalanine, diastereoisomer 1 and Example 15: N-{6-ethyl-5-(naphthalen-1-yl)-7-[2-(naphthalen-1-yloxy)ethyl]-7H-pyrrolo[2,3-d]pyrimidin-4-yl}-D-phenylalanine, diastereoisomer 2

Step A: 5-bromo-4-chloro-6-ethyl-7-[2-(1-naphthyloxy)ethyl]pyrrolo[2,3-d]pyrimidine 94 mg 2-(1-naphthyloxy)ethanol (0.5 mmol), 131 mg PPh₃ (0.5 mmol) and 66 mg Preparation 1b (0.25 mmol) were dissolved in 2.5 mL dry THF under N₂ atmosphere and cooled to 0° C. Then 230 µL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-[2-(1-naphthyloxy)ethyl]pyrrolo[2,3-d]pyrimidine.

$^1$H NMR (400 MHz, DMSO-d₆) δ: 8.69 (s, 1H), 7.80 (dd, 2H), 7.51-7.31 (m, 4H), 6.94 (d, 1H), 4.90 (t, 2H), 4.52 (t, 2H), 3.08 (q, 2H), 1.26 (t, 3H)

MS: (M+H)⁺=430.0

Step B: (2R)-2-[[5-bromo-6-ethyl-7-[2-(1-naphthyloxy)ethyl]pyrrolo[2,3-d]pyrimidin-4-yl]amino]-3-phenyl-propanoic Acid Using General Procedure III and 5-bromo-4-chloro-6-ethyl-7-[2-(1-naphthyloxy) ethyl]pyrrolo[2,3-d]pyrimidine as the appropriate 4-chloro-pyrrolo[2,3-d]pyrimidine derivative and D-phenylalanine as the appropriate amino acid derivative (2R)-2-[[5-bromo-6-ethyl-7-[2-(1-naphthyloxy)ethyl]pyrrolo[2,3-d]pyrimidin-4-yl]amino]-3-phenyl-propanoic acid was obtained.

$^1$H NMR (400 MHz, DMSO-d₆) δ: 12.96 (br s, 1H), 8.24 (s, 1H), 7.88 (d, 1H), 7.82 (d, 1H), 7.52-7.32 (m, 4H), 7.29-7.15 (m, 5H), 6.94 (d, 1H), 6.38 (d, 1H), 4.94 (q, 1H), 4.72 (t, 2H), 4.45 (t, 2H), 3.28 (m, 1H), 3.18 (dd, 1H), 2.92 (q, 2H), 1.19 (t, 3H)

MS: (M+H)⁺=559.2

Step C: Examples 14 and 15

Using General Procedure IVa and (2R)-2-[[5-bromo-6-ethyl-7-[2-(1-naphthyloxy) ethyl]pyrrolo[2,3-d]pyrimidin-4-yl]amino]-3-phenyl-propanoic acid as the appropriate 5-bromo-pyrrolo[2,3-d]pyrimidine derivative and 1-naphthaleneboronic acid neopentyl glycol ester as the appropriate boronic acid derivative, Example 14 was obtained as the earlier eluting diastereoisomer. HRMS calculated for $C_{39}H_{34}N_4O_3$: 606.2631, found: 607.2711 (M+H). Example 15 was obtained as the later eluting diastereoisomer. HRMS calculated for $C_{39}H_{34}N_4O_3$: 606.2631, found: 607.2705 (M+H).

Example 16: N-[6-ethyl-5-(naphthalen-1-yl)-7-(2-phenylethyl)-7H-pyrrolo[2,3-d]pyrimidin-4-yl]-D-phenylalanine, diastereoisomer 1 and Example 17: N-[6-ethyl-5-(naphthalen-1-yl)-7-(2-phenylethyl)-7H-pyrrolo[2,3-d]pyrimidin-4-yl]-D-phenylalanine, diastereoisomer 2

Step A: 5-bromo-4-chloro-6-ethyl-7-phenethyl-pyrrolo[2,3-d]pyrimidine 3.1 mL 2-phenylethanol (25.9 mmol), 3.397 g PPh₃ (12.95 mmol) and 3.40 g Preparation 1b (12.95 mmol) were dissolved in 110 mL dry THF under N₂ atmosphere and cooled to 0° C. Then 11.87 mL DEAD (40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-phenethyl-pyrrolo[2,3-d]pyrimidine.

¹H NMR (400 MHz, DMSO-d₆) δ: 8.61 (s, 1H), 7.32-7.16 (m, 3H), 7.11 (m, 2H), 4.51 (t, 2H), 3.06 (t, 2H), 2.70 (q, 2H), 1.10 (t, 3H)
MS: (M+H)⁺=364.0

Step B: (2R)-2-[(5-bromo-6-ethyl-7-phenethyl-pyrrolo[2,3-d]pyrimidin-4-yl)amino]-3-phenyl-propanoic Acid Using General Procedure III and 5-bromo-4-chloro-6-ethyl-7-phenethyl-pyrrolo[2,3-d]pyrimidine as the appropriate 4-chloro-pyrrolo[2,3-d]pyrimidine derivative and D-phenylalanine as the appropriate amino acid derivative (2R)-2-[(5-bromo-6-ethyl-7-phenethyl-pyrrolo[2,3-d]pyrimidin-4-yl)amino]-3-phenyl-propanoic acid was obtained.
¹H NMR (400 MHz, DMSO-d₆) δ: 12.80 (br s, 1H), 8.20 (s, 1H), 7.34-7.17 (m, 8H), 7.13 (m, 2H), 6.45 (d, 1H), 4.91 (q, 1H), 4.33 (t, 2H), 3.31 (dd, 1H), 3.18 (dd, 1H), 3.00 (t, 2H), 2.55 (q, 2H), 1.04 (t, 3H)
MS: (M+H)⁺=493.2

Step C: Examples 16 and 17

Using General Procedure IVa and (2R)-2-[(5-bromo-6-ethyl-7-phenethyl-pyrrolo[2,3-d]pyrimidin-4-yl)amino]-3-phenyl-propanoic acid as the appropriate 5-bromo-pyrrolo[2,3-d]pyrimidine derivative and 1-naphthaleneboronic acid neopentyl glycol ester as the appropriate boronic acid derivative, Example 16 was obtained as the earlier eluting diastereoisomer. HRMS calculated for $C_{35}H_{32}N_4O_2$: 540.2525, found: 541.2592 (M+H). Example 17 was obtained as the later eluting diastereoisomer. HRMS calculated for $C_{35}H_{32}N_4O_2$: 540.2525, found: 541.2619 (M+H).

Example 18: N-[6-ethyl-5-(naphthalen-1-yl)-7-(3-phenylpropyl)-7H-pyrrolo[2,3-d]pyrimidin-4-yl]-D-phenylalanine, diastereoisomer 1 and Example 19: N-[6-ethyl-5-(naphthalen-1-yl)-7-(3-phenylpropyl)-7H-pyrrolo[2,3-d]pyrimidin-4-yl]-D-phenylalanine, diastereoisomer 2

Step A: 5-bromo-4-chloro-6-ethyl-7-(3-phenylpropyl)pyrrolo[2,3-d]pyrimidine 3.52 mL 3-phenyl-propanol (25.9 mmol), 3.397 g PPh₃ (12.95 mmol) and 3.4 g Preparation 1b (12.95 mmol) were dissolved in 110 mL dry THF under N₂ atmosphere and cooled to 0° C. Then 11.87 mL DEAD (40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-(3-phenylpropyl)pyrrolo[2,3-d]pyrimidine.
¹H NMR (400 MHz, DMSO-d₆) δ: 8.60 (s, 1H), 7.31-7.22 (m, 2H), 7.21-7.13 (m, 3H), 4.32 (t, 2H), 2.85 (q, 2H), 2.65 (t, 2H), 2.05 (m, 2H), 1.16 (t, 3H)
MS: (M+H)⁺=378.0

Step B: (2R)-2-[[5-bromo-6-ethyl-7-(3-phenylpropyl)pyrrolo[2,3-d]pyrimidin-4-yl]amino]-3-phenyl-propanoic Acid Using General Procedure III and 5-bromo-4-chloro-6-ethyl-7-(3-phenylpropyl)pyrrolo[2,3-d]pyrimidine as the appropriate 4-chloro-pyrrolo[2,3-d]pyrimidine derivative and D-phenylalanine as the appropriate amino acid derivative, (2R)-2-[[5-bromo-6-ethyl-7-(3-phenylpropyl)pyrrolo[2,3-d]pyrimidin-4-yl]amino]-3-phenyl-propanoic acid was obtained. ¹H NMR (400 MHz, DMSO-d₆) δ: 12.95 (br s, 1H), 8.15 (s, 1H), 7.33-7.12 (m, 10H), 6.35 (d, 1H), 4.94 (q, 1H), 4.16 (t, 2H), 3.28 (dd, 1H), 3.16 (dd, 1H), 2.68 (q, 2H), 2.61 (t, 2H), 1.97 (m, 2H), 1.09 (t, 3H)
MS: (M+H)⁺=507.2

Step C: Examples 18 and 19

Using General Procedure IVa and (2R)-2-[[5-bromo-6-ethyl-7-(3-phenylpropyl) pyrrolo[2,3-d] pyrimidin-4-yl] amino]-3-phenyl-propanoic acid as the appropriate 5-bromo-pyrrolo[2,3-d] pyrimidine derivative and 1-naphthaleneboronic acid neopentyl glycol ester as the appropriate boronic acid derivative, Example 18 was obtained as the earlier eluting diastereoisomer. HRMS calculated for $C_{36}H_{34}N_4O_2$: 554.2682, found: 555.2742 (M+H). Example 19 was obtained as the later eluting diastereoisomer. HRMS calculated for $C_{36}H_{34}N_4O_2$: 554.2682, found: 555.2756 (M+H).

Example 20: N-[(5R$_a$)-5-(3-chloro-2-methylphenyl)-6-ethyl-7-methyl-7H-pyrrolo[2,3-d]pyrimidin-4-yl]-D-phenylalanine and Example 21: N-[(5S$_a$)-5-(3-chloro-2-methylphenyl)-6-ethyl-7-methyl-7H-pyrrolo[2,3-d]pyrimidin-4-yl]-D-phenylalanine Step A: 5-bromo-4-chloro-6-ethyl-7-methyl-pyrrolo[2,3-d]pyrimidine 65 mg Preparation 1b (0.25 mmol) was dissolved in 1 mL dry THF, then 20.3 µL dry MeOH (0.5 mmol) and 0.5 mL cyanomethylenetributylphosphorane solution (0.5 mmol, IM in toluene) was added. The mixture was stirred at r.t. until no further conversion was observed. The volatiles were removed under reduced pressure. The residue was purified via flash chromatography using heptane and EtOAc as eluents to obtain 5-bromo-4-chloro-6-ethyl-7-methyl-pyrrolo[2,3-d]pyrimidine.
H NMR (400 MHz, CDCl₃) δ: 8.56 (s, 1H), 3.84, (s, 3H), 2.91 (q, 2H), 1.26 (t, 3H)
MS: (M+H)⁺=274.0

Step B: (2R)-2-[[5-bromo-6-ethyl-7-methyl-pyrrolo[2,3-d]pyrimidin-4-yl]amino]-3-phenyl-propanoic Acid Using General Procedure III and 5-bromo-4-chloro-6-ethyl-7-methyl-pyrrolo[2,3-d]pyrimidine as the appropriate 4-chloro-pyrrolo[2,3-d]pyrimidine derivative and D-phenylalanine as the appropriate amino acid derivative, (2R)-2-[[5-bromo-6-ethyl-7-methyl-pyrrolo[2,3-d] pyrimidin-4-yl] amino]-3-phenyl-propanoic acid was obtained.
¹H NMR (500 MHz, DMSO-d₆) δ: 13.05 (br s, 1H), 8.17 (s, 1H), 7.32-7.25 (m, 2H), 7.25-7.18 (m, 3H), 6.32 (d, 1H), 4.97 (m, 1H), 3.68, (s, 3H), 3.29 (dd, 1H), 3.18 (dd, 1H), 2.75 (q, 2H), 1.13 (t, 3H)
MS: (M+H)⁺=403.0

Step C: Examples 20 and 21

Using General Procedure IVa and (2R)-2-[[5-bromo-6-ethyl-7-methyl-pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 20 was obtained as the earlier eluting diastereoisomer. HRMS calculated for $C_{25}H_{25}ClN_4O_2$: 448.1666, found: 449.1753 (M+H). Example 21 was obtained as the later eluting diastereoisomer. HRMS calculated for $C_{25}H_{25}ClN_4O_2$: 448.1666, found: 449.1752 (M+H).

Example 22: N-[($5R_a$)-5-(3-chloro-2-methylphenyl)-7-(cyclopropylmethyl)-6-ethyl-7H-pyrrolo[2,3-d]pyrimidin-4-yl]-D-phenylalanine and Example 23: N-[($5S_a$)-5-(3-chloro-2-methylphenyl)-7-(cyclopropylmethyl)-6-ethyl-7H-pyrrolo[2,3-d]pyrimidin-4-yl]-D-phenylalanine Step A: 5-bromo-4-chloro-7-(cyclopropylmethyl)-6-ethyl-pyrrolo[2,3-d]pyrimidine 65 mg Preparation 1b (0.25 mmol) was dissolved in 1 mL dry THF, then 40 µL cyclopropanemethanol (0.5 mmol) and 0.5 mL cyanomethylenetributylphosphorane solution (0.5 mmol, IM in toluene) was added. The mixture was stirred at r.t. until no further conversion was observed. The volatiles were removed under reduced pressure. The residue was purified via flash chromatography using heptane and EtOAc as eluents to obtain 5-bromo-4-chloro-7-(cyclopropylmethyl)-6-ethyl-pyrrolo[2,3-d]pyrimidine.

$^1$H NMR (400 MHz, CDCl$_3$) δ: 8.54 (s, 1H), 4.18 (d, 2H), 2.94 (q, 2H), 1.29 (t, 3H), 1.24-1.14 (m, 1H), 0.60-0.51 (m, 2H), 0.51-0.43 (m, 2H)

MS: (M+H)$^+$=314.0

Step B: (2R)-2-[[5-bromo-7-(cyclopropylmethyl)-6-ethyl-pyrrolo[2,3-d]pyrimidin-4-yl]amino]-3-phenyl-propanoic Acid Using General Procedure III and 5-bromo-4-chloro-7-(cyclopropylmethyl)-6-ethyl-pyrrolo[2,3-d]pyrimidine as the appropriate 4-chloro-pyrrolo[2,3-d]pyrimidine derivative and D-phenylalanine as the appropriate amino acid derivative, (2R)-2-[[5-bromo-7-(cyclopropylmethyl)-6-ethyl-pyrrolo[2,3-d]pyrimidin-4-yl]amino]-3-phenyl-propanoic acid was obtained.

$^1$H NMR (500 MHz, DMSO-d$_6$) δ: 13.05 (br s, 1H), 8.15 (s, 1H), 7.32-7.26 (m, 2H), 7.26-7.20 (m, 3H), 6.34 (d, 1H), 4.94 (m, 1H), 4.05 (d, 2H) 3.29 (dd, 1H), 3.18 (dd, 1H), 2.78 (q, 2H), 1.28-1.20 (m, 1H), 1.16 (t, 3H), 0.47-0.42 (m, 2H), 0.42-0.37 (m, 2H)

MS: (M+H)$^+$=443.0

Step C: Examples 22 and 23

Using General Procedure IVa and (2R)-2-[[5-bromo-7-(cyclopropylmethyl)-6-ethyl-pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 22 was obtained as the earlier eluting diastereoisomer. HRMS calculated for $C_{28}H_{29}ClN_4O_2$: 488.1979, found: 489.2064 (M+H). Example 23 was obtained as the later eluting diastereoisomer. HRMS calculated for $C_{28}H_{29}ClN_4O_2$: 488.1979, found: 489.2048 (M+H).

Example 24: N-[($5R_a$)-5-(3-chloro-2-methylphenyl)-6-ethyl-7-(prop-2-en-1-yl)-7H-pyrrolo[2,3-d]pyrimidin-4-yl]-D-phenylalanine and Example 25: N-[($5S_a$)-5-(3-chloro-2-methylphenyl)-6-ethyl-7-(prop-2-en-1-yl)-7H-pyrrolo[2,3-d]pyrimidin-4-yl]-D-phenylalanine Step A: 7-allyl-5-bromo-4-chloro-6-ethyl-pyrrolo[2,3-d]pyrimidine 65 mg Preparation 1b (0.25 mmol) was dissolved in 1 mL dry THF, then 34 µL allyl-alcohol (0.5 mmol) and 0.5 mL cyanomethylenetributylphosphorane solution (0.5 mmol, IM in toluene) was added. The mixture was stirred at r.t. until no further conversion was observed. The volatiles were removed under reduced pressure. The residue was purified via flash chromatography using heptane and EtOAc as eluents to obtain 7-allyl-5-bromo-4-chloro-6-ethyl-pyrrolo[2,3-d]pyrimidine.

$^1$H NMR (400 MHz, CDCl$_3$) δ: 8.57 (s, 1H), 6.02-5.90 (m, 1H), 5.25-5.16 (m, 1H), 5.00-4.85 (m, 3H), 2.87 (q, 2H), 1.26 (t, 3H)

MS: (M+H)$^+$=300.0

Step B: (2R)-2-[[7-allyl-5-bromo-6-ethyl-pyrrolo[2,3-d]pyrimidin-4-yl]amino]-3-phenyl-propanoic Acid Using General Procedure III and 7-allyl-5-bromo-4-chloro-6-ethyl-pyrrolo[2,3-d]pyrimidine as the appropriate 4-chloro-pyrrolo[2,3-d]pyrimidine derivative and D-phenylalanine as the appropriate amino acid derivative, (2R)-2-[[7-allyl-5-bromo-6-ethyl-pyrrolo[2,3-d]pyrimidin-4-yl]amino]-3-phenyl-propanoic acid was obtained.

$^1$H NMR (500 MHz, DMSO-d$_6$) δ: 13.06 (br s, 1H), 8.16 (s, 1H), 7.34-7.26 (m, 2H), 7.26-7.19 (m, 3H), 6.35 (d, 1H), 6.01-5.89 (m, 1H), 5.10 (dd, 1H), 5.01-4.93 (m, 1H), 4.87-4.73 (m, 3H), 3.29 (dd, 1H), 3.18 (dd, 1H), 2.70 (q, 2H), 1.12 (t, 3H)

MS: (M+H)$^+$=429.0

Step C: Examples 24 and 25

Using General Procedure IVa and (2R)-2-[[7-allyl-5-bromo-6-ethyl-pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 24 was obtained as the earlier eluting diastereoisomer. HRMS calculated for $C_{27}H_{27}ClN_4O_2$: 474.1823, found: 475.1908. Example 25 was obtained as the later eluting diastereoisomer. HRMS calculated for $C_{27}H_{27}ClN_4O_2$: 474.1823, found: 475.1909.

Example 26: N-[7-(but-2-yn-1-yl)-($5R_a$)-5-(3-chloro-2-methylphenyl)-6-ethyl-7H-pyrrolo[2,3-d]pyrimidin-4-yl]-D-phenylalanine and Example 27: N-[7-(but-2-yn-1-yl)-($5S_a$)-5-(3-chloro-2-methylphenyl)-6-ethyl-7H-pyrrolo[2,3-d]pyrimidin-4-yl]-D-phenylalanine Step A: 5-bromo-7-but-2-ynyl-4-chloro-6-ethyl-pyrrolo[2,3-d]pyrimidine 37 µL 2-butyn-1-ol (0.5 mmol), 131 mg PPh$_3$ (0.5 mmol) and 66 mg Preparation 1b (0.25 mmol) were dissolved in 2.5 mL dry THF under N$_2$ atmosphere and cooled to 0° C. Then 230 µL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-7-but-2-ynyl-4-chloro-6-ethyl-pyrrolo[2,3-d] pyrimidine.

$^1$H NMR (400 MHz, CDCl$_3$) δ: 8.59 (s, 1H), 5.03 (q, 2H), 2.99 (q, 2H), 1.77 (t, 3H), 1.33 (t, 3H)

MS: (M+H)$^+$=312.0

Step B: (2R)-2-[(5-bromo-7-but-2-ynyl-6-ethyl-pyrrolo[2,3-d]pyrimidin-4-yl)amino]-3-phenyl-propanoic Acid Using General Procedure III and 5-bromo-7-but-2-ynyl-4-chloro-6-ethyl-pyrrolo[2,3-d]pyrimidine as the appropriate 4-chloro-pyrrolo[2,3-d]pyrimidine derivative and D-phenylalanine as the appropriate amino acid derivative (2R)-2-[(5-bromo-7-but-2-ynyl-6-ethyl-pyrrolo[2,3-d]pyrimidin-4-yl)amino]-3-phenyl-propanoic acid was obtained.

$^1$H NMR (500 MHz, DMSO-d$_6$) δ: 13.25 (br s, 1H), 8.19 (s, 1H), 7.30-7.24 (m, 2H), 7.24-7.16 (m, 3H), 6.45 (d, 1H), 5.02-4.96 (m, 2H), 4.93 (q, 1H), 3.30 (dd, 1H), 3.19 (dd, 1H), 2.80 (q, 2H), 1.74 (t, 3H), 1.19 (t, 3H)

MS: (M+H)$^+$=441.0

Step C: Examples 26 and 27

Using General Procedure IVa and (2R)-2-[(5-bromo-7-but-2-ynyl-6-ethyl-pyrrolo[2,3-d]pyrimidin-4-yl)amino]-3-phenyl-propanoic acid as the appropriate 5-bromo-pyrrolo[2,3-d]pyrimidine derivative and Preparation 3c as the appropriate boronic acid derivative, Example 26 was obtained as the earlier eluting diastereoisomer. HRMS calculated for C$_{28}$H$_{27}$ClN$_4$O$_2$: 486.1823, found: 487.1893 (M+H). Example 27 was obtained as the later eluting diastereoisomer. HRMS calculated for C$_{28}$H$_{27}$ClN$_4$O$_2$: 486.1823, found: 487.1893 (M+H).

Example 28: N-[(5R$_a$)-5-(3-chloro-2-methylphenyl)-6-ethyl-7-(2,2,2-trifluoroethyl)-7H-pyrrolo[2,3-d]pyrimidin-4-yl]-D-phenylalanine and Example 29: N-[(5S$_a$)-5-(3-chloro-2-methylphenyl)-6-ethyl-7-(2,2,2-trifluoroethyl)-7H-pyrrolo[2,3-d]pyrimidin-4-yl]-D-phenylalanine Step A: 5-bromo-4-chloro-6-ethyl-7-(2,2,2-trifluoroethyl)pyrrolo[2,3-d]pyrimidine 72 µL trifluoroethanol (1 mmol), 262 mg PPh$_3$ (1 mmol) and 130 mg Preparation 1b (0.5 mmol) were dissolved in 5 mL dry THF under N$_2$ atmosphere and cooled to 0° C. Then 460 µL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-(2,2,2-trifluoro ethyl) pyrrolo[2,3-d] pyrimidine.

$^1$H NMR (400 MHz, CDCl$_3$) δ: 8.62 (s, 1H), 4.90 (q, 2H), 2.94 (q, 2H), 1.28 (t, 3H)

MS: (M+H)$^+$=342.0

Step B: (2R)-2-[[5-bromo-6-ethyl-7-(2,2,2-trifluoroethyl)pyrrolo[2,3-d]pyrimidin-4-yl]amino]-3-phenyl-propanoic Acid Using General Procedure III and 5-bromo-4-chloro-6-ethyl-7-(2,2,2-trifluoroethyl)pyrrolo[2,3-d]pyrimidine as the appropriate 4-chloro-pyrrolo[2,3-d]pyrimidine derivative and D-phenylalanine as the appropriate amino acid derivative (2R)-2-[[5-bromo-6-ethyl-7-(2,2,2-trifluoroethyl)pyrrolo[2,3-d]pyrimidin-4-yl]amino]-3-phenyl-propanoic acid was obtained.

$^1$H NMR (500 MHz, DMSO-d$_6$) δ: 13.11 (br s, 1H), 8.23 (s, 1H), 7.33-7.26 (m, 2H), 7.26-7.19 (m, 3H), 6.44 (d, 1H), 5.12 (q, 2H), 5.00-4.93 (m, 1H), 3.30 (dd, 1H), 3.20 (dd, 1H), 2.78 (q, 2H), 1.14 (t, 3H)

MS: (M+H)$^+$=471.0

Step C: Examples 28 and 29

Using General Procedure IVa and (2R)-2-[[5-bromo-6-ethyl-7-(2,2,2-trifluoroethyl) pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 28 was obtained as the earlier eluting diastereoisomer. HRMS calculated for C$_{26}$H$_{24}$ClF$_3$N$_4$O$_2$: 516.1540, found: 517.1624 (M+H). Example 29 was obtained as the later eluting diastereoisomer. HRMS calculated for C$_{26}$H$_{24}$ClF$_3$N$_4$O$_2$: 516.1540, found: 517.1606 (M+H).

Example 30: N-[(5R$_a$)-5-(3-chloro-2-methylphenyl)-7-(2-cyclopentylethyl)-6-ethyl-7H-pyrrolo[2,3-d]pyrimidin-4-yl]-D-phenylalanine and Example 31: N-[(5S$_a$)-5-(3-chloro-2-methylphenyl)-7-(2-cyclopentylethyl)-6-ethyl-7H-pyrrolo[2,3-d]pyrimidin-4-yl]-D-phenylalanine Step A: 5-bromo-4-chloro-7-(2-cyclopentylethyl)-6-ethyl-pyrrolo[2,3-d]pyrimidine 124 µL 2-cyclopentylethanol (1 mmol), 262 mg PPh$_3$ (1 mmol) and 130 mg Preparation 1b (0.5 mmol) were dissolved in 5 mL dry THF under N$_2$ atmosphere and cooled to 0° C. Then 460 µL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-7-(2-cyclopentylethyl)-6-ethyl-pyrrolo[2,3-d]pyrimidine.

$^1$H NMR (400 MHz, CDCl$_3$) δ: 8.55 (s, 1H), 4.31-4.20 (m, 2H), 2.89 (q, 2H), 1.91-1.72 (m, 5H), 1.69-1.57 (m, 2H), 1.57-1.46 (m, 2H), 1.28 (t, 3H), 1.23-1.05 (m, 2H)

MS: (M+H)$^+$=356.0

Step B: (2R)-2-[[5-bromo-7-(2-cyclopentylethyl)-6-ethyl-pyrrolo[2,3-d]pyrimidin-4-yl]amino]-3-phenyl-propanoic Acid Using General Procedure III and 5-bromo-4-chloro-7-(2-cyclopentylethyl)-6-ethyl-pyrrolo[2,3-d]pyrimidine as the appropriate 4-chloro-pyrrolo[2,3-d]pyrimidine derivative and D-phenylalanine as the appropriate amino acid derivative (2R)-2-[[5-bromo-7-(2-cyclopentylethyl)-6-ethyl-pyrrolo[2,3-d]pyrimidin-4-yl]amino]-3-phenyl-propanoic acid was obtained.

¹H NMR (500 MHz, DMSO-d₆) δ: 13.04 (br s, 1H), 8.17 (s, 1H), 7.32-7.26 (m, 2H), 7.25-7.19 (m, 3H), 6.32 (d, 1H), 5.00-4.92 (m, 1H), 4.17-4.09 (m, 2H), 3.29 (dd, 1H), 3.18 (dd, 1H), 2.74 (q, 2H), 1.79-1.70 (m, 3H), 1.70-1.62 (m, 2H), 1.60-1.50 (m, 2H), 1.50-1.42 (m, 2H), 1.15 (t, 3H), 1.12-1.01 (m, 2H)
MS: (M+H)⁺=485.2

Step C: Examples 30 and 31

Using General Procedure IVa and (2R)-2-[[5-bromo-7-(2-cyclopentylethyl)-6-ethyl-pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 30 was obtained as the earlier eluting diastereoisomer. HRMS calculated for C₃₁H₃₅ClN₄O₂: 530.2449, found: 531.2528 (M+H). Example 31 was obtained as the later eluting diastereoisomer. HRMS calculated for C₃₁H₃₅ClN₄O₂: 530.2449, found: 531.2547 (M+H).

Example 32: N-[(5R$_a$)-5-(3-chloro-2-methylphenyl)-6-ethyl-7-(naphthalen-1-ylmethyl)-7H-pyrrolo[2,3-d]pyrimidin-4-yl]-D-phenylalanine and Example 33: N-[(5S$_a$)-5-(3-chloro-2-methylphenyl)-6-ethyl-7-(naphthalen-1-ylmethyl)-7H-pyrrolo[2,3-d]pyrimidin-4-yl]-D-phenylalanine Step A: 5-bromo-4-chloro-6-ethyl-7-(1-naphthylmethyl)pyrrolo[2,3-d]pyrimidine 158 mg 1-naphthalenemethanol (1 mmol), 262 mg PPh₃ (1 mmol) and 130 mg Preparation 1b (0.5 mmol) were dissolved in 5 mL dry THF under N₂ atmosphere and cooled to 0° C. Then 460 μL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-(1-naphthylmethyl)pyrrolo[2,3-d]pyrimidine.
¹H NMR (400 MHz, CDCl₃) δ: 8.58 (s, 1H), 8.09 (d, 1H), 7.95-7.89 (m, 1H), 7.79 (d, 1H), 7.66-7.54 (m, 2H), 7.25 (t, 1H), 6.45 (dd, 1H), 6.03 (s, 2H), 2.76 (q, 2H), 1.08 (t, 3H)
MS: (M+H)⁺=400.0

Step B: (2R)-2-[[5-bromo-6-ethyl-7-(1-naphthylmethyl)pyrrolo[2,3-d]pyrimidin-4-yl]amino]-3-phenyl-propanoic Acid Using General Procedure III and 5-bromo-4-chloro-6-ethyl-7-(1-naphthylmethyl)pyrrolo[2,3-d]pyrimidine as the appropriate 4-chloro-pyrrolo[2,3-d]pyrimidine derivative and D-phenylalanine as the appropriate amino acid derivative (2R)-2-[[5-bromo-6-ethyl-7-(1-naphthylmethyl)pyrrolo[2,3-d]pyrimidin-4-yl]amino]-3-phenyl-propanoic acid was obtained.
¹H NMR (500 MHz, DMSO-d₆) δ: 13.14 (br s, 1H), 8.27 (d, 1H), 8.15 (s, 1H), 7.98 (d, 1H), 7.83 (d, 1H), 7.66-7.56 (m, 2H), 7.37-7.20 (m, 6H), 6.48 (d, 1H), 6.40 (d, 1H), 5.94 (s, 2H), 4.99 (q, 1H), 3.33 (dd, 1H), 3.22 (dd, 1H), 2.62 (q, 2H), 0.89 (t, 3H)
MS: (M+H)⁺=529.0

Step C: Examples 32 and 33

Using General Procedure IVa and (2R)-2-[[5-bromo-6-ethyl-7-(1-naphthylmethyl)pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 32 was obtained as the earlier eluting diastereoisomer. HRMS calculated for C₃₅H₃₁ClN₄O₂: 574.2136, found: 575.2211 (M+H). Example 33 was obtained as the later eluting diastereoisomer. HRMS calculated for C₃₅H₃₁ClN₄O₂: 574.2136, found: 575.2203 (M+H).

Example 34: N-[(5R$_a$)-5-(3-chloro-2-methylphenyl)-6-ethyl-7-(4-methoxybenzyl)-7H-pyrrolo[2,3-d]pyrimidin-4-yl]-D-phenylalanine and Example 35: N-[(5S$_a$)-5-(3-chloro-2-methylphenyl)-6-ethyl-7-(4-methoxybenzyl)-7H-pyrrolo[2,3-d]pyrimidin-4-yl]-D-phenylalanine Step A: 5-bromo-4-chloro-6-ethyl-7-[(4-methoxyphenyl)methyl]pyrrolo[2,3-d]pyrimidine 138 mg 4-methoxybenzyl alcohol (1 mmol), 262 mg PPh₃ (1 mmol) and 130 mg Preparation 1b (0.5 mmol) were dissolved in 5 mL dry THF under N₂ atmosphere and cooled to 0° C. Then 460 μL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-[(4-methoxyphenyl)methyl]pyrrolo[2,3-d]pyrimidine. MS: (M+H)⁺=380.0

Step B: (2R)-2-[[5-bromo-6-ethyl-7-[(4-methoxyphenyl)methyl]pyrrolo[2,3-d]pyrimidin-4-yl]amino]-3-phenyl-propanoic Acid Using General Procedure III and 5-bromo-4-chloro-6-ethyl-7-[(4-methoxyphenyl) methyl]pyrrolo[2,3-d]pyrimidine as the appropriate 4-chloro-pyrrolo[2,3-d]pyrimidine derivative and D-phenylalanine as the appropriate amino acid derivative, (2R)-2-[[5-bromo-6-ethyl-7-[(4-methoxyphenyl)methyl]pyrrolo[2,3-d]pyrimidin-4-yl]amino]-3-phenyl-propanoic acid was obtained.
¹H NMR (500 MHz, DMSO-d₆) δ: 13.07 (br s, 1H), 8.20 (s, 1H), 7.33-7.17 (m, 5H), 7.03 (d, 2H), 6.85 (d, 2H), 6.37 (d, 1H), 5.37 (s, 2H), 4.99 (q, 1H), 3.69 (s, 3H), 3.31 (dd, 1H), 3.20 (dd, 1H), 2.65 (q, 2H), 0.91 (t, 3H)
MS: (M+H)⁺=508.8

Step C: Examples 34 and 35

Using General Procedure IVa and (2R)-2-[[5-bromo-6-ethyl-7-[(4-methoxyphenyl) methyl]pyrrolo[2,3-d]pyrimidin-4-yl]amino]-3-phenyl-propanoic acid as the appropriate 5-bromo-pyrrolo[2,3-d]pyrimidine derivative and Preparation 3c as the appropriate boronic acid derivative, Example 34 was obtained as the earlier eluting diastereoisomer. HRMS calculated for C₃₂H₃₁ClN₄O₃: 554.2085, found: 555.2176 (M+H). Example 35 was obtained as the later eluting diastereoisomer. HRMS calculated for C₃₂H₃₁ClN₄O₃: 554.2085, found: 555.2140 (M+H).

Example 36: N-[7-benzyl-(5R$_a$)-5-(3-chloro-2-methylphenyl)-6-ethyl-7H-pyrrolo[2,3-d]pyrimidin-4-yl]-D-phenylalanine and Example 37: N-[7-benzyl-(5S$_a$)-5-(3-chloro-2-methylphenyl)-6-ethyl-7H-pyrrolo[2,3-d]pyrimidin-4-yl]-D-phenylalanine Using General Procedure IVa and Preparation 6 as the appropriate 5-bromo-pyrrolo[2,3-d]pyrimidine derivative and Preparation 3c as the appropriate boronic acid derivative, Example 36 was obtained as the earlier eluting diastereoisomer. HRMS calculated for $C_{31}H_{29}ClN_4O_2$: 524.1979, found: 525.2048 (M+H). Example 37 was obtained as the later eluting diastereoisomer. HRMS calculated for $C_{31}H_{29}ClN_4O_2$: 524.1979, found: 525.2064 (M+H).

Example 38: N-[(5R$_a$)-5-(3-chloro-2-methylphenyl)-6-ethyl-7-(propan-2-yl)-7H-pyrrolo[2,3-d]pyrimidin-4-yl]-D-phenylalanine and Example 39: N-[(5S$_a$)-5-(3-chloro-2-methylphenyl)-6-ethyl-7-(propan-2-yl)-7H-pyrrolo[2,3-d]pyrimidin-4-yl]-D-phenylalanine Step A: 5-bromo-4-chloro-6-ethyl-7-isopropyl-pyrrolo[2,3-d]pyrimidine 76 µL 2-propanol (1 mmol), 262 mg PPh$_3$ (1 mmol) and 130 mg Preparation 1b (0.5 mmol) were dissolved in 5 mL dry THF under N$_2$ atmosphere and cooled to 0° C.

Then 460 µL DEAD (0.5 mmol, 40% in toluene) was added dropwise. The mixture was stirred at 40° C. until no further conversion was observed. Then the volatiles were removed under reduced pressure and the residue was purified via flash chromatography using heptane and EtOAc as eluents to obtain 5-bromo-4-chloro-6-ethyl-7-isopropyl-pyrrolo[2,3-d]pyrimidine.
$^1$H NMR (400 MHz, CDCl$_3$) δ: 8.53 (s, 1H), 4.71 (sp, 1H), 2.92 (q, 2H), 1.72 (d, 6H), 1.25 (t, 3H)
MS: (M+H)$^+$=302.0

Step B: (2R)-2-[(5-bromo-6-ethyl-7-isopropyl-pyrrolo[2,3-d]pyrimidin-4-yl)amino]-3-phenyl-propanoic Acid Using General Procedure III and 5-bromo-4-chloro-6-ethyl-7-isopropyl-pyrrolo[2,3-d]pyrimidine as the appropriate 4-chloro-pyrrolo[2,3-d]pyrimidine derivative and D-phenylalanine as the appropriate amino acid derivative (2R)-2-[(5-bromo-6-ethyl-7-isopropyl-pyrrolo[2,3-d]pyrimidin-4-yl)amino]-3-phenyl-propanoic acid was obtained.
$^1$H NMR (500 MHz, DMSO-d$_6$) δ: 13.04 (br s, 1H), 8.14 (s, 1H), 7.35-7.17 (m, 5H), 6.33 (d, 1H), 4.95 (q, 1H), 4.64 (sp, 1H), 3.28 (dd, 1H), 3.17 (dd, 1H), 2.76 (q, 2H), 1.59 (d, 6H), 1.11 (t, 3H)
MS: (M+H)$^+$=431.2

Step C: Examples 38 and 39

Using General Procedure IVa and (2R)-2-[(5-bromo-6-ethyl-7-isopropyl-pyrrolo[2,3-d]pyrimidin-4-yl)amino]-3-phenyl-propanoic acid as the appropriate 5-bromo-pyrrolo[2,3-d]pyrimidine derivative and Preparation 3c as the appropriate boronic acid derivative, Example 38 was obtained as the earlier eluting diastereoisomer. HRMS calculated for $C_{27}H_{29}ClN_4O_2$: 476.1979, found: 477.2057 (M+H). Example 39 was obtained as the later eluting diastereoisomer. HRMS calculated for $C_{27}H_{29}ClN_4O_2$: 476.1979, found: 477.2063 (M+H).

Example 40: (2R)-2-[(7-benzyl-(5S$_a$)-5-{3-chloro-2-methyl-4-[2-(4-methylpiperazin-1-yl)ethoxy]phenyl}-6-ethyl-7H-pyrrolo[2,3-d]pyrimidin-4-yl)oxy]-3-phenylpropanoic Acid Step A: 7-benzyl-5-bromo-4-chloro-6-ethyl-pyrrolo[2,3-d]pyrimidine 255 mg NaH (6.38 mmol) and 50 mL dry THF were charged into a 50 mL Schlenk tube under N$_2$ atmosphere and the slurry was cooled to 0° C. Then 1.792 g Preparation 1b (5.8 mmol) was added. After stirring the mixture for 30 minutes at 0° C., 773 µL benzyl bromide (6.38 mmol) was added and the mixture was allowed to warm up to r.t., and stirred until no further conversion was observed. The mixture was then diluted with saturated aqueous NH$_4$Cl solution, and extracted with DCM. The combined organic layers were washed with brine, dried over MgSO$_4$, filtered and the filtrate was concentrated under reduced pressure. The crude product was purified via flash chromatography using heptane and EtOAc as eluents to obtain 7-benzyl-5-bromo-4-chloro-6-ethyl-pyrrolo[2,3-d]pyrimidine. $^1$H NMR (400 MHz, CDCl$_3$) δ: 8.58 (s, 1H), 7.35-7.20 (m, 3H), 7.10-6.96 (m, 2H), 5.52 (s, 2H), 2.78 (q, 2H), 1.05 (t, 3H)

Step B: Methyl (2R)-2-(7-benzyl-5-bromo-6-ethyl-pyrrolo[2,3-d]pyrimidin-4-yl)oxy-3-phenyl-propanoate 1.639 g 7-benzyl-5-bromo-4-chloro-6-ethyl-pyrrolo[2,3-d]pyrimidine (4.67 mmol) was dissolved in 47 mL dry DMSO, then 2.948 g methyl (2R)-2-hydroxy-3-phenyl-propanoate (16.4 mmol) and 7.234 g Cs$_2$CO$_3$ (22.2 mmol) were added and the mixture was stirred at 100° C. under N$_2$ atmosphere until no further conversion was observed. Then it was diluted with water and brine, extracted with DCM. The organic layer was dried over Na$_2$SO$_4$, filtered and the filtrate was concentrated under reduced pressure. The crude product was purified via flash chromatography using heptane and $^i$Pr$_2$O as eluents to obtain methyl (2R)-2-(7-benzyl-5-bromo-6-ethyl-pyrrolo[2,3-d]pyrimidin-4-yl)oxy-3-phenyl-propanoate.
$^1$H NMR (400 MHz, CDCl$_3$) δ: 8.29 (s, 1H), 7.47 (d, 2H), 7.36-7.19 (m, 6H), 7.06-6.96 (m, 2H), 5.60 (dd, 1H), 5.47 (s, 2H), 3.73 (s, 3H), 3.41-3.28 (m, 2H), 2.72 (q, 2H), 1.03 (t, 3H)
MS: (M+H)$^+$=494.2

Step C: Methyl (2R)-2-[7-benzyl-(5S$_a$)-5-[3-chloro-2-methyl-4-hydroxyphenyl]-6-ethyl-pyrrolo[2,3-d]pyrimidin-4-yl]oxy-3-phenyl-propanoate A mixture of 1.20 g methyl (2R)-2-(7-benzyl-5-bromo-6-ethyl-pyrrolo[2,3-d]pyrimidin-4-yl)oxy-3-phenyl-propanoate (2.43 mmol), 1.98 g Preparation 3a (7.21 mmol), 110 mg Pd(OAc)$_2$ (0.49 mmol), 350 mg butyl-diadamantylphosphine (0.98 mmol), and 7.35 mL 1M aqueous TBAOH in 18 mL DME was heated under MW irradiation at 100° C. until no further conversion was observed. The reaction mixture was filtered through Celite. Water was added to the filtrate, it was acidified to pH=4 and extracted with MTBE. The combined organic phases were dried over Na$_2$SO$_4$, filtered and the filtrate was concentrated under reduced pressure.

The residue was heated in a mixture of 10 mL MeOH and 40 µL cc. H$_2$SO$_4$ until no further conversion was observed. The volatiles were removed under reduced pressure, the residue was diluted with water, the pH was set to 5, and it was extracted with DCM. The combined organic layers were dried over Na$_2$SO$_4$, filtered and the filtrate was concentrated under reduced pressure. The crude product was purified via flash chromatography using heptane and EtOAc as eluents to obtain methyl (2R)-2-[7-benzyl-(5S$_a$)-5-[3-chloro-2-methyl-4-hydroxphenyl]-6-ethyl-pyrrolo[2,3-d]pyrimidin-4-yl]oxy-3-phenyl-propanoate as the later eluting diastereoisomer. $^1$H NMR (500 MHz, DMSO-d$_6$) δ: 10.14 (s, 1H), 8.27 (s, 1H), 7.34-7.27 (m, 2H), 7.27-7.22 (m, 1H), 7.17-7.07 (m, 4H), 7.05 (d, 2H), 6.98 (dd, 1H), 6.64 (d, 2H), 5.60

(d, 1H), 5.51 (d, 1H), 5.43 (dd, 1H), 3.56 (s, 3H), 3.00 (dd, 1H), 2.85 (dd, 1H), 2.60-2.51 (m, 1H), 2.48-2.38 (m, 1H), 2.04 (s, 3H), 0.84 (t, 3H)

Step D: Example 40

139 mg methyl (2R)-2-[7-benzyl-(5S$_a$)-5-[3-chloro-2-methyl-4-hydroxyphenyl]-6-ethyl-pyrrolo[2,3-d]pyrimidin-4-yl]oxy-3-phenyl-propanoate (0.25 mmol), 72 mg 1-(2-hydroxyethyl)-4-methylpiperazine (0.50 mmol) and 166 mg resin bound PPh$_3$ (0.5 mmol) were dissolved in 3 mL dry toluene under N$_2$ atmosphere, then 115 mg DTAD (0.5 mmol) was added. The mixture was stirred at 50° C. until no further conversion was observed. The mixture was then diluted with DCM, filtered and the filtrate concentrated under reduced pressure, and purified via flash chromatography using heptane, EtOAc and MeOH as eluents. The obtained intermediate was dissolved in 10 mL MeOH, then 500 mg LiOH×H$_2$O was added, and the mixture was stirred at 50° C. until no further conversion was observed. The mixture was diluted with brine, neutralized with IM aqueous HCl solution and extracted with DCM. The organic layer was dried over Na$_2$SO$_4$, filtered and the filtrate was concentrated under reduced pressure. The crude product was purified via preparative reversed phase chromatography using 40 mM aqueous NH$_4$OAc solution (pH=4, adjusted with AcOH) and MeCN as eluents to obtain Example 40. HRMS calculated for C$_{38}$H$_{42}$ClN$_5$O$_4$: 667.2925, found: 668.2992 (M+H).

Example 41: N-[6-bromo-7-(but-3-en-1-yl)-(5R$_a$)-5-(3-chloro-2-methylphenyl)-7H-pyrrolo[2,3-d]pyrimidin-4-yl]-D-phenylalanine and Example 42: N-[6-bromo-7-(but-3-en-1-yl)-(5S$_a$)-5-(3-chloro-2-methylphenyl)-7H-pyrrolo[2,3-d]pyrimidin-4-yl]-D-phenylalanine Step A: 7-but-3-enyl-4-chloro-5-iodo-pyrrolo[2,3-d]pyrimidine 5.0 g 4-chloro-5-iodo-7H-pyrrolo[2,3-d]pyrimidine (17 mmol), 2.842 g K$_2$CO$_3$ (20.57 mmol), 2.15 mL 4-bromo-1-butene (20.57 mmol) and 26 mL dry DMF were stirred at r.t. under N$_2$ atmosphere until no further conversion was observed. Then the mixture was poured into water and extracted with EtOAc. The combined organic layers were washed with water, dried over MgSO$_4$, filtered and the filtrate was concentrated under reduced pressure. The crude product was purified via flash chromatography using heptane and EtOAc to obtain 7-but-3-enyl-4-chloro-5-iodo-pyrrolo[2,3-d]pyrimidine.
$^1$H NMR (400 MHz, CDCl$_3$) δ: 8.62 (s, 1H), 7.38 (s, 1H), 5.82-5.69 (m, 1H), 5.08 (s, 1H), 5.04 (dd, 1H), 4.33 (t, 2H), 2.60 (q, 2H)
MS: (M+H)$^+$=334.0

Step B: (2R)-2-[(7-but-3-enyl-5-iodo-pyrrolo[2,3-d]pyrimidin-4-yl)amino]-3-phenyl-propanoic Acid Using General Procedure III and 7-but-3-enyl-4-chloro-5-iodo-pyrrolo[2,3-d]pyrimidine as the appropriate 4-chloro-pyrrolo[2,3-d]pyrimidine derivative and D-phenylalanine as the appropriate amino acid derivative, (2R)-2-[(7-but-3-enyl-5-iodo-pyrrolo[2,3-d]pyrimidin-4-yl)amino]-3-phenyl-propanoic acid was obtained. $^1$H NMR (400 MHz, CDCl$_3$) δ: 8.32 (s, 1H), 7.38 (s, 1H), 7.35-7.28 (m, 3H), 7.28-7.22 (m, 2H), 7.02 (s, 1H), 6.28 (d, 1H), 5.80-5.67 (m, 1H), 5.09-5.04 (m, 1H), 5.04-5.00 (s, 1H), 4.94-4.85 (m, 1H), 4.22 (t, 2H), 3.51 (dd, 1H), 3.30 (dd, 1H), 2.54 (q, 2H)

Step C: (2R)-2-[[7-but-3-enyl-5-(3-chloro-2-methyl-phenyl)pyrrolo[2,3-d]pyrimidin-4-yl]amino]-3-phenyl-propanoic Acid Using General Procedure IVb and (2R)-2-[(7-but-3-enyl-5-iodo-pyrrolo[2,3-d]pyrimidin-4-yl)amino]-3-phenyl-propanoic acid as the appropriate 5-iodo-pyrrolo[2,3-d]pyrimidine derivative and Preparation 3c as the appropriate boronic acid derivative, (2R)-2-[[7-but-3-enyl-5-(3-chloro-2-methyl-phenyl)pyrrolo[2,3-d]pyrimidin-4-yl]amino]-3-phenyl-propanoic acid was obtained. $^1$H NMR (500 MHz, DMSO-d$_6$) δ: 12.86 (br s, 1H), 8.24 (s, 1H), 7.55-7.43 (m, 1H), 7.33-6.95 (m, 6H), 6.89-6.80 (m, 2H), 5.84-5.40 (m, 1H), 5.08-4.93 (m, 3H), 4.84 (br s, 1H), 4.37-4.15 (m, 2H), 3.16 (d, 1H), 2.85 (dd, 1H), 2.56 (q, 2H), 2.22-2.04 (s, 3H).

Step D: Examples 41 and 42

512 mg (2R)-2-[[7-but-3-enyl-5-(3-chloro-2-methyl-phenyl)pyrrolo[2,3-d]pyrimidin-4-yl]amino]-3-phenyl-propanoic acid (1 mmol) was dissolved in 4.5 mL dry DMF and 187 mg NBS (1 mmol) was added. The mixture was stirred at r.t. until no further conversion was observed. The mixture was then poured into water, extracted with EtOAc. The combined organic layers were washed with brine, dried over Na$_2$SO$_4$, filtered and the filtrate was concentrated under reduced pressure. The crude product was purified via preparative reversed phase chromatography using 0.1% aqueous TFA solution and MeCN as eluents to obtain Example 41 as the earlier eluting diastereoisomer. HRMS calculated for C$_{26}$H$_{24}$BrClN$_4$O$_2$: 538.0771, found: 541.0831 (M+H). Example 42 was obtained as the later eluting diastereoisomer. HRMS calculated for C$_{26}$H$_{24}$BrClN$_4$O$_2$: 538.0771, found: 541.0835 (M+H).

Example 43: N-[6-bromo-(5R$_a$)-5-(3-chloro-2-methylphenyl)-7-(prop-2-en-1-yl)-7H-pyrrolo[2,3-d]pyrimidin-4-yl]-D-phenylalanine and Example 44: N-[6-bromo-(5S$_a$)-5-(3-chloro-2-methylphenyl)-7-(prop-2-en-1-yl)-7H-pyrrolo[2,3-d]pyrimidin-4-yl]-D-phenylalanine Step A: 7-allyl-4-chloro-5-iodo-pyrrolo[2,3-d]pyrimidine 176.5 mg 4-chloro-5-iodo-7H-pyrrolo[2,3-d]pyrimidine (0.6 mmol), 100.7 mg K$_2$CO$_3$ (0.73 mmol), 63 µL allyl bromide (0.73 mmol) and 1 mL dry DMF were stirred at r.t. under N$_2$ atmosphere until no further conversion was observed. Then the mixture was poured into water and extracted with EtOAc. The combined organic layers were washed with water, dried over MgSO$_4$, filtered and the filtrate was concentrated under reduced pressure. The crude product was purified via flash chromatography using heptane and EtOAc to obtain 7-allyl-4-chloro-5-iodo-pyrrolo[2,3-d]pyrimidine. MS: (M+H)$^+$=320.0

Step B: (2R)-2-[(7-allyl-5-iodo-pyrrolo[2,3-d]pyrimidin-4-yl)amino]-3-phenyl-propanoic Acid Using General Procedure III and 7-allyl-4-chloro-5-iodo-pyrrolo[2,3-d]pyrimidine as the appropriate 4-chloro-pyrrolo[2,3-d]pyrimidine derivative and D-phenylalanine as the appropriate amino acid derivative, (2R)-2-[(7-allyl-5-iodo-pyrrolo[2,3-d]pyrimidin-4-yl) amino]-3-phenyl-propanoic acid was obtained.

$^1$H NMR (400 MHz, DMSO-d$_6$) δ: 13.09 (br s, 1H), 8.20 (s, 1H), 7.43 (s, 1H), 7.34-7.18 (m, 5H), 6.52 (bd, 1H), 6.05-5.90 (m, 1H), 5.15 (dd, 1H), 5.07-4.94 (m, 2H), 4.74 (d, 2H), 3.38 (dd, 1H), 3.15 (dd, 1H)

MS: (M+H)$^+$=449.0

Step C: (2R)-2-[[7-allyl-5-(3-chloro-2-methyl-phenyl)pyrrolo[2,3-d]pyrimidin-4-yl]amino]-3-phenyl-propanoic Acid Using General Procedure IVb and (2R)-2-[(7-allyl-5-iodo-pyrrolo[2,3-d]pyrimidin-4-yl) amino]-3-phenyl-propanoic acid as the appropriate 5-iodo-pyrrolo[2,3-d]pyrimidine derivative and Preparation 3c as the appropriate boronic acid derivative, (2R)-2-[[7-allyl-5-(3-chloro-2-methyl-phenyl)pyrrolo[2,3-d]pyrimidin-4-yl]amino]-3-phenyl-propanoic acid was obtained.

$^1$H NMR (400 MHz, DMSO-d$_6$) δ: 12.89 (br s, 1H), 8.23 (s, 1H), 7.59-7.42 (br, 1H), 7.31-7.10 (m, 6H), 6.91-6.81 (br, 2H), 6.12-5.98 (m, 1H), 5.16 (dd, 1H), 5.09-4.96 (m, 2H), 4.90-4.76 (br, 3H), 3.17 (dd, 1H), 2.86 (dd, 1H), 2.23-2.04 (br s, 3H)

MS: (M+H)$^+$=447.0

Step D: Examples 43 and 44

447 mg (2R)-2-[[7-allyl-5-(3-chloro-2-methyl-phenyl)pyrrolo[2,3-d]pyrimidin-4-yl]amino]-3-phenyl-propanoic acid (1 mmol) was dissolved in 4.5 mL dry DMF and 187 mg NBS (1 mmol) was added. The mixture was stirred at r.t. until no further conversion was observed. The mixture was then poured into water, extracted with EtOAc. The combined organic layers were washed with brine, dried over Na$_2$SO$_4$, filtered and the filtrate was concentrated under reduced pressure. The crude product was purified via preparative reversed phase chromatography using 0.1% aqueous TFA solution and MeCN as eluents to obtain Example 43 as the earlier eluting diastereoisomer. HRMS calculated for C$_{25}$H$_{22}$BrClN$_4$O$_2$: 524.0615, found: 525.0675 (M+H). Example 44 was obtained as the later eluting diastereoisomer. HRMS calculated for C$_{25}$H$_{22}$BrClN$_4$O$_2$: 524.0615, found: 525.0674 (M+H).

Example 45: (2R)-2-[(7-benzyl-5-{3-chloro-2-methyl-4-[2-(4-methylpiperazin-1-yl) ethoxy]phenyl}-7H-pyrrolo[2,3-d]pyrimidin-4-yl)oxy]-3-phenylpropanoic Acid

Step A: 7-benzyl-4-chloro-5-iodo-pyrrolo[2,3-d]pyrimidine 1.68 g 4-chloro-5-iodo-7H-pyrrolo[2,3-d]pyrimidine (6 mmol), 1.24 mL benzyl alcohol (12 mmol), 3.144 g PPh$_3$ (12 mmol) and 60 mL dry THF were cooled to 0° C. under N$_2$ atmosphere, then 5.5 mL DEAD solution (12 mmol, 40% in toluene) was added and the mixture was stirred at 40° C. until no further conversion was observed. Then the mixture was poured into water and extracted with Et$_2$O. The combined organic layers were washed with water, dried over MgSO$_4$, filtered and the filtrate was concentrated under reduced pressure. The crude product was purified via flash chromatography using heptane and EtOAc to obtain 7-benzyl-4-chloro-5-iodo-pyrrolo[2,3-d]pyrimidine.

$^1$H NMR (500 MHz, DMSO-d$_6$) δ: 8.67 (s, 1H), 8.12 (s, 1H), 7.32 (t, 2H), 7.28 (t, 1H), 7.28 (d, 2H), 5.47 (s, 2H)

MS (M+H): 369.9

Step B: Methyl (2R)-2-(7-benzyl-5-iodo-pyrrolo[2,3-d]pyrimidin-4-yl)oxy-3-phenyl-propanoate 1 eq. 7-benzyl-4-chloro-5-iodo-pyrrolo[2,3-d]pyrimidine, 3 eq. methyl (2R)-2-hydroxy-3-phenyl-propanoate, 3 eq. Cs$_2$CO$_3$ and dry DMSO (6 mL/mmol) were stirred at 100° C. until no further conversion was observed. The mixture was acidified with IM aqueous HCl solution, and extracted with DCM. The organic layer was dried over Na$_2$SO$_4$, filtered and the filtrate was concentrated under reduced pressure. The crude product was purified via flash chromatography using heptane and EtOAc as eluents to give methyl (2R)-2-(7-benzyl-5-iodo-pyrrolo[2,3-d]pyrimidin-4-yl)oxy-3-phenyl-propanoate. MS (M+H): 514.1

Step C: Example 45

Using General Procedure IVb and methyl (2R)-2-(7-benzyl-5-iodo-pyrrolo[2,3-d]pyrimidin-4-yl)oxy-3-phenyl-propanoate as the appropriate 5-iodo-pyrrolo[2,3-d]pyrimidine derivative and Preparation 3b as the appropriate boronic acid derivative, methyl (2R)-2-[7-benzyl-5-[3-chloro-2-methyl-4-[2-(4-methylpiperazin-1-yl)ethoxy]phenyl]pyrrolo[2,3-d]pyrimidin-4-yl]oxy-3-phenyl-propanoate was obtained. It was dissolved in dioxane:water 1:1 (20 mL/mmol) and 10 eq. LiOH×H$_2$O was added. The mixture was stirred at r.t. until no further conversion was observed. Then it was diluted with brine, neutralized with 2M aqueous HCl solution, extracted with DCM. The combined organic phases were dried over Na$_2$SO$_4$, filtered and the filtrate was concentrated under reduced pressure. The crude product was purified via preparative reversed phase chromatography using 0.1% aqueous TFA solution and MeCN as eluents to obtain Example 45. HRMS calculated for C$_{36}$H$_{38}$ClN$_5$O$_4$: 639.2612, found: 640.2654 (M+H).

Example 46: N-[5-(3-chloro-2-methylphenyl)-7,8-dihydro-6H-pyrimido[5,4-b]pyrrolizin-4-yl]-D-phenylalanine 210 mg 1:1 mixture of Examples 43 and 44 (mixture of the two diastereoisomers, 0.4 mmol) was dissolved in 3 mL MeOH and 70 μL cc. H$_2$SO$_4$ (1.2 mmol) was added. The mixture was stirred at r.t. until no further conversion was observed. The mixture was poured into icy water, neutralized with saturated aqueous NaHCO$_3$ solution and extracted with EtOAc. The combined organic phases were washed with brine, dried over MgSO$_4$, filtered and the filtrate was concentrated under reduced pressure. Then it was dissolved in dry THF (6 mL/mmol), and was cooled to 0° C. 5 eq. 9-borabicyclo[3.3.1]nonane solution (0.5M in THF) was added and the mixture was stirred at r.t. until no further conversion was observed. Then 20 eq. 2M aqueous NaOH solution and 20 mol % PdCl$_2$×dppf was added. The mixture was stirred at 80° C. until no further conversion was observed. Then it was filtered through Celite, washed with EtOAc. The layers of the filtrate were separated, the aqueous layer was acidified to pH 3 with 2M aqueous HCl solution, then extracted with EtOAc. The combined organic phases were dried over Na$_2$SO$_4$, filtered and the filtrate was concentrated under reduced pressure. The crude product was purified via preparative reversed phase chromatography using 40 mM aqueous NH$_4$OAc solution (pH=4, adjusted with AcOH) and MeCN as eluents to obtain Example 46 as a mixture of diastereoisomers. HRMS calculated for $C_{25}H_{23}ClN_4O_2$: 446.1510, found: 447.159 and 447.1591 (M+H).

Example 47: N-[(5R$_a$)-5-(3-chloro-2-methylphenyl)-6,7,8,9-tetrahydropyrimido[5,4-b]indolizin-4-yl]-D-phenylalanine and Example 48: N-[(5S$_a$)-5-(3-chloro-2-methylphenyl)-6,7,8,9-tetrahydropyrimido[5,4-b]indolizin-4-yl]-D-phenylalanine 1.29 g 1:1 mixture of Examples 41 and 42 (mixture of the two diastereoisomers, 2.3 mmol) was dissolved in 10 mL MeOH and 0.4 mL cc. $H_2SO_4$ (6.9 mmol) was added.

The mixture was stirred at r.t. until no further conversion was observed. The mixture was poured into icy water, neutralized with saturated aqueous $NaHCO_3$ solution and extracted with EtOAc. The combined organic phases were washed with brine, dried over $MgSO_4$, filtered and the filtrate was concentrated under reduced pressure. Then it was dissolved in dry THF (6 mL/mmol), and was cooled to 0° C. 5 eq. 9-borabicyclo[3.3.1]nonane solution (0.5M in THF) was added and the mixture was stirred at r.t. until no further conversion was observed. Then 20 eq. 2M aqueous NaOH solution and 20 mol % $PdCl_2 \times dppf$ was added. The mixture was stirred at 80° C. until no further conversion was observed. Then it was filtered through Celite, washed with EtOAc. The layers of the filtrate were separated, the aqueous layer was acidified to pH 3 with 2M aqueous HCl solution, then extracted with EtOAc. The combined organic phases were dried over $Na_2SO_4$, filtered and the filtrate was concentrated under reduced pressure. The crude product was purified via preparative reversed phase chromatography using 0.1% aqueous TFA solution and MeCN as eluents. Example 47 was obtained as the earlier eluting diastereoisomer. HRMS calculated for $C_{26}H_{25}ClN_4O_2$: 460.1666, found: 461.1747 (M+H). Example 48 was obtained as the later eluting diastereoisomer. HRMS calculated for $C_{26}H_{25}ClN_4O_2$: 460.1666, found: 461.1752 (M+H).

Example 49: (2R)-2-{[(3S$_a$)-3-(3-chloro-4-hydroxy-2-methylphenyl)-2-ethyl-1-benzothiophen-4-yl]oxy}-3-phenylpropanoic Acid and Example 50: (2R)-2-{[(3R$_a$)-3-(3-chloro-4-hydroxy-2-methylphenyl)-2-ethyl-1-benzothiophen-4-yl]oxy}-3-phenylpropanoic Acid Step A: (2R)-2-(2-ethylbenzothiophen-4-yl)oxy-3-phenyl-propanoic Acid 270 mg (2R)-2-hydroxy-3-phenyl-propanoic acid (1.63 mmol), 40 mg CuI (0.21 mmol) and 325 mg $Cs_2CO_3$ (1 mmol) were measured into a 7 mL vial equipped with screw cap and rubber septum. The vial was purged with argon and 5 mL dry DMF and 288 mg 2-ethyl-4-iodo-benzo[b]thiophene (1 mmol) were added by syringe. The mixture was stirred at 110° C. in dark for 20 hours. All further steps were carried out in dark or at red light. 10 mL water was added and the pH was set to 3 with 2M aqueous HCl solution. Then it was extracted with EtOAc. The combined organic layer was dried over $Na_2SO_4$, filtered and the filtrate was concentrated under reduced pressure. The crude product was purified on a preparative TLC plate (silica layer, toluene:AcOH 9:1 eluent) to obtain (2R)-2-(2-ethylbenzothiophen-4-yl)oxy-3-phenyl-propanoic acid. $^1$H NMR (500 MHz, DMSO-d$_6$) δ: 12.53 (br s, 1H), 7.42-7.36 (m, 3H), 7.30 (t, 2H), 7.25-7.18 (m, 1H), 7.13 (t, 1H), 7.07 (br, 1H), 6.65 (d, 1H), 4.98 (dd, 1H), 3.29 (dd, 1H), 3.22 (dd, 1H), 2.89 (q, 2H), 1.30 (t, 3H)

Step B: Methyl (2R)-2-(2-ethylbenzothiophen-4-yl)oxy-3-phenyl-propanoate 1.434 g (2R)-2-(2-ethylbenzothiophen-4-yl)oxy-3-phenyl-propanoic acid (4.39 mmol) was dissolved in 20 mL MeOH and 20 μL cc. $H_2SO_4$ was added. The mixture was stirred at 80° C. until no further conversion was observed. The mixture was concentrated under reduced pressure, then diluted with water, neutralized with saturated aqueous $NaHCO_3$ solution and extracted with DCM. The combined organic phases were washed with brine, dried over $MgSO_4$, filtered and the filtrate was concentrated under reduced pressure to obtain methyl (2R)-2-(2-ethylbenzothiophen-4-yl)oxy-3-phenyl-propanoate. $^1$H NMR (400 MHz, CDCl$_3$) δ: 7.46-7.33 (m, 5H), 7.33-7.26 (m, 1H), 7.16 (bd, 1H), 7.13 (t, 1H), 6.65 (d, 1H), 4.99 (dd, 1H), 3.75 (s, 3H), 3.46-3.32 (m, 2H), 3.01-2.91 (m, 2H), 1.42 (t, 3H)

Step C: Methyl (2R)-2-(2-ethyl-3-iodo-benzothiophen-4-yl)oxy-3-phenyl-propanoate 1.278 g methyl-(2R)-2-(2-ethylbenzothiophen-4-yl)oxy-3-phenyl-propanoate (3.75 mmol), 2.284 g $I_2$ (9 mmol), and 2.5 g $Ag_2SO_4$ (8 mmol) were dissolved in 10 mL EtOH and stirred at r.t. until no further conversion was observed. The mixture was then filtered, the filtrate was concentrated under reduced pressure and purified via flash chromatography using heptane and EtOAc as eluents to obtain 860 mg methyl (2R)-2-(2-ethyl-3,7-diiodo-benzothiophen-4-yl)oxy-3-phenyl-propanoate that was dissolved in 20 mL THF, 150 mg 10% Pd/C was added and the mixture was stirred at r.t. under 4 bar $H_2$ atmosphere until no further conversion was observed. Then it was filtered through Celite, the filtrate was concentrated under reduced pressure and purified via flash chromatography using heptane and EtOAc as eluents to obtain methyl (2R)-2-(2-ethyl-3-iodo-benzothiophen-4-yl)oxy-3-phenyl-propanoate. $^1$H NMR (500 MHz, DMSO-d$_6$) δ: 7.53 (d, 1H), 7.49-7.41 (m, 2H), 7.34-7.27 (m, 2H), 7.26-7.18 (m, 2H), 6.77 (d, 1H), 5.33 (dd, 1H), 3.61 (s, 3H), 3.43 (dd, 1H), 3.32 (dd, 1H), 2.94-2.85 (m, 2H), 1.25 (t, 3H)

Step D: Examples 49 and 50

320 mg methyl (2R)-2-(2-ethyl-3-iodo-benzothiophen-4-yl)oxy-3-phenyl-propanoate (0.686 mmol) and 368 mg Preparation 3a (1.37 mmol) were dissolved in 4 mL 2-Me-THF under $N_2$ atmosphere, then 1.37 mL TBAOH solution (1.37 mmol, IM in THF) and 49 mg AtaPhos (0.069 mmol) were added and the mixture was stirred at 90° C. in a closed vial until no further conversion was observed. Then it was diluted with 30 mL DCM, washed with 10 mL IM aqueous HCl solution. The organic layer was concentrated under reduced pressure, then dissolved in 5 mL MeOH. 100 mg LiOH×$H_2O$ was added, and the mixture was stirred at 50° C. until no further conversion was observed. Then it was diluted with brine, neutralized with IM aqueous HCl solution and extracted with DCM. The organic layer was dried over $Na_2SO_4$, filtered and the filtrate was concentrated under reduced pressure. The crude product was purified via preparative reversed phase chromatography using 0.1% aqueous TFA solution and MeCN as eluents. Example 49 was obtained as the later eluting diastereoisomer. HRMS calculated for $C_{26}H_{23}ClO_4S$: 466.1006, found: 465.0956 (M–H). Example 50 was obtained as the earlier eluting diastereoisomer. HRMS calculated for $C_{26}H_{23}ClO_4S$: 466.1006, found: 465.0971 (M–H).

Example 51: (2R)-2-[((3S$_a$)-3-{3-chloro-2-methyl-4-[2-(4-methylpiperazin-1-yl)ethoxy]phenyl}-2-ethyl-1-benzothiophen-4-yl)oxy]-3-phenylpropanoic Acid Step A: Methyl (2R)-2-[3-(3-chloro-4-hydroxy-2-methyl-phenyl)-2-ethyl-benzothiophen-4-yl]oxy-3-phenyl-propanoate 140 mg Example 49 (0.3 mmol) was dissolved in 3 mL MeOH and 50 μL cc. $H_2SO_4$ was added. The mixture was stirred at 80° C. until no further conversion was observed. The mixture was concentrated under reduced pressure and the residue was diluted with water, neutralized with saturated aqueous $NaHCO_3$ solution and extracted with DCM. The combined organic phases were washed with brine, dried over $MgSO_4$, filtered and the filtrate was concentrated under reduced pressure. The crude product was purified via flash chromatography using heptane and EtOAc as eluents to obtain methyl (2R)-2-[3-(3-chloro-4-hydroxy-2-methyl-phenyl)-2-ethyl-benzothiophen-4-yl]oxy-3-phenyl-propanoate.

$^1$H NMR (500 MHz, DMSO-d$_6$) δ: 10.02 (s, 1H), 7.49 (d, 1H), 7.23-7.12 (m, 4H), 7.02 (d, 1H), 6.92 (d, 1H), 6.89-6.86 (m, 2H), 6.62 (d, 1H), 5.01 (dd, 1H), 3.50 (s, 3H), 2.72 (dd, 1H), 2.60-2.51 (m, 2H), 2.38 (dd, 1H), 1.96 (s, 3H), 1.12 (t, 3H)

Step B: Example 51

63 mg methyl (2R)-2-[3-(3-chloro-4-hydroxy-2-methyl-phenyl)-2-ethyl-benzothiophen-4-yl]oxy-3-phenyl-propanoate (0.13 mmol), 23 mg 1-(2-hydroxyethyl)-4-methyl-piperazine (0.156 mmol) and 41 mg $PPh_3$ (0.156 mmol) were dissolved in 2 mL dry THF under $N_2$ atmosphere, then 36 mg DTAD (0.156 mmol) was added. The mixture was stirred at 50° C. until no further conversion was observed. The mixture was then concentrated under reduced pressure, and purified via flash chromatography using heptane, EtOAc and MeOH as eluents. The obtained intermediate was dissolved in 5 mL MeOH, then 100 mg LiOH×$H_2O$ was added, and the mixture was stirred at 50° C. until no further conversion was observed. Then it was diluted with brine, neutralized with 1 M aqueous HCl solution and extracted with DCM. The organic layer was dried over $Na_2SO_4$, filtered and the filtrate was concentrated under reduced pressure. The crude product was purified via preparative reversed phase chromatography using 40 mM aqueous $NH_4OAc$ solution (pH=4, adjusted with AcOH) and MeCN as eluents to obtain Example 51. HRMS calculated for $C_{33}H_{37}ClN_2O_4S$: 592.2163, found: 593.2238 (M+H).

Example 52: (2R)-2-{[(3R$_a$)-3-{3-chloro-2-methyl-4-[2-(4-methylpiperazin-1-yl)ethoxy]phenyl}-2-(4-fluorophenyl)-1-benzothiophen-4-yl]oxy}-3-(2-{[2-(2-methoxyphenyl)pyrimidin-4-yl] methoxy}phenyl) propanoic Acid and Example 53: (2R)-2-{[(3S$_a$)-3-{3-chloro-2-methyl-4-[2-(4-methylpiperazin-1-yl)ethoxy]phenyl}-2-(4-fluorophenyl)-1-benzothiophen-4-yl]oxy}-3-(2-{[2-(2-methoxyphenyl) pyrimidin-4-yl]methoxy}phenyl) propanoic Acid Step A: (3-bromophenyl) N,N-diethylcarbamate 5.0 g 3-bromophenol (28.9 mmol) and 4.31 g diethylcarbamoyl chloride (31.8 mmol) were dissolved in 50 mL pyridine and stirred at 100° C. until no further conversion was observed. Then the mixture was concentrated under reduced pressure and purified via flash chromatography using heptane and EtOAc as eluents to obtain (3-bromophenyl) N,N-diethylcarbamate. MS (EI, 70 eV) m/z (% relative intensity, [ion]): 56 (9), 72 (42), 100 (100), 174 (4), 176 (4), 271 (4, [M$^+$]), 273 (4, [M$^+$])

Step B: (3-bromo-2-iodo-phenyl) N,N-diethylcarbamate 2.72 g (3-bromophenyl) N,N-diethylcarbamate (10 mmol) was dissolved in 50 mL dry THF under $N_2$ atmosphere and cooled to −78° C. 6 mL LDA solution (12 mmol, 2M in THF, heptane, ethyl benzene) was added and the mixture was stirred at −78° C. for 30 minutes. Then 3.18 g $I_2$ (12.5 mmol) was added and the mixture was stirred at −78° C. for 30 minutes then it was allowed to warm up to r.t. Then the mixture was concentrated under reduced pressure and purified via flash chromatography using heptane and EtOAc as eluents to obtain (3-bromo-2-iodo-phenyl) N,N-diethylcarbamate. $^1$H NMR (400 MHz, DMSO-d$_6$) δ: 7.60 (dd, 1H), 7.35 (t, 1H), 7.17 (dd, 1H), 3.47 (q, 2H), 3.31 (q, 2H), 1.27 (t, 3H), 1.14 (t, 3H)

Step C: [3-bromo-2-[2-(4-fluorophenyl)ethynyl] phenyl] N,N-diethylcarbamate 2.60 g (3-bromo-2-iodo-phenyl) N,N-diethylcarbamate (6.53 mmol), 863 mg 1-ethynyl-4-fluorobenzene (7.19 mmol), 229 mg $Pd(PPh_3)_2Cl_2$ (0.33 mmol), 130 mg copper (I) iodide (0.65 mmol) and 1.43 g diethylamine (19.6 mmol) were dissolved in 25 mL dry DMF and stirred at 50° C. until no further conversion was observed. The mixture was diluted with water and extracted with EtOAc. The combined organic layers were washed with brine, dried over $MgSO_4$, filtered and the filtrate was concentrated under reduced pressure. The crude product was purified via flash chromatography using heptane and EtOAc as eluents to obtain [3-bromo-2-[2-(4-fluorophenyl)ethynyl]phenyl] N,N-diethylcarbamate. MS (EI, 70 eV) m/z (% relative intensity, [ion]): 56 (2), 72 (35), 100 (100), 261 (2), 263 (2), 389 (2, [M$^+$]), 391 (2, [M$^+$])

Step D: [2-[2-(4-fluorophenyl)ethynyl]-3-methylsulfanyl-phenyl] N,N-diethylcarbamate 2.5 g [3-bromo-2-[2-(4-fluorophenyl)ethynyl]phenyl] N,N-diethylcarbamate (6.56 mmol) was dissolved in 65 mL dry THF and cooled to −78° C., then 4.3 mL "BuLi solution (6.88 mmol, 1.6M in hexanes) was added. The mixture was stirred at −78° C. for 30 minutes. Then 742 mg S₂Me₂ (7.87 mmol) was added and the mixture was stirred at −78° C. for 30 minutes, then it was allowed to warm up to r.t. The mixture was then concentrated under reduced pressure and purified via flash chromatography using heptane and EtOAc as eluents to obtain [2-[2-(4-fluorophenyl)ethynyl]-3-methylsulfanyl-phenyl]N,N-diethylcarbamate. MS (EI, 70 eV) m/z (% relative intensity, [ion]): 56 (2), 72 (46), 100 (100), 342 (40), 357 (1, [M⁺])

Step E: [2-(4-fluorophenyl)-3-iodo-benzothiophen-4-yl] N,N-diethylcarbamate 1100 mg 2-[2-(4-fluorophenyl)ethynyl]-3-methylsulfanyl-phenyl] N,N-diethylcarbamate (3.08 mmol) and 937 mg I₂ (3.7 mmol) were dissolved in 20 mL DCM and stirred at r.t. until no further conversion was observed. The mixture was then diluted with 10% aqueous Na₂SO₃ solution and extracted with DCM. The combined organic layers were washed with brine, to give [2-(4-fluorophenyl)-3-iodo-benzothiophen-4-yl] N,N-diethylcarbamate. $^1$H NMR (400 MHz, CDCl₃) δ: 7.74 (dd, 1H), 7.56 (m, 2H), 7.40 (t, 1H), 7.18 (m, 2H), 7.12 (dd, 1H), 3.60 (q, 2H), 3.46 (q, 2H), 1.36 (t, 3H), 1.26 (t, 3H) MS (EI, 70 eV) m/z (% relative intensity, [ion]): 72 (42), 100 (100), 170 (16), 342 (37), 369 (5), 469 (1, [M⁺])

Step F: [3-[3-chloro-2-methyl-4-[2-(4-methylpiperazin-1-yl)ethoxy]phenyl]-2-(4-fluoro phenyl)benzothiophen-4-yl] N,N-diethylcarbamate 1 eq. [2-(4-fluorophenyl)-3-iodo-benzothiophen-4-yl] N,N-diethylcarbamate, 2 eq. Preparation 3b, 2 eq. Cs₂CO₃, 0.1 eq. Ataphos and THF:water 3:1 (10 mL/mmol benzothiophene derivative) were stirred under N₂ atmosphere at 70° C. until no further conversion was observed. The mixture was diluted with water and extracted with DCM.

The organic phase was dried over MgSO₄, filtered and the filtrate was concentrated under reduced pressure. The crude product was purified via flash chromatography using heptane and EtOAc as eluents to give [3-[3-chloro-2-methyl-4-[2-(4-methylpiperazin-1-yl)ethoxy]phenyl]-2-(4-fluorophenyl)benzothiophen-4-yl] N,N-diethylcarbamate. MS: (M+H)⁺=610.2

Step G: 3-[3-chloro-2-methyl-4-[2-(4-methylpiperazin-1-yl)ethoxy]phenyl]-2-(4-fluoro phenyl)benzothiophen-4-ol 1.8 g [3-[3-chloro-2-methyl-4-[2-(4-methylpiperazin-1-yl)ethoxy]phenyl]-2-(4-fluoro phenyl)benzothiophen-4-yl] N,N-diethylcarbamate (3 mmol) was dissolved in 80 mL EtOH and 1.2 g NaOH (30 mmol) was added. The mixture was stirred at 80° C. until no further conversion was observed. The mixture was concentrated under reduced pressure and purified via flash chromatography using DCM and MeOH as eluents to obtain 3-[3-chloro-2-methyl-4-[2-(4-methylpiperazin-1-yl)ethoxy]phenyl]-2-(4-fluorophenyl)benzothiophen-4-ol. MS: (M+H)⁺=511.2

Step H: Examples 52 and 53

470 mg 3-[3-chloro-2-methyl-4-[2-(4-methylpiperazin-1-yl)ethoxy]phenyl]-2-(4-fluoro phenyl)benzothiophen-4-ol (0.92 mmol), 1.12 g Preparation 2d (2.76 mmol) and 726 mg PPh₃ (2.76 mmol) were dissolved in 10 mL dry toluene, then 635 mg DTAD (2.76 mmol) was added. The mixture was stirred at 50° C. until no further conversion was observed. The mixture was then concentrated under reduced pressure and purified via flash chromatography using heptane and EtOAc as eluents. The formed intermediate was dissolved in 10 mL dioxane:water 1:1, 400 mg LiOH×H₂O was added, and the mixture was stirred at r.t. until no further conversion was observed. It was neutralized with 2M aqueous HCl solution and extracted with DCM. The combined organic phases were dried over Na₂SO₄, filtered and the filtrate was concentrated under reduced pressure. The crude product was purified via preparative reversed phase chromatography using 25 mM aqueous NH₄HCO₃ solution and MeCN as eluents. Example 52 was obtained as the earlier eluting diastereoisomer. HRMS calculated for C₄₉H₄₆ClFN₄O₆S: 872.2811, found: 437.1457 (M+2H). Example 53 was obtained as the later eluting diastereoisomer. HRMS calculated for C₄₉H₄₆ClFN₄O₆S: 872.2811, found: 437.1491 (M+2H).

Example 54: 2-benzyl-3-[3-(3-chloro-4-hydroxy-2-methylphenyl)-2-ethyl-1-benzothiophen-4-yl]propanoic Acid Step A: Methyl (Z)-2-benzyl-3-(2-ethylbenzothiophen-4-yl)prop-2-enoate 576 mg 2-ethyl-4-iodo-benzo[b]thiophene (2 mmol), 717 mg methyl 2-benzylacrylate (4 mmol), 556 μL TEA (4 mmol) and 24 mg PdCl₂ (0.1 mmol) were dissolved in 10 mL DMF and stirred at 130° C. in a MW reactor until no further conversion was observed. The mixture was concentrated under reduced pressure and purified via flash chromatography using heptane and EtOAc as eluents to obtain methyl (Z)-2-benzyl-3-(2-ethylbenzothiophen-4-yl)prop-2-enoate. $^1$H NMR (400 MHz, CDCl₃) ratio of diastereoisomers 1.00/0.77=major/minor, δ: 8.06-8.28 (s, 1H), 7.68-7.76 (d, 1H), 7.44-6.98 (m, 8H), 4.25-3.93 (s, 2H), 3.78-3.82 (s, 3H), 2.97-2.99 (q, 2H), 1.41-1.43 (t, 3H)

Step B: Methyl 2-benzyl-3-(2-ethylbenzothiophen-4-yl)propanoate 432 mg methyl (Z)-2-benzyl-3-(2-ethylbenzothiophen-4-yl)prop-2-enoate (1.28 mmol), 137 mg 10% Pd/C, 5 mL AcOH and 20 mL MeOH were stirred under 4 bar H₂ atmosphere at r.t. until no further conversion was observed. The mixture was filtered through Celite, the filtrate was concentrated under reduced pressure and purified via flash chromatography using heptane and EtOAc as eluents to obtain methyl 2-benzyl-3-(2-ethylbenzothiophen-4-yl)propanoate. $^1$H NMR (400 MHz, CDCl₃) δ: 7.61 (d, 1H), 7.38-7.05 (m, 7H), 6.80 (s, 1H), 3.50 (s, 3H), 3.28-3.18 (m, 1H), 3.11-3.00 (m, 3H), 2.90 (q, 2H), 2.86-2.77 (m, 1H), 1.35 (t, 3H)

Step C: Methyl 2-benzyl-3-(2-ethyl-3-iodo-benzothiophen-4-yl)propanoate 346 mg methyl 2-benzyl-3-(2-ethylbenzothiophen-4-yl)propanoate (1.02 mmol), 305 mg I₂ (1.2 mmol) and 468 mg Ag₂SO₄ (1.5 mmol) were dissolved in 5 mL EtOH and stirred at r.t. until no further conversion was observed. The mixture was filtered, the filtrate was concentrated under reduced pressure and purified via flash chromatography using heptane and EtOAc as eluents to obtain methyl 2-benzyl-3-(2-ethyl-3-iodo-benzothiophen-4-yl)propanoate. $^1$H NMR (400 MHz, CDCl₃) δ: 7.67 (dd, 1H), 7.28-7.06 (m, 7H), 4.29-4.17 (m, 1H), 3.80-3.71 (m, 1H), 3.32 (s, 3H), 3.28-3.21 (m, 1H), 3.08-3.00 (m, 2H), 2.97 (q, 2H), 1.35 (t, 3H)

Step D: Example 54

1 eq. methyl 2-benzyl-3-(2-ethyl-3-iodo-benzothiophen-4-yl)propanoate, 2 eq. Preparation 3a, 2 eq. TBAOH solution (IM in water), 0.1 eq. Ataphos and 2-Me-THF (5 mL/mmol benzothiophene derivative) were stirred under $N_2$ atmosphere at 100° C. until no further conversion was observed. The mixture was diluted with water and extracted with DCM. The organic layer was dried over $Na_2SO_4$, filtered and the filtrate was concentrated under reduced pressure. The formed intermediate was dissolved in MeOH (5 mL/mmol benzothiophene derivative), 10 eq. LiOH×$H_2O$ was added, and the mixture was stirred at r.t. until no further conversion was observed. It was neutralized with 2M aqueous HCl solution and extracted with DCM. The combined organic phases were dried over $Na_2SO_4$, filtered and the filtrate was concentrated under reduced pressure. The crude product was purified using preparative reversed phase chromatography using 0.1% aqueous TFA solution and MeCN as eluents to give Example 54. HRMS calculated for $C_{27}H_{25}ClO_3S$: 464.1213, found: 463.1158 (M−H).

Example 55: (2R)-2-{[(1R$_a$)-1-{3-chloro-2-methyl-4-[2-(4-methylpiperazin-1-yl)ethoxy]phenyl}-2-(4-fluorophenyl)-1H-indol-7-yl]oxy}-3-(2-methoxyphenyl)propanoic Acid and Example 56: (2R)-2-{[(1S$_a$)-1-{3-chloro-2-methyl-4-[2-(4-methylpiperazin-1-yl)ethoxy]phenyl}-2-(4-fluorophenyl)-1H-indol-7-yl]oxy}-3-(2-methoxyphenyl)propanoic Acid 600 mg Preparation 7b (0.86 mmol) was dissolved in 20 mL dioxane:water 1:1 and 600 mg LiOH×$H_2O$ was added. The mixture was stirred at r.t. until no further conversion was observed. Then it was diluted with water, acidified with IM aqueous HCl solution and extracted with DCM. The combined organic phases were dried over $Na_2SO_4$, filtered and the filtrate was concentrated under reduced pressure and purified via preparative reversed phase chromatography using 25 mM aqueous $NH_4HCO_3$ solution and MeCN as eluents. Example 55 was obtained as the earlier eluting diastereoisomer. HRMS calculated for $C_{38}H_{39}ClFN_3O_5$: 671.2562, found: 672.2618 (M+H). Example 56 was obtained as the later eluting diastereoisomer. HRMS calculated for $C_{38}H_{39}ClFN_3O_5$: 671.2562, found: 672.2652 (M+H).

Example 57: (2R)-2-{[3-chloro-(1S$_a$)-1-{3-chloro-2-methyl-4-[2-(4-methylpiperazin-1-yl)ethoxy]phenyl}-2-(4-fluorophenyl)-1H-indol-7-yl]oxy}-3-(2-methoxyphenyl)propanoic Acid 240 mg Preparation 7b (0.34 mmol) was dissolved in 3 mL DCM and 46 mg NCS (0.34 mmol) was added. The mixture was stirred at r.t. until no further conversion was observed. Then it was diluted with water and extracted with DCM. The combined organic phases were dried over $Na_2SO_4$, filtered and the filtrate was concentrated under reduced pressure. Then it was dissolved in 5 mL dioxane:water 1:1 and 140 mg LiOH×$H_2O$ was added. The mixture was stirred at r.t. until no further conversion was observed. Then it was diluted with water, acidified with IM aqueous HCl solution and extracted with DCM. The combined organic phases were dried over $Na_2SO_4$, filtered and the filtrate was concentrated under reduced pressure. The crude product was purified via preparative reversed phase chromatography using 25 mM aqueous $NH_4HCO_3$ solution and MeCN as eluents. Example 57 was obtained as the later eluting diastereoisomer. HRMS calculated for $C_{38}H_{38}Cl_2FN_3O_5$: 705.2173, found: 706.2227 (M+H).

Example 58: (2R)-2-{[(1R$_a$)-1-{3-chloro-2-methyl-4-[2-(4-methylpiperazin-1-yl)ethoxy]phenyl}-2-(furan-2-yl)-1H-indol-7-yl]oxy}-3-(2-methoxyphenyl)propanoic Acid and Example 59: (2R)-2-{[(1S$_a$)-1-{3-chloro-2-methyl-4-[2-(4-methylpiperazin-1-yl)ethoxy]phenyl}-2-(furan-2-yl)-1H-indol-7-yl]oxy}-3-(2-methoxyphenyl)propanoic Acid and Example 60: (2R)-2-{[(1S$_a$)-1-{3-chloro-2-methyl-4-[2-(4-methylpiperazin-1-yl)ethoxy]phenyl}-2-(5-fluorofuran-2-yl)-1H-indol-7-yl]oxy}-3-(2-methoxyphenyl)propanoic Acid Step A: 4-[7-benzyloxy-2-(5-fluoro-2-furyl)indol-1-yl]-2-chloro-3-methyl-phenol 1360 mg Preparation 7a (2 mmol), 848 mg 2-(5-fluoro-2-furyl)-4,4,5,5-tetramethyl-1,3,2-dioxaborolane (4 mmol), 2123 mg $K_3PO_4$ (10 mmol), 45 mg Pd(OAc)$_2$ (0.2 mmol) and 164 mg SPhos (0.4 mmol) were dissolved in 30 mL dry toluene and stirred at 75° C. until no further conversion was observed. The solvent was then removed under reduced pressure, the residue was purified via flash chromatography using heptane and EtOAc as eluents. Then 2 mL TBAF solution (2 mmol, IM in THF) and 25 mL THF were added and the mixture was stirred at r.t. until no further conversion was observed. Then the mixture was concentrated under reduced pressure, and the residue was purified via flash chromatography using heptane and EtOAc as eluents to give 4-[7-benzyloxy-2-(5-fluoro-2-furyl)indol-1-yl]-2-chloro-3-methyl-phenol. MS: (M+H)$^+$=448.0

Step B: 7-benzyloxy-1-[3-chloro-2-methyl-4-[2-(4-methylpiperazin-1-yl)ethoxy]phenyl]-2-(5-fluoro-2-furyl)indole 650 mg 4-[7-benzyloxy-2-(5-fluoro-2-furyl)indol-1-yl]-2-chloro-3-methyl-phenol (1.01 mmol), 288 mg 1-(2-hydroxyethyl)-4-methylpiperazine (2 mmol) and 786 mg PPh$_3$ (3 mmol) were dissolved in 20 mL dry toluene. Then 690 mg DTAD (3 mmol) was added and the mixture was stirred at 45° C. until no further conversion was observed. Then it was concentrated under reduced pressure, and was purified via flash chromatography using DCM and MeOH as eluents to give 7-benzyloxy-1-[3-chloro-2-methyl-4-[2-(4-methyl piperazin-1-yl)ethoxy]phenyl]-2-(5-fluoro-2-furyl)indole. MS: (M+H)$^+$=574.2

Step C: The mixture of 1-[3-chloro-2-methyl-4-[2-(4-methylpiperazin-1-yl)ethoxy]phenyl]-2-(2-furyl)indol-7-ol and 1-[3-chloro-2-methyl-4-[2-(4-methyl-piperazin-1-yl)ethoxy]phenyl]-2-(5-fluoro-2-furyl)indol-7-ol 1300 mg 7-benzyloxy-1-[3-chloro-2-methyl-4-[2-(4-methylpiperazin-1-yl)ethoxy]phenyl]-2-(5-fluoro-2-furyl)

indole (2.26 mmol) was dissolved in 100 mL MeOH and 100 mg 10% Pd/C was added. The mixture was stirred under 1 bar $H_2$ atmosphere at r.t. overnight. The mixture was filtered through Celite and the filtrate was concentrated under reduced pressure to give a 7:3 mixture of 1-[3-chloro-2-methyl-4-[2-(4-methylpiperazin-1-yl)ethoxy]phenyl]-2-(2-furyl)indol-7-ol (MS: $(M+H)^+=466.2$) and 1-[3-chloro-2-methyl-4-[2-(4-methylpiperazin-1-yl)ethoxy]phenyl]-2-(5-fluoro-2-furyl)indol-7-ol (MS: $(M+H)^+=484.2$).

Step D: Examples 58, 59 and 60

465 mg of the 7:3 mixture of 1-[3-chloro-2-methyl-4-[2-(4-methylpiperazin-1-yl)ethoxy]phenyl]-2-(2-furyl)indol-7-ol and 1-[3-chloro-2-methyl-4-[2-(4-methylpiperazin-1-yl)ethoxy]phenyl]-2-(5-fluoro-2-furyl)indol-7-ol (1 mmol), 449 mg ethyl (2S)-2-hydroxy-3-phenyl-propanoate (2 mmol) and 786 mg $PPh_3$ (3 mmol) were dissolved in 10 mL dry toluene. Then 691 mg DTAD (3 mmol) was added and the mixture was stirred at 45° C. until no further conversion was observed. Then it was concentrated under reduced pressure, and the residue was purified via flash chromatography using DCM and MeOH as eluents. Then it was dissolved in 5 mL dioxane:water 1:1 and 140 mg LiOH× $H_2O$ was added. The mixture was stirred at r.t. until no further conversion was observed. Then it was diluted with water, acidified with 1M aqueous HCl solution and extracted with DCM. The combined organic phases were dried over $Na_2SO_4$, filtered and the filtrate was concentrated under reduced pressure. The crude product was purified via preparative reversed phase chromatography using 25 mM aqueous $NH_4HCO_3$ solution and MeCN as eluents. Example 58 was obtained as the earlier eluting diastereoisomer. HRMS calculated for $C_{36}H_{38}ClN_3O_6$: 643.2449, found: 644.2512 (M+H). Example 59 was obtained as the later eluting diastereoisomer. HRMS calculated for $C_{36}H_{38}ClN_3O_6$: 643.2449, found: 644.2521 (M+H). Example 60 was obtained as the later eluting diastereoisomer. HRMS calculated for $C_{36}H_{37}ClFN_3O_6$: 661.2355, found: 662.2411 (M+H).

Example 61: (2R)-2-{[(3R$_a$)-3-{3-chloro-2-methyl-4-[2-(4-methylpiperazin-1-yl)ethoxy]phenyl}-2-(4-fluorophenyl)-1-benzofuran-4-yl]oxy}-3-(2-methoxyphenyl)propanoic Acid and Example 62: (2R)-2-{[(3S$_a$)-3-{3-chloro-2-methyl-4-[2-(4-methylpiperazin-1-yl)ethoxy]phenyl}-2-(4-fluorophenyl)-1-benzofuran-4-yl]oxy}-3-(2-methoxyphenyl)propanoic Acid Step A: Ethyl (2S)-3-(2-methoxyphenyl)-2-(p-tolylsulfonyloxy)propanoate 3000 mg Preparation 2f (13.38 mmol) was dissolved in 10 mL pyridine and 2933 mg TsCl (15.38 mmol) was added at 0° C. The mixture was stirred at r.t. until no further conversion was observed. Then the mixture was diluted with water and extracted with EtOAc. The combined organic phases were washed with 1M aqueous citric acid solution, dried over $Na_2SO_4$, filtered and the filtrate was concentrated under reduced pressure to give ethyl (2S)-3-(2-methoxyphenyl)-2-(p-tolylsulfonyloxy)propanoate. MS (EI, 70 eV) m/z (% relative intensity, [ion]): 65 (7), 77 (14), 91 (49), 123 (33), 133 (33), 165 (100), 207 (65), 307 (13), 512 (7, [M$^+$])

Step B: Ethyl (2R)-2-[3-bromo-2-(4-fluorophenyl)benzofuran-4-yl]oxy-3-(2-methoxy phenyl)propanoate 1 eq. Preparation 1c, 1.5 eq. ethyl (2S)-3-(2-methoxyphenyl)-2-(p-tolylsulfonyloxy) propanoate, 2 eq. $K_2CO_3$ and DMSO (10 mL/mmol benzofurane derivative) were stirred at 60° C. under $N_2$ atmosphere until no further conversion was observed. Then it was diluted with brine, neutralized with 1M aqueous HCl solution and extracted with DCM. The combined organic phases were dried over $Na_2SO_4$, filtered and the filtrate was concentrated under reduced pressure. The crude product was purified via flash chromatography using heptane and EtOAc as eluents to give ethyl (2R)-2-[3-bromo-2-(4-fluorophenyl)benzofuran-4-yl]oxy-3-(2-methoxyphenyl)propanoate. MS (EI, 70 eV) m/z (% relative intensity, [ion]): 91 (56), 133 (41), 165 (100), 207 (93), 281 (26), 305 (9), 512 (3, [M$^+$]), 514 (3, [M$^+$])

Step C: Examples 61 and 62

Using General Procedure VI and ethyl (2R)-2-[3-bromo-2-(4-fluorophenyl)benzofuran-4-yl]oxy-3-(2-methoxyphenyl)propanoate as the appropriate 3-bromo-benzofuran derivative and Preparation 3b as the appropriate boronic acid derivative, Example 61 was obtained as the earlier eluting diastereoisomer. HRMS calculated for $C_{38}H_{38}ClFN_2O_6$: 672.2402, found: 673.2465 (M+H). Example 62 was obtained as the later eluting diastereoisomer.
HRMS calculated for $C_{38}H_{38}ClFN_2O_6$: 672.2402, found: 673.2486 (M+H).

Example 63: (2R)-2-{[(3R$_a$)-3-{3-chloro-2-methyl-4-[2-(4-methylpiperazin-1-yl)ethoxy]phenyl}-2-(4-fluorophenyl)-1-benzofuran-4-yl]oxy}-3-(2-{[2-(2-methoxyphenyl)pyrimidin-4-yl]methoxy}phenyl) propanoic Acid and Example 64: (2R)-2-{[(3S$_a$)-3-{3-chloro-2-methyl-4-[2-(4-methylpiperazin-1-yl)ethoxy]phenyl}-2-(4-fluorophenyl)-1-benzofuran-4-yl]oxy}-3-(2-{[2-(2-methoxyphenyl) pyrimidin-4-yl]methoxy}phenyl) propanoic Acid Step A: Ethyl (2R)-2-[3-bromo-2-(4-fluorophenyl)benzofuran-4-yl]oxy-3-[2-[2-(2-methoxy phenyl)pyrimidin-4-yl]oxyphenyl]propanoate Using General Procedure V and Preparation 1c as the appropriate benzofuran-4-ol derivative and Preparation 2d as the appropriate lactic ester derivative, ethyl (2R)-2-[3-bromo-2-(4-fluorophenyl)benzofuran-4-yl]oxy-3-[2-[2-(2-methoxyphenyl)pyrimidin-4-yl]oxyphenyl] propanoate was obtained. MS: $(M+H)^+=699.2$ Step B: Examples 63 and 64

Using General Procedure VI and ethyl (2R)-2-[3-bromo-2-(4-fluorophenyl)benzofuran-4-yl]oxy-3-[2-[2-(2-methoxyphenyl)pyrimidin-4-yl]oxyphenyl]propanoate as the appropriate 3-bromo-benzofuran derivative and Preparation 3b as the appropriate boronic acid derivative, Example 63 was obtained as the earlier eluting diastereoisomer. HRMS calculated for $C_{49}H_{46}ClFN_4O_7$: 856.3039, found: 429.1582 (M+2H). Example 64 was obtained as the later eluting diastereoisomer. HRMS calculated for C$_{49}$H$_{46}$ClFN$_4$O$_7$: 856.3039, found: 429.1604 (M+2H).

Example 65: (2R)-2-{[(3S$_a$)-3-{3-chloro-2-methyl-4-[2-(4-methylpiperazin-1-yl)ethoxy]phenyl}-2-(4-fluorophenyl)-1-benzofuran-4-yl]oxy}-3-[2-(2,2,2-trifluoroethoxy) phenyl]propanoic Acid Step A: Ethyl (2R)-2-[3-bromo-2-(4-fluorophenyl) benzofuran-4-yl]oxy-3-[2-(2,2,2-trifluoroethoxy) phenyl]propanoate Using General Procedure V and Preparation 1c as the appropriate benzofuran-4-ol derivative and Preparation 2h as the appropriate lactic ester derivative, ethyl (2R)-2-[3-bromo-2-(4-fluorophenyl)benzofuran-4-yl]oxy-3-[2-(2,2,2-trifluoroethoxy)phenyl]propanoate was obtained. MS: (M+Na)$^+$=604.4

Step B: Example 65

Using General Procedure VI and ethyl (2R)-2-[3-bromo-2-(4-fluorophenyl)benzofuran-4-yl]oxy-3-[2-(2,2,2-trifluoroethoxy)phenyl]propanoate as the appropriate 3-bromo-benzofuran derivative and Preparation 3b as the appropriate boronic acid derivative, Example 65 was obtained as the later eluting diastereoisomer. HRMS calculated for C$_{39}$H$_{37}$ClF$_4$N$_2$O$_6$: 740.2276, found: 741.2372 (M+H).

Example 66: (2R)-2-{[(3S$_a$)-3-{3-chloro-2-methyl-4-[2-(4-methylpiperazin-1-yl)ethoxy]phenyl}-6-fluoro-2-(4-fluorophenyl)-1-benzofuran-4-yl]oxy}-3-[2-(2,2,2-trifluoro ethoxy)phenyl] propanoic Acid Step A: Ethyl (2R)-2-[3-bromo-6-fluoro-2-(4-fluorophenyl)benzofuran-4-yl]oxy-3-[2-(2,2,2-trifluoroethoxy)phenyl]propanoate Using General Procedure V and Preparation 1d as the appropriate benzofuran-4-ol derivative and Preparation 2h as the appropriate lactic ester derivative, ethyl (2R)-2-[3-bromo-6-fluoro-2-(4-fluorophenyl)benzofuran-4-yl]oxy-3-[2-(2,2,2-trifluoroethoxy) phenyl]propanoate was obtained. $^1$H NMR (400 MHz, DMSO-d$_6$): 8.07 (m, 2H), 7.43 (m, 3H), 7.27 (m, 2H), 7.11 (m, 1H), 6.98 (m, 1H), 6.55 (dd, 1H), 5.23 (m, 1H), 4.82 (q, 2H), 4.12 (q, 2H), 3.37 (m, 1H), 3.25 (m, 1H), 1.10 (t, 3H)

Step B: Example 66

Using General Procedure VI and ethyl (2R)-2-[3-bromo-6-fluoro-2-(4-fluorophenyl) benzofuran-4-yl]oxy-3-[2-(2,2,2-trifluoroethoxy)phenyl]propanoate as the appropriate 3-bromo-benzofuran derivative and Preparation 3b as the appropriate boronic acid derivative, Example 66 was obtained as the later eluting diastereoisomer. HRMS calculated for C$_{39}$H$_{36}$ClF$_5$N$_2$O$_6$: 758.2182, found: 759.2244 (M+H).

Example 67: (2R)-2-{[(3S$_a$)-3-{3-chloro-2-methyl-4-[2-(4-methylpiperazin-1-yl)ethoxy]phenyl}-6-fluoro-2-(4-fluorophenyl)-1-benzofuran-4-yl]oxy}-3-(2-{[2-(2-methoxy phenyl)pyrimidin-4-yl]methoxy}phenyl)propanoic Acid Step A: Ethyl (2R)-2-[3-bromo-6-fluoro-2-(4-fluorophenyl)benzofuran-4-yl]oxy-3-[2-[[2-(2-methoxyphenyl)pyrimidin-4-yl]methoxy]phenyl]propanoate Using General Procedure V and Preparation 1d as the appropriate benzofuran-4-ol derivative and Preparation 2d as the appropriate lactic ester derivative, ethyl (2R)-2-[3-bromo-6-fluoro-2-(4-fluorophenyl)benzofuran-4-yl]oxy-3-[2-[[2-(2-methoxyphenyl) pyrimidin-4-yl]methoxy]phenyl] propanoate was obtained. $^1$H NMR (400 MHz, DMSO-d$_6$): 8.86 (d, 1H), 8.05 (m, 2H), 7.61 (d, 1H), 7.52 (dd, 1H), 7.48-7.38 (m, 4H), 7.25 (m, 1H), 7.21 (m, 1H), 7.12 (m, 2H), 7.03 (td, 1H), 6.94 (td, 1H), 6.67 (dd, 1H), 5.40 (m, 1H), 5.26 (s, 2H), 4.15 (q, 2H), 3.75 (s, 3H), 3.56 (m, 1H), 3.30 (m, 1H), 1.12 (t, 3H)

Step B: Example 67

Using General Procedure VI and ethyl (2R)-2-[3-bromo-6-fluoro-2-(4-fluorophenyl) benzofuran-4-yl]oxy-3-[2-[[2-(2-methoxyphenyl)pyrimidin-4-yl]methoxy]phenyl]propanoate as the appropriate 3-bromo-benzofuran derivative and Preparation 3b as the appropriate boronic acid derivative, Example 67 was obtained as the later eluting diastereoisomer. HRMS calculated for C$_{49}$H$_{45}$ClF$_2$N$_4$O$_7$: 874.2945, found: 438.1543 (M+2H).

Example 68: (2R)-2-{[(3R$_a$)-3-{3-chloro-2-methyl-4-[2-(4-methylpiperazin-1-yl)ethoxy]phenyl}-2-(4-fluorophenyl)-1-methyl-H-indol-4-yl]oxy}-3-(2-{[2-(2-methoxyphenyl)pyrimidin-4-yl]methoxy}phenyl) propanoic Acid and Example 69: (2R)-2-{[(3S$_a$)-3-{3-chloro-2-methyl-4-[2-(4-methylpiperazin-1-yl)ethoxy]phenyl}-2-(4-fluorophenyl)-1-methyl-1H-indol-4-yl]oxy}-3-(2-{[2-(2-methoxyphenyl) pyrimidin-4-yl] methoxy}phenyl)propanoic Acid Step A: 1-(benzenesulfonyl)-4-benzyloxy-indole 7.0 g 4-benzyloxy-1H-indole (31.35 mmol) was dissolved in 60 mL dry DMF and 1.317 g NaH (32.92 mmol, 60% on mineral oil) was added at 0° C. The mixture was stirred for 1 hour, then 6.09 g benzenesulfonyl chloride (34.48 mmol) was added dropwise and the mixture was stirred at 0° C. until no further conversion was observed. Then it was diluted with water and extracted with DCM. The combined organic phases were dried over Na$_2$SO$_4$, filtered and the filtrate was concentrated under reduced pressure and purified via flash chromatography using heptane and EtOAc as eluents to obtain 1-(benzenesulfonyl)-4-benzyloxy-indole.
$^1$H NMR (400 MHz, DMSO-d$_6$) δ: 7.97 (d, 2H), 7.72 (d, 1H), 7.69 (t, 1H), 7.59 (t, 2H), 7.54 (d, 1H), 7.47 (d, 2H), 7.39 (t, 2H), 7.33 (d, 1H), 7.27 (t, 1H), 6.89 (d, 1H), 6.85 (d, 1H), 5.20 (s, 2H) MS (EI, 70 eV) m/z (% relative intensity, [ion]): 77 (32), 91 (100), 141 (18), 222 (6), 272 (11), 363 (10, [M$^+$])

Step B: 1-(benzenesulfonyl)-4-benzyloxy-2-iodo-indole 5.08 g 1-(benzenesulfonyl)-4-benzyloxy-indole (13.98 mmol) was dissolved in 140 mL dry THF. 8.54 mL LDA solution (15.38 mmol, 1.8M in THF-heptane-ethylbenzene) was added at −78° C. and the mixture was stirred for 1 hour. Then 4.26 g iodine (16.8 mmol) was added and the mixture was stirred for 1 hour at −78° C. The mixture was quenched with saturated aqueous NH$_4$Cl solution, extracted with EtOAc. The combined organic phases were washed with aqueous Na$_2$SO$_3$ solution and water, then dried over Na$_2$SO$_4$, filtered and the filtrate was concentrated under reduced pressure. The crude product was purified via flash chromatography using heptane and EtOAc as eluents to obtain 1-(benzenesulfonyl)-4-benzyloxy-2-iodo-indole. $^1$H NMR (400 MHz, DMSO-d$_6$) δ: 7.86 (dd, 2H), 7.75 (d, 1H), 7.70 (d, 1H), 7.61 (t, 2H), 7.47 (dd, 2H), 7.39 (t, 2H), 7.33 (d, 1H), 7.23 (t, 1H), 7.18 (s, 1H), 6.90 (d, 1H), 5.20 (s, 2H)

Step C: 1-(benzenesulfonyl)-4-benzyloxy-2-(4-fluorophenyl)indole 5.8 g 1-(benzenesulfonyl)-4-benzyloxy-2-iodo-indole (11.86 mmol) and 3.16 g 4-(4,4,5,5-tetramethyl-1,3,2-dioxaborolan-2-yl)fluorobenzene (14.22 mmol) were dissolved in 75 mL THF, then 7.73 g Cs$_2$CO$_3$ (23.72 mmol), 420 mg Ataphos (0.59 mmol) and 25 mL water were added and the mixture was stirred at 70° C. under N$_2$ atmosphere until no further conversion was observed. The mixture was then concentrated under reduced pressure and purified via flash chromatography using heptane and EtOAc as eluents to obtain 1-(benzenesulfonyl)-4-benzyloxy-2-(4-fluorophenyl) indole. $^1$H NMR (400 MHz, DMSO-d$_6$) δ: 7.79 (d, 1H), 7.67 (m, 1H), 7.60-7.48 (m, 6H), 7.43-7.25 (m, 8H), 7.00 (d, 1H), 5.57 (s, 1H), 5.22 (s, 2H)

Step D: 1-(benzenesulfonyl)-4-benzyloxy-2-(4-fluorophenyl)-3-iodo-indole 4.92 g 1-(benzenesulfonyl)-4-benzyloxy-2-(4-fluorophenyl)indole (10.75 mmol), 3.69 g Ag$_2$SO$_4$ (11.83 mmol) and 3.0 g iodine (11.83 mmol) were stirred in 100 mL EtOH at r.t. until no further conversion was observed. Then the mixture was concentrated under reduced pressure and purified via flash chromatography using heptane and EtOAc as eluents to obtain 1-(benzenesulfonyl)-4-benzyloxy-2-(4-fluorophenyl)-3-iodo-indole. MS: (M+H)$^+$=584.2

Step E: 1-(benzenesulfonyl)-4-benzyloxy-3-[3-chloro-2-methyl-4-[2-(4-methylpiperazin-1-yl) ethoxy]phenyl]-2-(4-fluorophenyl)indole 5.5 g 1-(benzenesulfonyl)-4-benzyloxy-2-(4-fluorophenyl)-3-iodo-indole (9.42 mmol), 4.46 g Preparation 3b (11.31 mmol), 6.14 g Cs$_2$CO$_3$ (18.84 mmol) and 354 mg Ataphos (0.5 mmol) were dissolved in 100 mL THF:water 3:1 and stirred at 70° C. under N$_2$ until no further conversion was observed. The mixture was concentrated under reduced pressure and purified via flash chromatography using heptane, EtOAc and MeOH as eluents to obtain 1-(benzenesulfonyl)-4-benzyloxy-3-[3-chloro-2-methyl-4-[2-(4-methyl-piperazin-1-yl)ethoxy] phenyl]-2-(4-fluorophenyl)indole.
$^1$H NMR (400 MHz, DMSO-d$_6$) δ: 7.85 (d, 1H), 7.67 (t, 1H), 7.61-6.90 (m, 2H), 7.53-7.47 (m, 4H), 7.4 (t, 1H), 7.20-7.07 (m, 5H), 6.96 (d, 1H), 6.77 (d, 1H), 6.73 (d, 1H), 6.66 (d, 2H), 4.96 (d, 1H), 4.86 (d, 1H), 4.09 (m, 1H), 4.00 (m, 1H), 3.34 (br s, 4H), 2.75 (t, 2H), 2.58 (br s, 4H), 2.30 (s, 3H), 1.81 (s, 3H)
MS: (M+H)$^+$=724.2

Step F: 4-benzyloxy-3-[3-chloro-2-methyl-4-[2-(4-methylpiperazin-1-yl)ethoxy]phenyl]-2-(4-fluorophenyl)-1H-indole 6.5 g 1-(benzenesulfonyl)-4-benzyloxy-3-[3-chloro-2-methyl-4-[2-(4-methylpiperazin-1-yl)ethoxy]phenyl]-2-(4-fluorophenyl)indole (8.97 mmol) was dissolved in 100 mL THF and 100 mL MeOH, then 28.3 g Ba(OH)$_2$×8 H$_2$O (89.7 mmol) was added and the mixture was stirred at 70° C. until no further conversion was observed. The mixture was then filtered, the filtrate was concentrated under reduced pressure and purified via flash chromatography using DCM and MeOH as eluents to obtain 4-benzyloxy-3-[3-chloro-2-methyl-4-[2-(4-methylpiperazin-1-yl)ethoxy]phenyl]-2-(4-fluorophenyl)-1H-indole. MS: (M+H)$^+$=584.2

Step G: 4-benzyloxy-3-[3-chloro-2-methyl-4-[2-(4-methylpiperazin-1-yl)ethoxy]phenyl]-2-(4-fluorophenyl)-1-methyl-indole 1.626 g 4-benzyloxy-3-[3-chloro-2-methyl-4-[2-(4-methylpiperazin-1-yl)ethoxy]phenyl]-2-(4-fluorophenyl)-1H-indole (2.78 mmol) was dissolved in 25 mL dry DMF and cooled to 0° C. Then 123 mg NaH (3.06 mmol, 60% on mineral oil) was added and the mixture was stirred for 1 hour. Then 395 mg methyl iodide (2.78 mmol) was added and the mixture was stirred for 1 hour. The mixture was then poured into water and extracted with DCM. The combined organic phases were washed with brine, dried over MgSO$_4$, filtered and the filtrate was concentrated under reduced pressure. The crude product was purified via flash chromatography using DCM and MeOH as eluents to obtain 4-benzyloxy-3-[3-chloro-2-methyl-4-[2-(4-methylpiperazin-1-yl)ethoxy]phenyl]-2-(4-fluorophenyl)-1-methyl-indole.
$^1$H NMR (400 MHz, DMSO-d$_6$) δ: 7.31 (dd, 2H), 7.24-7.10 (m, 7H), 6.97 (d, 1H), 6.83-6.76 (m, 3H), 6.68 (dd, 1H), 5.01 (d, 1H), 4.93 (d, 1H), 4.14 (m, 1H), 4.06 (m, 1H), 3.63 (s, 3H), 3.10-2.60 (br s, 8H), 2.84 (br s, 2H), 2.58 (s, 3H), 2.04 (s, 3H)

Step H: 3-[3-chloro-2-methyl-4-[2-(4-methylpiperazin-1-yl)ethoxy]phenyl]-2-(4-fluoro phenyl)-1-methyl-indol-4-ol 1.6 g 4-benzyloxy-3-[3-chloro-2-methyl-4-[2-(4-methylpiperazin-1-yl)ethoxy]phenyl]-2-(4-fluorophenyl)-1-methyl-indole (2.68 mmol) was dissolved in 10 mL DCM and 1 eq.
HBr (33% solution in AcOH) was added. The mixture was stirred at r.t. until no further conversion was observed. The mixture was then diluted with 10% aqueous K$_2$CO$_3$ solution and extracted with DCM. The combined organic phases were washed with brine, dried over MgSO$_4$, filtered and the filtrate was concentrated under reduced pressure. The crude product was purified via flash chromatography using DCM and MeOH as eluents, then via preparative reversed phase chromatography using 25 mM aqueous NH$_4$HCO$_3$ solution and MeCN as eluents to obtain 3-[3-chloro-2-methyl-4-[2-(4-methylpiperazin-1-yl)ethoxy]phenyl]-2-(4-fluorophenyl)-1-methyl-indol-4-ol.
$^1$H NMR (400 MHz, DMSO-d$_6$) δ: 9.02 (s, 1H), 7.29-7.15 (m, 4H), 7.06-6.92 (m, 2H), 6.86 (d, 1H), 6.78 (d, 1H), 6.38 (dd, 1H), 4.07 (m, 2H), 3.58 (s, 3H), 2.70 (t, 2H), 2.58-2.40 (br s, 4H), 2.40-2.19 (br s, 4H), 2.19 (s, 3H), 2.09 (s, 3H)
MS: (M+H)$^+$=508.2

Step I: Ethyl (2S)-3-[2-[[2-(2-methoxyphenyl)pyrimidin-4-yl]methoxy]phenyl]-2-(p-tolyl sulfonyloxy)propanoate 3.668 g Preparation 2d (8.97 mmol) was dissolved in 12 mL pyridine and 1.97 g TsCl (10.31 mmol) was added at 0° C. The mixture was stirred at r.t. until no further conversion was observed. Then the mixture was diluted with water and extracted with EtOAc. The combined organic phases were washed with IM aqueous citric acid solution, dried over MgSO$_4$, filtered and the filtrate was concentrated under reduced pressure to give ethyl (2S)-3-[2-[[2-(2-methoxyphenyl)pyrimidin-4-yl]methoxy]phenyl]-2-(p-tolylsulfonyloxy)propanoate.

$^1$H NMR (400 MHz, DMSO-d$_6$) δ: 8.93 (d, 1H), 7.58 (dd, 1H), 7.52-7.43 (m, 2H), 7.43-7.34 (m, 2H), 7.26-7.15 (m, 4H), 7.13-7.04 (m, 2H), 6.93-6.83 (m, 2H), 5.12 (d, 1H), 5.03-4.92 (m, 2H), 4.01 (q, 2H), 3.79 (s, 3H), 3.26 (dd, 1H), 3.01 (dd, 1H), 2.36 (s, 3H), 1.12 (t, 3H)

MS: (M+H)$^+$=563.2

Step J: Examples 68 and 69

60 mg 3-[3-chloro-2-methyl-4-[2-(4-methylpiperazin-1-yl)ethoxy]phenyl]-2-(4-fluoro phenyl)-1-methyl-indol-4-ol (0.12 mmol), 101 mg ethyl (2S)-3-[2-[[2-(2-methoxy phenyl)pyrimidin-4-yl]methoxy]phenyl]-2-(p-tolylsulfonyloxy)propanoate (0.18 mmol) and 80 mg Cs$_2$CO$_3$ (0.24 mmol) were dissolved in 2 mL dry DMF and stirred at 50° C. until no further conversion was observed. Then 2 eq. LiOH×H$_2$O was added and mixture was stirred at r.t. until no further conversion was observed. The mixture was concentrated and purified by preparative reversed phase chromatography using 25 mM aqueous NH$_4$HCO$_3$ solution and MeCN as eluents to obtain Example 68 as the earlier eluting diastereoisomer. HRMS calculated for C$_{50}$H$_{49}$ClFN$_5$O$_6$: 869.3355, found: 435.6743 (M+2H). Example 69 was obtained as the later eluting diastereoisomer. HRMS calculated for C$_{50}$H$_{49}$ClFN$_5$O$_6$: 869.3355, found: 435.6767 (M+2H).

Example 70: N-[3-(3-chloro-2-methylphenyl)thieno[3,2-c]pyridin-4-yl]-D-phenylalanine

Step A: 4-bromo-N-(dimethoxymethyl)thiophene-3-carboxamide 5.01 g 4-bromothiophene-3-carboxylic acid (24.2 mmol) was dissolved in 25 mL isopropyl acetate and 17.9 mL SOCl$_2$ (242 mmol) was added and the mixture was stirred at 50° C. for 2 hours. Then the excess SOCl$_2$ was distilled and the residue was dissolved in 25 mL isopropyl acetate and cooled to 10° C. 10.6 mL DIPEA (60.5 mmol) and 4.0 mL aminoacetaldehyde dimethyl acetal (36.3 mmol) were added. The mixture was allowed to warm up to r.t. and stirred under N$_2$ atmosphere overnight. The mixture was diluted with 10% aqueous H$_3$PO$_4$ solution and extracted with isopropyl acetate. The combined organic phases were washed with 10% aqueous KH$_2$PO$_4$ solution and brine, then dried over Na$_2$SO$_4$, filtered and the filtrate was concentrated under reduced pressure to obtain 4-bromo-N-(dimethoxymethyl)thiophene-3-carboxamide.

$^1$H NMR (400 MHz, DMSO-d$_6$) δ: 8.36 (t, 1H), 7.93 (d, 1H), 7.72 (d, 1H), 4.48 (t, 1H), 3.31-3.28 (m, 8H)

MS (M+H): 294.0

Step B: 3-bromo-5H-thieno[3,2-c]pyridin-4-one 32 mg 4-bromo-N-(dimethoxymethyl)thiophene-3-carboxamide (0.102 mmol) was dissolved in 1 mL PPA and stirred at 100° C. under argon atmosphere until no further conversion was observed. The mixture was then poured into ice, the formed precipitate was filtered and washed with water to obtain 3-bromo-5H-thieno[3,2-c]pyridin-4-one. MS (M+H): 229.9

Step C: 3-bromo-4-chloro-thieno[3,2-c]pyridine 1.06 g 3-bromo-5H-thieno[3,2-c]pyridin-4-one (4.4 mmol), 560 μL N,N-dimethylaniline (4.4 mmol) and 8.37 mL POCl$_3$ (88 mmol) were stirred at 100° C. until no further conversion observed. The reaction mixture was then poured into ice and extracted with DCM. The combined organic phases were washed with saturated aqueous NaHCO$_3$ solution and brine, dried over Na$_2$SO$_4$, filtered and the filtrate was concentrated under reduced pressure. The crude product was purified via flash chromatography using heptane and EtOAc as eluents to obtain 3-bromo-4-chloro-thieno[3,2-c]pyridine. MS (M+H): 247.9

Step D: 3,4-dibromothieno[3,2-c]pyridine 735 mg 3-bromo-4-chloro-thieno[3,2-c]pyridine (2.8 mmol) and 2.288 g bromotrimethylsilane (14.5 mmol) were dissolved in 15 mL propionitrile and stirred at 100° C. until no further conversion was observed. The reaction mixture was then concentrated under reduced pressure and purified via preparative reversed phase chromatography using 40 mM aqueous NH$_4$OAc solution (pH=4, adjusted with AcOH) and MeCN as eluents to obtain 3,4-dibromothieno[3,2-c]pyridine. MS (M+H): 291.8

Step E: (2R)-2-[(3-bromothieno[3,2-c]pyridin-4-yl)amino]-3-phenyl-propanoic Acid 340 mg 3,4-dibromothieno[3,2-c]pyridine (1.16 mmol) and 718 mg D-phenylalanine (4.35 mmol) were dissolved in 7.5 mL sulfolane, then 421 mg potassium fluoride (7.25 mmol) and 2.23 g 4,7,13,16,21,24-hexaoxa-1,10-diazabicyclo[8.8.8]hexacosane (5.8 mmol) were added and the mixture was stirred at 175° C. under argon atmosphere until no further conversion was observed. The reaction mixture was directly injected and purified via preparative reversed phase chromatography using 40 mM aqueous NH$_4$OAc solution (pH=4, adjusted with AcOH) solution and MeCN as eluents to obtain (2R)-2-[(3-bromothieno[3,2-c]pyridin-4-yl)amino]-3-phenyl-propanoic acid.

Step F: Example 70

189 mg (2R)-2-[(3-bromothieno[3,2-c]pyridin-4-yl)amino]-3-phenyl-propanoic acid (0.5 mmol), 341 mg (3-chloro-2-methylphenyl)boronic acid (2 mmol) were dissolved in 3.5 mL DME, then 72 mg butyldi-1-adamantylphosphine (0.2 mmol), 22 mg Pd(OAc)$_2$ (0.1 mmol) and 389 mg TBAOH (1.5 mmol) were added and the mixture was stirred at 100° C. under argon atmosphere until no further conversion was observed. Then the mixture was poured into icy water, extracted with MTBE. The aqueous phase was acidified to pH 2 and extracted with DCM. The combined organic phases were dried over Na$_2$SO$_4$, filtered and the filtrate was concentrated under reduced pressure. The crude product was purified via preparative reversed phase chromatography using 25 mM aqueous NH$_4$HCO$_3$ solution and MeCN as eluents to obtain Example 70. HRMS calculated for C$_{23}$H$_{19}$ClN$_2$O$_2$S: 422.0856, found: 423.0937 and 423.0919 for the two diastereomers (M+H).

Example 71: (2R)-2-{[(3S$_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl) pyrimidin-4-yl]methoxy}phenyl)propanoic Acid

Step A: 2-chloro-3-[2-(4-fluorophenyl)ethynyl]pyridine

In a dry flask 3.85 g 3-bromo-2-chloro-pyridine (20 mmol), 0.23 g CuI (1.2 mmol), 0.42 g PdCl$_2$(PPh$_3$)$_2$ (0.6 mmol) were added in 40 mL dry TEA. After stirring for 10 minutes, 2.64 g 1-ethynyl-4-fluoro-benzene (22 mmol) was added and the solution was heated to 100° C. and stirred overnight. The reaction mixture was cooled down, diluted with water and then it was extracted with EtOAc. The combined organic layers were dried over $Na_2SO_4$, filtered and concentrated under reduced pressure. The crude product was purified via flash chromatography using heptane and EtOAc as eluents to obtain 2-chloro-3-[2-(4-fluorophenyl) ethynyl]pyridine. $^1$H NMR (500 MHz, DMSO-$d_6$) δ 8.44 (dd, 1H), 8.14 (dd, 1H), 7.68 (t, 2H), 7.51 (dd, 1H), 7.33 (t, 2H)

Step B: 2-(4-fluorophenyl)thieno[2,3-b]pyridine 2.95 g 2-chloro-3-[2-(4-fluorophenyl)ethynyl]pyridine (12.7 mmol) and 3.97 g $Na_2S$ (51 mmol) were placed in a 250 mL flask. 120 mL DMF was added and the mixture was stirred at 130° C. for 2 hours. Then the reaction mixture was cooled down, diluted with water and then it was extracted with EtOAc. The combined organic layers were dried over $Na_2SO_4$, filtered and concentrated under reduced pressure. The crude product was purified via flash chromatography using heptane and EtOAc as eluents to obtain 2-(4-fluorophenyl)thieno[2,3-b]pyridine. MS (M+H): 230.2

Step C: 2-(4-fluorophenyl)thieno[2,3-b]pyridine N-oxide 1.94 g 2-(4-fluorophenyl)thieno[2,3-b]pyridine (8.4 mmol) was dissolved in DCM (50 mL) and cooled to 0° C. 3.12 g MCPBA (12.6 mmol) was added portionwise and stirred at r.t. for 6 hours. Then it was concentrated under reduced pressure and the crude product was purified via flash chromatography using DCM and methanol as eluents. MS (M+H): 246.2

Step D: 4-chloro-2-(4-fluorophenyl)thieno[2,3-b] pyridine 1.56 g 2-(4-fluorophenyl)-7-oxido-thieno[2,3-b]pyridin-7-ium (6.4 mmol) was dissolved in 50 mL $CHCl_3$. 15.7 mL $POCl_3$ (25.76 g, 168 mmol) was added and the reaction mixture was stirred at reflux temperature for 3 hours. Then it was cooled down, ice and saturated aqueous $NaHCO_3$ was added and it was extracted with $CHCl_3$. The combined organic layers were dried over $Na_2SO_4$, filtered and concentrated under reduced pressure. The crude product was purified via flash chromatography using DCM and methanol as eluents to obtain 4-chloro-2-(4-fluorophenyl)thieno[2,3-b]pyridine. MS (M+H): 264.0

Step E: 3-bromo-4-chloro-2-(4-fluorophenyl)thieno [2,3-b]pyridine 1.15 g $Br_2$ (7.2 mmol) was added dropwise to a mixture of 1.46 g 4-chloro-2-(4-fluorophenyl)thieno[2,3-b]pyridine (5.5 mmol), 0.52 g $K_2HPO_4$ (3.0 mmol), 0.46 g $NaHCO_3$ (5.5 mmol) and 1.12 g $MgSO_4$ (9.2 mmol) in 20 mL $CHCl_3$. The mixture was stirred overnight at reflux temperature. Then, the reaction was cooled down and filtered. The filtrate was concentrated under reduced pressure. The crude product was purified via flash chromatography using DCM and methanol as eluents to obtain 3-bromo-4-chloro-2-(4-fluorophenyl)thieno[2,3-b]pyridine. $^1$H NMR (500 MHz, DMSO-$d_6$) δ 8.59 (d, 1H), 7.76 (m, 2H), 7.71 (d, 1H), 7.42 (m, 2H)

Step F: 3-bromo-2-(4-fluorophenyl)thieno[2,3-b] pyridin-4-ol

The mixture of 0.206 g 3-bromo-4-chloro-2-(4-fluorophenyl)thieno[2,3-b]pyridine (0.6 mmol), 0.492 g sodium acetate (6 mmol), 12 mL AcOH and 0.18 mL $H_2O$ was heated at 150° C. via MW irradiation for 5 hours. Water was added and the product was collected by filtration. $^1$H NMR (500 MHz, DMSO-$d_6$) δ 11.63 (br s, 1H), 8.30 (br s, 1H), 7.72 (m, 2H), 7.38 (m, 2H), 6.87 (br s, 1H)

Step G: Ethyl (2R)-2-[3-bromo-2-(4-fluorophenyl) thieno[2,3-b]pyridin-4-yl]oxy-3-[2-[[2-(2-methoxyphenyl)pyrimidin-4-yl]methoxy]phenyl]propanoate 0.324 g 3-bromo-2-(4-fluorophenyl)thieno[2,3-b]pyridin-4-ol (1 mmol), 0.613 g Preparation 2d (1.5 mmol), 0.691 g DTAD (3 mmol) and 0.787 g $PPh_3$ (3 mmol) were dissolved in 10 mL dry THF under $N_2$ atmosphere and the mixture was stirred at r.t. until no further conversion was observed. The solvent was then removed under reduced pressure, the residue was purified via flash chromatography using heptane and EtOAc as eluents to give ethyl (2R)-2-[3-bromo-2-(4-fluorophenyl)thieno[2,3-b]pyridin-4-yl]oxy-3-[2-[[2-(2-methoxyphenyl)pyrimidin-4-yl]methoxy]phenyl]propanoate. $^1$H NMR (500 MHz, DMSO-$d_6$) δ 8.86 (d, 1H), 8.33 (d, 1H), 7.72 (m, 2H), 7.61 (d, 1H), 7.51 (dd, 1H), 7.45 (td, 1H), 7.44 (d, 1H), 7.39 (m, 2H), 7.25 (td, 1H), 7.14 (d, 1H), 7.10 (d, 1H), 7.03 (td, 1H), 6.93 (t, 1H), 6.88 (d, 1H), 5.55 (dd, 1H), 5.30 (d, 1H), 5.26 (d, 1H), 4.16 (m, 2H), 3.75 (s, 3H), 3.58 (dd, 1H), 3.35 (dd, 1H), 1.13 (t, 3H)

Step H: Example 71

0.288 g (2R)-2-[3-bromo-2-(4-fluorophenyl)thieno[2,3-b]pyridin-4-yl]oxy-3-[2-[[2-(2-methoxyphenyl)pyrimidin-4-yl]methoxy]phenyl]propanoate (0.4 mmol), 0.472 g Preparation 3b (1.2 mmol), 0.028 g Ataphos (0.004 mmol) and 0.392 g $Cs_2CO_3$ (1.2 mmol) were dissolved in a mixture of dioxane (4 mL) and water (3 mL) and stirred under $N_2$ at 70° C. until no further conversion was observed. Then the mixture was diluted with water and extracted with DCM. The combined organic phases were dried over $Na_2SO_4$ and concentrated under reduced pressure. The crude product was purified was purified via flash chromatography using DCM and methanol as eluents. The obtained intermediate was dissolved in a mixture of dioxane (7 mL) and water (7 mL) and 0.168 g LiOH×$H_2O$ (4 mmol) was added. The mixture was stirred at r.t. until no further conversion was observed. Then it was diluted with brine, neutralized with 2M aqueous HCl, extracted with DCM. The combined organic phases were dried over $Na_2SO_4$, filtered and the filtrate was concentrated under reduced pressure. The diastereoisomers were purified and separated by preparative reversed phase chromatography using 5 mM aqueous $NH_4HCO_3$ solution and MeCN as eluents. The diastereomer eluting later was collected as Example 71. HRMS calculated for $C_{48}H_{45}ClFN_5O_6S$: 873.2763; found 437.6441 (M+2H).

Example 72: (2R)-2-[5-[3-chloro-2-methyl-4-[2-(4-methylpiperazin-1-yl)ethoxy]phenyl]-6-(4-fluorophenyl)-7-methyl-pyrrolo[2,3-d]pyrimidin-4-yl]oxy-3-[2-[[2-(2-methoxyphenyl)pyrimidin-4-yl]methoxy] phenyl]propanoic Acid Step A: Ethyl 2-amino-5-(4-fluorophenyl)-1H-pyrrole-3-carboxylate The solution of 3330 mg ethyl 3-amino-3-imino-propanoate (20 mmol) and 4340 mg 2-bromo-1-(4-fluorophenyl) ethanone (20 mmol) in 40 mL ethanol was stirred at r.t. for 30 minutes, then 20 mL lM NaOEt solution in ethanol (20 mmol) was added at 0° C., then it was stirred at 60° C. for 90 minutes. Additional 13 mL lM NaOEt solution in ethanol (13 mmol) was added at room temperature and it was stirred at 60° C. for further 1 hour. The reaction mixture was concentrated under reduced pressure, diluted with 40 mL water then it was extracted with ethyl acetate. The combined organic phase was dried over $MgSO_4$, filtered and the filtrate was concentrated under reduced pressure. The residue was purified via flash chromatography using heptane and EtOAc as eluents to obtain ethyl 2-amino-5-(4-fluorophenyl)-1H-pyrrole-3-carboxylate. $^1H$ NMR (400 MHz, DMSO-$d_6$) δ: 10.75 (br s, 1H), 7.52 (m, 2H), 7.14 (m, 2H), 6.44 (d, 1H), 5.68 (br s, 2H), 4.14 (q, 2H), 1.25 (t, 3H)

Step B: 6-(4-fluorophenyl)-3,7-dihydropyrrolo[2,3-d]pyrimidin-4-one

The solution of 6.83 g ethyl 2-amino-5-(4-fluorophenyl)-1H-pyrrole-3-carboxylate (27.5 mmol) and 12 mL formic acid in 50 mL formamide and 24 mL DMF was stirred at 160° C. for 16 hours in a sealed reaction vessel. The reaction mixture was cooled to room temperature; 150 mL 2-propanol was added. The precipitate was filtered, washed with heptane, then it was dried under reduced pressure to obtain 6-(4-fluorophenyl)-3,7-dihydropyrrolo[2,3-d]pyrimidin-4-one. $^1H$ NMR (400 MHz, DMSO-$d_6$) δ: 12.36 (br s, 1H), 11.88 (br s, 1H), 7.88 (m, 3H), 7.27 (t, 2H), 6.93 (s, 1H)

Step C: 4-chloro-6-(4-fluorophenyl)-7H-pyrrolo[2,3-d]pyrimidine

The solution of 4.50 g 6-(4-fluorophenyl)-3,7-dihydropyrrolo[2,3-d]pyrimidin-4-one (19.6 mmol) in 46 mL $POCl_3$ (491 mmol) was stirred at 90° C. for 3 hours. It was concentrated under reduced pressure, the residue was poured onto ice. The pH was adjusted to 7 using solid $K_2CO_3$, then the mixture was extracted with ethyl acetate. The combined organic phase was washed with brine, then it was dried over $MgSO_4$, filtered and the filtrate was concentrated under reduced pressure to give 4-chloro-6-(4-fluorophenyl)-7H-pyrrolo[2,3-d]pyrimidine. $^1H$ NMR (400 MHz, DMSO-$d_6$) δ: 13.04 (br s, 1H), 8.60 (s, 1H), 8.08 (m, 2H), 7.37 (t, 2H), 7.10 (d, 1H)

Step D: 4-chloro-6-(4-fluorophenyl)-7-methyl-pyrrolo[2,3-d]pyrimidine

To the solution of 1.87 g 4-chloro-6-(4-fluorophenyl)-7H-pyrrolo[2,3-d]pyrimidine (7.55 mmol) in 38 mL DMF 1.286 g MeI (9.06 mmol) then 1.15 g $K_2CO_3$ (8.30 mmol) was added and it was stirred at r.t. for 1 hour. The reaction mixture was concentrated under reduced pressure. The residue was diluted with brine, and it was extracted with dichloromethane. The combined organic phase was dried over $MgSO_4$, filtered and the filtrate was concentrated under reduced pressure, then the residue was purified via flash chromatography using heptane and ethyl acetate as eluents to obtain 4-chloro-6-(4-fluorophenyl)-7-methyl-pyrrolo[2,3-d]pyrimidine. $^1H$ NMR (400 MHz, DMSO-$d_6$) δ: 8.69 (s, 1H), 7.79 (m, 2H), 7.42 (m, 2H), 6.80 (s, 1H), 3.83 (s, 3H)

Step E: 5-bromo-4-chloro-6-(4-fluorophenyl)-7-methyl-pyrrolo[2,3-d]pyrimidine

To the solution of 1.36 g 4-chloro-6-(4-fluorophenyl)-7-methyl-pyrrolo[2,3-d]pyrimidine (5.20 mmol) in 16 mL acetic acid 5.46 mL lM $Br_2$ solution in acetic acid (5.46 mmol) was added dropwise at 0° C., then the reaction mixture was stirred at r.t. for 30 minutes. The reaction mixture was concentrated under reduced pressure, then the residue was diluted with saturated aqueous $NaHCO_3$ solution and it was extracted with ethyl acetate. The combined organic phase was dried over $MgSO_4$, filtered and the filtrate was concentrated under reduced pressure. The crude product was purified via flash chromatography using heptane and ethyl acetate as eluents to obtain 5-bromo-4-chloro-6-(4-fluorophenyl)-7-methyl-pyrrolo[2,3-d]pyrimidine. $^1H$ NMR (400 MHz, DMSO-$d_6$) δ: 8.73 (s, 1H), 7.70 (m, 2H), 7.47 (m, 2H), 3.69 (s, 3H)

Step F: Ethyl (2R)-2-[5-bromo-6-(4-fluorophenyl)-7-methyl-pyrrolo[2,3-d]pyrimidin-4-yl]oxy-3-[2-[[2-(2-methoxyphenyl)pyrimidin-4-yl]methoxy]phenyl]propanoate 845 mg 5-bromo-4-chloro-6-(4-fluorophenyl)-7-methyl-pyrrolo[2,3-d]pyrimidine (2.48 mmol), 1.27 g Preparation 2c (3.11 mmol) was dissolved in 10 mL DMF, then 2.43 g $Cs_2CO_3$ (7.44 mmol) was added and the mixture was stirred at 60° C. for 6 hours. The reaction mixture was concentrated under reduced pressure, it was diluted with brine, and then the mixture was extracted with ethyl acetate. The combined organic phase was dried over $MgSO_4$, filtered and the filtrate was concentrated under reduced pressure, then the residue was purified via flash chromatography using heptane and ethyl acetate as eluents to obtain ethyl (2R)-2-[5-bromo-6-(4-fluorophenyl)-7-methyl-pyrrolo[2,3-d]pyrimidin-4-yl]oxy-3-[2-[[2-(2-methoxyphenyl)pyrimidin-4-yl]methoxy]phenyl]propanoate. MS (M+H): 712.0

Step G: Example 72

Using General Procedure II and ethyl (2R)-2-[5-bromo-6-(4-fluorophenyl)-7-methyl-pyrrolo[2,3-d]pyrimidin-4-yl]oxy-3-[2-[[2-(2-methoxyphenyl)pyrimidin-4-yl]methoxy]phenyl]propanoate instead of 5-bromo-furo[2,3-d]pyrimidyl-lactic ester, and using Preparation 3b as the appropriate boronic acid derivative, Example 72 was obtained as a mixture of diastereoisomers. HRMS calculated for $C_{48}H_{47}ClFN_7O_6$: 871.3260; found 436.6703 and 436.6710 (M+2H).

Example 73: 2-{[3-{3,5-dichloro-2,6-dimethyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl) pyrimidin-4-yl]methoxy}phenyl) propanoic Acid Example 74: 2-{[3-{2,6-dimethyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl) propanoic Acid Example 75: 1-[(dimethylcarbamoyl)oxy]ethyl (2R)-2-{[(3S$_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl) propanoate 591 mg dimethylamine hydrochloride (7.25 mmol) and 1.20 mL pyridine (14.9 mmol) were dissolved in 18 mL dry DCM under nitrogen atmosphere, then the mixture was cooled to −78° C. and 990 mg 1-chloroethyl chloroformate (6.9 mmol) was added. The reaction mixture was stirred at −78° C. until no further conversion was observed. The cold mixture was filtered and the filtrate was concentrated under reduced pressure (30 mbar) using a 30° C. bath. Then it was dissolved in 2 mL dry DMF under nitrogen atmosphere, 60 mg Example 71 (0.069 mmol) and 223 mg $Cs_2CO_3$ (0.55 mmol) were added and the reaction mixture was stirred at r.t. until no further conversion was observed. Then the mixture was diluted with brine, extracted with EtOAc. The combined organic layer was dried over $Na_2SO_4$, filtered and the filtrate was concentrated under reduced pressure. The crude product was purified via reversed phase chromatography using 5 mM aqueous $NH_4HCO_3$ solution and MeCN as eluents to obtain Example 75 as a mixture of diastereoisomers. HRMS calculated for $C_{53}H_{54}ClFN_6O_8S$: 988.3397; found: 495.1782 and 495.1772 (M+2H).

Example 76: 1-[(ethoxycarbonyl)oxy]ethyl (2R)-2-{[(3S$_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl) propanoate 668 mg EtOH (14.5 mmol) and 1.26 g pyridine (15.6 mmol) were dissolved in 18 mL dry DCM under nitrogen atmosphere, then the mixture was cooled to −78° C. and 1.98 g 1-chloroethyl chloroformate (13.8 mmol) was added. The reaction mixture was stirred at −78° C. until no further conversion was observed. The cold mixture was filtered and the filtrate was concentrated under reduced pressure (30 mbar) using a 30° C. bath. Then it was dissolved in 2 mL dry DMF under nitrogen atmosphere, 60 mg Example 71 (0.069 mmol) and 223 mg $Cs_2CO_3$ (0.55 mmol) were added and the reaction mixture was stirred at r.t. until no further conversion was observed. Then the mixture was filtered and the filtrate was purified via reversed phase chromatography using 5 mM aqueous $NH_4HCO_3$ solution and MeCN as eluents to obtain Example 76 as a mixture of diastereoisomers. HRMS calculated for $C_{53}H_{53}ClFN_5O_9S$: 989.3237; found: 990.3342 and 990.3314 (M+H).

Example 77: 2-{[3-{3-chloro-2-methyl-4-[2-(4-methylpiperazin-1-yl)ethoxy]phenyl}-2-(4-fluorophenyl)thieno[2,3-b]pyridin-4-yl]oxy}-3-hydroxy-3-(2-{[2-(2-methoxyphenyl) pyrimidin-4-yl]methoxy}phenyl)propanoic Acid Example 78: 2-{[3-{3-chloro-2-methyl-4-[2-(4-methylpiperazin-1-yl)ethoxy]phenyl}-2-(4-fluorophenyl)thieno[2,3-b]pyridin-4-yl]oxy}-4-hydroxy-3-(2-{[2-(2-methoxyphenyl) pyrimidin-4-yl]methoxy}phenyl)butanoic Acid Example 79: 2-O-[3-{3-chloro-2-methyl-4-[2-(4-methylpiperazin-1-yl)ethoxy]phenyl}-2-(4-fluorophenyl)thieno[2,3-b]pyridin-4-yl]-3,4-dideoxy-3-(2-{[2-(2-methoxyphenyl) pyrimidin-4-yl]methoxy}phenyl)pentonic Acid Example 80: 2-{[3-{3-chloro-2-methyl-4-[2-(4-methylpiperazin-1-yl)ethoxy]phenyl}-2-(4-fluorophenyl)thieno[2,3-b]pyridin-4-yl]oxy}-3-[2-({2-[5-(hydroxymethyl)pyridin-3-yl]pyrimidin-4-yl}methoxy)phenyl]propanoic Acid Example 81: 2-{[3-{3-chloro-2-methyl-4-[2-(4-methylpiperazin-1-yl)ethoxy]phenyl}-2-(4-fluorophenyl)thieno[2,3-b]pyridin-4-yl]oxy}-3-{2-[(2-{2-[(2-hydroxyethoxy)methyl]phenyl}pyrimidin-4-yl)methoxy]phenyl}propanoic Acid Example 82: 2-{[3-{3-chloro-2-methyl-4-[2-(4-methylpiperazin-1-yl)ethoxy]phenyl}-2-(4-fluorophenyl)thieno[2,3-b]pyridin-4-yl]oxy}-3-{2-[(2-{4-[2-(dimethylamino)ethoxy]phenyl}pyrimidin-4-yl)methoxy]phenyl}propanoic Acid Example 83: 2-{[3-{3-chloro-2-methyl-4-[2-(4-methylpiperazin-1-yl)ethoxy]phenyl}-2-(4-fluorophenyl)thieno[2,3-b]pyridin-4-yl]oxy}-3-[2-({2-[3-(phosphonooxy)phenyl]pyrimidin-4-yl}methoxy) phenyl]propanoic Acid Example 84: N-[3-{3-chloro-2-methyl-4-[2-(4-methylpiperazin-1-yl)ethoxy]phenyl}-2-(4-fluorophenyl)thieno[2,3-b]pyridin-4-yl]-2-{[2-(2-methoxyphenyl)pyrimidin-4-yl]methoxy}-D-phenylalanine Step A: ethyl (2R)-2-[[3-bromo-2-(4-fluorophenyl)thieno[2,3-b]pyridin-4-yl]amino]-3-[2-[[2-(2-methoxyphenyl)pyrimidin-4-yl]methoxy]phenyl]propanoate 343 mg 3-bromo-4-chloro-2-(4-fluorophenyl)thieno[2,3-b]pyridine (Step E in Example 71, 1.0 mmol) and 455 mg Preparation 2i (1.20 mmol) were dissolved in 5 mL dry DMSO, then 978 mg $Cs_2CO_3$ (3.0 mmol) was added and the mixture was stirred under nitrogen atmosphere at 100° C.

until no further conversion was observed. Then it was diluted with brine, neutralized with 2 M aqueous HCl solution, and extracted with DCM. The combined organic phase was dried over $Na_2SO_4$, filtered and the filtrate was concentrated under reduced pressure. Then it was dissolved 1.5 mL 1.25 M HCl solution in EtOH, and the mixture was stirred at 60° C. until the ester formation was complete. Then it was carefully neutralized with saturated aqueous $NaHCO_3$ solution, extracted with DCM. The combined organic phase was dried over $Na_2SO_4$, filtered and the filtrate was concentrated under reduced pressure. The crude product was purified via flash chromatography using heptane and EtOAc as eluents.

$^1$H NMR (500 MHz, DMSO-$d_6$) δ: 8.77 (d, 1H), 8.07 (d, 1H), 7.6 (m, 2H), 7.52-6.88 (m, 8H), 7.37 (d, 1H), 7.34 (m, 2H), 7.05 (d, 1H), 6.57 (d, 1H), 5.23/5.19 (d+d, 2H), 4.92 (m, 1H), 4.12 (m, 2H), 3.73 (s, 3H), 3.44/3.25 (dd+dd, 2H), 1.14 (t, 3H)

HRMS calculated for $C_{36}H_{30}BrFN_4O_4S$: 712.1155; found: 357.0649 (M+2H).

Step B: ethyl (2R)-2-[[3-(3-chloro-4-hydroxy-2-methyl-phenyl)-2-(4-fluorophenyl)thieno[2,3-b]pyridin-4-yl]amino]-3-[2-[[2-(2-methoxyphenyl)pyrimidin-4-yl]methoxy]phenyl]propanoate 178 mg ethyl (2R)-2-[[3-bromo-2-(4-fluorophenyl)thieno[2,3-b]pyridin-4-yl]amino]-3-[2-[[2-(2-methoxyphenyl)pyrimidin-4-yl]methoxy]phenyl]propanoate (0.249 mmol) and 107 mg Preparation 3a (0.4 mmol) were dissolved in 1 mL 1,4-dioxane under nitrogen atmosphere, then 163 mg $Cs_2CO_3$ (0.50 mmol), 0.5 mL water and 28 mg AtaPhos (0.04 mmol) were added and the mixture was stirred in a microwave reactor at 111° C. for 15 minutes. Then it was diluted with brine, neutralized with 2 M aqueous HCl solution, and extracted with DCM. The combined organic phase was dried over $Na_2SO_4$, filtered and the filtrate was concentrated under reduced pressure. The crude product was purified via flash chromatography using heptane and EtOAc as eluents to obtain ethyl (2R)-2-[[3-(3-chloro-4-hydroxy-2-methyl-phenyl)-2-(4-fluorophenyl)thieno[2,3-b]pyridin-4-yl]amino]-3-[2-[[2-(2-methoxyphenyl)pyrimidin-4-yl]methoxy]phenyl]propanoate as a mixture of atropoisomers. HRMS calculated for $C_{43}H_{36}ClFN_4O_5S$: 774.2079; found: 388.1113 (M+2H).

Step C: Example 84

80 mg ethyl (2R)-2-[[3-(3-chloro-4-hydroxy-2-methyl-phenyl)-2-(4-fluorophenyl)thieno[2,3-b]pyridin-4-yl]amino]-3-[2-[[2-(2-methoxyphenyl)pyrimidin-4-yl]methoxy]phenyl]propanoate (0.103 mmol), 43 mg 2-(4-methylpiperazin-1-yl)ethanol (0.30 mmol), and 79 mg $PPh_3$ (0.30 mmol) were dissolved in 1 mL dry toluene, then 69 mg DTAD (0.30 mmol) was added and the mixture was stirred at 50° C. under nitrogen atmosphere until no further conversion was observed. Then the mixture was concentrated under reduced pressure and the residue was purified via flash chromatography using EtOAc and MeOH as eluents. The obtained ester derivative was dissolved in 1 mL THF, then 80 mg LiOH×$H_2O$ and 1 mL water were added and the mixture was stirred at r.t. until the hydrolysis was complete. Then it was diluted with brine, neutralized with 2 M aqueous HCl solution, and extracted with DCM. The combined organic phase was dried over $Na_2SO_4$, filtered and the filtrate was concentrated under reduced pressure. The crude product was purified via reversed phase chromatography using 25 mM aqueous $NH_4HCO_3$ solution and MeCN as eluents to obtain Example 84 as a 7:3 mixture of diastereoisomers. HRMS calculated for $C_{48}H_{46}ClFN_6O_5S$: 872.2923; found: 437.1540 and 437.1538 (M+2H).

Example 85: 2-{[3-{3-chloro-2-methyl-4-[2-(4-methylpiperazin-1-yl)ethoxy]phenyl}-2-(4-fluorophenyl)thieno[3,2-c]pyridin-4-yl]oxy}-3-(2-{[2-(2-methoxyphenyl)pyrimidin-4-yl]methoxy}phenyl) propanoic Acid Example 86: N-[3-{3-chloro-2-methyl-4-[2-(4-methylpiperazin-1-yl)ethoxy]phenyl}-2-(4-fluorophenyl)thieno[3,2-c]pyridin-4-yl]-2-{[2-(2-methoxyphenyl)pyrimidin-4-yl]methoxy}phenylalanine Step A: 3-bromo-4-chloro-2-iodo-thieno[3,2-c]pyridine 4.97 g 3-bromo-4-chloro-thieno[3,2-c]pyridine (20.0 mmol) was dissolved in 50 mL dry THF under argon atmosphere and the mixture was cooled to −45° C. Then 22 mL Mg(TMP)Cl×LiCl solution (22 mmol, 1 M in THF) was added dropwise and the mixture was stirred for 1 hour at −45° C., then 1 hour at 0° C., then it was cooled to −45° C. again.

Then 5.58 g iodine (22 mmol, dissolved in 20 mL dry, cold THF) was added dropwise and the mixture was stirred at −45° C. for 2 hours. Then it was allowed to warm up to r.t. and concentrated under reduced pressure. The residue was poured onto 300 mL brine, and extracted with EtOAc. The combined organic phase was washed with saturated aqueous $Na_2SO_3$ solution, saturated aqueous $NH_4Cl$ solution, then with water and then dried over $Na_2SO_4$, filtered and the filtrate was concentrated under reduced pressure.

The crude product was purified via flash chromatography using hexanes and EtOAc as eluents.

$^1$H NMR (500 MHz, DMSO-d$_6$) δ: 8.27 (d, 1H), 8.17 (d, 1H)

HRMS calculated for C$_7$H$_2$BrClINS: 372.7824; found: 373.7916 (M+H).

Step B: 3-bromo-4-chloro-2-(4-fluorophenyl)thieno [3,2-c]pyridine 2.62 g 3-bromo-4-chloro-2-iodo-thieno[3,2-c]pyridine (7.0 mmol) and 2.33 g 2-(4-fluorophenyl)-4,4,5,5-tetramethyl-1,3,2-dioxaborolane (10.5 mmol) were dissolved in 18 mL THF under argon atmosphere, then 6.84 g Cs$_2$CO$_3$ (21 mmol), 18 mL water, 79 mg Pd(OAc)$_2$ (0.35 mmol) and 297 mg $^t$BuXPhos (0.70 mmol) were added and the mixture was stirred at 70° C. until no further conversion was observed. Then the volatiles were evaporated under reduced pressure. The residue was diluted with water and extracted with EtOAc. The combined organic phase was washed with saturated aqueous NH$_4$Cl solution, then with brine and then dried over Na$_2$SO$_4$, filtered and the filtrate was concentrated under reduced pressure. The crude product was purified via flash chromatography using hexanes and EtOAc as eluents.

$^1$H NMR (500 MHz, DMSO-d$_6$) δ: 8.35 (d, 1H), 8.26 (d, 1H), 7.74 (dd, 2H), 7.42 (t, 2H) HRMS calculated for C$_{13}$H$_6$BrClFNS: 340.9077; found: 341.9144 (M+H).

Step C: ethyl (2R)-2-[[3-bromo-2-(4-fluorophenyl) thieno[3,2-c]pyridin-4-yl]amino]-3-[2-[[2-(2-methoxyphenyl)pyrimidin-4-yl]methoxy]phenyl] propanoate 343 mg 3-bromo-4-chloro-2-(4-fluorophenyl)thieno[3,2-c]pyridine (1.0 mmol) and 455 mg Preparation 2i (1.20 mmol) were dissolved in 5 mL dry DMSO, then 978 mg Cs$_2$CO$_3$ (3.00 mmol) was added and the mixture was stirred under nitrogen atmosphere at 100° C. until no further conversion was observed. Then it was diluted with brine, neutralized with 2 M aqueous HCl solution, and extracted with DCM. The combined organic phase was dried over Na$_2$SO$_4$, filtered and the filtrate was concentrated under reduced pressure. Then it was dissolved 1.5 mL 1.25 M HCl solution in EtOH, and the mixture was stirred at 60° C. until the ester formation was complete. Then it was carefully neutralized with saturated aqueous NaHCO$_3$ solution, extracted with DCM. The combined organic phase was dried over Na$_2$SO$_4$, filtered and the filtrate was concentrated under reduced pressure. The crude product was purified via flash chromatography using heptane and EtOAc as eluents. HRMS calculated for C$_{36}$H$_{30}$BrFN$_4$O$_4$S: 712.1155; found: 713.1209 (M+H).

Step D: ethyl (2R)-2-[[3-(3-chloro-4-hydroxy-2-methyl-phenyl)-2-(4-fluorophenyl)thieno[3,2-c]pyridin-4-yl]amino]-3-[2-[[2-(2-methoxyphenyl)pyrimidin-4-yl]methoxy]phenyl]propanoate 31 mg ethyl (2R)-2-[[3-bromo-2-(4-fluorophenyl)thieno[3,2-c]pyridin-4-yl]amino]-3-[2-[[2-(2-methoxyphenyl)pyrimidin-4-yl]methoxy]phenyl]propanoate (0.043 mmol) and 24 mg Preparation 3a (0.09 mmol) were dissolved in 0.5 mL 1,4-dioxane under nitrogen atmosphere, then 33 mg Cs$_2$CO$_3$ (0.10 mmol), 0.5 mL water and 9.4 mg AtaPhos (0.013 mmol) were added and the mixture was stirred in a microwave reactor at 111° C. for 10 minutes. Then it was diluted with brine, neutralized with 2 M aqueous HCl solution, and extracted with DCM. The combined organic phase was dried over Na$_2$SO$_4$, filtered and the filtrate was concentrated under reduced pressure. The crude product was purified via flash chromatography using heptane and EtOAc as eluents to obtain ethyl (2R)-2-[[3-(3-chloro-4-hydroxy-2-methyl-phenyl)-2-(4-fluorophenyl)thieno[3,2-c]pyridin-4-yl]amino]-3-[2-[[2-(2-methoxyphenyl)pyrimidin-4-yl]methoxy]phenyl] propanoate as a mixture of atropoisomers. HRMS calculated for C$_{43}$H$_{36}$ClFN$_4$O$_5$S: 774.2079; found: 775.2134 (M+H).

Step E: Example 86

33 mg ethyl (2R)-2-[[3-(3-chloro-4-hydroxy-2-methylphenyl)-2-(4-fluorophenyl)thieno[3,2-c]pyridin-4-yl] amino]-3-[2-[[2-(2-methoxyphenyl)pyrimidin-4-yl] methoxy]phenyl]propanoate (0.04 mmol), 15 mg 2-(4-methylpiperazin-1-yl)ethanol (0.10 mmol), and 26 mg PPh$_3$ (0.10 mmol) were dissolved in 1 mL dry toluene, then 23 mg DTAD (0.10 mmol) was added and the mixture was stirred at 50° C. under nitrogen atmosphere until no further conversion was observed. Then the mixture was concentrated under reduced pressure and the residue was purified via flash chromatography using EtOAc and MeOH as eluents. The obtained ester derivative was dissolved in 1 mL THF, then 80 mg LiOH×H$_2$O and 1 mL water were added and the mixture was stirred at rt until the hydrolysis was complete. Then it was diluted with brine, neutralized with 2 M aqueous HCl solution, and extracted with DCM. The combined organic phase was dried over Na$_2$SO$_4$, filtered and the filtrate was concentrated under reduced pressure. The crude product was purified via reversed phase chromatography using 25 mM aqueous NH$_4$HCO$_3$ solution and MeCN as eluents to obtain Example 86 as a 10:3 mixture of diastereoisomers. HRMS calculated for C$_{48}$H$_{46}$ClFN$_6$O$_5$S: 872.2923; found: 437.1549 and 437.1532 (M+2H).

Example 87: 2-{[3-{3-chloro-2-methyl-4-[2-(4-methylpiperazin-1-yl)ethoxy]phenyl}-2-(4-fluorophenyl)thieno[2,3-c]pyridin-4-yl]oxy}-3-(2-{[2-(2-methoxyphenyl)pyrimidin-4-yl]methoxy}phenyl) propanoic Acid Example 88: N-[3-{3-chloro-2-methyl-4-[2-(4-methylpiperazin-1-yl)ethoxy]phenyl}-2-(4-fluorophenyl)thieno[2,3-c]pyridin-4-yl]-2-{[2-(2-methoxyphenyl)pyrimidin-4-yl]methoxy}phenylalanine Example 89: 2-{[3-{3-chloro-2-methyl-4-[2-(4-methylpiperazin-1-yl)ethoxy]phenyl}-2-(4-fluorophenyl)thieno[2,3-d]pyridazin-4-yl]oxy}-3-(2-{[2-(2-methoxyphenyl) pyrimidin-4-yl]methoxy}phenyl) propanoic Acid Example 90: N-[3-{3-chloro-2-methyl-4-[2-(4-methylpiperazin-1-yl)ethoxy]phenyl}-2-(4-fluorophenyl)thieno[2,3-d]pyridazin-4-yl]-2-{[2-(2-methoxyphenyl)pyrimidin-4-yl] methoxy}phenylalanine Example 91: 2-{[5-{3-chloro-2-methyl-4-[2-(4-methylpiperazin-1-yl)ethoxy]phenyl}-6-(4-fluorophenyl)thieno[2,3-c]pyridazin-4-yl]oxy}-3-(2-{[2-(2-methoxyphenyl) pyrimidin-4-yl]methoxy}phenyl) propanoic Acid Example 92: N-[5-{3-chloro-2-methyl-4-[2-(4-methylpiperazin-1-yl)ethoxy]phenyl}-6-(4-fluorophenyl)thieno[2,3-c]pyridazin-4-yl]-2-{[2-(2-methoxyphenyl)pyrimidin-4-yl] methoxy}phenylalanine Example 93: 2-{[3-{3-chloro-2-methyl-4-[2-(4-methylpiperazin-1-yl)ethoxy]phenyl}-2-(4-fluorophenyl)furo[2,3-b]pyridin-4-yl]oxy}-3-(2-{[2-(2-methoxyphenyl)pyrimidin-4-yl]methoxy}phenyl) propanoic Acid Example 94: N-[3-{3-chloro-2-methyl-4-[2-(4-methylpiperazin-1-yl)ethoxy]phenyl}-2-(4-fluorophenyl)furo[2,3-b]pyridin-4-yl]-2-{[2-(2-methoxyphenyl)pyrimidin-4-yl]methoxy}phenylalanine Example 95: 2-{[3-{3-chloro-2-methyl-4-[2-(4-methylpiperazin-1-yl)ethoxy]phenyl}-2-(4-fluorophenyl)furo[3,2-c]pyridin-4-yl]oxy}-3-(2-{[2-(2-methoxyphenyl)pyrimidin-4-yl]methoxy}phenyl) propanoic Acid Example 96: N-[3-{3-chloro-2-methyl-4-[2-(4-methylpiperazin-1-yl)ethoxy]phenyl}-2-(4-fluorophenyl)furo[3,2-c]pyridin-4-yl]-2-{[2-(2-methoxyphenyl)pyrimidin-4-yl]methoxy}phenylalanine Example 97a: 2-{[(3S$_a$)-3-{3-chloro-2-methyl-4-[2-(4-methylpiperazin-1-yl)ethoxy]phenyl}-2-(4-fluorophenyl)imidazo[1,2-c]pyrimidin-5-yl]oxy}-3-(2-{[2-(2-methoxyphenyl)pyrimidin-4-yl]methoxy}phenyl) propanoic Acid and Example 97b: 2-[{(3R$_a$)-3-{3-chloro-2-methyl-4-[2-(4-methylpiperazin-1-yl)ethoxy]phenyl}-2-(4-fluorophenyl)imidazo[1,2-c]pyrimidin-5-yl]oxy}-3-(2-{[2-(2-methoxyphenyl)pyrimidin-4-yl]methoxy}phenyl) propanoic Acid Step A: 1-(2-bromo-1,1-dimethoxy-ethyl)-4-fluoro-benzene 8.68 g 2-bromo-1-(4-fluorophenyl)ethanone (40.0 mmol) was dissolved in 80 mL MeOH, then 8.75 mL CH(OMe)$_3$ (80.0 mmol) and 380 mg TsOH×H$_2$O (2.00 mmol) was added and the mixture was stirred at reflux temperature until no further conversion was observed. Then it was concentrated under reduced pressure and diluted with Et$_2$O. It was washed with 10% aqueous K$_2$CO$_3$ solution, dried over Na$_2$SO$_4$, filtered and the filtrate was concentrated under reduced pressure. $^1$H NMR (250 MHz, CDCl$_3$) δ: 7.53-7.44 (m, 2H), 7.11-7.01 (m, 2H), 3.60 (s, 2H), 3.22 (s, 6H)

Step B: 5-chloro-2-(4-fluorophenyl)imidazo[1,2-c] pyrimidine

A high pressure reaction vessel made of steel was charged with 648 mg 2-chloropyrimidin-4-amine (5.0 mmol), 1.58 g 1-(2-bromo-1,1-dimethoxy-ethyl)-4-fluoro-benzene (6.0 mmol), 123 mg Sc(OTf)$_3$ (0.25 mmol) and 50 mL MeCN and the mixture was stirred at 120° C. for 24 hours. Then it was diluted with DCM and washed with saturated aqueous NaHCO$_3$ solution. The aqueous layer was extracted with DCM. The combined organic layer was dried over MgSO$_4$, filtered and the filtrate was concentrated under reduced pressure. The crude product was purified via flash chromatography using hexanes and EtOAc as eluents. HRMS calculated for C$_{12}$H$_7$ClFN$_3$: 247.0312; found: 248.0397 (M+H).

Step C: 3-bromo-5-chloro-2-(4-fluorophenyl)imidazo[1,2-c]pyrimidine 198 mg 5-chloro-2-(4-fluorophenyl)imidazo[1,2-c]pyrimidine (0.80 mmol) was dissolved in 4.8 mL DMF then 142 mg NBS (0.80 mmol) was added and the mixture was stirred at r.t. until the consumption of the starting material. Then the mixture was poured onto saturated aqueous NaHCO$_3$ solution and the formed precipitate was filtered, washed with water. The crude product was purified via flash chromatography using hexanes and EtOAc as eluents.
$^1$H NMR (500 MHz, DMSO-d$_6$) δ: 8.03 (m, 2H), 7.90 (d, 1H), 7.73 (d, 1H), 7.39 (m, 2H) HRMS calculated for C$_{12}$H$_6$BrClFN$_3$: 324.9418; found: 325.9496 (M+H).

Step D: ethyl (2R)-2-[3-bromo-2-(4-fluorophenyl) imidazo[1,2-c]pyrimidin-5-yl]oxy-3-[2-[[2-(2-methoxyphenyl)pyrimidin-4-yl]methoxy]phenyl] propanoate 102 mg 3-bromo-5-chloro-2-(4-fluorophenyl)imidazo[1,2-c]pyrimidine (0.312 mmol) and 140 mg Preparation 2c (0.344 mmol) were dissolved in 3 mL dry DMSO under nitrogen atmosphere, then 305 mg Cs$_2$CO$_3$ (0.936 mmol) was added and the mixture was stirred at r.t. until no further desired conversion was observed. Then it was diluted with brine and water, neutralized with 2 M aqueous HCl solution, and extracted with DCM. The combined organic phase was dried over Na$_2$SO$_4$, filtered and the filtrate was concentrated under reduced pressure. The crude product was purified via flash chromatography using heptane and EtOAc as eluents.
$^1$H NMR (500 MHz, DMSO-d$_6$) δ: 8.20 (d, 1H), 8.03 (m, 2H), 7.62 (d, 1H), 7.56 (d, 1H), 7.50 (dd, 1H), 7.49 (dd, 1H), 7.42 (ddd, 1H), 7.35 (m, 2H), 7.27 (ddd, 1H), 7.23 (d, 1H), 7.13 (d, 1H), 7.11 (d, 1H), 7.01 (td, 1H), 6.96 (td, 1H), 5.80 (dd, 1H), 5.31/5.27 (d+d, 2H), 4.18/4.15 (m+m, 2H), 3.75 (s, 3H), 3.62/3.36 (dd+dd, 2H), 1.12 (t, 3H)

HRMS calculated for $C_{35}H_{29}BrFN_5O_5$: 697.1336; found: 698.1419 (M+H).

Step E: ethyl (2R)-2-[3-(3-chloro-4-hydroxy-2-methyl-phenyl)-2-(4-fluorophenyl)imidazo[1,2-c]pyrimidin-5-yl]oxy-3-[2-[[2-(2-methoxyphenyl)pyrimidin-4-yl]methoxy]phenyl]propanoate 150 mg ethyl (2R)-2-[3-bromo-2-(4-fluorophenyl)imidazo[1,2-c]pyrimidin-5-yl]oxy-3-[2-[[2-(2-methoxyphenyl)pyrimidin-4-yl]methoxy]phenyl]propanoate (0.215 mmol) and 80.8 mg Preparation 3a (0.301 mmol) were dissolved in 1 mL THF under nitrogen atmosphere, then 140 mg $Cs_2CO_3$ (0.430 mmol), 0.2 mL water and 30.4 mg AtaPhos (0.043 mmol) were added and the mixture was stirred in a microwave reactor at 100° C. for 5 minutes. Then the mixture was diluted with brine, neutralized with 2 M aqueous HCl solution and extracted with DCM. The combined organic phase was dried over $Na_2SO_4$, filtered and the filtrate was concentrated under reduced pressure. The crude product was purified via flash chromatography using heptane and EtOAc as eluents to obtain a mixture of diastereoisomers. HRMS calculated for $C_{42}H_{35}ClFN_5O_6$: 759.2260; found: 760.2370 and 760.2344 (M+H).

Step F: Examples 97a and 97b 11.4 mg ethyl (2R)-2-[3-(3-chloro-4-hydroxy-2-methyl-phenyl)-2-(4-fluorophenyl) imidazo[1,2-c]pyrimidin-5-yl]oxy-3-[2-[[2-(2-methoxyphenyl)pyrimidin-4-yl]methoxy]phenyl]propanoate (0.015 mmol), 7.2 mg 2-(4-methylpiperazin-1-yl)ethanol (0.050 mmol), and 13.1 mg $PPh_3$ (0.050 mmol) were dissolved in 1 mL dry toluene, then 11.5 mg DTAD (0.050 mmol) was added and the mixture was stirred at 50° C. under nitrogen atmosphere until no further conversion was observed. Then the mixture was concentrated under reduced pressure and the residue was purified via flash chromatography using EtOAc and MeOH as eluents. The obtained ester derivative was dissolved in 1 mL THF, then 42 mg LiOH×$H_2O$ and 1 mL water were added and the mixture was stirred at r.t. until the hydrolysis was complete. Then it was diluted with brine, neutralized with 2 M aqueous HCl solution, and extracted with DCM. The combined organic phase was dried over $Na_2SO_4$, filtered and the filtrate was concentrated under reduced pressure. The crude product was purified via reversed phase chromatography using 25 mM aqueous $NH_4HCO_3$ solution and MeCN as eluents. Example 97a was obtained as the earlier eluting diastereoisomer. HRMS calculated for $C_{47}H_{45}ClFN_7O_6$: 857.3104; found: 429.6626 (M+2H).

Example 97b was obtained as the later eluting diastereoisomer. HRMS calculated for $C_{47}H_{45}ClFN_7O_6$: 857.3104; found: 429.6638 (M+2H).

Example 98: N-[3-{3-chloro-2-methyl-4-[2-(4-methylpiperazin-1-yl)ethoxy]phenyl}-2-(4-fluorophenyl)imidazo[1,2-c]pyrimidin-5-yl]-2-{[2-(2-methoxyphenyl)pyrimidin-4-yl]methoxy}phenylalanine Example 99: 2-{[3-{3-chloro-2-methyl-4-[2-(4-methylpiperazin-1-yl)ethoxy]phenyl}-2-(4-fluorophenyl)imidazo[1,2-a]pyrazin-5-yl]oxy}-3-(2-{[2-(2-methoxyphenyl) pyrimidin-4-yl]methoxy}phenyl) propanoic Acid Example 100: N-[3-{3-chloro-2-methyl-4-[2-(4-methylpiperazin-1-yl)ethoxy]phenyl}-2-(4-fluorophenyl)imidazo[1,2-a]pyrazin-5-yl]-2-{[2-(2-methoxyphenyl)pyrimidin-4-yl]methoxy}phenylalanine Example 101: 2-{[3-{3-chloro-2-methyl-4-[2-(4-methylpiperazin-1-yl)ethoxy]phenyl}-2-(4-fluorophenyl)imidazo[1,2-a]pyrimidin-5-yl]oxy}-3-(2-{[2-(2-methoxyphenyl) pyrimidin-4-yl]methoxy}phenyl) propanoic Acid Example 102: N-[3-{3-chloro-2-methyl-4-[2-(4-methylpiperazin-1-yl)ethoxy]phenyl}-2-(4-fluorophenyl)imidazo[1,2-a]pyrimidin-5-yl]-2-{[2-(2-methoxyphenyl)pyrimidin-4-yl]methoxy}-D-phenylalanine Step A: 2-(4-fluorophenyl)-1H-imidazo[1,2-a]pyrimidin-5-one 10.0 g 2-amino-1H-pyrimidin-4-one (90.0 mmol) and 9.77 g 2-bromo-1-(4-fluorophenyl) ethanone (45.0 mmol) were dissolved in 100 mL DMF and the mixture was stirred at 120° C. until no further conversion was observed. Then it was concentrated under reduced pressure and was diluted with EtOAc. Celite was added and the volatiles were evaporated under reduced pressure. The mixture was purified via flash chromatography using heptane and EtOAc as eluents. The regioisomer eluting earlier was collected as 2-(4-fluorophenyl)-1H-imidazo[1,2-a]pyrimidin-5-one. $^1$H NMR (500 MHz, DMSO-$d_6$) δ: 12.98 (br s, 1H), 8.14 (s, 1H), 7.97 (m, 2H), 7.90 (d, 1H), 7.27 (m, 2H), 5.57 (d, 1H)

Step B: 5-chloro-2-(4-fluorophenyl)imidazo[1,2-a]pyrimidine 1.36 g 2-(4-fluorophenyl)-1H-imidazo[1,2-a]pyrimidin-5-one (5.9 mmol) and 16.6 mL $POCl_3$ was stirred at 93° C. for 90 minutes, then the mixture was cooled to r.t. and concentrated under reduced pressure. The residue was poured onto icy-water. After the ice melted the formed precipitate was filtered, washed with water. $^1$H NMR (500 MHz, DMSO-$d_6$) δ: 8.65 (s, 1H), 8.55 (d, 1H), 8.17 (m, 2H), 7.45 (d, 1H), 7.33 (m, 2H)

Step C: 3-bromo-5-chloro-2-(4-fluorophenyl)imidazo[1,2-a]pyrimidine 715 mg 5-chloro-2-(4-fluorophenyl)imidazo[1,2-a]pyrimidine (2.89 mmol) was dissolved in 10 mL chloroform then 570 mg NBS (3.20 mmol) was added and the mixture was stirred at r.t. until the consumption of the starting material. Then the mixture was concentrated under reduced pressure and purified via flash chromatography using heptane and EtOAc as eluents.

$^1$H NMR (500 MHz, DMSO-$d_6$) δ: 8.52 (d, 1H), 8.10 (m, 2H), 7.39 (m, 2H), 7.38 (d, 1H) HRMS calculated for $C_{12}H_6BrClFN_3$: 324.9418; found: 325.9481 (M+H).

Step D: 5-chloro-3-[3-chloro-2-methyl-4-[2-(4-methylpiperazin-1-yl)ethoxy]phenyl]-2-(4-fluorophenyl)imidazo[1,2-a]pyrimidine 620 mg 3-bromo-5-chloro-2-(4-fluorophenyl)imidazo[1,2-a]pyrimidine (1.93 mmol) and 2.37 g Preparation 3b (6.0 mmol) were dissolved in 10 mL THF under nitrogen atmosphere, then 1.30 g $Cs_2CO_3$ (4.00 mmol), 3 mL water and 273 mg AtaPhos (0.386 mmol) were added and the mixture was stirred in a microwave reactor at 110° C. for 10 minutes. Then the mixture was diluted with brine and extracted with DCM. The combined organic phase was dried over $Na_2SO_4$, filtered and the filtrate was concentrated under reduced pressure. The crude product was purified via flash chromatography using EtOAc and MeOH as eluents. LRMS calculated for $C_{26}H_{26}Cl_2FN_5O$: 513.15; found: 514.1 (M+H).

Step E: Example 102

341 mg 5-chloro-3-[3-chloro-2-methyl-4-[2-(4-methylpiperazin-1-yl)ethoxy]phenyl]-2-(4-fluorophenyl)imidazo[1,2-a]pyrimidine (0.66 mmol) and 300 mg Preparation 2i (0.76 mmol) were dissolved in 3 mL dry DMSO under nitrogen atmosphere, then 652 mg $Cs_2CO_3$ (2.0 mmol) was added and the mixture was stirred in a microwave reactor at 160° C. for 10 minutes. Then it was diluted with brine and water, neutralized with 2 M aqueous HCl solution, and extracted with DCM. The combined organic phase was dried over $Na_2SO_4$, filtered and the filtrate was concentrated under reduced pressure. The crude product was purified via reversed phase chromatography using 25 mM aqueous $NH_4HCO_3$ solution and MeCN as eluents to obtain Example 102 as a mixture of diastereoisomers. HRMS calculated for $C_{47}H_{46}ClFN_8O_5$: 856.3264; found: 429.1687 and 429.1705 (M+2H).

Example 103: 2-{[3-{3-chloro-2-methyl-4-[2-(4-methylpiperazin-1-yl)ethoxy]phenyl}-2-(4-fluorophenyl)imidazo[1,2-a]pyridin-5-yl]oxy}-3-(2-{[2-(2-methoxyphenyl) pyrimidin-4-yl]methoxy}phenyl) propanoic Acid Example 104: N-[3-{3-chloro-2-methyl-4-[2-(4-methylpiperazin-1-yl)ethoxy]phenyl}-2-(4-fluorophenyl)imidazo[1,2-a]pyridin-5-yl]-2-{[2-(2-methoxyphenyl)pyrimidin-4-yl]methoxy}phenylalanine Pharmacological Study Example A: Inhibition of Mcl-1 by the Fluorescence Polarisation Technique The relative binding potency of each compound was determined via Fluorescence Polarisation (FP). The method utilised a Fluorescein labelled ligand (Fluorescein-βAla-Ahx-A-REIGAQLRRMADDLNAQY-OH; mw 2,765) which binds to the Mcl-1 protein (such that Mcl-1 corresponds to the UniProtKB® primary accession number: Q07820) leading to an increased anisotropy measured in milli-polarisation (mP) units using a reader. The addition of a compound which binds competitively to the same site as the ligand will result in a greater proportion of unbound ligand in the system indicated by a decrease in mP units.

Method 1:

An 11 point serial dilution of each compound was prepared in DMSO and 2 μl transferred into flat bottomed, low binding, 384-well plate (final DMSO concentration 5%). 38 μl of buffer (10 mM 4-(2-hydroxyethyl)-1-piperazineethanesulfonic acid [HEPES], 150 mM NaCl, 0.05% Tween 20, pH 7.4), containing the Fluorescein labelled ligand (final concentration 1 nM) and Mcl-1 protein (final concentration 5 nM) was then added.

Assay plates were incubated ~2 hours at room temperature before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls. 11-point dose response curves were plotted with XL-Fit software using a 4-Parameter Logistic Model (Sigmoidal Dose-Response Model) and the inhibitory concentrations that gave a 50% reduction in mP ($IC_{50}$) were determined. Results obtained using Method 1 are presented in Table 1 below; $IC_{50}$ of Mcl-1 inhibition obtained using Method 1 are not underlined.

Method 2:

An 11 point serial dilution of each compound was prepared in DMSO and 2 μl transferred into flat bottomed, low binding, 384-well plate (final DMSO concentration 5%). 38 μl of buffer (20 mM $Na_2HPO_4$, 1 mM EDTA, 50 mM NaCl, pH 7.4), containing the Fluorescein labelled ligand (final concentration 10 nM) and Mcl-1 protein (final concentration 10 nM) was then added.

Assay plates were incubated ~2 hours at room temperature before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls (50 aM unlabelled ligand). 11-point dose response curves were plotted with XL-Fit software using a 4-Parameter Logistic Model (Sigmoidal Dose-Response Model) and the inhibitory concentrations that gave a 50% reduction in mP ($IC_{50}$) were determined. Results obtained using Method 2 are presented in Table 1 below; $IC_{50}$ of Mcl-1 inhibition obtained using Method 2 are underlined.

The results show that the compounds of the invention inhibit interaction between the Mcl-1 protein and the fluorescent peptide described hereinbefore.

Example B: In Vitro Cytotoxicity

The cytotoxicity studies were carried out on the H929 multiple myeloma tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

IC$_{50}$ of Mcl-1 inhibition (fluorescence polarisation test) and of cytotoxicity for H929 cells

| | IC$_{50}$ (M) Mcl-1 FP | IC$_{50}$ (M) MTT H929 |
|---|---|---|
| Example 1 | 3.8E−09 | 2.41E−08 |
| Example 2 | 6.0E−09 | 1.45E−08 |
| Example 3 | 1.7E−08 | 3.64E−07 |
| Example 4 | 2.9E−08 | 3.29E−07 |
| Example 5 | 1.5E−08 | 6.19E−07 |
| Example 6 | 8.9E−09 | ND |
| Example 7 | 1.1E−07 | 7.57E−07 |
| Example 8 | 6.6E−09 | 1.78E−08 |
| Example 9 | 8.6E−08 | 6.89E−08 |
| Example 10 | <u>1.8E−05</u> | ND |
| Example 11 | <u>3.4E−05</u> | ND |
| Example 12 | <u>5.6E−07</u> | ND |
| Example 13 | <u>6.6E−07</u> | ND |
| Example 14 | <u>1.2E−05</u> | ND |
| Example 15 | <u>7.3E−06</u> | ND |
| Example 16 | <u>1.8E−06</u> | ND |
| Example 17 | <u>3.8E−06</u> | ND |
| Example 18 | <u>3.1E−06</u> | ND |
| Example 19 | <u>3.3E−06</u> | ND |
| Example 20 | <u>64.8% @ 50 µM</u> | ND |
| Example 21 | <u>8.7E−06</u> | ND |
| Example 22 | <u>74.2% @ 50 µM</u> | ND |
| Example 23 | <u>6.8E−06</u> | ND |
| Example 24 | <u>1.8E−05</u> | ND |
| Example 25 | <u>9.1E−06</u> | ND |
| Example 26 | <u>5.9E−06</u> | ND |
| Example 27 | <u>3.3E−07</u> | ND |
| Example 28 | <u>63.25% @ 50 µM</u> | ND |
| Example 29 | <u>8.5E−06</u> | ND |
| Example 30 | <u>6.4E−06</u> | ND |
| Example 31 | <u>7.9E−07</u> | ND |
| Example 32 | <u>3.5E−06</u> | ND |
| Example 33 | <u>2.6E−07</u> | ND |
| Example 34 | <u>6.4E−06</u> | ND |
| Example 35 | <u>2.9E−07</u> | ND |
| Example 36 | <u>6.5E−06</u> | ND |
| Example 37 | <u>5.3E−07</u> | ND |
| Example 38 | <u>67% @ 50 µM</u> | ND |
| Example 39 | <u>77.75% @ 50 µM</u> | ND |
| Example 40 | 8.6E−07/<u>3.3E−08</u> | ND |
| Example 41 | <u>1.3E−05</u> | ND |
| Example 42 | <u>4.5E−07</u> | ND |
| Example 43 | <u>66.9% @ 50 µM</u> | ND |
| Example 44 | <u>2.5E−06</u> | ND |
| Example 45 | <u>1.8E−06</u> | ND |
| Example 46 | <u>71% @ 50 µM</u> | ND |
| Example 47 | <u>1.1E−05</u> | ND |
| Example 48 | <u>5.9E−06</u> | ND |
| Example 49 | <u>3.9E−08</u> | ND |
| Example 50 | <u>65.85% @ 10 µM</u> | ND |
| Example 51 | 3.6E−07/<u>5.5E−09</u> | 1.10E−05 |
| Example 52 | 1.6E−06 | ND |
| Example 53 | 2.2E−08 | 2.53E−08 |
| Example 54 | <u>1.2E−07</u> | ND |
| Example 55 | <u>55.35% @ 10 µM</u> | ND |
| Example 56 | 4.7E−08 | ND |
| Example 57 | 1.7E−07 | ND |
| Example 58 | <u>51.9% @ 10 µM</u> | ND |
| Example 59 | 3.6E−08 | 1.24E−06 |
| Example 60 | 1.9E−08 | 5.68E−07 |
| Example 61 | <u>52.8% @ 10 µM</u> | ND |
| Example 62 | 8.2E−07 | ND |
| Example 63 | 1.7E−07 | ND |
| Example 64 | 7.4E−09 | 4.71E−08 |
| Example 65 | 1.0E−06 | ND |
| Example 66 | 1.6E−06 | ND |
| Example 67 | 1.4E−08 | 8.36E−08 |
| Example 68 | 1.2E−06 | ND |
| Example 69 | 2.4E−08 | 1.04E−07 |
| Example 70 | <u>13.55% @ 10 µM</u> | ND |
| Example 71 | 5.02E−09 | 9.08E−09 |
| Example 72 | 1.55E−08 | 3.2E−08 |
| Example 73 | ND | ND |
| Example 74 | ND | ND |
| Example 75 | 5.61E−07 | 7.55E−08 |
| Example 76 | 1.34E−07 | 1.01E−08 |
| Example 77 | ND | ND |
| Example 78 | ND | ND |
| Example 79 | ND | ND |
| Example 80 | ND | ND |
| Example 81 | ND | ND |
| Example 82 | ND | ND |
| Example 83 | ND | ND |
| Example 84 | 5.45E−09 | 1.09E−08 |
| Example 85 | ND | ND |
| Example 86 | 3.05E−08 | 3.59E−08 |
| Example 87 | ND | ND |
| Example 88 | ND | ND |
| Example 89 | ND | ND |
| Example 90 | ND | ND |
| Example 91 | ND | ND |
| Example 92 | ND | ND |
| Example 93 | ND | ND |
| Example 94 | ND | ND |
| Example 95 | ND | ND |
| Example 96 | ND | ND |
| Example 97a | 55% @ <u>10 µM</u> | 1.16E−05 |
| Example 97b | 4.10E−08 | 4.59E−07 |
| Example 98 | ND | ND |
| Example 99 | ND | ND |
| Example 100 | ND | ND |
| Example 101 | ND | ND |
| Example 102 | no curve | >3.00E−05 |
| Example 103 | ND | ND |
| Example 104 | ND | ND |

Note:
IC$_{50}$ of Mcl-1 inhibition obtained using Method 2 are underlined.
ND: not determined
For partial inhibitors, the percentage fluorescence polarization inhibition for a given concentration of the test compound is indicated. Accordingly, 45.1% @ 10 µM means that 45.1% fluorescence polarization inhibition is observed for a concentration of test compound equal to 10 µM.

Example C: Quantification of the cleaved form of PARP in vivo

The ability of the compounds of the invention to induce apoptosis, by measuring cleaved PARP levels, is evaluated in a xenograft model of AMO-1 multiple myeloma cells. 1·10$^7$ AMO-1 cells are grafted sub-cutaneously into immunosuppressed mice (SCID strain). 12 to 14 days after the graft, the animals are treated by intraveinous or oral routes with the various compounds. After treatment, the tumour masses are recovered and lysed, and the cleaved form of PARP is quantified in the tumour lysates.

The quantification is carried out using the "Meso Scale Discovery (MSD) ELISA platform" test, which specifically assays the cleaved form of PARP. It is expressed in the form of an activation factor corresponding to the ratio between the quantity of cleaved PARP in the treated mice divided by the quantity of cleaved PARP in the control mice.

The results (presented in Table 2 below) show that the compounds of the invention are capable of inducing apoptosis in AMO-1 tumour cells in vivo.

TABLE 2

Quantification of the cleaved form of PARP in vivo

| | PARP fold |
|---|---|
| Example 1 | 157.5 |
| Example 2 | 216.3 |

TABLE 2-continued

Quantification of the cleaved form of PARP in vivo

| | PARP fold |
|---|---|
| Example 8 | 55.4 |
| Example 53 | 40.2 |
| Example 67 | 29.3 |
| Example 72 | 15.7 |

Example D: Anti-Tumour Activity In Vivo

The anti-tumour activity of the compounds of the invention is evaluated in a xenograft model of AMO-1 multiple myeloma cells.

$1 \times 10^7$ AMO-1 cells are grafted sub-cutaneously into immunosuppressed mice (SCID strain).

6 to 8 days after the graft, when the tumour mass has reached about 150 mm$^3$, the mice are treated with the various compounds in a daily schedule (5-day treatment). The tumour mass is measured twice weekly from the start of treatment.

The compound of the invention has anti-tumour activity (tumour regression) in the AMO-1 multiple myeloma model with ΔT/C (qualification parameter of the activity of a product, which is measured by subtracting the median tumor volume on the day of last treatment from the median tumor volume on the day of first treatment/tumour volume of the untreated control group on the day of last treatment) of −27%. The results obtained show that the compounds of the invention induce significant tumour regression during the treatment period.

Example E: Pharmaceutical Composition: Tablets

| 1000 tablets containing a dose of 5 mg of a compound selected from Examples 1 to 104 | 5 g |
|---|---|
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A method of treating multiple myeloma in a subject in need thereof, comprising administration of an effective amount of a compound of formula (I), its enantiomers, diastereoisomers and atropisomers, and addition salts thereof with a pharmaceutically acceptable acid or base, alone or in combination with one or more pharmaceutically acceptable excipients:

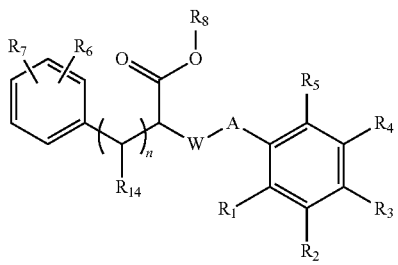

(I)

wherein:

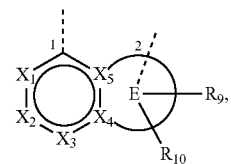

A represents the group
in which 1 is linked to the W group and 2 is linked to the phenyl ring, wherein:
the ring system

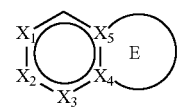

is selected from the group consisting of:

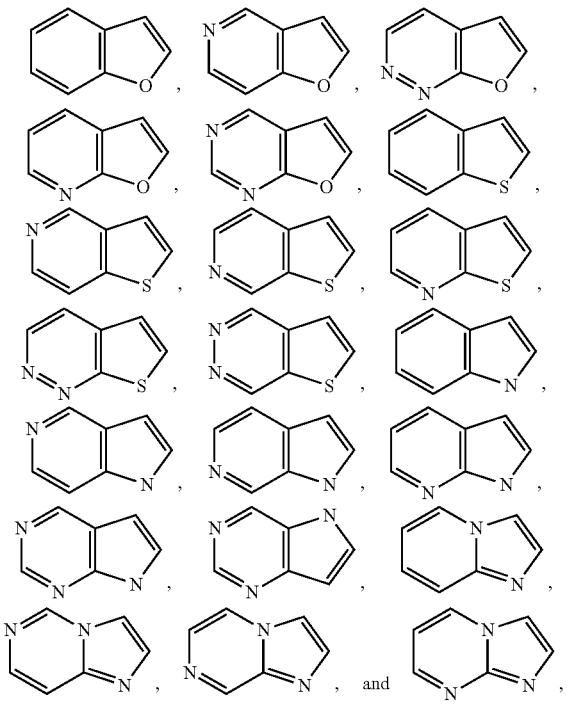

$R_1$ represents a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl group, a hydroxy group, a hydroxy$(C_1-C_6)$alkyl group, a linear or branched $(C_1-C_6)$alkoxy group, —S—$(C_1-C_6)$alkyl, a cyano group, a nitro group, -alkyl$(C_0-C_6)$—$NR_{11}R_{11}'$, —O-alkyl$(C_1-C_6)$—$NR_{11}R_{11}'$, —O-alkyl$(C_1-C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1-C_6)$—$NR_{11}$—C(O)—$R_{11}'$, —$SO_2$—$NR_{11}R_{11}'$, —$SO_2$-alkyl$(C_1-C_6)$, $R_2$, $R_3$, $R_4$ and $R_5$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a hydroxy$(C_1-C_6)$alkyl group, a linear or branched $(C_1-C_6)$alkoxy group, a —S—$(C_1-C_6)$alkyl group, a cyano group, a nitro group, -alkyl$(C_0-C_6)$—$NR_{11}R_{11}'$, —O-alkyl$(C_1-C_6)$—$NR_{11}R_{11}'$, —O-alkyl$(C_1-C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1-C_6)$—$NR_{11}$—C(O)—$R_{11}'$, —$SO_2$—$NR_{11}R_{11}'$, or —$SO_2$-alkyl$(C_1-C_6)$, or the substituents of the pair ($R_1$, $R_2$), together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by from 1 to 2 groups selected from halogen, linear or branched $(C_1-C_6)$alkyl, -alkyl$(C_0-C_6)$—$NR_{11}R_{11}'$, —$NR_{13}R_{13}'$, -alkyl$(C_0-C_6)$-$Cy_1$ and oxo, $R_6$ and $R_7$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a linear or branched $(C_1-C_6)$alkoxy group, a —S—$(C_1-C_6)$alkyl group, a cyano group, a nitro group, -alkyl$(C_0-C_6)$—$NR_{11}R_{11}'$, —O-$Cy_1$, -alkyl$(C_0-C_6)$-$Cy_1$, -alkenyl$(C_2-C_6)$-$Cy_1$, -alkynyl$(C_2-C_6)$-$Cy_1$, —O-alkyl$(C_1-C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1-C_6)$—$NR_{11}$—C(O)—$R_{11}'$, —$SO_2$—$NR_{11}R_{11}'$, —$SO_2$-alkyl$(C_1-C_6)$, or the substituents of the pair ($R_6$, $R_7$), when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched $(C_1-C_6)$alkyl group, —$NR_{13}R_{13}'$, -alkyl$(C_0-C_6)$-$Cy_1$ and oxo, W represents a —$CH_2$— group, a —NH— group or an oxygen atom, $R_8$ represents a hydrogen atom, a linear or branched $(C_1-C_8)$alkyl group, a —$CHR_aR_b$ group, an aryl group, a heteroaryl group, an arylalkyl$(C_1-C_6)$ group, or a heteroarylalkyl$(C_1-C_6)$ group, $R_9$ represents a hydrogen atom, a linear or branched $(C_1-C_6)$alkyl group, a linear or branched $(C_2-C_6)$alkenyl group, a linear or branched $(C_2-C_6)$alkynyl group, -$Cy_2$, -alkyl$(C_1-C_6)$-$Cy_2$, -alkenyl$(C_2-C_6)$-$Cy_2$, -alkynyl$(C_2-C_6)$-$Cy_2$, -$Cy_2$-$Cy_3$, -alkynyl$(C_2-C_6)$—O-$Cy_2$, -$Cy_2$-alkyl$(C_0-C_6)$—O-alkyl$(C_0-C_6)$-$Cy_3$, a halogen atom, a cyano group, —C(O)—$R_{15}$, or —C(O)—$NR_{15}R_{15}'$, $R_{10}$ represents a hydrogen atom, a linear or branched $(C_1-C_6)$alkyl group, a linear or branched $(C_2-C_6)$alkenyl group, a linear or branched $(C_2-C_6)$alkynyl group, an arylalkyl$(C_1-C_6)$ group, a cycloalkylalkyl$(C_1-C_6)$ group, a linear or branched $(C_1-C_6)$polyhaloalkyl, -alkyl$(C_1-C_6)$—O-$Cy_4$, or the substituents of the pair ($R_9$, $R_{10}$), when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, $R_{11}$ and $R_{11}'$ independently of one another represent a hydrogen atom, a linear or branched $(C_1-C_6)$alkyl group, or the substituents of the pair ($R_{11}$, $R_{11}'$), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched $(C_1-C_6)$alkyl group, $R_{12}$ represents -$Cy_5$, -$Cy_5$-alkyl$(C_0-C_6)$—O-alkyl$(C_0-C_6)$-$Cy_6$, -$Cy_5$-alkyl$(C_0-C_6)$-$Cy_6$, -$Cy_5$-alkyl$(C_0-C_6)$—$NR_{11}$-alkyl$(C_0-C_6)$-$Cy_6$, -$Cy_5$-$Cy_6$-O-alkyl$(C_0-C_6)$-$Cy_7$, —C(O)—$NR_{11}R_{11}'$, —$NR_{11}R_{11}'$, —$OR_{11}$, —$NR_{11}$—C(O)—$R_{11}'$, —O-alkyl$(C_1-C_6)$—$OR_{11}$, —$SO_2$—$R_{11}$, —C(O)—$OR_{11}$, or —NH—C(O)—NH—$R_{11}$, $R_{13}$, $R_{13}'$, $R_{15}$ and $R_{15}'$, independently of one another, represent a hydrogen atom, or an optionally substituted linear or branched $(C_1-C_6)$alkyl group, $R_{14}$ represents a hydrogen atom, a hydroxy group, or a hydroxy$(C_1-C_6)$alkyl group, $R_a$ represents a hydrogen atom or a linear or branched $(C_1-C_6)$alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$, independently of one another, represent a hydrogen atom, a linear or branched $(C_1-C_8)$alkyl group, a cycloalkyl group, a $(C_1-C_6)$alkoxy$(C_1-C_6)$alkyl group, a $(C_1-C_6)$alkoxycarbonyl$(C_1-C_6)$alkyl group, or the substituents of the pair ($R_c$, $R_c'$), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched $(C_1-C_6)$alkyl group, $Cy_1$, $Cy_2$, $Cy_3$, $Cy_4$, $Cy_5$, $Cy_6$ and $Cy_7$, independently of one another, represent a cycloalkyl group, a heterocycloalkyl group, an aryl group, or a heteroaryl group, n is an integer equal to 0 or 1,
wherein:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems,
wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched ($C_1$-$C_6$)alkyl, optionally substituted linear or branched ($C_2$-$C_6$)alkenyl, optionally substituted linear or branched ($C_2$-$C_6$)alkynyl, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched ($C_1$-$C_6$)polyhaloalkyl, trifluoromethoxy, halogen, or an aldohexose of formula:

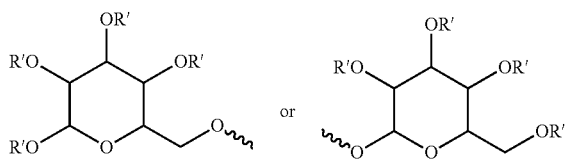

in which each R' is independent;
wherein R' and R", independently of one another, represent a hydrogen atom or an optionally substituted linear or branched ($C_1$-$C_6$)alkyl group, and M$^+$ represents a pharmaceutically acceptable monovalent cation.

2. The method according to claim 1, wherein:
$R_1$ and $R_2$ independently of one another represent a halogen atom, a linear or branched ($C_1$-$C_6$)alkyl group, a hydroxy group, a linear or branched ($C_1$-$C_6$)alkoxy group,
or the substituents of the pair ($R_1$, $R_2$), together with the carbon atoms carrying them, form an aromatic ring having from 5 to 7 ring members, which ring may contain from 1 to 3 nitrogen atoms,
$R_3$ represents a hydrogen atom, a halogen atom, a linear or branched ($C_1$-$C_6$)alkyl group, a hydroxy group, a linear or branched ($C_1$-$C_6$)alkoxy group, or —O-alkyl($C_1$-$C_6$)—NR$_{11}$R$_{11}$',
$R_4$ and $R_5$ independently of one another represent a hydrogen atom, a halogen atom, a linear or branched ($C_1$-$C_6$)alkyl group, a hydroxy group, a linear or branched ($C_1$-$C_6$)alkoxy group,
$R_6$ and $R_7$ independently of one another represent a hydrogen atom, a halogen atom, a linear or branched ($C_1$-$C_6$)alkyl group, a linear or branched ($C_1$-$C_6$)polyhaloalkyl group, a hydroxy group, a linear or branched ($C_1$-$C_6$)alkoxy group, a cyano group, a nitro group, -alkyl($C_0$-$C_6$)—NR$_{11}$R$_{11}$', -alkyl($C_0$-$C_6$)-Cy$_1$, —O-alkyl($C_1$-$C_6$)—R$_{12}$, or —C(O)—NR$_{11}$R$_{11}$',
$R_8$ represents a hydrogen atom, a linear or branched ($C_1$-$C_8$)alkyl group, or a —CHR$_a$R$_b$ group,
$R_9$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, -Cy$_2$, or a halogen atom,
$R_{10}$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, an arylalkyl($C_1$-$C_6$) group, a cycloalkylalkyl($C_1$-$C_6$) group, a linear or branched ($C_1$-$C_6$)polyhaloalkyl, or -alkyl($C_1$-$C_6$)—O-Cy$_4$,
or the substituents of the pair ($R_9$, $R_{10}$), when grafted onto two adjacent carbon atoms, together with the carbon atoms carrying them, form a non-aromatic ring having from 5 to 7 ring members, which ring may contain from 1 to 3 heteroatoms selected from oxygen, sulphur and nitrogen,
$R_{11}$ and $R_{11}$' independently of one another represent a hydrogen atom, a linear or branched ($C_1$-$C_6$)alkyl group,
or the substituents of the pair ($R_{11}$, $R_{11}$'), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen be substituted by a linear or branched ($C_1$-$C_6$)alkyl group,
$R_{12}$ represents -Cy$_5$ or -Cy$_5$-alkyl($C_0$-$C_6$)-Cy$_6$,
W represents a —NH— group or an oxygen atom,
wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched ($C_1$-$C_6$)alkyl, optionally substituted linear or branched ($C_1$-$C_6$) alkoxy, hydroxy, oxo (or N-oxide where appropriate), —C(O)—OR', —C(O)—NR'R", —O—C(O)—NR' R", —NR'R", —O—P(O)(OR')$_2$, —O—P(O)(O$^-$M$^+$)$_2$, linear or branched ($C_1$-$C_6$)polyhaloalkyl, halogen, or an aldohexose of formula:

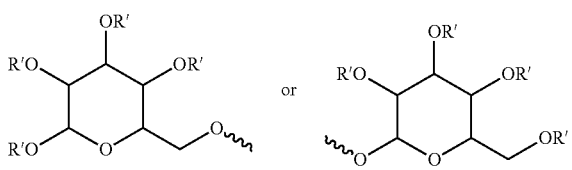

in which each R' is independent;
wherein R' and R", independently of one another, represent a hydrogen atom or an optionally substituted linear or branched ($C_1$-$C_6$)alkyl group and M$^+$ represents a pharmaceutically acceptable monovalent cation.

3. The method according to claim 1, wherein n is an integer equal to 1.

4. The method according to claim 1, wherein the compound of formula (I) is compound of formula (I-a):

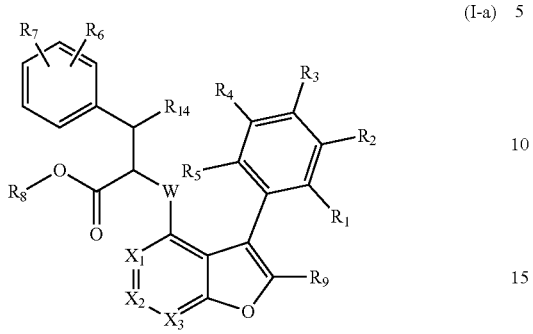

wherein
the ring system

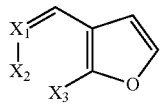

is selected from the group consisting of:

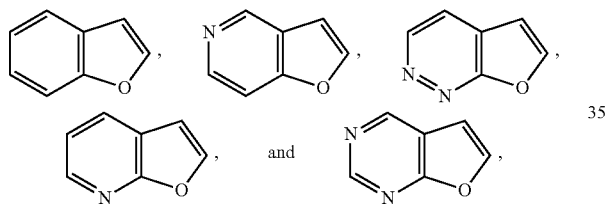

R₁ represents a halogen atom, a linear or branched (C₁-C₆)alkyl group, a linear or branched (C₂-C₆)alkenyl group, a linear or branched (C₂-C₆)alkynyl group, a linear or branched (C₁-C₆)polyhaloalkyl group, a hydroxy group, a hydroxy(C₁-C₆)alkyl group, a linear or branched (C₁-C₆)alkoxy group, —S—(C₁-C₆)alkyl, a cyano group, a nitro group, -alkyl(C₀-C₆)—NR₁₁R₁₁', —O-alkyl(C₁-C₆)—NR₁₁R₁₁', —O-alkyl(C₁-C₆)—R₁₂, —C(O)—OR₁₁, —O—C(O)—R₁₁, —C(O)—NR₁₁R₁₁', —NR₁₁—C(O)—R₁₁', —NR₁₁—C(O)—OR₁₁', -alkyl(C₁-C₆)—NR₁₁—C(O)—R₁₁', —SO₂—NR₁₁R₁₁', or —SO₂-alkyl(C₁-C₆), R₂, R₃, R₄ and R₅ independently of one another represent a hydrogen atom, a halogen atom, a linear or branched (C₁-C₆)alkyl group, a linear or branched (C₂-C₆)alkenyl group, a linear or branched (C₂-C₆)alkynyl group, a linear or branched (C₁-C₆)polyhaloalkyl, a hydroxy group, a hydroxy(C₁-C₆)alkyl group, a linear or branched (C₁-C₆)alkoxy group, a —S—(C₁-C₆)alkyl group, a cyano group, a nitro group, -alkyl(C₀-C₆)—NR₁₁R₁₁', —O-alkyl(C₁-C₆)—NR₁₁R₁₁', —O-alkyl(C₁-C₆)—R₁₂, —C(O)—OR₁₁, —O—C(O)—R₁₁, —C(O)—NR₁₁R₁₁', —NR₁₁—C(O)—R₁₁', —NR₁₁—C(O)—OR₁₁', -alkyl(C₁-C₆)—NR₁₁—C(O)—R₁₁', —SO₂—NR₁₁R₁₁', or —SO₂-alkyl(C₁-C₆), or the substituents of the pair (R₁, R₂), together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by from 1 to 2 groups selected from halogen, linear or branched (C₁-C₆)alkyl, -alkyl(C₀-C₆)—NR₁₁R₁₁', —NR₁₃R₁₃', -alkyl(C₀-C₆)-Cy₁ and oxo, R₆ and R₇ independently of one another represent a hydrogen atom, a halogen atom, a linear or branched (C₁-C₆)alkyl group, a linear or branched (C₂-C₆)alkenyl group, a linear or branched (C₂-C₆)alkynyl group, a linear or branched (C₁-C₆)polyhaloalkyl, a hydroxy group, a linear or branched (C₁-C₆)alkoxy group, a —S—(C₁-C₆)alkyl group, a cyano group, a nitro group, -alkyl(C₀-C₆)—NR₁₁R₁₁', —O-Cy₁, -alkyl(C₀-C₆)-Cy₁, -alkenyl(C₂-C₆)-Cy₁, -alkynyl(C₂-C₆)-Cy₁, —O-alkyl(C₁-C₆)—R₁₂, —C(O)—OR₁₁, —O—C(O)—R₁₁, —C(O)—NR₁₁R₁₁', —NR₁₁—C(O)—R₁₁', —NR₁₁—C(O)—OR₁₁', -alkyl(C₁-C₆)—NR₁₁—C(O)—R₁₁', —SO₂—NR₁₁R₁₁', —SO₂-alkyl(C₁-C₆), or the substituents of the pair (R₆, R₇), when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched (C₁-C₆)alkyl group, —NR₁₃R₁₃', -alkyl(C₀-C₆)-Cy₁ and oxo, W represents a —CH₂— group, a —NH— group or an oxygen atom, R₈ represents a hydrogen atom, a linear or branched (C₁-C₈)alkyl group, a —CHR_aR_b group, an aryl group, a heteroaryl group, an arylalkyl(C₁-C₆) group, or a heteroarylalkyl(C₁-C₆) group, R₉ represents a hydrogen atom, a linear or branched (C₁-C₆)alkyl group, a linear or branched (C₂-C₆)alkenyl group, a linear or branched (C₂-C₆)alkynyl group, -Cy₂, -alkyl(C₁-C₆)-Cy₂, -alkenyl(C₂-C₆)-Cy₂, -alkynyl(C₂-C₆)-Cy₂, —Cy₂-Cy₃, -alkynyl(C₂-C₆)—O-Cy₂, -Cy₂-alkyl(C₀-C₆)—O-alkyl(C₀-C₆)-Cy₃, a halogen atom, a cyano group, —C(O)—R₁₅, or —C(O)—NR₁₅R₁₅', R₁₁ and R₁₁' independently of one another represent a hydrogen atom, a linear or branched (C₁-C₆)alkyl group, or the substituents of the pair (R₁₁, R₁₁'), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched (C₁-C₆)alkyl group, R₁₂ represents -Cy₅, -Cy₅-alkyl(C₀-C₆)—O-alkyl(C₀-C₆)-Cy₆, -Cy₅-alkyl(C₀-C₆)-Cy₆, -Cy₅-alkyl(C₀-C₆)—NR₁₁-alkyl(C₀-C₆)-Cy₆, —Cy₅-Cy₆-O-alkyl(C₀-C₆)-Cy₇, —C(O)—NR₁₁R₁₁', —NR₁₁R₁₁', —OR₁₁, —NR₁₁—C(O)—R₁₁', —O-alkyl(C₁-C₆)—OR₁₁, —SO₂—R₁₁, —C(O)—OR₁₁, or —NH—C(O)—NH—R₁₁, R$_{13}$, R$_{13}$', R$_{15}$ and R$_{15}$', independently of one another, represent a hydrogen atom, or an optionally substituted linear or branched (C$_1$-C$_6$)alkyl group, R$_{14}$ represents a hydrogen atom, a hydroxy group, or a hydroxy(C$_1$-C$_6$)alkyl group, R$_a$ represents a hydrogen atom or a linear or branched (C$_1$-C$_6$)alkyl group, R$_b$ represents a —O—C(O)—O—R$_c$ group, a —O—C(O)—NR$_c$R$_c$' group, or a —O—P(O)(OR$_c$)$_2$ group, R$_c$ and R$_c$', independently of one another, represent a hydrogen atom, a linear or branched (C$_1$-C$_8$)alkyl group, a cycloalkyl group, a (C$_1$-C$_6$)alkoxy(C$_1$-C$_6$)alkyl group, a (C$_1$-C$_6$)alkoxycarbonyl(C$_1$-C$_6$)alkyl group, or the substituents of the pair (R$_c$, R$_c$'), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched (C$_1$-C$_6$)alkyl group, Cy$_1$, Cy$_2$, Cy$_3$, Cy$_4$, Cy$_5$, Cy$_6$ and Cy$_7$, independently of one another, represent a cycloalkyl group, a heterocycloalkyl group, an aryl group, or a heteroaryl group, n is an integer equal to 0 or 1, wherein:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched (C$_1$-C$_6$)alkyl, optionally substituted linear or branched (C$_2$-C$_6$)alkenyl, optionally substituted linear or branched (C$_2$-C$_6$)alkynyl, optionally substituted linear or branched (C$_1$-C$_6$)alkoxy, optionally substituted (C$_1$-C$_6$)alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched (C$_1$-C$_6$)polyhaloalkyl, trifluoromethoxy, halogen, or an aldohexose of formula:

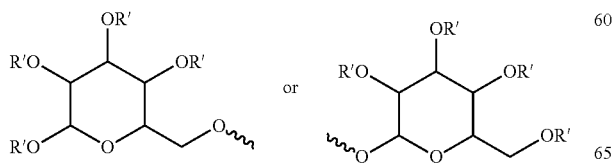

in which each R' is independent;

wherein R' and R", independently of one another, represent a hydrogen atom or an optionally substituted linear or branched (C$_1$-C$_6$)alkyl group, and M$^+$ represents a pharmaceutically acceptable monovalent cation, its enantiomers, diastereoisomers and atropisomers, and addition salts thereof with a pharmaceutically acceptable acid or base.

5. The method according to claim 1, wherein the compound of formula (I) is a compound of formula (I-b):

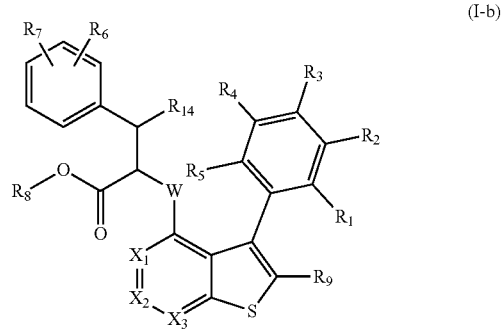

(I-b)

wherein
the ring system

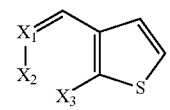

is selected from the group consisting of:

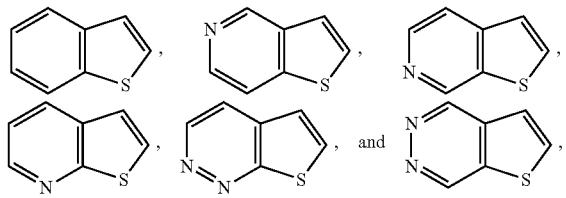

R$_1$ represents a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl group, a hydroxy group, a hydroxy(C$_1$-C$_6$)alkyl group, a linear or branched (C$_1$-C$_6$)alkoxy group, —S—(C$_1$-C$_6$)alkyl, a cyano group, a nitro group, -alkyl(C$_0$-C$_6$)—NR$_{11}$R$_{11}$', —O-alkyl(C$_1$-C$_6$)—NR$_{11}$R$_{11}$', —O-alkyl(C$_1$-C$_6$)—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$—NR$_{11}$R$_{11}$', —SO$_2$-alkyl(C$_1$-C$_6$), R$_2$, R$_3$, R$_4$ and R$_5$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a hydroxy(C$_1$-C$_6$)alkyl group, a linear or branched $(C_1\text{-}C_6)$alkoxy group, a —S—$(C_1\text{-}C_6)$alkyl group, a cyano group, a nitro group, -alkyl$(C_0\text{-}C_6)$—$NR_{11}R_{11}'$, —O-alkyl$(C_1\text{-}C_6)$—$NR_{11}R_{11}'$, —O-alkyl$(C_1\text{-}C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1\text{-}C_6)$—$NR_{11}$—C(O)—$R_{11}'$, —$SO_2$—$NR_{11}R_{11}'$, or —$SO_2$-alkyl$(C_1\text{-}C_6)$, or the substituents of the pair $(R_1, R_2)$, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by from 1 to 2 groups selected from halogen, linear or branched $(C_1\text{-}C_6)$alkyl, -alkyl$(C_0\text{-}C_6)$—$NR_{11}R_{11}'$, —$NR_{13}R_{13}'$, -alkyl$(C_0\text{-}C_6)$-$Cy_1$ and oxo, $R_6$ and $R_7$ independently of one another represent a hydrogen atom, a halogen atom, a linear or branched $(C_1\text{-}C_6)$alkyl group, a linear or branched $(C_2\text{-}C_6)$alkenyl group, a linear or branched $(C_2\text{-}C_6)$alkynyl group, a linear or branched $(C_1\text{-}C_6)$polyhaloalkyl, a hydroxy group, a linear or branched $(C_1\text{-}C_6)$alkoxy group, a —S—$(C_1\text{-}C_6)$alkyl group, a cyano group, a nitro group, -alkyl$(C_0\text{-}C_6)$—$NR_{11}R_{11}'$, —O-$Cy_1$, -alkyl$(C_0\text{-}C_6)$-$Cy_1$, -alkenyl$(C_2\text{-}C_6)$-$Cy_1$, -alkynyl$(C_2\text{-}C_6)$-$Cy_1$, —O-alkyl$(C_1\text{-}C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1\text{-}C_6)$—$NR_{11}$—C(O)—$R_{11}'$, —$SO_2$—$NR_{11}R_{11}'$, —$SO_2$-alkyl$(C_1\text{-}C_6)$, or the substituents of the pair $(R_6, R_7)$, when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched $(C_1\text{-}C_6)$alkyl group, —$NR_{13}R_{13}'$, -alkyl$(C_0\text{-}C_6)$-$Cy_1$ and oxo, W represents a —$CH_2$— group, a —NH— group or an oxygen atom, $R_8$ represents a hydrogen atom, a linear or branched $(C_1\text{-}C_8)$alkyl group, a —$CHR_aR_b$ group, an aryl group, a heteroaryl group, an arylalkyl$(C_1\text{-}C_6)$ group, or a heteroarylalkyl$(C_1\text{-}C_6)$ group, $R_9$ represents a hydrogen atom, a linear or branched $(C_1\text{-}C_6)$alkyl group, a linear or branched $(C_2\text{-}C_6)$alkenyl group, a linear or branched $(C_2\text{-}C_6)$alkynyl group, -$Cy_2$, -alkyl$(C_1\text{-}C_6)$-$Cy_2$, -alkenyl$(C_2\text{-}C_6)$-$Cy_2$, -alkynyl$(C_2\text{-}C_6)$-$Cy_2$, —$Cy_2$-$Cy_3$, -alkynyl$(C_2\text{-}C_6)$—O-$Cy_2$, -$Cy_2$-alkyl$(C_0\text{-}C_6)$—O-alkyl$(C_0\text{-}C_6)$-$Cy_3$, a halogen atom, a cyano group, —C(O)—$R_{15}$, or —C(O)—$NR_{15}R_{15}'$, $R_{11}$ and $R_{11}'$ independently of one another represent a hydrogen atom, a linear or branched $(C_1\text{-}C_6)$alkyl group, or the substituents of the pair $(R_{11}, R_{11}')$, together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched $(C_1\text{-}C_6)$alkyl group, $R_{12}$ represents -$Cy_5$, -$Cy_5$-alkyl$(C_0\text{-}C_6)$—O-alkyl$(C_0\text{-}C_6)$-$Cy_6$, -$Cy_5$-alkyl$(C_0\text{-}C_6)$-$Cy_6$, -$Cy_5$-alkyl$(C_0\text{-}C_6)$—$NR_{11}$-alkyl$(C_0\text{-}C_6)$-$Cy_6$, -$Cy_5$-$Cy_6$-O-alkyl$(C_0\text{-}C_6)$-$Cy_7$, —C(O)—$NR_{11}R_{11}'$, —$NR_{11}R_{11}'$, —$OR_{11}$, —$NR_{11}$—C(O)—$R_{11}'$, —O-alkyl$(C_1\text{-}C_6)$—$OR_{11}$, —$SO_2$—$R_{11}$, —C(O)—$OR_{11}$, or —NH—C(O)—NH—$R_{11}$, $R_{13}$, $R_{13}'$, $R_{15}$ and $R_{15}'$, independently of one another, represent a hydrogen atom, or an optionally substituted linear or branched $(C_1\text{-}C_6)$alkyl group, $R_{14}$ represents a hydrogen atom, a hydroxy group, or a hydroxy$(C_1\text{-}C_6)$alkyl group, $R_a$ represents a hydrogen atom or a linear or branched $(C_1\text{-}C_6)$alkyl group, $R_b$ represents a —O—C(O)—O—$R_c$ group, a —O—C(O)—$NR_cR_c'$ group, or a —O—P(O)$(OR_c)_2$ group, $R_c$ and $R_c'$, independently of one another, represent a hydrogen atom, a linear or branched $(C_1\text{-}C_8)$alkyl group, a cycloalkyl group, a $(C_1\text{-}C_6)$alkoxy$(C_1\text{-}C_6)$alkyl group, a $(C_1\text{-}C_6)$alkoxycarbonyl$(C_1\text{-}C_6)$alkyl group, or the substituents of the pair $(R_c, R_c')$, together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched $(C_1\text{-}C_6)$alkyl group, $Cy_1$, $Cy_2$, $Cy_3$, $Cy_4$, $Cy_5$, $Cy_6$ and $Cy_7$, independently of one another, represent a cycloalkyl group, a heterocycloalkyl group, an aryl group, or a heteroaryl group, n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched $(C_1\text{-}C_6)$alkyl, optionally substituted linear or branched $(C_2\text{-}C_6)$alkenyl, optionally substituted linear or branched $(C_2\text{-}C_6)$alkynyl, optionally substituted linear or branched $(C_1\text{-}C_6)$alkoxy, optionally substituted $(C_1\text{-}C_6)$alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)$(OR')_2$, —O—P(O)$(O^-M^+)_2$, linear or branched $(C_1\text{-}C_6)$polyhaloalkyl, trifluoromethoxy, halogen, or an aldohexose of formula:

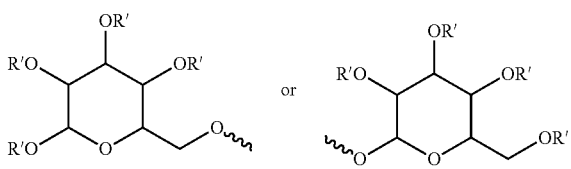

in which each R' is independent;
wherein R' and R'', independently of one another, represent a hydrogen atom or an optionally substituted linear or branched $(C_1-C_6)$alkyl group, and $M^+$ represents a pharmaceutically acceptable monovalent cation,
its enantiomers, diastereoisomers and atropisomers, and addition salts thereof with a pharmaceutically acceptable acid or base.

6. The method according to claim 1, wherein the compound of formula (I) is a compound of formula (I-c):

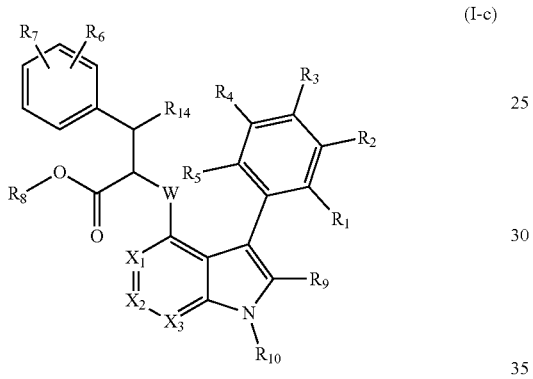

wherein
the ring system

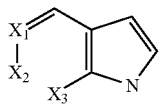

is selected from the group consisting of:

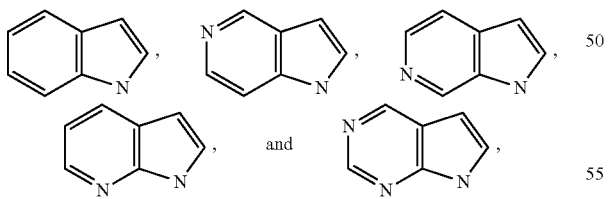

$R_1$ represents a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl group, a hydroxy group, a hydroxy$(C_1-C_6)$alkyl group, a linear or branched $(C_1-C_6)$alkoxy group, —S—$(C_1-C_6)$alkyl group, a cyano group, a nitro group, -alkyl$(C_0-C_6)$—$NR_{11}R_{11}'$, —O-alkyl$(C_1-C_6)$—$NR_{11}R_{11}'$, —O-alkyl$(C_1-C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1-C_6)$—$NR_{11}$—C(O)—$R_{11}'$, —$SO_2$—$NR_{11}R_{11}'$, —$SO_2$-alkyl$(C_1-C_6)$, $R_2$, $R_3$, $R_4$ and $R_5$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a hydroxy$(C_1-C_6)$alkyl group, a linear or branched $(C_1-C_6)$alkoxy group, a —S—$(C_1-C_6)$alkyl group, a cyano group, a nitro group, -alkyl$(C_0-C_6)$—$NR_{11}R_{11}'$, —O-alkyl$(C_1-C_6)$—$NR_{11}R_{11}'$, —O-alkyl$(C_1-C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1-C_6)$—$NR_{11}$—C(O)—$R_{11}'$, —$SO_2$—$NR_{11}R_{11}'$, or —$SO_2$-alkyl$(C_1-C_6)$, or the substituents of the pair $(R_1, R_2)$, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by from 1 to 2 groups selected from halogen, linear or branched $(C_1-C_6)$alkyl, -alkyl$(C_0-C_6)$—$NR_{11}R_{11}'$, —$NR_{13}R_{13}'$, -alkyl$(C_0-C_6)$-$Cy_1$ and oxo, $R_6$ and $R_7$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a linear or branched $(C_1-C_6)$alkoxy group, a —S—$(C_1-C_6)$alkyl group, a cyano group, a nitro group, -alkyl$(C_0-C_6)$—$NR_{11}R_{11}'$, —O-$Cy_1$, -alkyl$(C_0-C_6)$-$Cy_1$, -alkenyl$(C_2-C_6)$-$Cy_1$, -alkynyl$(C_2-C_6)$-$Cy_1$, —O-alkyl$(C_1-C_6)$—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl$(C_1-C_6)$—$NR_{11}$—C(O)—$R_{11}'$, —$SO_2$—$NR_{11}R_{11}'$, —$SO_2$-alkyl$(C_1-C_6)$, or the substituents of the pair $(R_6, R_7)$, when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched $(C_1-C_6)$alkyl group, —$NR_{13}R_{13}'$, -alkyl$(C_0-C_6)$-$Cy_1$ and oxo, W represents a —$CH_2$— group, a —NH— group or an oxygen atom, $R_8$ represents a hydrogen atom, a linear or branched $(C_1-C_8)$alkyl group, a —$CHR_aR_b$ group, an aryl group, a heteroaryl group, an arylalkyl$(C_1-C_6)$ group, or a heteroarylalkyl$(C_1-C_6)$ group, $R_9$ represents a hydrogen atom, a linear or branched $(C_1-C_6)$alkyl group, a linear or branched $(C_2-C_6)$alkenyl group, a linear or branched $(C_2-C_6)$alkynyl group, -$Cy_2$, -alkyl$(C_1-C_6)$-$Cy_2$, -alkenyl$(C_2-C_6)$-$Cy_2$, -alkynyl$(C_2-C_6)$-$Cy_2$, -$Cy_2$-$Cy_3$, -alkynyl$(C_2-C_6)$—O-$Cy_2$, -$Cy_2$-alkyl$(C_0-C_6)$—O-alkyl$(C_0-C_6)$-$Cy_3$, a halogen atom, a cyano group, —C(O)—$R_{15}$, or —C(O)—$NR_{15}R_{15}'$, $R_{10}$ represents a hydrogen atom, a linear or branched $(C_1-C_6)$alkyl group, a linear or branched $(C_2-C_6)$alkenyl group, a linear or branched $(C_2-C_6)$alkynyl group, an arylalkyl($C_1$-$C_6$) group, a cycloalkylalkyl ($C_1$-$C_6$) group, a linear or branched ($C_1$-$C_6$)polyhaloalkyl, or -alkyl($C_1$-$C_6$)—O-$Cy_4$, or the substituents of the pair ($R_9$, $R_{10}$), when grafted onto two adjacent carbon atoms, together with the carbon atoms carrying them, form a non-aromatic ring having from 5 to 7 ring members, which ring may contain from 1 to 3 heteroatoms selected from oxygen, sulphur and nitrogen, $R_{11}$ and $R_{11}'$ independently of one another represent a hydrogen atom, a linear or branched ($C_1$-$C_6$)alkyl group, or the substituents of the pair ($R_{11}$, $R_{11}'$), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched ($C_1$-$C_6$)alkyl group, $R_{12}$ represents -$Cy_5$, -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl($C_0$-$C_6$)-$Cy_7$, —C(O)—$NR_{11}R_{11}'$, —$NR_{11}R_{11}'$, —$OR_{11}$, —$NR_{11}$—C(O)—$R_{11}$', —O-alkyl($C_1$-$C_6$)—$OR_{11}$, —$SO_2$—$R_{11}$, —C(O)—$OR_{11}$, or —NH—C(O)—NH—$R_{11}$, $R_{13}$, $R_{13}'$, $R_{15}$ and $R_{15}'$, independently of one another, represent a hydrogen atom, or an optionally substituted linear or branched ($C_1$-$C_6$)alkyl group, $R_{14}$ represents a hydrogen atom, a hydroxy group, or a hydroxy($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$, independently of one another, represent a hydrogen atom, a linear or branched ($C_1$-$C_8$)alkyl group, a cycloalkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched ($C_1$-$C_6$)alkyl group, $Cy_1$, $Cy_2$, $Cy_3$, $Cy_4$, $Cy_5$, $Cy_6$ and $Cy_7$, independently of one another, represent a cycloalkyl group, a heterocycloalkyl group, an aryl group, or a heteroaryl group, n is an integer equal to 0 or 1, wherein:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched ($C_1$-$C_6$)alkyl, optionally substituted linear or branched ($C_2$-$C_6$)alkenyl, optionally substituted linear or branched ($C_2$-$C_6$)alkynyl, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched ($C_1$-$C_6$)polyhaloalkyl, trifluoromethoxy, halogen, or an aldohexose of formula:

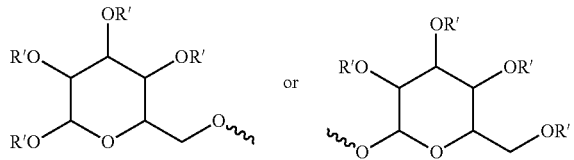

in which each R' is independent;

wherein R' and R", independently of one another, represent a hydrogen atom or an optionally substituted linear or branched ($C_1$-$C_6$)alkyl group, and M$^+$ represents a pharmaceutically acceptable monovalent cation, its enantiomers, diastereoisomers and atropisomers, and addition salts thereof with a pharmaceutically acceptable acid or base.

7. The method according to claim 6, wherein $R_{10}$ represents hydrogen; methyl; isopropyl; 2,2,2-trifluoroethyl; benzyl; 4-methoxybenzyl; phenethyl; 3-phenyl-propyl; cyclopropylmethyl; cyclopentylethyl; naphthalen-1-ylmethyl; 2-(naphthalen-1-yloxy)ethyl; but-2-yn-1-yl; prop-2-en-1-yl; or but-3-en-1-yl.

8. The method according to claim 1, wherein the compound of formula (I) is a compound of formula (I-d):

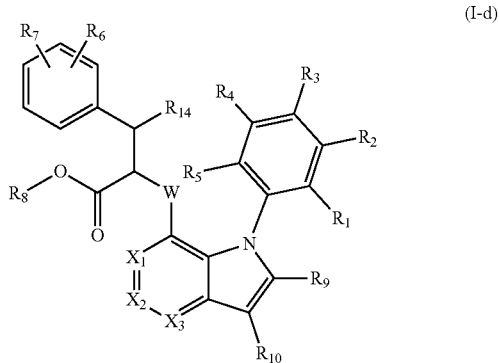

wherein
the ring system

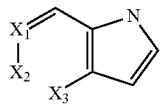

is selected from the group consisting of:

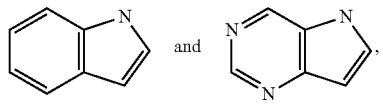 [SMILES: c1ccc2[nH]ccc2c1 ; c1ncc2[nH]ccc2n1]

$R_1$ represents a halogen atom, a linear or branched ($C_1$-$C_6$)alkyl group, a linear or branched ($C_2$-$C_6$) alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl, a cyano group, a nitro group, -alkyl($C_0$-$C_6$)—$NR_{11}R_{11}'$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, —$SO_2$-alkyl($C_1$-$C_6$), $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$), or the substituents of the pair ($R_1$, $R_2$), together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by from 1 to 2 groups selected from halogen, linear or branched ($C_1$-$C_6$)alkyl, -alkyl($C_0$-$C_6$)—$NR_{11}R_{11}'$, —$NR_{13}R_{13}'$, -alkyl($C_0$-$C_6$)-$Cy_1$ and oxo, $R_6$ and $R_7$ independently of one another represent a hydrogen atom, a halogen atom, a linear or branched ($C_1$-$C_6$)alkyl group, a linear or branched ($C_2$-$C_6$) alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl ($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, —$SO_2$-alkyl($C_1$-$C_6$), or the substituents of the pair ($R_6$, $R_7$), when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched ($C_1$-$C_6$)alkyl group, —$NR_{13}R_{13}'$, -alkyl($C_0$-$C_6$)-$Cy_1$ and oxo, W represents a —$CH_2$— group, a —NH— group or an oxygen atom, $R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_9$ represents a hydrogen atom, a linear or branched ($C_1$-$C_6$)alkyl group, a linear or branched ($C_2$-$C_6$) alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, —$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{15}$, or —C(O)—$NR_{15}R_{15}'$, $R_{10}$ represents a hydrogen atom, a linear or branched ($C_1$-$C_6$)alkyl group, a linear or branched ($C_2$-$C_6$) alkenyl group, a linear or branched ($C_2$-$C_6$)alkynyl group, an arylalkyl($C_1$-$C_6$) group, a cycloalkylalkyl ($C_1$-$C_6$) group, a linear or branched ($C_1$-$C_6$)polyhaloalkyl, or -alkyl($C_1$-$C_6$)—O-$Cy_4$, or the substituents of the pair ($R_9$, $R_{10}$), when grafted onto two adjacent carbon atoms, together with the carbon atoms carrying them, form a non-aromatic ring having from 5 to 7 ring members, which ring may contain from 1 to 3 heteroatoms selected from oxygen, sulphur and nitrogen, $R_{11}$ and $R_{11}'$ independently of one another represent a hydrogen atom, a linear or branched ($C_1$-$C_6$)alkyl group, or the substituents of the pair ($R_{11}$, $R_{11}'$), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched ($C_1$-$C_6$)alkyl group, $R_{12}$ represents -$Cy_5$, -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl ($C_0$-$C_6$)-$Cy_7$, —C(O)—$NR_{11}R_{11}'$, —$NR_{11}R_{11}'$, —$OR_{11}$, —$NR_{11}$—C(O)—$R_{11}'$, —O-alkyl($C_1$-$C_6$)—$OR_{11}$, —$SO_2$—$R_{11}$, —C(O)—$OR_{11}$, or —NH—C(O)—NH—$R_{11}$, $R_{13}$, $R_{13}'$, $R_{15}$ and $R_{15}'$, independently of one another, represent a hydrogen atom, or an optionally substituted linear or branched ($C_1$-$C_6$)alkyl group, $R_{14}$ represents a hydrogen atom, a hydroxy group, or a hydroxy($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C (O)—$NR_cR_c'$ group, or a —O—P(O)($OR_c$)$_2$ group, $R_c$ and $R_c'$, independently of one another, represent a hydrogen atom, a linear or branched ($C_1$-$C_8$)alkyl group, a cycloalkyl group, a $(C_1-C_6)$alkoxy$(C_1-C_6)$alkyl group, a $(C_1-C_6)$alkoxycarbonyl$(C_1-C_6)$alkyl group, or the substituents of the pair $(R_c, R_c')$, together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched $(C_1-C_6)$alkyl group, $Cy_1$, $Cy_2$, $Cy_3$, $Cy_4$, $Cy_5$, $Cy_6$ and $Cy_7$, independently of one another, represent a cycloalkyl group, a heterocycloalkyl group, an aryl group, or a heteroaryl group, n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched $(C_1-C_6)$alkyl, optionally substituted linear or branched $(C_2-C_6)$alkenyl, optionally substituted linear or branched $(C_2-C_6)$alkynyl, optionally substituted linear or branched $(C_1-C_6)$alkoxy, optionally substituted $(C_1-C_6)$alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched $(C_1-C_6)$polyhaloalkyl, trifluoromethoxy, halogen, or an aldohexose of formula:

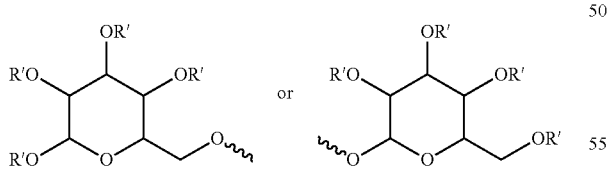

in which each R' is independent;

wherein R' and R", independently of one another, represent a hydrogen atom or an optionally substituted linear or branched $(C_1-C_6)$alkyl group, and M$^+$ represents a pharmaceutically acceptable monovalent cation, its enantiomers, diastereoisomers and atropisomers, and addition salts thereof with a pharmaceutically acceptable acid or base.

9. The method according to claim 8, wherein $R_{10}$ represents a hydrogen atom or a halogen atom.

10. The method according to claim 1, wherein the compound of formula (I) is a compound of formula (I-e):

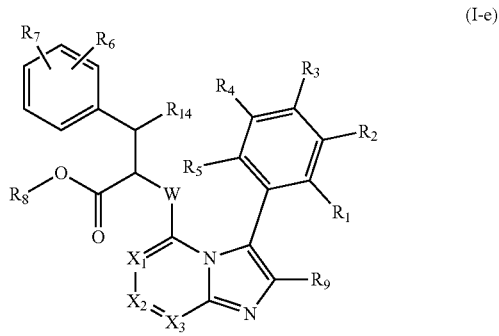

(I-e)

wherein the ring system

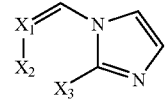

is selected from the group consisting of:

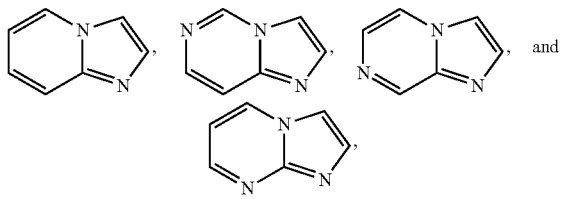

$R_1$ represents a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl group, a hydroxy group, a hydroxy$(C_1-C_6)$alkyl group, a linear or branched $(C_1-C_6)$alkoxy group, —S—$(C_1-C_6)$alkyl, a cyano group, a nitro group, -alkyl$(C_0-C_6)$—NR$_{11}$R$_{11}$', —O-alkyl$(C_1-C_6)$—NR$_{11}$R$_{11}$', —O-alkyl$(C_1-C_6)$—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl$(C_1-C_6)$—NR$_{11}$—C(O)—R$_{11}$', —SO$_2$—NR$_{11}$R$_{11}$', —SO$_2$-alkyl$(C_1-C_6)$, $R_2$, $R_3$, $R_4$ and $R_5$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a hydroxy$(C_1-C_6)$alkyl group, a linear or branched $(C_1-C_6)$alkoxy group, a —S—$(C_1-C_6)$alkyl group, a cyano group, a nitro group, -alkyl$(C_0-C_6)$—NR$_{11}$R$_{11}$', —O-alkyl$(C_1-C_6)$—NR$_{11}$R$_{11}$', —O-alkyl$(C_1-C_6)$—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl$(C_1-C_6)$—NR$_{11}$—C(O)—R$_{11}$', —SO$_2$—NR$_{11}$R$_{11}$', or —SO$_2$-alkyl$(C_1-C_6)$, or the substituents of the pair (R$_1$, R$_2$), together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by from 1 to 2 groups selected from halogen, linear or branched (C$_1$-C$_6$)alkyl, -alkyl(C$_0$-C$_6$)—NR$_{11}$R$_{11}$', —NR$_{13}$R$_{13}$', -alkyl(C$_0$-C$_6$)-Cy$_1$ and oxo, R$_6$ and R$_7$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a linear or branched (C$_1$-C$_6$)alkoxy group, a —S—(C$_1$-C$_6$)alkyl group, a cyano group, a nitro group, -alkyl(C$_0$-C$_6$)—NR$_{11}$R$_{11}$', —O-Cy$_1$, -alkyl(C$_0$-C$_6$)-Cy$_1$, -alkenyl(C$_2$-C$_6$)-Cy$_1$, -alkynyl (C$_2$-C$_6$)-Cy$_1$, —O-alkyl(C$_1$-C$_6$)—R$_{12}$, —C(O)— OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$— NR$_{11}$R$_{11}$', —SO$_2$-alkyl(C$_1$-C$_6$), or the substituents of the pair (R$_6$, R$_7$), when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched (C$_1$-C$_6$)alkyl group, —NR$_{13}$R$_{13}$', -alkyl(C$_0$-C$_6$)-Cy$_1$ and oxo, W represents a —CH$_2$— group, a —NH— group or an oxygen atom, R$_8$ represents a hydrogen atom, a linear or branched (C$_1$-C$_8$)alkyl group, a —CHR$_a$R$_b$ group, an aryl group, a heteroaryl group, an arylalkyl(C$_1$-C$_6$) group, or a heteroarylalkyl(C$_1$-C$_6$) group, R$_9$ represents a hydrogen atom, a linear or branched (C$_1$-C$_6$)alkyl group, a linear or branched (C$_2$-C$_6$)alkenyl group, a linear or branched (C$_2$-C$_6$)alkynyl group, -Cy$_2$, -alkyl(C$_1$-C$_6$)-Cy$_2$, -alkenyl(C$_2$-C$_6$)-Cy$_2$, -alkynyl(C$_2$-C$_6$)-Cy$_2$, -Cy$_2$-Cy$_3$, -alkynyl(C$_2$-C$_6$)—O-Cy$_2$, -Cy$_2$-alkyl(C$_0$-C$_6$)—O-alkyl(C$_0$-C$_6$)-Cy$_3$, a halogen atom, a cyano group, —C(O)—R$_{15}$, or —C(O)—NR$_{15}$R$_{15}$', R$_{11}$ and R$_{11}$' independently of one another represent a hydrogen atom, a linear or branched (C$_1$-C$_6$)alkyl group, or the substituents of the pair (R$_{11}$, R$_{11}$'), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched (C$_1$-C$_6$)alkyl group, R$_{12}$ represents -Cy$_5$, -Cy$_5$-alkyl(C$_0$-C$_6$)—O-alkyl(C$_0$-C$_6$)-Cy$_6$, -Cy$_5$-alkyl(C$_0$-C$_6$)-Cy$_6$, -Cy$_5$-alkyl(C$_0$-C$_6$)—NR$_{11}$-alkyl(C$_0$-C$_6$)-Cy$_6$, -Cy$_5$-Cy$_6$-O-alkyl (C$_0$-C$_6$)-Cy$_7$, —C(O)—NR$_{11}$R$_{11}$', —NR$_{11}$R$_{11}$', —OR$_{11}$, —NR$_{11}$—C(O)—R$_{11}$', —O-alkyl(C$_1$-C$_6$)—OR$_{11}$, —SO$_2$—R$_{11}$, —C(O)—OR$_{11}$, or —NH—C (O)—NH—R$_{11}$, R$_{13}$, R$_{13}$', R$_{15}$ and R$_{15}$', independently of one another, represent a hydrogen atom, or an optionally substituted linear or branched (C$_1$-C$_6$)alkyl group, R$_{14}$ represents a hydrogen atom, a hydroxy group, or a hydroxy(C$_1$-C$_6$)alkyl group, R$_a$ represents a hydrogen atom or a linear or branched (C$_1$-C$_6$)alkyl group, R$_b$ represents a —O—C(O)—O—R$_c$ group, a —O—C (O)—NR$_c$R$_c$' group, or a —O—P(O)(OR$_c$)$_2$ group, R$_c$ and R$_c$', independently of one another, represent a hydrogen atom, a linear or branched (C$_1$-C$_8$)alkyl group, a cycloalkyl group, a (C$_1$-C$_6$)alkoxy(C$_1$-C$_6$) alkyl group, a (C$_1$-C$_6$)alkoxycarbonyl(C$_1$-C$_6$)alkyl group, or the substituents of the pair (R$_c$, R$_c$'), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched (C$_1$-C$_6$)alkyl group, Cy$_1$, Cy$_2$, Cy$_3$, Cy$_4$, Cy$_5$, Cy$_6$ and Cy$_7$, independently of one another, represent a cycloalkyl group, a heterocycloalkyl group, an aryl group, or a heteroaryl group, n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched (C$_1$-C$_6$)alkyl, optionally substituted linear or branched (C$_2$-C$_6$)alkenyl, optionally substituted linear or branched (C$_2$-C$_6$)alkynyl, optionally substituted linear or branched (C$_1$-C$_6$)alkoxy, optionally substituted (C$_1$-C$_6$)alkyl-S—, hydroxy, oxo (or N-oxide where appropriate), nitro, cyano, —C(O)—OR', —O— C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched (C$_1$-C$_6$)polyhaloalkyl, trifluoromethoxy, halogen, or an aldohexose of formula:

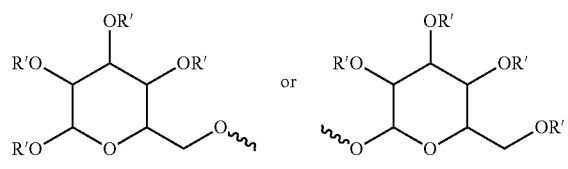

in which each R' is independent;

wherein R' and R", independently of one another, represent a hydrogen atom or an optionally substituted linear or branched $(C_1-C_6)$alkyl group, and $M^+$ represents a pharmaceutically acceptable monovalent cation, its enantiomers, diastereoisomers and atropisomers, and addition salts thereof with a pharmaceutically acceptable acid or base.

11. The method according to claim 1, wherein at least one of the groups selected from $R_2$, $R_3$, $R_4$ and $R_5$ does not represent a hydrogen atom.

12. The method according to claim 1, wherein $R_{14}$ represents a hydrogen atom.

13. The method according to claim 1, wherein $R_1$ represents a linear or branched $(C_1-C_6)$alkyl group or a halogen atom.

14. The method according to claim 1, wherein $R_2$ represents a linear or branched $(C_1-C_6)$alkoxy group, a hydroxy group or a halogen atom.

15. The method according to claim 1, wherein $R_3$ represents a hydrogen atom, a hydroxy group, a linear or branched $(C_1-C_6)$alkoxy group or —O-alkyl$(C_1-C_6)$—$NR_{11}R_{11}'$.

16. The method according to claim 1, wherein $R_4$ and $R_5$ represent a hydrogen atom.

17. The method according to claim 1, wherein

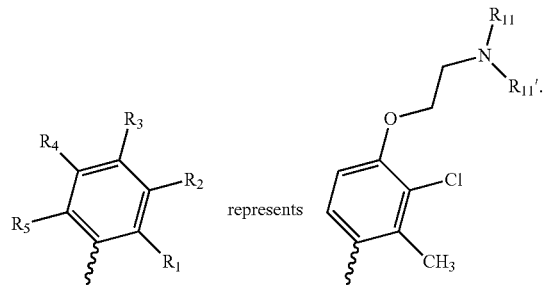

18. The method according to claim 1, wherein the substituents of the pair $(R_1, R_5)$ are identical and the substituents of the pair $(R_2, R_4)$ are identical.

19. The method according to claim 1, wherein $R_6$ represents a hydrogen atom, an optionally substituted linear or branched $(C_1-C_6)$alkoxy group or a —O-alkyl$(C_1-C_6)$—$R_{12}$ group.

20. The method according to claim 1, wherein $R_7$ represents a hydrogen atom.

21. The method according to claim 1, wherein

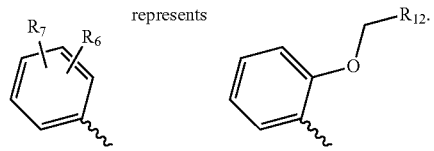

22. The method according to claim 1, wherein the compound of formula (I) is a compound of formula (I-g):

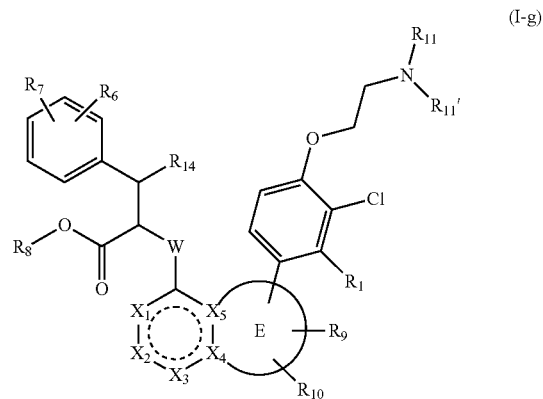

wherein
the ring system

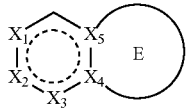

is selected from the group consisting of:

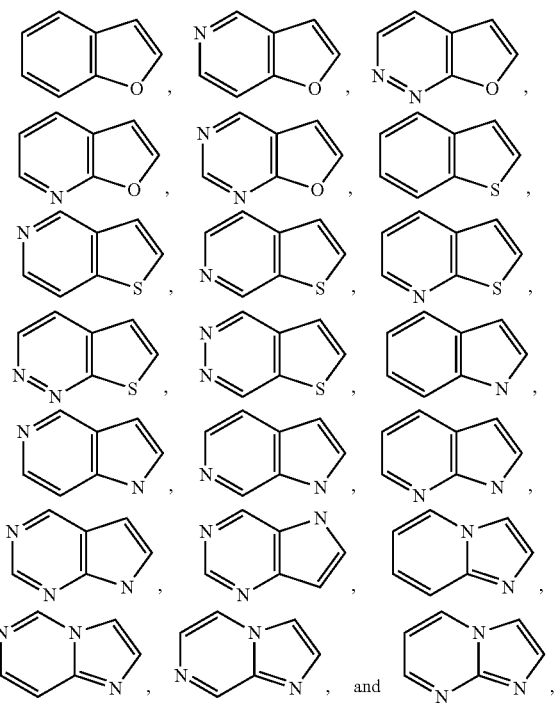

$R_1$ represents a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl group, a hydroxy group, a hydroxy$(C_1-C_6)$alkyl group, a linear or branched $(C_1-C_6)$alkoxy group, —S—(C$_1$-C$_6$)alkyl, a cyano group, a nitro group, -alkyl(C$_0$-C$_6$)—NR$_{11}$R$_{11}$', —O-alkyl(C$_1$-C$_6$)—NR$_{11}$R$_{11}$', —O-alkyl(C$_1$-C$_6$)—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$—NR$_{11}$R$_{11}$', —SO$_2$-alkyl(C$_1$-C$_6$), R$_6$ and R$_7$ independently of one another represent a hydrogen atom, a halogen atom, a linear or branched (C$_1$-C$_6$)alkyl group, a linear or branched (C$_2$-C$_6$) alkenyl group, a linear or branched (C$_2$-C$_6$)alkynyl group, a linear or branched (C$_1$-C$_6$)polyhaloalkyl, a hydroxy group, a linear or branched (C$_1$-C$_6$)alkoxy group, a —S—(C$_1$-C$_6$)alkyl group, a cyano group, a nitro group, -alkyl(C$_0$-C$_6$)—NR$_{11}$R$_{11}$', —O-Cy$_1$, -alkyl(C$_0$-C$_6$)-Cy$_1$, -alkenyl(C$_2$-C$_6$)-Cy$_1$, -alkynyl (C$_2$-C$_6$)-Cy$_1$, —O-alkyl(C$_1$-C$_6$)—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$—NR$_{11}$R$_{11}$', —SO$_2$-alkyl(C$_1$-C$_6$), or the substituents of the pair (R$_6$, R$_7$), when grafted onto two adjacent carbon atoms, together with the carbon atoms carrying them, form an aromatic or non-aromatic ring composed of from 5 to 7 ring members, which ring may contain from 1 to 3 heteroatoms selected from oxygen, sulphur and nitrogen, wherein the resulting ring may be substituted by a group selected from a linear or branched (C$_1$-C$_6$)alkyl group, —NR$_{13}$R$_{13}$', -alkyl(C$_0$-C$_6$)-Cy$_1$ and oxo, W represents a —CH$_2$— group, a —NH— group or an oxygen atom, R$_8$ represents a hydrogen atom, a linear or branched (C$_1$-C$_8$)alkyl group, a —CHR$_a$R$_b$ group, an aryl group, a heteroaryl group, an arylalkyl(C$_1$-C$_6$) group, or a heteroarylalkyl(C$_1$-C$_6$) group, R$_9$ represents a hydrogen atom, a linear or branched (C$_1$-C$_6$)alkyl group, a linear or branched (C$_2$-C$_6$) alkenyl group, a linear or branched (C$_2$-C$_6$)alkynyl group, -Cy$_2$, -alkyl(C$_1$-C$_6$)-Cy$_2$, -alkenyl(C$_2$-C$_6$)-Cy$_2$, -alkynyl(C$_2$-C$_6$)-Cy$_2$, -Cy$_2$-Cy$_3$, -alkynyl(C$_2$-C$_6$)—O-Cy$_2$, -Cy$_2$-alkyl(C$_0$-C$_6$)—O-alkyl(C$_0$-C$_6$)-Cy$_3$, a halogen atom, a cyano group, —C(O)—R$_{15}$, or —C(O)—NR$_{15}$R$_{15}$', R$_{11}$ and R$_{11}$' independently of one another represent a hydrogen atom, a linear or branched (C$_1$-C$_6$)alkyl group, or the substituents of the pair (R$_{11}$, R$_{11}$'), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched (C$_1$-C$_6$)alkyl group, R$_{12}$ represents -Cy$_5$, -Cy$_5$-alkyl(C$_0$-C$_6$)—O-alkyl(C$_0$-C$_6$)-Cy$_6$, -Cy$_5$-alkyl(C$_0$-C$_6$)-Cy$_6$, -Cy$_5$-alkyl(C$_0$-C$_6$)—NR$_{11}$-alkyl(C$_0$-C$_6$)-Cy$_6$, -Cy$_5$-Cy$_6$-O-alkyl (C$_0$-C$_6$)-Cy$_7$, —C(O)—NR$_{11}$R$_{11}$', —NR$_{11}$R$_{11}$', —OR$_{11}$, —NR$_{11}$—C(O)—R$_{11}$', —O-alkyl(C$_1$-C$_6$)—OR$_{11}$, —SO$_2$—R$_{11}$, —C(O)—OR$_{11}$, or —NH—C(O)—NH—R$_{11}$, R$_{13}$, R$_{13}$', R$_{15}$ and R$_{15}$', independently of one another, represent a hydrogen atom, or an optionally substituted linear or branched (C$_1$-C$_6$)alkyl group, R$_{14}$ represents a hydrogen atom, a hydroxy group, or a hydroxy(C$_1$-C$_6$)alkyl group, R$_a$ represents a hydrogen atom or a linear or branched (C$_1$-C$_6$)alkyl group, R$_b$ represents a —O—C(O)—O—R$_c$ group, a —O—C(O)—NR$_c$R$_c$' group, or a —O—P(O)(OR$_c$)$_2$ group, R$_c$ and R$_c$', independently of one another, represent a hydrogen atom, a linear or branched (C$_1$-C$_8$)alkyl group, a cycloalkyl group, a (C$_1$-C$_6$)alkoxy(C$_1$-C$_6$) alkyl group, a (C$_1$-C$_6$)alkoxycarbonyl(C$_1$-C$_6$)alkyl group, or the substituents of the pair (R$_c$, R$_c$'), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen in question may be substituted by a linear or branched (C$_1$-C$_6$)alkyl group, Cy$_1$, Cy$_2$, Cy$_3$, Cy$_4$, Cy$_5$, Cy$_6$ and Cy$_7$, independently of one another, represent a cycloalkyl group, a heterocycloalkyl group, an aryl group, or a heteroaryl group, n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from optionally substituted linear or branched (C$_1$-C$_6$)alkyl, optionally substituted linear or branched (C$_2$-C$_6$)alkenyl, optionally substituted linear or branched (C$_2$-C$_6$)alkynyl, optionally substituted linear or branched (C$_1$-C$_6$)alkoxy, optionally substituted (C$_1$-C$_6$)alkyl-S—, hydroxy, oxo (or N-oxide where appropriate), nitro, cyano, —C(O)—OR', —O—C(O)—R', —C(O)—NR'R", —O—C(O)—NR'R", —NR'R", —(C=NR')—OR", —O—P(O)(OR')$_2$, —O—P(O)(O$^-$M$^+$)$_2$, linear or branched (C$_1$-C$_6$)polyhaloalkyl, trifluoromethoxy, halogen, or an aldohexose of formula:

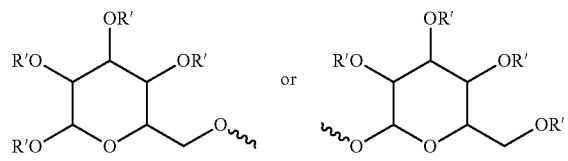

in which each R' is independent;
wherein R' and R", independently of one another, represent a hydrogen atom or an optionally substituted linear or branched $(C_1-C_6)$alkyl group, and $M^+$ represents a pharmaceutically acceptable monovalent cation, its enantiomers, diastereoisomers and atropisomers, and addition salts thereof with a pharmaceutically acceptable acid or base.

23. The method according to claim 1, wherein $R_8$ represents a hydrogen atom, a —$CHR_aR_b$ group, an optionally substituted linear or branched $(C_1-C_8)$alkyl group, or a heteroarylalkyl$(C_1-C_6)$ group.

24. The method according to claim 1, wherein $R_9$ represents a hydrogen atom, a halogen atom, a linear or branched $(C_1-C_6)$alkyl group, a linear or branched $(C_2-C_6)$alkenyl group, a linear or branched $(C_2-C_6)$alkynyl group, an aryl group or a heteroaryl group.

25. The method according to claim 1, wherein $R_{11}$ and $R_{11}'$, independently of one another, represent a linear or branched $(C_1-C_6)$alkyl group, or the substituents of the pair $(R_{11}, R_{11}')$, together with the nitrogen atom carrying them, form a non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched $(C_1-C_6)$alkyl group.

26. The method according to claim 1, wherein $R_{12}$ represents -$Cy_5$ or -$Cy_5$-alkyl$(C_0-C_6)$-$Cy_6$.

27. The method according to claim 26, wherein $Cy_5$ represents a heteroaryl group.

28. The method according to claim 26, wherein $Cy_6$ represents a phenyl group.

29. The method according to claim 26, wherein $R_{12}$ represents

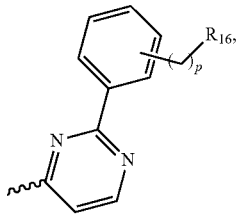

wherein p is an integer equal to 0 or 1 and $R_{16}$ represents a hydrogen atom, a hydroxy group, an optionally substituted linear or branched $(C_1-C_6)$alkyl group, a linear or branched $(C_1-C_6)$alkoxy group, a —O—$(CHR_{17}$—$CHR_{18}$—O$)_q$—R' group, a —O—P(O)(OR')$_2$ group, a —O—P(O)(O$^-$M$^+$)$_2$ group, a —O—C(O)—$NR_{19}R_{20}$ group, a di$(C_1-C_6)$alkylamino$(C_1-C_6)$alkoxy group, a halogen atom, or an aldohexose of formula:

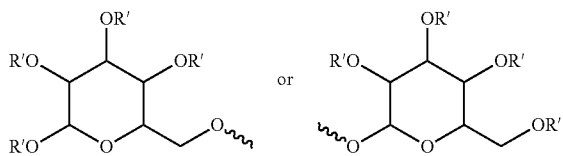

in which each R' is independent;
wherein:
R' represents a hydrogen atom or a linear or branched $(C_1-C_6)$alkyl group, $R_{17}$ represents a hydrogen atom or a $(C_1-C_6)$alkoxy$(C_1-C_6)$alkyl group,
$R_{18}$ represents a hydrogen atom or a hydroxy$(C_1-C_6)$alkyl group,
$R_{19}$ represents a hydrogen atom or a $(C_1-C_6)$alkoxy$(C_1-C_6)$alkyl group,
$R_{20}$ represents a $(C_1-C_6)$alkoxy$(C_1-C_6)$alkyl group, a —$(CH_2)_r$—$NR_{11}R_{11}'$ group or a —$(CH_2)_r$—O—$(CHR_{17}$—$CHR_{18}$—O$)_q$—R' group,
q is an integer equal to 1, 2 or 3 and r is an integer equal to 0 or 1,
$M^+$ represents a pharmaceutically acceptable monovalent cation.

30. The method according to claim 29, wherein the aldexose is D-mannose.

31. The method according to claim 1, wherein the compound of formula (I) is selected from the group consisting of:

(2R)-2-[5-{3-chloro-2-methyl-4-[2-(4-methylpiperazin-1-yl)ethoxy]phenyl}-6-(4-fluorophenyl)furo[2,3-d]pyrimidin-4-yl]oxy}-3-(2-{[2-(2-methoxyphenyl)pyrimidin-4-yl]methoxy}phenyl)propanoic acid;

(2R)-2-{[5-{3-chloro-2-ethyl-4-[2-(4-methylpiperazin-1-yl)ethoxy]phenyl}-6-(4-fluorophenyl)furo[2,3-d]pyrimidin-4-yl]oxy}-3-(2-{[2-(2-methoxyphenyl)pyrimidin-4-yl]methoxy}phenyl)propanoic acid;

N-[(5$S_a$)-5-{3-chloro-2-methyl-4-[2-(4-methylpiperazin-1-yl)ethoxy]phenyl}-6-(4-fluorophenyl)furo[2,3-d]pyrimidin-4-yl]-2-{[2-(2-methoxyphenyl)pyrimidin-4-yl]methoxy}-D-phenylalanine;

(2R)-2-{[(3$S_a$)-3-{3-chloro-2-methyl-4-[2-(4-methylpiperazin-1-yl)ethoxy]phenyl}-2-(4-fluorophenyl)-1-benzothiophen-4-yl]oxy}-3-(2-{[2-(2-methoxyphenyl)pyrimidin-4-yl]methoxy}phenyl)propanoic acid;

(2R)-2-{[(3$S_a$)-3-{3-chloro-2-methyl-4-[2-(4-methylpiperazin-1-yl)ethoxy]phenyl}-2-(4-fluorophenyl)-1-benzofuran-4-yl]oxy}-3-(2-{[2-(2-methoxyphenyl)pyrimidin-4-yl]methoxy}phenyl)propanoic acid;

(2R)-2-{[(3$S_a$)-3-{3-chloro-2-methyl-4-[2-(4-methylpiperazin-1-yl)ethoxy]phenyl}-6-fluoro-2-(4-fluorophenyl)-1-benzofuran-4-yl]oxy}-3-(2-{[2-(2-methoxyphenyl) pyrimidin-4-yl]methoxy}phenyl)propanoic acid;

(2R)-2-{[3-{(3$S_a$)-3-chloro-2-methyl-4-[2-(4-methylpiperazin-1-yl)ethoxy]phenyl}-2-(4-fluorophenyl)-1-methyl-1H-indol-4-yl]oxy}-3-(2-{[2-(2-methoxyphenyl) pyrimidin-4-yl]methoxy}phenyl)propanoic acid;

(2R)-2-{[(3$S_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl) pyrimidin-4-yl]methoxy}phenyl)propanoic acid;

(2R)-2-[5-[3-chloro-2-methyl-4-[2-(4-methylpiperazin-1-yl)ethoxy]phenyl]-6-(4-fluorophenyl)-7-methyl-pyrrolo[2,3-d]pyrimidin-4-yl]oxy-3-[2-[[2-(2-methoxy phenyl)pyrimidin-4-yl]methoxy]phenyl]propanoic acid;

1-[(dimethylcarbamoyl)oxy]ethyl (2R)-2-1 [(3$S_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl)propanoate;

1-[(ethoxycarbonyl)oxy]ethyl (2R)-2-{[(3$S_a$)-3-{3-chloro-2-methyl-4-[2-(4-methylpiperazin-1-yl)ethoxy]phenyl}-2-(4-fluorophenyl)thieno[2,3-b]pyridin-4-yl]oxy}-3-(2-{[2-(2-methoxyphenyl)pyrimidin-4-yl]methoxy}phenyl)propanoate;

N-[3-{3-chloro-2-methyl-4-[2-(4-methylpiperazin-1-yl)ethoxy]phenyl}-2-(4-fluorophenyl)thieno[2,3-b]pyridin-4-yl]-2-{[2-(2-methoxyphenyl)pyrimidin-4-yl]
methoxy}-D-phenylalanine;

N-[3-{3-chloro-2-methyl-4-[2-(4-methylpiperazin-1-yl)
ethoxy]phenyl}-2-(4-fluorophenyl)thieno[3,2-c]pyridin-4-yl]-2-{[2-(2-methoxyphenyl)pyrimidin-4-yl]
methoxy}phenylalanine; and 2-{[(3R$_a$)-3-{3-chloro-2-methyl-4-[2-(4-methylpiperazin-1-yl)ethoxy]phenyl}-2-(4-fluorophenyl)imidazo
[1,2-c]pyrimidin-5-yl]oxy}-3-(2-{[2-(2-methoxyphenyl) pyrimidin-4-yl]methoxy}phenyl)propanoic acid.

32. The method according to claim 1, wherein the compound of formula (I) is administered in combination with an anti-cancer agent selected from genotoxic agents, mitotic poisons, anti-metabolites, proteasome inhibitors, kinase inhibitors and antibodies, wherein the compound of formula (I) and the anti-cancer agent may be administered in combination with one or more pharmaceutically acceptable excipients.

33. The method of according to claim 1, wherein the compound of formula (I) is administered in combination with radiotherapy.

* * * * *

UNITED STATES PATENT AND TRADEMARK OFFICE
CERTIFICATE OF CORRECTION

PATENT NO. : 10,618,909 B2
APPLICATION NO. : 16/394308
DATED : April 14, 2020
INVENTOR(S) : Balázs Bálint et al.

It is certified that error appears in the above-identified patent and that said Letters Patent is hereby corrected as shown below:

In the Claims

Column 99, Line 37: "—$NR_{13}R^{13}$"" should read -- —$NR_{13}R_{13'}$ --

Column 124, Line 19: "(2R)-2-[5-" should read -- (2R)-2-{[5- --

Column 124, Line 56: "(2R)-2-1 [(3S$_\alpha$)" should read -- (2R)-2-{[(3S$_\alpha$) --

Column 125, Line 19: delete "of"

Signed and Sealed this
Eighth Day of September, 2020

Andrei Iancu
*Director of the United States Patent and Trademark Office*